United States Patent
Griffith et al.

(10) Patent No.: US 11,952,579 B2
(45) Date of Patent: Apr. 9, 2024

(54) INTERFERING WITH HD-ZIP TRANSCRIPTION FACTOR REPRESSION OF GENE EXPRESSION TO PRODUCE PLANTS WITH ENHANCED TRAITS

(71) Applicant: Monsanto Technology LLC, St. Louis, MO (US)

(72) Inventors: Cara L. Griffith, Catawissa, MO (US); Abha Khandelwal, Chesterfield, MO (US); Paul J. Loida, Kirkwood, MO (US); Elena A. Rice, Olivette, MO (US); Rebecca L. Thompson, St. Charles, MO (US); Sivalinganna Manjunath, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 114 days.

(21) Appl. No.: 17/071,231

(22) Filed: Oct. 15, 2020

(65) Prior Publication Data

US 2021/0095300 A1    Apr. 1, 2021

Related U.S. Application Data

(62) Division of application No. 15/028,381, filed as application No. PCT/US2014/058594 on Oct. 1, 2014, now Pat. No. 10,829,773.

(60) Provisional application No. 61/888,980, filed on Oct. 9, 2013.

(51) Int. Cl.
*C12N 15/82* (2006.01)

(52) U.S. Cl.
CPC .................. *C12N 15/8216* (2013.01)

(58) Field of Classification Search
None
See application file for complete search history.

(56) References Cited

U.S. PATENT DOCUMENTS

| | | |
|---|---|---|
| 5,627,061 A | 5/1997 | Barry et al. |
| 6,196,636 B1 | 3/2001 | Mills et al. |
| 6,248,876 B1 | 6/2001 | Barry et al. |
| 6,399,861 B1 | 6/2002 | Anderson et al. |
| 6,417,428 B1 | 7/2002 | Thomashow et al. |
| 6,777,589 B1 | 8/2004 | Lundquist et al. |
| 7,135,616 B2 | 11/2006 | Heard et al. |
| H2191 H | 6/2007 | Wang |
| 7,365,185 B2 | 4/2008 | Boukharov et al. |
| 7,371,848 B2 | 5/2008 | Conner et al. |
| 7,511,190 B2 | 3/2009 | Sherman et al. |
| 7,674,955 B2 | 3/2010 | Chan et al. |
| 7,956,242 B2 | 6/2011 | Zhang et al. |
| 8,673,557 B2 | 3/2014 | Scharenberg et al. |
| 8,895,818 B2 | 11/2014 | Chomet et al. |
| 9,447,425 B2 | 9/2016 | Heard et al. |
| 9,469,880 B2 | 10/2016 | Adams et al. |
| 10,233,507 B2 | 3/2019 | Adams et al. |
| 10,392,626 B1 | 8/2019 | Ahrens et al. |
| 10,407,741 B2 | 9/2019 | Adams et al. |
| 10,829,773 B2 | 11/2020 | Griffith et al. |
| 10,858,710 B2 | 12/2020 | Adams et al. |
| 11,466,330 B2 | 10/2022 | Adams et al. |
| 11,884,986 B2 | 1/2024 | Adams et al. |
| 2003/0121070 A1 | 6/2003 | Adam et al. |
| 2004/0010815 A1 | 1/2004 | Lange et al. |
| 2004/0016025 A1 | 1/2004 | Budworth et al. |
| 2004/0214272 A1 | 10/2004 | La Rosa et al. |
| 2004/0216190 A1 | 10/2004 | Kovalic |
| 2005/0160493 A9 | 7/2005 | Ratcliffe et al. |
| 2005/0283856 A1 | 12/2005 | Conner et al. |
| 2006/0147961 A1 | 7/2006 | Dong et al. |
| 2007/0054278 A1 | 3/2007 | Cargill |
| 2007/0214517 A1 | 9/2007 | Alexandrov et al. |
| 2008/0028482 A1 | 1/2008 | Beazley et al. |
| 2008/0127365 A1 | 5/2008 | Sanz Molinero et al. |
| 2008/0229439 A1* | 9/2008 | La Rosa ............ C12N 15/8218 800/278 |
| 2009/0049566 A1 | 2/2009 | Zhang et al. |
| 2009/0158452 A1 | 6/2009 | Johnson et al. |
| 2009/0205085 A1 | 8/2009 | Goldman et al. |
| 2010/0162427 A1 | 6/2010 | Riechmann et al. |
| 2010/0218278 A1 | 8/2010 | Kaster, Jr. et al. |
| 2011/0138499 A1 | 6/2011 | Zhang et al. |
| 2011/0138504 A1 | 6/2011 | Beazley et al. |

(Continued)

FOREIGN PATENT DOCUMENTS

| | | |
|---|---|---|
| CA | 2456979 | 6/2014 |
| CN | 1933723 | 3/2007 |

(Continued)

OTHER PUBLICATIONS

Yang et al. (PNAS, 98:11438-11443, 2001).*
Nishimura et al. (Plant Cell Physiol., 41(5):583-590, 2000).*
McConnell et al. (Nature, 411:709-713, 2001).*
Guo et al. (PNAS, 101: 9205-9210, 2004).*
Keskin et al. (Protein Science, 13:1043-1055, 2004).*
Wells, Biochemistry 29:8509-8517, 1990.*
Ngo et al., (The Protein Folding Problem and Tertiary Structure Prediction, K. Merz., and S. Le Grand (eds.) pp. 492-495, 1994).*
Doerks et al., (TIG, 14:248-250, 1998).*
Smith et al. (Nature Biotechnology, 15:1222-1223, 1997).*
Bork et al. (TIG, 12:425-427, 1996).*

(Continued)

*Primary Examiner* — Vinod Kumar
(74) *Attorney, Agent, or Firm* — Dentons US LLP; David Lanzotti

(57) ABSTRACT

A recombinant DNA construct is disclosed. When the recombinant DNA construct is expressed in a plant or a plant cell, endogenous HD-Zip class II proteins become less able to repress DNA transcription of the genes they typically regulate. The recombinant DNA construct can be expressed in plant cells to produce plants with enhanced phenotypes. Methods of making transgenic plants comprising the recombinant DNA construct, and plants produced thereby are also disclosed.

8 Claims, 12 Drawing Sheets

Specification includes a Sequence Listing.

(56) References Cited

U.S. PATENT DOCUMENTS

| | | |
|---|---|---|
| 2011/0252501 A1 | 10/2011 | Abad et al. |
| 2012/0137382 A1 | 5/2012 | Repetti et al. |
| 2015/0047069 A1 | 2/2015 | Chomet et al. |
| 2015/0052633 A1 | 2/2015 | Creelman et al. |
| 2016/0257968 A1 | 9/2016 | Griffith et al. |
| 2017/0088904 A1 | 3/2017 | Adams et al. |
| 2019/0382778 A1 | 12/2019 | Ahrens et al. |
| 2020/0080102 A1 | 3/2020 | Chomet et al. |
| 2020/0087738 A1 | 3/2020 | Adams et al. |
| 2021/0108277 A1 | 4/2021 | Adams et al. |

FOREIGN PATENT DOCUMENTS

| | | | |
|---|---|---|---|
| CN | 100999549 | 12/2010 | |
| CN | 102154321 | 8/2011 | |
| EP | 1797754 | 10/2010 | |
| WO | 0215675 | 2/2002 | |
| WO | 0216655 | 2/2002 | |
| WO | WO 2003/008540 | 1/2003 | |
| WO | 03013227 | 2/2003 | |
| WO | 03013228 | 2/2003 | |
| WO | 2005059103 | 6/2005 | |
| WO | 2006069017 | 6/2006 | |
| WO | 2006130156 | 12/2006 | |
| WO | 2007023190 | 3/2007 | |
| WO | 2008015263 | 2/2008 | |
| WO | 2009049373 | 4/2009 | |
| WO | WO-2009049373 A1 * | 4/2009 | ........... C07K 14/415 |
| WO | 2010083178 A1 | 7/2010 | |
| WO | 2011025840 | 3/2011 | |
| WO | 2011088065 | 7/2011 | |
| WO | 2013012775 | 1/2013 | |
| WO | 2013155001 | 10/2013 | |
| WO | 2015054000 | 4/2015 | |

OTHER PUBLICATIONS

Thornton et al. (Nature structural Biology, structural genomics supplement, Nov. 2000).*
Steindler et al. (Development, 126:4235-4245, 1999).*
Bou-Torrent et al. (Plant Signalling & Behavior, 7:1382-1387; Published Nov. 2012).*
United States U.S. Appl. No. 09/713,994, filed Nov. 16, 2000, Keddie et al.
Agalou et al., "A genome-wide survey of HD-Zip genes in rice and analysis of drought responsive family members," Plant Mol Biol, 66:87-103, 2007.
Ariel et al., "The true story of the HD-Zip family," Trends in Plant Science 12(9):419-426, 2007.
Aso et al., "Characterization of Homeodomain-Leucine zipper genes in the fern Ceratopteris richardii and the evolution of the Homeodomain-Leucine zipper gene family in vascular plants," Mol Biol. Evol. 16(4):544-552, 1999.
Bou-Torrent et al., "ATBH4 and HAT3, two class II HD-Zip transcription factors, control leaf development in *Arabidopsis*," Plant Signal Behavior 7(11):1382-1387, 2012.
Cao et al., "The *Arabidopsis* NPR1 Gene That Controls Systemic Acquired Resistance Encodes a Novel Protein Containing Ankyrin Repeats," Cell 88:57-63, 1997.
Chan et al., "Homeoboxes in plant development," Biochimica et Biophysica Acta 1442:1-19, 1998.
Ciarbelli et al, "The *Arabidopsis* homeodomain-leucine zipper II gene family: diversity and redundancy," Plant Mol Biol 68:465-478, 2008.
Collins et al., "Molecular Characterization of the Maize Rp1-D Rust Resistance Haplotype and Its Mutants," The Plant Cell, 11:1365-1376, 1999.
Comelli et al., "Conserved homeodomain cysteines confer redox sensitivity and influence the DNA binding properties of plant class III HD-Zip proteins," Arch Biochem Biophys,467:41-47 2007.

Deng et al., "Characterization of five novel dehydration-responsive homeodomain leucine zipper genes from the resurrection plant Craterostigma plantagineum," Plant Mol Biol, 49:601-610, 2002.
Frank et al., "Two dehydration-inducible transcripts from the resurrection plant Craterostigma plantagineum encode interacting homeodomain-leucine zipper proteins," Plant J Cell Molec Biol 15:413-421 1998.
Harris et al., "Modulation of plant growth by HD-Zip class I and II transcription factors in response to environmental stimuli," New Phytol 190:823-837, 2011.
Hymus et al., "Application of HB17, an *Arabidopsis* class II homeodomain-leucine zipper transcription factor, to regulate chloroplast number and photosynthetic capacity," Journal of Experimental Botany 64(14):4479-4490, 2013.
Ikeda et al., "A novel group of transcriptional repressors in *Arabidopsis*," Plant Cell Physiol 50(5):970-975, 2009.
Larkin et al., "Roles of the GLABROUS1 and Transparent Testa Glabra genes in *Arabidopsis* trichome development," The Plant Cell 6:1065-1076, 1994.
Lazar et al., "Transforming growth factor α: mutation of aspartic acid 47 and Leucine 48 results in different biological activities," Mol Cell Biol. 8(3):1247-1252, 1988.
Liu et al., "Two Transcription Factors, DREB1 and DREB2, with an EREBP/AP2 DNA binding domain separate two cellular signal transduction pathways in drought- and low-temperature-responsive gene expressing respectively, in *Arabidopsis*," The Plant Cell 10:1391-1406, 1998.
McElwain et al, "A wheat cDNA clone which is homologous to the 17 kd heat-chock protein gene family of soybean," Nucleic Acids Res 17(4):1764-1764, 1989.
Meijer et al., "HD-Zip proteins of families I and II from rice interactions and functional properties," Molecular and General Genetics 263:12-21, 2000.
Newman et al.," Genes galore: a summary of methods for accessing results from large-scale partial sequencing of anonymous *Arabidopsis* cDNA clones," Plant Physiology 106:1241-1255, 1994.
Nishimura et al, "Over-expression of tobacco knotted1-type class1 homeobox genes alters various leaf morphology," Plant Cell Physiology, 41(5):583-590, 2000.
Olsen et al., "NAC transcription factors: structurally distinct, functionally diverse," Trends in Plant Science 10(2):79-87, 2005.
O'Shea et al., "X-ray structure of the GCN4 leucine zipper, a two-stranded, parallel coiled coil," Science, 254:539-544, 1991.
Palena et al., "A monomer-dimer equilibrium modulates the interaction of the sunflower homeodomain leucine-zipper protein Hahb-4 with DNA," Biochem J, 341:81-87, 1999.
Park et al., "ATHB17 is a positive regulator of abscisic acid response during early seedling growth," Mol Cells 35:125-133, 2013.
Rice et al., "Expression of a Truncated ATHB17 Protein in Maize Increases Ear Weight at Silking," PLOS One 9(4):e94238, 2014.
Ruberti et al., "A novel class of plant proteins containing a homeodomain with a. closely linked leucine zipper motif,"EMBO J. 10(7):1789-91, 1991.
Sakakibara et al., "Isolation of homeodomain-leucine zipper genes from the moss physcomitrella patens and the evolution of homeodomain-leucine zippergenes in land plants," Molecular Biology and Evolution, 18(4):491-502, 2001.
Schena et al., "Structure of homeobox-leucine zipper genes suggests a model for the evolution of gene families"; Proc Nati Acad Sci USA 91:8393-8397, 1994.
Schena et al., "The HAT4 gene of *Arabidopsis* encodes a developmental regulator," Genes and Dev., 7:367-379, 1993.
Seo et al., "Competitive inhibition of transcription factors by small interfering peptides," Trends Plant Sci, 16:541-549, 2011.
Sessa et al., "DNA-binding specificity of the homeodomain-leucine zipper domain," J Mol Biol, 274: 343-309, 1997.
Sessa et al., "The Athb-1 and -2 HD-Zip domains homodimerize forming complexes of different DNA binding specificities," EMBO J, 12:3507-3517, 1993.
Turchi et al., "*Arabidopsis* HD-Zip it transcription factors control apical embryo development and meristem function," Development 140:2118-2129, 2013.

(56) References Cited

OTHER PUBLICATIONS

Uberlacker et al., "Ectopic expression of the maize homeobox genes ZmHox1a or ZmHox1b causes pleiotropic alterations in the vegetative and floral development of transgenic tobacco," The Plant Cell 8:349-362, 1996.
Wenkel et al., "A Feedback Regulatory Module Formed by Little Zipper and HD-ZIPIII Genes," Plant Cell, 19:3379-3390, 2007.
Whisstock et al., "Prediction of protein function form protein sequence and structure," Q. Rev. Biophys. 36(3):307-340, 2003.
Zhao et al., "Systematic Analysis of Sequences and Expression Patterns of Drought-Responsive Members of the HD-Zip Gene Family in Maize," PLOS ONE, 6:e28488, 2011.
GenBank Accession No. AAC67320, dated Mar. 11, 2002.
GenBank Accession No. AC005560, dated Mar. 11, 2002.
GenBank Accession No. NM_126204, dated Jun. 5, 2013.
GenBank Accession No. NP_178252, dated Jun. 5, 2013.
GenBank Accession No. H76651, dated Jan. 5, 1998.
GenBank Database Accession No. AF145727, dated Mar. 17, 2000.
GenBank Database Accession No. AJ431181, dated Apr. 22, 2008.
GenBank Database Accession No. EU966190, dated Dec. 10, 2008.
GenBank Database Accession No. NM_001050228, dated Feb. 14, 2008.
GenPept Database Accession No. ACG38308, dated Dec. 10, 2008.
GenPept Database Accession No. EAY75147, dated Dec. 17, 2008.
U.S. Appl. No. 17/819,853, filed Aug. 15, 2022, Adams et al.
GenPept Database Accession No. NP_001043693, dated Feb. 14, 2008.
GenBank Database Accession No. GE573225.1, dated Nov. 3, 2008.
NCBI Protein Sequence Accession No. Q8S9N6, Natl Lib of Medicine, NIH, Bethesda, MD, submitted Feb. 19, 2014.
Cranston et al., "Dicamba resistance in kochia," Weed Science 49:164-170, 2001.
Guo et al., "Protein tolerance to random amino acid change," PNAS 101(25):9205-9210, 2004.
Oh et al., "Transcriptional regulation of secondary growth in *Arabidopsis thaliana*," Journal of Experimental Botany 54(393):2709-2722, 2003.
Zhang, "Overexpression analysis of plant transcription factors," Current Opinion in Plant Biology 6:430-440, 2003.
USPTO: Final Office Action regarding U.S. Appl. No. 14/511,107, dated Jan. 23, 2017.
European Supplementary Search Report regarding European Application No. 14852873.0, dated Feb. 14, 2017.
European Supplementary Search Report regarding European Application No. 14851966.3, dated Mar. 2, 2017.
Rice et al., "Expression of *Arabidopsis thaliana* HB17 Gene in Corn Leads to Improved Sink Potential," In Vitro Cellular Developmental Biology—Animal 49:S22, 2013. (Abstract).
Office Action regarding Chinese Application No. 201480055624.1, dated Mar. 9, 2017.
Zeng et al., "Genetic Engineering Technology," China Light Industry Press pp. 67-74, 2010.
USPTO: Interview Summary regarding U.S. Appl. No. 14/511,107, dated Apr. 12, 2017.
Steindler et al., "Shade avoidance responses are mediated by the ATHB-2 HD-Zip protein, a negative regulator of gene expression," Development 126:4235-4245, 1999.
Ohgishi et al., "Negative autoregulation of the *Arabidopsis* homeobox gene ATHB-2," The Plant Journal 25(4):389-398, 2001.
Qin et al., "Progress in HD-Zip Transcription Factors of Plants," Chinese Journal of Cell Biology 31(4):514-520, 2009.
USPTO: Non-Final Office Action regarding U.S. Appl. No. 14/511,107, dated Jan. 17, 2018.
Ruzza et al., ATB17 Arath, 2002.
Sentoku et al., "Overexpression of Rice OSH Genes Induces Ectopic Shoots on Leaf Sheaths of Transgenic Rice Plants," Developmental Biology 220:358-364, 2000.
Silverstone et al., "Gibberellins and the Green Revolution," Trends in Plant Science 5(1):1-2, 2000.
Ueki et al., "Functional transient genetic transformation of *Arabidopsis* leaves by biolistic bombardment," Nature Protocols 4(1):71-77, 2009.
Hallauer, Principles of Cultivar Development, vol. 2, Walter Fehr ed., "Maize," pp. 249-294, 1987.
Hill et al., "Functional Analysis of Conserved Histidines in ADP-Glucose Pyrophosphorylase from *Excherichia coli*," Biochem. Biophys. Res. Commun. 244(2):573¬577, 1998.
Hulbert et al., "Structure and Evolution of the rp1 Complex Conferring Rust Resistance in Maize," Annual Review of Phytopathology 35:293-310, 1997.
Examination Report regarding Europe Application No. 14852873.0, dated Jul. 8, 2019, 6 pages.
Ait-Ali et al., "Flexible control of plant architecture and yield via switchable expression of *Arabidopsis* gai," Plant Biotechnology Journal 1:337-343, 2003.
Reynolds et al., "Achieving yield gains in wheat," Plant, Cell and Environment 35:1799-1823, 2012.
USPTO: Non-Final Office Action regarding U.S. Appl. No. 16/427,309, dated Jul. 14, 2020.
Alexandrov et al. (NCBI, BenBank Accession No. EU968120; Published Dec. 10, 2008).

\* cited by examiner

Cont. on Fig.4b

SEQUENCE LISTING

<160> NUMBER OF SEQ ID NOS: 270

<210> SEQ ID NO 1
<211> LENGTH: 678
<212> TYPE: DNA
<213> ORGANISM: Zea mays

<400> SEQUENCE: 1

```
atggggtcca cttctccttc aggcctggag ctcaccatgg ctgtcccggg cctcagctcc      60
tcctctggct cagaggggtt tggatgcaac aacaacaacg ggagcgggaa cgggaacaac     120
atgagggacc tggacatgaa ccagccggcg agcggcggcg aggaggagga gttcccaatg     180
gggagcgtgg aggaggagga ggacgagcgc ggcggcgccg gcgggccgca ccgcgccaag     240
aagctccggc tgtccaagga gcagtcccgc ctcctggagg agagcttccg cctcaaccac     300
accctcacac cgaagcaaaa ggaggccttg gctgtcaagc tcaagctgcg gcccaggcag     360
gtggaggtct ggttccagaa ccgcagggct aggacgaagc ttaagcagac ggagctggag     420
tgcgagtacc tgaagcgctg cttcggctcg ctgaccgagg agaacggcg gctgcagcgg     480 gaggtggagg agctgcgcgc gatgcgggtg gccccgccca ccgtgctctc cccgcacacc     540
cggcagccgc tccggcgtc cgcgctcacc atgtgcccgc gctgcgagcg catcaccgcc     600
gcaacggccg cgcgcacccc acgcccgccg ccgccgcga gccccttcca cccgcgccgc     660
ccgtccgcgg cgttttag                                                  678
```

<210> SEQ ID NO 2
<211> LENGTH: 888
<212> TYPE: DNA
<213> ORGANISM: Zea mays

<400> SEQUENCE: 2

```
atgatgcccc aggccagcgc tagcctcgac ctcggcctca gcctgggcct caccctcacc      60
tcccagggca gcctctcctc ctccaccacc accgccggct cctcctcccc ctgggcagcc     120
gcgctcagct ccgtcgtggc cgacgtcgcc agggcgcggg gtgacgcgta cgcgcagcac     180
cacgccggcg ccgcgatgac gatgcgcgcg tccacgtcgc ccgacagcgg cgacaccacc     240
accgccaaga gggagaggga gggggagctc gagcgcaccg gctccgccgg aggcgtccgc     300
agcgacgagg aggacggcgc ggacggcggc gccggcgggc gcaagaagct caggctctcc     360
aaggaccagg ccgccgtcct cgaggagtgc ttcaagacgc acagcacgct caaccccaag     420
```

| | |
|---|---|
| cagaaggtgc agctggccaa ccgcctgggc ctccggccgc ggcaggtgga ggtgtggttc | 480 |
| cagaaccgcc gcgcgcggac caagctgaag cagacgcagg tggactgcga gtacctcaag | 540 |
| cgctggtgcg accgcctcgc cgacgagaac aagcgcctcg agaaggagct ggccgacctc | 600 |
| agggcgctca aggccgcgcc gccgtcgtcg gccgccgcgc agcccgcctc ggccgccgcc | 660 |
| accctcacaa tgtgcccgtc ctgccgccgc gtcgcggccg ccgctagcca ccaccaccag | 720 |
| ccgcccccgc cgcaatgcca ccccaagcct accgtcgccg ccggtggcgg cagcgtcgtg | 780 |
| cccaggccca gccactgcca gttcttcccg gccgccgccg ttgaccggac gagccagggc | 840 |
| acgtggaaca ccgccgcgcc gccgctcgtc accagagaac tcttctga | 888 |

<210> SEQ ID NO 3
<211> LENGTH: 948
<212> TYPE: DNA
<213> ORGANISM: Zea mays

<400> SEQUENCE: 3

| | |
|---|---|
| atggcggatt ccgggagcga cctcgtgctt gggcttggga tggggtcgg ggtgcggagg | 60 |
| gaggaggaaa cgcagagagg gaggagggat agggaggcga ggaggagct tgagtttgag | 120 |
| acggggaggt gcgcccggcc gtcgccgagg ccggcggtgc gactcacgct cctgccaggc | 180 |
| ctggtgccta gccttggcct cccgtggccg ctgtcgtccg agaccaatcg tgaggtgtcg | 240 |
| acgcgtggct tcgacgacgt gaaccggcg ctgtccgtgg ccggtgctgg gcggaggag | 300 |
| gacgaggcgg ccgtggccgc agccacggcg gcagcatcct cgtcgcctaa taacagctcg | 360 |
| ggctccttcg cgatggacat ctccgcgcag ggccagggcc agggcagga ccaggcggcg | 420 |
| cccgccgccg accgcgcgtg ctcgcgcgcc agcgacgagg acgacggcgg ctcggcgcgc | 480 |
| aagaagctgc gcctctccaa ggaacagtcc gcgttcctgg aggagagctt caaggtgcgc | 540 |
| gccacgccga acccgaagca gaagctggcg ctggcgaggc agctcaacct gcgggcgcgc | 600 |
| caggtggagg tgtggttcca gaaccgcagg gccaggacga agctgaagca gacggaggtg | 660 |
| gactgcgagc acctgaagcg ctgctgcgag acgctgacgg gggagaaccg gcggctgcac | 720 |
| aaggagctag ccgagctccg cgcgctcaag gcggtgcgcc ccttgttgca catgcacctc | 780 |
| ccggccacca ccctctccat gtgcccctcc tgcgagcgcg tcgcctccac cagctccgcg | 840 |
| gccccgccg cgccggcgcc agcgtcgccc tcacctgctg ctggtgctgg cattgcggcg | 900 |
| tcggccccgg acccggatca gaggccctcg tcgtcgttcg cggcgtga | 948 |

<210> SEQ ID NO 4
<211> LENGTH: 786
<212> TYPE: DNA
<213> ORGANISM: Zea mays

<400> SEQUENCE: 4

| | |
|---|---|
| atggcgcctc aaagcctgga tctcgggctg agtctcggcc tgggcgtggc ggcattccag | 60 |
| cccagcttct gccacccggc cggcaatgac gcggcggagc gggaggccag cccgaccgcg | 120 |
| gacgagaggg agcggaggtg ctcgcccgcc ggcagcccga cgtcgagcgg cagcgggaag | 180 |
| cgcgtcgcgg cggagaggtc ggccggcagc ggcagcggc acgaggacga cgacgggggc | 240 |
| gctcgcaaga agctgcggct gtccaaggac caggccgccg tgctcgagga gtgcttcaaa | 300 |
| acgcaccaca ccctcactcc gaagcagaag gcagcgctgg ccagccgcct gggcctccgg | 360 |
| gcgcggcagg tggaggtgtg gttccagaac cggcgcgccc ggaccaagct gaagcagacg | 420 |
| gaggtcgact gcgagtacct caggcgctgg tgcgagcagc tcgccgagga gaaccggcgc | 480 |

```
ctgggcaagg aggtcgccga gctcagggcg ctgagcgccg cgcccgcgcc agcggcccct    540
ctcaccgccc tcacaatgtg cctctcctgc aggcgcgtct cctcttcatc ctgctcatcc    600
tcgccgccta acacgcacgc gcatgccgct gcagctggca ctggcaggag cgtggcggcg    660
gcggcggcga cgacgttgcc cgcccaccgg cagttcttgt gcgggttcag agacggcggg    720
gcggccgccg ccgcagtgta cgggacctca tcggctctcg caaaggccct cagggcggcc    780
agatag                                                               786

<210> SEQ ID NO 5
<211> LENGTH: 672
<212> TYPE: DNA
<213> ORGANISM: Zea mays

<400> SEQUENCE: 5
atgtacagct gcactcgtgc catggaggaa gaggggtcg ggaagtcatg gctcgggctg       60
gggataggcg gcggcggcga tctgatgaag cggaataacc gaccaccggt gcagttggac     120
gacctgctgt cgttcccgcc gcagagcgta gctgctgcga gcaagaagca ggcggagaaa     180
ggcggcggtg ggcgcaagag gcacaagatc gtcgttacgg ccgacgaaga tggccgccag     240
tcgccgcacg gcggcgcgag gaagaagctc cggctcacca aggcgcagtc cacgctgctc     300
gaggacacct tccgcgccca caacatactc tcccacgctc agaagcagga gcttgcacgg     360
caggtgaatc tcagcgccag gcaggtggaa gtgtggttcc agaacaggag agcaagaacg     420
aagctgaagc aaacggaggc ggactgcgag gtcctgaagc gctactgcga gagactgacc     480
ggcgagaacc agcggctgag gctggagctc cgcgcagctg cagcggtcgcc ggcggcggag     540 gaggctgggt tctacgtcca gtcgtcgttc ccgttcccgc cgctggccac ggccatggcc     600
agcgtctgcc cgtcgtgcga caaggtcgtc gccgtgacga gcggcaagag ctccaccagc     660
tactcctcgt ga                                                         672

<210> SEQ ID NO 6
<211> LENGTH: 726
<212> TYPE: DNA
<213> ORGANISM: Zea mays

<400> SEQUENCE: 6
atggaggaag aggggtcgg caagtcatgg cttgcgctgg ggataggcgg cggcgatctg       60
atgaagcgga caaccgacc accggtgcag ttcgacctgc tgttcccgcc gcagagcgtc     120
aaggaagaag gtgccgcgag caagaaggca gagaaaggcg gtgggcggaa gaggctcaag     180
gttgtcacgg ccgacgagga tggccgccag tcgccgcacg gcggtccagg ccccagcgac     240
ggctccggcg caggcgcgag gaagaagctc cggctcacca atgagcagtc gacgctgctc     300
gaggacacct tccgcgccca caacatactc tccaacgcgc agaagcagga gctcgcacgg     360
caggtggatc tcagcgccag gcaggtggaa gtgtggttcc agaacaggag agcaagaaca     420
aagctgaagc aaacggaggt ggactgcgag atcctgaagc gctgctgcga gagcctgacc     480
ggcgagaacc agcggctgag gctggagctc cgcgcagctg cagcggtcagc ggcggcggcg     540 gcggaggctg ggctctacgt ccagtcgtcg ttccgccgc tggccacggc cacggccacg     600
gccagcgtct gccgtcgtg cgacaaggta attgccgtgt cgagcggcgg cgagacaagc     660
ggcaagagct ccaccagcta ctcctcgcga cgcgctgggt tcccttcaat aatgggcagt     720
cgttga                                                                726
```

<210> SEQ ID NO 7
<211> LENGTH: 804
<212> TYPE: DNA
<213> ORGANISM: Zea mays

<400> SEQUENCE: 7

```
atgtcgagcc tcaccacggc cgccagcagc agcagcagca tggaggagca ctgctactcc    60
gtgtccgcgg aggaggtcgt cggcacgcac ctgtccttag ggatcggcgg cggcggcgga   120
ggaggaggag ataagaggac gatgctaacg ctgccgccgt ctcggacggt gcagctgttc   180
ggcgaggtgc tgtcggtgca ggacggtgac ggaacgcaag ctcttcgtca tcatcacacg   240
ggccggccac cagcagcgag cagcaggaag aagaagagga aggacgccgc cgccgctggt   300
ggcgccagcg ccactgacgc cgctgccaat ggccatcatc atcagagcaa gaaaaccaag   360
acgacggcgg cgcgccgaga cgacggaggc ggcggcagga agaagctccg gctcacctcc   420
gcgcaggcca ccttgctcga ggacagcttc cgcgcccaca acatcctctc tcacggggag   480
aagcaggagc tggcgcggca ggcggggctg agcgcgcggc aggtggaggt gtggttccag   540
aaccggaggg cccggaccaa gctcaagcag acggaggtyg actgcgacct gctccgccgc   600
tggtgcgccc gcctctccga cgacaacgac cgactccgcc gagacctcgc cgacctccgc   660
cgggcggcgt cgtcgtccgc gggcctcggc gccgtcgtct gctgcgcctc atgcggcgcc   720
gacaggcagc tcgccctcgc cgccgccgcc gacaacgtgc tgccgtcggt cgcctcgcct   780
agtcactcac ctcacctcac ctga                                          804
```

<210> SEQ ID NO 8
<211> LENGTH: 960
<212> TYPE: DNA
<213> ORGANISM: Zea mays

<400> SEQUENCE: 8

```
atggatatta tggcgcttaa tgcgagagac gaggagcagt acgggaacaa ccatctcggg    60
ctcgggctga gcctcagcct cggcctcggc gtcgccaccg cggctccggt cgaggtcgag   120
ccccccgccac cgccgcggca gcagcagcag cgagctatca gctcgcgcc catcacctcc   180
ctccccgcgc cgcagtggtg gaagtggaac ggccccggtc tcttcttcgg acgacaatg   240
gatcagcagc agcagccggc ggccgcgcgc acggccacg agatgccgtt cctgcgggg    300
gtggacgtga accgggcccc tgccggggat accaggaggg gtagctgcag cgaggacgac   360
gaggagcctg gcggcgcgtc gtcgtcgcca aacagcacgc tctccagcag cctcagcggg   420
aagcgcgcag ctccggcgag gagcggcgga gaggtggccg accacacccc gagagccgga   480
ggcggcagcg acgacgagga ctccggcggt gggtcgcgca agaagctccg cctgtccaag   540
gaccaggccg ccgtcctcga ggagagcttc aaggagcata acacactcaa ccccaagcag   600
aaggcggcgc tggcgaagca gctgaacctg aagccgcgtc aggtggaggt gtggttccag   660
aaccgcagag ccaggacgaa gctgaagcag acggaggtgg actgcgagtt cctgaagcgc   720
tgctgcgaga cgctgacgga ggagaaccgg cggctgcagc gggaggtggc ggagctgcgc   780
gtgctcaagc tctggcgcc gcaccactac gcgcgcatgc cgccgcccac cacgctcacc   840
atgtgcccct cctgcgagcg cctcgcctcc gcgtccgcgt ccgccgacca gcgggccgt   900
gcagggccct gctggggccc tctccccgtg ttcgtcgacg gcccagcccg gaggccgtga   960
```

<210> SEQ ID NO 9
<211> LENGTH: 1065

```
<212> TYPE: DNA
<213> ORGANISM: Zea mays

<400> SEQUENCE: 9
atggagctgg ggctgagcct gggcgacgcg gcagtgccgg acgccggcag ggcggctccg      60
gagctgggcc tggggcttgg ggtcgggatt ggatccaacg ccgccggaac cggcagggga     120
agcaaggcgg cggggacgac gggaactact gggtggtggg cggcgccggc acaccggag     180 tcggcagtgc ggctcagcct cgtgtccagc ctcggccttc agtggccacc tccgacggc     240 ggcatctgtc atgtagggcg cgacgaggcg ccggcgcgcg gcttcgacgt gaaccgggcg     300
ccgtcggtgg cggggagcgc cctggcgctg gaggatgacg aggaggagcc gggcgccgcg     360
gcactgtcgt cgtcgcccaa cgacagcgcg ggctccttcc cgctggacct gggaggccca     420
cgcgcccacg ccgagggcgc cgcggcgcgg ccggcggcg agcggtcctc gtctcgcgcc     480
agcgatgagg acgagggcgc gtccgcgcgc aagaagctgc gcctctccaa ggagcagtct     540
gcgttcctgg aggagagctt caaggagcac agcacccctca accctaagca gaaggcggcg     600
ctggcgaagc agctcaacct ccggccgcga caggtagaag tctggttcca gaaccgccga     660
gccaggacga agctgaagca gacggaggtg gactgcgagt acctgaagcg ctgctgcgag     720
acgctgacgg aggagaaccg gcggctgcac aaggagctcg cggagctgcg cgcgctcaag     780
acggcgccgc ccttcttcat cgcgcctcccg gccaccaccc tctccatgtg ccctcctgc     840 gagcgcgtcg cctccggccc cagccctgcc tccacctcgg cacctgcgtc gtccacgccg     900
cctgccacag ccgccaccac cgccatctcg tacgctgcag cagccgccgc acccgtgcga     960
gccgaccacc ggccctcgtc gttcgccgcg ctgttcgcgg cgacccgcag cttcccgctg    1020
gcgtcccagc cgcggccgcc cgcgccggcg agcaactgcc tgtag                     1065

<210> SEQ ID NO 10
<211> LENGTH: 996
<212> TYPE: DNA
<213> ORGANISM: Zea mays

<400> SEQUENCE: 10
atggaacttg agcttagtct gggggattct agagctccag caaagagcgc ttccacgcct      60
gctgcactga ctcctataca cgcaggtgcg ggaggagaag gccatgagct tgcgctggag     120
ctaggagtag gagctgccaa aagagctgaa caagacaacc aaaagacacc cgtgcaacca     180
gaacatgtgc aggaagaaga agaagaggaa gaaacatgcc catacagcga gtcacctgcc     240
gagctgagcc tcatcggctg cccttttgctg cctgcggcct cagcagaaat agggtccgtg     300
aattcttcag aggtgtgcgt gcgacgagga tttggtgtgg acgctgttct cgtggatgga     360
ggagacgcag cacaaggaag accggctttg tcgacttcgt tcttgccttc ggagtttctc     420
gttcggcggc aggctgatga tcaagaagct gctgcagagg atgaggagat gagtgggtt     480 ggcgggggag cgaggaagaa gctgaggctg tccaaggagc agtctgcgtt cctggaggat     540
agcttcaagg cgcacagcac actgacccca aaacagaaga gtgatttagc gaagcggctg     600
aaacttcgac cgcgccaggt ggaggtctgg ttccagaaca gaagagcaag aagtaagcta     660
aagcagacgg aggtggactg cgagtacctg aagcgttggt gcgagaagct agcgcaggag     720
aaccggaggc tgcagaggga ggtggcggag ctgcggcgtc tttgctccgc cgcctacccg     780
ttttacggtg cagcagcagg gttcggcgtg ccacagccc gagtgtgccc tagctcatgc     840
gataacgacg tcagcgaggc tgctatcagt ggcgctccat cagcagcggc accaccgcca     900
```

```
tccaccttgt cgccagctg gcctcctcat ttcggaccct tcaccgtcgt cgtcccccca    960
ctgctccgcc ggcagccgtc ggcgacgacc tcgtga                             996
```

<210> SEQ ID NO 11
<211> LENGTH: 666
<212> TYPE: DNA
<213> ORGANISM: Zea mays

<400> SEQUENCE: 11

```
atgtacagca ctcgtgagga agagggcgtc gggaagtcat ggcttgggct ggggataggc     60
ggcggcagcg gcggctgcga tctgatgcag cggaataacc gaccaccggt gcagttcgac    120
ctgctgttcc cgccgcaggg cgtcgtggaa ggagttgccg cgagcaagaa ggcggagaaa    180
ggcggtggtg gacggaagag gctcaaggtc gttacgggca cggccgacga ggatggccag    240
cagcccccag gcgcgaggaa gaagctccgg ctcaccaagg cgcagtcgac gctgctcgag    300
gacaccttcc gcgcccacag catactctcc aacgcgcaga agcaggagct cgcacgacaa    360
gtggatctca gcgccaggca ggtggaagta tggttccaga acaggagggc aagaacgaag    420
ctgaagcaaa cggaggcgga ctgcgagatc ctgaagcgct gctgcgagag cctgaccggc    480
gagaaccagc ggctgaggct ggagctcgcg cagctgcagg ggtcggaggc tgggctctac    540
ctccagtcgt cgttcccgcc gctggccgcg gccatggcga gcgtctgtcc gtcgtgcgac    600
aaggtcatca ccgtggcgag cggcggcgag acaagcggca gaagctcgac tagctactcc    660
tcgtga                                                              666
```

<210> SEQ ID NO 12
<211> LENGTH: 819
<212> TYPE: DNA
<213> ORGANISM: Zea mays

<400> SEQUENCE: 12

```
atggcgcctc aaagcttgga tcttgggctg agtctcggcc tgggcgtggc ggcgttccag     60
cccagcagct tctgccaccc cggcaatgcc gtcgtcgtcc ccgcggcggc ggagcgggag    120
gccagcccgg ccgcggcgga ggagagggag cggaggtgct cgcccgccgg cagcccggtg    180
tcgagcggca gcggcagcgg gaataagcgc gccgcggcgg agaggtcggc cggcgccggc    240
gccggtagcg gcgacgagga cgacgacggt gccgcacgca agaagctgcg gctgtccaaa    300
gaccaggccg ccgtgctcga ggagtgcttc aagacgcacc acacgctcac tccgaagcag    360
aaggtggcgc tggccagcag cctgggcctc cggccgcggc aggtggaggt gtggttccag    420
aaccggcgcg cccggaccaa gctgaagcag acggaggtgg actgcgagta cctcaagcgc    480
tggtgcgagc agctcgccga ggagaaccgc cgcctgggca aggaggtcgc cgagctcagg    540
gcgctcagcg ccgcgccggc ggccccgctc accaccctca cgatgtgcct ctcctgccgg    600
cgcgtcgcct cctcgtcccc gtcgtcgtcg tcgtcgccca ggcctagcat ccccggcgcc    660
gcagctgcca gtggcgggag catggcctct ccggcggcgg cggcgacgtt gcccgcccac    720
aggcagttct tctgcgggtt cagagacgcc ggggcggcgg ccgcggcgta cgggacagcc    780
tcggcggggc tcgcgaagcc tgtcagggct gccagatag                           819
```

<210> SEQ ID NO 13
<211> LENGTH: 738
<212> TYPE: DNA
<213> ORGANISM: Zea mays

<400> SEQUENCE: 13

-continued

| | |
|---|---|
| atggctcagg aggacgtgca cctggacgat gccggcctgg cgctgtgcct gtccctccac | 60 |
| ggtaccagca gcagccggct gagcacggag gcgccgcgca cgctggagcc gccgtcgctg | 120 |
| acgctgagca tgccggacga agcgaccgcg accgcgaccg gcgggtccgg cggcagcggc | 180 |
| ggggccgcgc gcagcgtgtc gtcgcggtca gtggagggcg tgaagcggga gcgcgtggac | 240 |
| gacgccgagg gcgagcgggc gtcgtcgacg gccgccgcgg cgcgggtctg cgccggcgcc | 300 |
| gaggacgacg acgacgggag cacgcggaag aagctgaggc tgaccaagga gcagtccaag | 360 |
| ctcctggagg accgcttcaa ggaccacagc accctcaacc cgaagcagaa aatcgcgttg | 420 |
| gcgaagcaac tgaagctgag gccacggcag gtggaggtgt ggttccaaaa caggcgagca | 480 |
| aggacgaagc tgaagcagac ggaggtggac tgcgagctgc tgaagcgctg ctgcgagtcg | 540 |
| ctgagcgagg agaaccggcg gctgcagcgg gagctacagg agctccgcgc gctcaagctc | 600 |
| gccggcccgc acccacaggc gccgtcgtcg tcgcccgccg ccgcgacgca gggcgtgccg | 660 |
| gtgccggtgc cgccgccgtt gtacgtgcag atgcagatgc agctcagcag ctgccgatgc | 720 |
| tgccggccgc cacgctga | 738 |

<210> SEQ ID NO 14
<211> LENGTH: 765
<212> TYPE: DNA
<213> ORGANISM: Zea mays

<400> SEQUENCE: 14

| | |
|---|---|
| atgtatacca ctactcgtgc catggagaaa gaagaggggt tcgggaagtc atggcttggc | 60 |
| ctggggatcg gcgcggtgg ccgcgatctg aatctgatga gcggagccg accactacga | 120 |
| ccggtgcggc tggacctgct gttcccgccg agtgtggagg gaggagaagc tgccgcgagg | 180 |
| agcaggaagg ctggtgcagg tgcactgcgg aatatgtcgt tgaagcaggt cgcaggcgac | 240 |
| gacgatggtg ggcagtcgtc gcacggtggt ccgagcccca gcgacgacga cgacggcgca | 300 |
| ggcgcgcgga agaagctccg gctcaccacg gagcagtcca gctgctcga ggacaccttc | 360 |
| cgcgcccaca acatactctc ccacgctcag aagcatgagg tggcgcggca ggtggatcta | 420 |
| agcgccaggc aggtggaagt gtggttccag aacaggaggg caagaacaaa gctgaagcaa | 480 |
| acggaggtgg actgcgagac cctgaggcgc tggcgcgaga gcctggcaga cgagaacctg | 540 |
| cggctgaggc tggagctgga gcagctgcag cggtgggcga ccgccgccgc tggtcagtcc | 600 |
| tccgcgtccc cgtcgccggc cacggccacg gcgagcgtct gtccgtcgtg cgacaaggtc | 660 |
| gtcgtcgtca ccgtgacgag ctgtggggag acaagcggca agagctccac cagcagctac | 720 |
| tcctccagtc ctcctcttga catgctcgat cgatcggttc aatga | 765 |

<210> SEQ ID NO 15
<211> LENGTH: 789
<212> TYPE: DNA
<213> ORGANISM: Zea mays

<400> SEQUENCE: 15

| | |
|---|---|
| atggagcaag aagaggttgg cctcgccctg ggcctctccc tcggctccgg ccaccaccac | 60 |
| caggagctca agcccaaca tccgtcgcat ccgtgtgcgg cgttgttgga gccttctctg | 120 |
| tcgctcagcg gccggcgac caaggatgat ggcccgaccg caccggtgag gaggttcgct | 180 |
| gccgtgaaga gggagctgca gacgatggag gggaacgacg acgaggccac cggcagggta | 240 |
| cttgtctact cagtggcgtc gtcggcggtg gttactgccg acgacgacga aggtgcaac | 300 |

```
agcagccgga agaagctgag gctgtccaag gagcagtcgg cgctgctgga ggaccacttc      360
aaggagcaca gcaccctcaa ccctaagcag aaggctgctt tggccagaca actgaacctg      420
agcccaaggc aagtggaggt ttggttccaa acagaagag ccagaaccaa gctgaagcag       480
acagaagtgg actgcgagat tctcaagcgc tgctgcgaga cgttaacaga ggagaaccgg      540
cgtctccacc gcgagctcca gcagctccgc gccctcagcc accgcacccc caccccggct      600
gcctttttca tgcccaccgc cgctgccgct cgctctccaa tctgcccctc ctgccagcgc      660
cttgttgcca ccggagcatc tgccgccgcc gcaaccaccg ccggtgcaga taataagcct      720
aaggcgggcg cccccggcgg ccgagcgcca cacgtgttca gcccttttcac caattctgcc     780 gcctgctga                                                              789

<210> SEQ ID NO 16
<211> LENGTH: 1008
<212> TYPE: DNA
<213> ORGANISM: Zea mays

<400> SEQUENCE: 16
atggagttgg cgctcagctt gggggagacc atggcggatg ccgggaggga cctcatgctg      60
gggcttggga tggggtcgg ggtgcggagg gaggaggaag cgcagagagg gaggagggac       120
agggaggtga ggcgggagct ggagttcacg gcgaggagcg cccggtcgtc gccggagccg      180
gctgtgcgac tcaccctcct gcacggcctc ggctcccgt ggccgccgcc gccgtcgtcc       240
gagaccaacc ggcacctgga ggcgtcggcg cgtggcttcg acgtgaaccg ggcgccgtcg      300
ctgtccgcgg ccggtgccgc cgcggaggag gacgaggagc aggacgaggc ggggcggcc      360 gcggcggcgg catcgtcgtc gcccaacaac agcgcgagct ccttcccgac ggacttctcc      420
gcgcacggcc agtggcgcc cggcgccgac cgcgcgtgct cccgcgccag cgacgaggac      480
gacggcggct ccgcgcgcaa gaagctgcgc ctctccaagg agcagtccgc gttcctggag      540
gacagcttca aggagcacgc cacgctgaac ccgaagcaga agctcgcgct ggcgaagcag      600
ctcaacctcc ggccgcgcca ggtggaggtg tggttccaga accgcagagc caggacgaag      660
ctgaagcaga cggaggtgga ctgcgagtac ctcaagcgat gctgcgagac gctgacggag      720
gagaaccggc ggctgcagaa ggagctatcc gagctccgcg cgctcaagac ggtgcaccc      780 ttctacatgc cctcccggc caccacccct tccatgtgcc cctcctgcga gcgcgtcgcc      840
tccaactccg cgccggcgcc cgcgtcatcg ccgtcccccg ctactggcat tgcggccccg      900
gcaccggagc agaggccctc gtcgttcgcg gctctgttct cgtcccctct gaaccgcccg      960
ctggccgccc aggcgcaacc gcaaccgcag cgccggcca actcgtga                   1008

<210> SEQ ID NO 17
<211> LENGTH: 684
<212> TYPE: DNA
<213> ORGANISM: Zea mays

<400> SEQUENCE: 17
atgatggaga gggtcgagga cttagggctc agcctcagcc tcagctcgtc cctcgcgtct      60
cctcgcactc accatgtcgc caccatgctg ctacgcgctc cagagaagag gttcctggag      120
atgccactgc tgctgcccgc gaagcggacg accgaggtca ccggcgagga tggcctgcga     180
ggcggcagcg atgaggagga cggcggctgc ggcatcgacg gctccaggaa gaagctccgg     240
ctgtccaagg accagtccgc ggtgctcgag atagcttcc gggagcaccc aactctcaac      300
cctcggcaga aggcagcctt ggcgcagcag ctaggcctgc ggccccgcca ggtggaggtg     360
```

```
tggttccaga acaggcgcgc caggacgaag ctgaagcaga cggaggtgga ctgcgagtac    420
ctgaagcgct gctgcgagac gctgacgag gagaaccggc ggctgcagaa ggaggtgcag    480
gagctccgcg cgctcaagct cgtgtcgccg cacctctaca tgcacatgtc cccgcccacc    540
accctcacca tgtgcccctc ctgcgagcgc gtctcctcgt ccaacggcaa ctccgcagct    600
gccacggcgg ccgcgcgcgc gcgcgccggc gccggcgccg cgccatcgt ctgccacccg     660 atcgaccgag ccactagtac gtag                                          684

<210> SEQ ID NO 18
<211> LENGTH: 879
<212> TYPE: DNA
<213> ORGANISM: Zea mays

<400> SEQUENCE: 18
atggctcagg aggacgtgca cctggacgac gcaggcctcg cgctgggcct gtccctcggc     60
agcggcagcg gcggcgcctc tggtgcggcg cgccacggtg gtatcagccg ccggctgagc    120
agggaggtgc ggctgccgtc gccgcacccg ctggagccgt cgctgacgct gagcttgccg    180
gacgaagcga ccgcgaccgg gtccggcggg gcgggggccg cgcacagcgt gtcgtcgctg    240
tcagtggcgg gcgtgaagag ggagcgcgtg gatgacgccg agggagagcg ggcgtcgtct    300
acggccgcgt tgccgcgggc ctgcgccggc gccgaggacg acgacgacga cgggagcacg    360
cggaagaagc tgaggctgac caaggagcag tccgcgctcc tggaggaccg cttcaaggag    420
cacagcaccc tgaacccgaa gcagaaagtc gcgttggcga agcaactgaa gctgaggcca    480
cggcaggtgg aggtgtggtt ccaaaacagg cgagcaagga cgaagctgaa gcagacggag    540
gtggactgcg agctgctgaa cgctgctgc gagtcgctga cggaggagaa ccggcggctg    600
cagcgggagc tgcaggagct ccgcgcgctc aagttcgccc acacccaca ggcgccgccg     660 tcgtccgcga cgcaggccgg cgcggcgcg ggcgtcgttc cggcgccgcc gccgccgttg    720
tacatgcaga tgcagatgcc ggccgccgcc acgctgagcc tgtgcccgtc ctgcgaccgc    780
ctggccgggc ccggcgccgc cgccaaggcc gagcccaggc ccaaggcagc cgccacccac    840
cacttcttca acccttcac ccactccgcc gcctgctga                           879

<210> SEQ ID NO 19
<211> LENGTH: 225
<212> TYPE: PRT
<213> ORGANISM: Zea mays

<400> SEQUENCE: 19

Met Gly Ser Thr Ser Pro Ser Gly Leu Glu Leu Thr Met Ala Val Pro
1               5                   10                  15

Gly Leu Ser Ser Ser Ser Gly Ser Glu Gly Phe Gly Cys Asn Asn Asn
                20                  25                  30

Asn Gly Ser Gly Asn Gly Asn Asn Met Arg Asp Leu Asp Met Asn Gln
            35                  40                  45

Pro Ala Ser Gly Gly Glu Glu Glu Phe Pro Met Gly Ser Val Glu
        50                  55                  60

Glu Glu Glu Asp Glu Arg Gly Gly Ala Gly Gly Pro His Arg Ala Lys
65                  70                  75                  80

Lys Leu Arg Leu Ser Lys Glu Gln Ser Arg Leu Leu Glu Glu Ser Phe
                85                  90                  95

Arg Leu Asn His Thr Leu Thr Pro Lys Gln Lys Glu Ala Leu Ala Val
                100                 105                 110
```

```
Lys Leu Lys Leu Arg Pro Arg Gln Val Glu Val Trp Phe Gln Asn Arg
            115                 120                 125

Arg Ala Arg Thr Lys Leu Lys Gln Thr Glu Leu Glu Cys Glu Tyr Leu
    130                 135                 140

Lys Arg Cys Phe Gly Ser Leu Thr Glu Glu Asn Arg Arg Leu Gln Arg
145                 150                 155                 160

Glu Val Glu Glu Leu Arg Ala Met Arg Val Ala Pro Thr Val Leu
                165                 170                 175

Ser Pro His Thr Arg Gln Pro Leu Pro Ala Ser Ala Leu Thr Met Cys
                180                 185                 190

Pro Arg Cys Glu Arg Ile Thr Ala Ala Thr Ala Ala Arg Thr Pro Arg
            195                 200                 205

Pro Pro Pro Ala Ala Ser Pro Phe His Pro Arg Arg Pro Ser Ala Ala
    210                 215                 220

Phe
225

<210> SEQ ID NO 20
<211> LENGTH: 295
<212> TYPE: PRT
<213> ORGANISM: Zea mays

<400> SEQUENCE: 20

Met Met Pro Gln Ala Ser Ala Ser Leu Asp Leu Gly Leu Ser Leu Gly
1               5                   10                  15

Leu Thr Leu Thr Ser Gln Gly Ser Leu Ser Ser Thr Thr Thr Ala
            20                  25                  30

Gly Ser Ser Ser Pro Trp Ala Ala Ala Leu Ser Ser Val Val Ala Asp
                35                  40                  45

Val Ala Arg Ala Arg Gly Asp Ala Tyr Ala Gln His His Ala Gly Ala
    50                  55                  60

Ala Met Thr Met Arg Ala Ser Thr Ser Pro Asp Ser Gly Asp Thr Thr
65                  70                  75                  80

Thr Ala Lys Arg Glu Arg Glu Gly Glu Leu Glu Arg Thr Gly Ser Ala
                85                  90                  95

Gly Gly Val Arg Ser Asp Glu Glu Asp Gly Ala Asp Gly Gly Ala Gly
            100                 105                 110

Gly Arg Lys Lys Leu Arg Leu Ser Lys Asp Gln Ala Ala Val Leu Glu
            115                 120                 125

Glu Cys Phe Lys Thr His Ser Thr Leu Asn Pro Lys Gln Lys Val Gln
    130                 135                 140

Leu Ala Asn Arg Leu Gly Leu Arg Pro Arg Gln Val Glu Val Trp Phe
145                 150                 155                 160

Gln Asn Arg Arg Ala Arg Thr Lys Leu Lys Gln Thr Glu Val Asp Cys
                165                 170                 175

Glu Tyr Leu Lys Arg Trp Cys Asp Arg Leu Ala Asp Glu Asn Lys Arg
            180                 185                 190

Leu Glu Lys Glu Leu Ala Asp Leu Arg Ala Leu Lys Ala Ala Pro Pro
        195                 200                 205

Ser Ser Ala Ala Ala Gln Pro Ala Ser Ala Ala Thr Leu Thr Met
    210                 215                 220

Cys Pro Ser Cys Arg Arg Val Ala Ala Ala Ser His His His Gln
225                 230                 235                 240

Pro Pro Pro Pro Gln Cys His Pro Lys Pro Thr Val Ala Ala Gly Gly
```

```
                    245                 250                 255
Gly Ser Val Val Pro Arg Pro Ser His Cys Gln Phe Phe Pro Ala Ala
                260                 265                 270

Ala Val Asp Arg Thr Ser Gln Gly Thr Trp Asn Thr Ala Ala Pro Pro
            275                 280                 285

Leu Val Thr Arg Glu Leu Phe
        290                 295

<210> SEQ ID NO 21
<211> LENGTH: 315
<212> TYPE: PRT
<213> ORGANISM: Zea mays

<400> SEQUENCE: 21

Met Ala Asp Ser Gly Ser Asp Leu Val Leu Gly Leu Gly Met Gly Val
1               5                   10                  15

Gly Val Arg Arg Glu Glu Glu Thr Gln Arg Gly Arg Arg Asp Arg Glu
            20                  25                  30

Ala Arg Arg Glu Leu Glu Phe Glu Thr Gly Arg Cys Ala Arg Pro Ser
        35                  40                  45

Pro Glu Pro Ala Val Arg Leu Thr Leu Leu Pro Gly Leu Val Pro Ser
    50                  55                  60

Leu Gly Leu Pro Trp Pro Leu Ser Ser Glu Thr Asn Arg Glu Val Ser
65                  70                  75                  80

Thr Arg Gly Phe Asp Asp Val Asn Arg Ala Leu Ser Val Ala Gly Ala
                85                  90                  95

Gly Ala Glu Glu Asp Glu Ala Ala Val Ala Ala Ala Thr Ala Ala Ala
            100                 105                 110

Ser Ser Ser Pro Asn Asn Ser Ser Gly Ser Phe Ala Met Asp Ile Ser
        115                 120                 125

Ala Gln Gly Gln Gly Gln Gly Gln Asp Gln Ala Ala Pro Ala Ala Asp
    130                 135                 140

Arg Ala Cys Ser Arg Ala Ser Asp Glu Asp Asp Gly Gly Ser Ala Arg
145                 150                 155                 160

Lys Lys Leu Arg Leu Ser Lys Glu Gln Ser Ala Phe Leu Glu Glu Ser
                165                 170                 175

Phe Lys Val Arg Ala Thr Pro Asn Pro Lys Gln Lys Leu Ala Leu Ala
            180                 185                 190

Arg Gln Leu Asn Leu Arg Ala Arg Gln Val Glu Val Trp Phe Gln Asn
        195                 200                 205

Arg Arg Ala Arg Thr Lys Leu Lys Gln Thr Glu Val Asp Cys Glu His
    210                 215                 220

Leu Lys Arg Cys Cys Glu Thr Leu Thr Gly Glu Asn Arg Arg Leu His
225                 230                 235                 240

Lys Glu Leu Ala Glu Leu Arg Ala Leu Lys Ala Val Arg Pro Leu Leu
                245                 250                 255

His Met His Leu Pro Ala Thr Thr Leu Ser Met Cys Pro Ser Cys Glu
            260                 265                 270

Arg Val Ala Ser Thr Ser Ser Ala Ala Pro Ala Ala Pro Ala Pro Ala
        275                 280                 285

Ser Pro Ser Pro Ala Ala Gly Ala Gly Ile Ala Ala Ser Ala Pro Asp
    290                 295                 300

Pro Asp Gln Arg Pro Ser Ser Ser Phe Ala Ala
305                 310                 315
```

<210> SEQ ID NO 22
<211> LENGTH: 261
<212> TYPE: PRT
<213> ORGANISM: Zea mays

<400> SEQUENCE: 22

```
Met Ala Pro Gln Ser Leu Asp Leu Gly Leu Ser Gly Leu Gly Val
1               5                   10                  15

Ala Ala Phe Gln Pro Ser Phe Cys His Pro Ala Gly Asn Asp Ala Ala
            20                  25                  30

Glu Arg Glu Ala Ser Pro Thr Ala Asp Glu Arg Glu Arg Arg Cys Ser
            35                  40                  45

Pro Ala Gly Ser Pro Thr Ser Ser Gly Ser Gly Lys Arg Val Ala Ala
50                  55                  60

Glu Arg Ser Ala Gly Ser Gly Ser Gly Asp Glu Asp Asp Gly Gly
65                  70                  75                  80

Ala Arg Lys Lys Leu Arg Leu Ser Lys Asp Gln Ala Ala Val Leu Glu
                85                  90                  95

Glu Cys Phe Lys Thr His His Thr Leu Thr Pro Lys Gln Lys Ala Ala
            100                 105                 110

Leu Ala Ser Arg Leu Gly Leu Arg Ala Arg Gln Val Glu Val Trp Phe
            115                 120                 125

Gln Asn Arg Arg Ala Arg Thr Lys Leu Lys Gln Thr Glu Val Asp Cys
130                 135                 140

Glu Tyr Leu Arg Arg Trp Cys Glu Gln Leu Ala Glu Glu Asn Arg Arg
145                 150                 155                 160

Leu Gly Lys Glu Val Ala Glu Leu Arg Ala Leu Ser Ala Ala Pro Ala
                165                 170                 175

Pro Ala Ala Pro Leu Thr Ala Leu Thr Met Cys Leu Ser Cys Arg Arg
            180                 185                 190

Val Ser Ser Ser Cys Ser Ser Pro Asn Thr His Ala His
            195                 200                 205

Ala Ala Ala Ala Gly Thr Gly Arg Ser Val Ala Ala Ala Ala Thr
210                 215                 220

Thr Leu Pro Ala His Arg Gln Phe Leu Cys Gly Phe Arg Asp Gly Gly
225                 230                 235                 240

Ala Ala Ala Ala Ala Val Tyr Gly Thr Ser Ser Ala Leu Ala Lys Ala
                245                 250                 255

Leu Arg Ala Ala Arg
            260
```

<210> SEQ ID NO 23
<211> LENGTH: 223
<212> TYPE: PRT
<213> ORGANISM: Zea mays

<400> SEQUENCE: 23

```
Met Tyr Ser Cys Thr Arg Ala Met Glu Glu Gly Val Gly Lys Ser
1               5                   10                  15

Trp Leu Gly Leu Gly Ile Gly Gly Gly Asp Leu Met Lys Arg Asn
            20                  25                  30

Asn Arg Pro Pro Val Gln Leu Asp Asp Leu Leu Ser Phe Pro Pro Gln
            35                  40                  45

Ser Val Ala Ala Ala Ser Lys Lys Gln Ala Glu Lys Gly Gly Gly Gly
50                  55                  60
```

```
Arg Lys Arg His Lys Ile Val Val Thr Ala Asp Glu Asp Gly Arg Gln
 65                  70                  75                  80

Ser Pro His Gly Gly Ala Arg Lys Lys Leu Arg Leu Thr Lys Ala Gln
                 85                  90                  95

Ser Thr Leu Leu Glu Asp Thr Phe Arg Ala His Asn Ile Leu Ser His
            100                 105                 110

Ala Gln Lys Gln Glu Leu Ala Arg Gln Val Asn Leu Ser Ala Arg Gln
        115                 120                 125

Val Glu Val Trp Phe Gln Asn Arg Arg Ala Arg Thr Lys Leu Lys Gln
    130                 135                 140

Thr Glu Ala Asp Cys Glu Val Leu Lys Arg Tyr Cys Glu Arg Leu Thr
145                 150                 155                 160

Gly Glu Asn Gln Arg Leu Arg Leu Glu Leu Ala Gln Leu Gln Arg Ser
                165                 170                 175

Pro Ala Ala Glu Glu Ala Gly Phe Tyr Val Gln Ser Ser Phe Pro Phe
            180                 185                 190

Pro Pro Leu Ala Thr Ala Met Ala Ser Val Cys Pro Ser Cys Asp Lys
        195                 200                 205

Val Val Ala Val Thr Ser Gly Lys Ser Ser Thr Ser Tyr Ser Ser
    210                 215                 220

<210> SEQ ID NO 24
<211> LENGTH: 241
<212> TYPE: PRT
<213> ORGANISM: Zea mays

<400> SEQUENCE: 24

Met Glu Glu Glu Gly Val Gly Lys Ser Trp Leu Ala Leu Gly Ile Gly
  1               5                  10                  15

Gly Gly Asp Leu Met Lys Arg Asn Asn Arg Pro Val Gln Phe Asp
             20                  25                  30

Leu Leu Phe Pro Pro Gln Ser Val Lys Glu Glu Gly Ala Ala Ser Lys
         35                  40                  45

Lys Ala Glu Lys Gly Gly Gly Arg Lys Arg Leu Lys Val Val Thr Ala
     50                  55                  60

Asp Glu Asp Gly Arg Gln Ser Pro His Gly Gly Pro Gly Pro Ser Asp
 65                  70                  75                  80

Gly Ser Gly Ala Gly Ala Arg Lys Lys Leu Arg Leu Thr Asn Glu Gln
                 85                  90                  95

Ser Thr Leu Leu Glu Asp Thr Phe Arg Ala His Asn Ile Leu Ser Asn
            100                 105                 110

Ala Gln Lys Gln Glu Leu Ala Arg Gln Val Asp Leu Ser Ala Arg Gln
        115                 120                 125

Val Glu Val Trp Phe Gln Asn Arg Arg Ala Arg Thr Lys Leu Lys Gln
    130                 135                 140

Thr Glu Val Asp Cys Glu Ile Leu Lys Arg Cys Cys Glu Ser Leu Thr
145                 150                 155                 160

Gly Glu Asn Gln Arg Leu Arg Leu Glu Leu Ala Gln Leu Gln Arg Ser
                165                 170                 175

Ala Ala Ala Ala Glu Ala Gly Leu Tyr Val Gln Ser Ser Phe Pro
            180                 185                 190

Pro Leu Ala Thr Ala Thr Ala Thr Ala Ser Val Cys Pro Ser Cys Asp
        195                 200                 205

Lys Val Ile Ala Val Ser Ser Gly Gly Glu Thr Ser Gly Lys Ser Ser
    210                 215                 220
```

Thr Ser Tyr Ser Ser Arg Arg Ala Gly Phe Pro Ser Ile Met Gly Ser
225                 230                 235                 240

Arg

<210> SEQ ID NO 25
<211> LENGTH: 267
<212> TYPE: PRT
<213> ORGANISM: Zea mays

<400> SEQUENCE: 25

Met Ser Ser Leu Thr Ala Ala Ser Ser Ser Ser Met Glu Glu
1               5                   10                  15

His Cys Tyr Ser Val Ser Ala Glu Glu Val Val Gly Thr His Leu Ser
                20                  25                  30

Leu Gly Ile Gly Gly Gly Gly Gly Gly Asp Lys Arg Thr Met
            35                  40                  45

Leu Thr Leu Pro Pro Ser Arg Thr Val Gln Leu Phe Gly Glu Val Leu
        50                  55                  60

Ser Val Gln Asp Gly Asp Gly Thr Gln Ala Leu Arg His His His Thr
65                  70                  75                  80

Gly Arg Pro Pro Ala Ala Ser Ser Arg Lys Lys Arg Lys Asp Ala
                85                  90                  95

Ala Ala Ala Gly Gly Ala Ser Ala Thr Asp Ala Ala Asn Gly His
            100                 105                 110

His His Gln Ser Lys Lys Thr Lys Thr Thr Ala Ala Arg Arg Asp Asp
                115                 120                 125

Gly Gly Gly Gly Arg Lys Lys Leu Arg Leu Thr Ser Ala Gln Ala Thr
            130                 135                 140

Leu Leu Glu Asp Ser Phe Arg Ala His Asn Ile Leu Ser His Gly Glu
145                 150                 155                 160

Lys Gln Glu Leu Ala Arg Gln Ala Gly Leu Ser Ala Arg Gln Val Glu
                165                 170                 175

Val Trp Phe Gln Asn Arg Arg Ala Arg Thr Lys Leu Lys Gln Thr Glu
            180                 185                 190

Val Asp Cys Asp Leu Leu Arg Arg Trp Cys Ala Arg Leu Ser Asp Asp
            195                 200                 205

Asn Asp Arg Leu Arg Arg Asp Leu Ala Asp Leu Arg Ala Ala Ser
        210                 215                 220

Ser Ser Ala Gly Leu Gly Ala Val Val Cys Ala Ser Cys Gly Ala
225                 230                 235                 240

Asp Arg Gln Leu Ala Leu Ala Ala Ala Asp Asn Val Leu Pro Ser
                245                 250                 255

Val Ala Ser Pro Ser His Ser Pro His Leu Thr
            260                 265

<210> SEQ ID NO 26
<211> LENGTH: 319
<212> TYPE: PRT
<213> ORGANISM: Zea mays

<400> SEQUENCE: 26

Met Asp Ile Met Ala Leu Asn Ala Arg Asp Glu Glu Gln Tyr Gly Asn
1               5                   10                  15

Asn His Leu Gly Leu Gly Leu Ser Leu Ser Leu Gly Leu Gly Val Ala
                20                  25                  30

-continued

```
Thr Ala Ala Pro Val Glu Val Glu Pro Pro Pro Pro Arg Gln Gln
         35                  40                  45

Gln Gln Arg Ala Ile Ser Val Ala Pro Ile Thr Ser Leu Pro Ala Pro
 50                  55                  60

Gln Trp Trp Lys Trp Asn Gly Pro Gly Leu Phe Phe Gly Thr Thr Met
65                  70                  75                  80

Asp Gln Gln Gln Pro Ala Ala Ala Arg His Gly His Glu Met Pro
                 85                  90                  95

Phe Leu Arg Gly Val Asp Val Asn Arg Ala Pro Ala Gly Asp Thr Arg
             100                 105                 110

Arg Gly Ser Cys Ser Glu Asp Glu Glu Pro Gly Gly Ala Ser Ser
         115                 120                 125

Ser Pro Asn Ser Thr Leu Ser Ser Ser Leu Ser Gly Lys Arg Ala Ala
130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
                 165                 170                 175

Arg Leu Ser Lys Asp Gln Ala Ala Val Leu Glu Glu Ser Phe Lys Glu
             180                 185                 190

His Asn Thr Leu Asn Pro Lys Gln Lys Ala Ala Leu Ala Lys Gln Leu
         195                 200                 205

Asn Leu Lys Pro Arg Gln Val Glu Val Trp Phe Gln Asn Arg Arg Ala
    210                 215                 220

Arg Thr Lys Leu Lys Gln Thr Glu Val Asp Cys Glu Phe Leu Lys Arg
225                 230                 235                 240

Cys Cys Glu Thr Leu Thr Glu Glu Asn Arg Arg Leu Gln Arg Glu Val
                 245                 250                 255

Ala Glu Leu Arg Val Leu Lys Leu Val Ala Pro His His Tyr Ala Arg
             260                 265                 270

Met Pro Pro Pro Thr Thr Leu Thr Met Cys Pro Ser Cys Glu Arg Leu
         275                 280                 285

Ala Ser Ala Ser Ala Ser Ala Asp Gln Ala Gly Arg Ala Gly Pro Cys
    290                 295                 300

Trp Gly Pro Leu Pro Val Phe Val Asp Gly Pro Ala Arg Arg Pro
305                 310                 315

<210> SEQ ID NO 27
<211> LENGTH: 354
<212> TYPE: PRT
<213> ORGANISM: Zea mays

<400> SEQUENCE: 27

Met Glu Leu Gly Leu Ser Leu Gly Asp Ala Ala Val Pro Asp Ala Gly
1               5                   10                  15

Arg Ala Ala Pro Glu Leu Gly Leu Gly Leu Gly Val Gly Ile Gly Ser
             20                  25                  30

Asn Ala Ala Gly Thr Gly Arg Gly Ser Lys Ala Ala Gly Thr Thr Gly
         35                  40                  45

Thr Thr Gly Trp Trp Ala Ala Pro Ala Thr Pro Glu Ser Ala Val Arg
     50                  55                  60

Leu Ser Leu Val Ser Ser Leu Gly Leu Gln Trp Pro Pro Asp Gly
65                  70                  75                  80

Gly Ile Cys His Val Gly Arg Asp Glu Ala Pro Ala Arg Gly Phe Asp
                 85                  90                  95
```

Val Asn Arg Ala Pro Ser Val Ala Gly Ser Ala Leu Ala Leu Glu Asp
                100                 105                 110

Asp Glu Glu Glu Pro Gly Ala Ala Leu Ser Ser Pro Asn Asp
            115                 120                 125

Ser Ala Gly Ser Phe Pro Leu Asp Leu Gly Pro Arg Ala His Ala
    130                 135                 140

Glu Gly Ala Ala Arg Ala Gly Glu Arg Ser Ser Arg Ala
145                 150                 155                 160

Ser Asp Glu Asp Glu Gly Ala Ser Ala Arg Lys Lys Leu Arg Leu Ser
                165                 170                 175

Lys Glu Gln Ser Ala Phe Leu Glu Glu Ser Phe Lys Glu His Ser Thr
                180                 185                 190

Leu Asn Pro Lys Gln Lys Ala Ala Leu Ala Lys Gln Leu Asn Leu Arg
                195                 200                 205

Pro Arg Gln Val Glu Val Trp Phe Gln Asn Arg Arg Ala Arg Thr Lys
                210                 215                 220

Leu Lys Gln Thr Glu Val Asp Cys Glu Tyr Leu Lys Arg Cys Cys Glu
225                 230                 235                 240

Thr Leu Thr Glu Glu Asn Arg Arg Leu His Lys Glu Leu Ala Glu Leu
                245                 250                 255

Arg Ala Leu Lys Thr Ala Pro Pro Phe Phe Met Arg Leu Pro Ala Thr
                260                 265                 270

Thr Leu Ser Met Cys Pro Ser Cys Glu Arg Val Ala Ser Gly Pro Ser
                275                 280                 285

Pro Ala Ser Thr Ser Ala Pro Ala Ser Ser Thr Pro Ala Thr Ala
                290                 295                 300

Ala Thr Thr Ala Ile Ser Tyr Ala Ala Ala Ala Ala Pro Val Arg
305                 310                 315                 320

Ala Asp His Arg Pro Ser Ser Phe Ala Ala Leu Phe Ala Ala Thr Arg
                325                 330                 335

Ser Phe Pro Leu Ala Ser Gln Pro Arg Pro Pro Ala Pro Ala Ser Asn
                340                 345                 350

Cys Leu

<210> SEQ ID NO 28
<211> LENGTH: 331
<212> TYPE: PRT
<213> ORGANISM: Zea mays

<400> SEQUENCE: 28

Met Glu Leu Glu Leu Ser Leu Gly Asp Ser Arg Ala Pro Ala Lys Ser
1               5                   10                  15

Ala Ser Thr Pro Ala Ala Leu Thr Pro Ile His Ala Gly Ala Gly Gly
                20                  25                  30

Glu Gly His Glu Leu Ala Leu Glu Leu Gly Val Gly Ala Ala Lys Arg
            35                  40                  45

Ala Glu Gln Asp Asn Gln Lys Thr Pro Val Gln Pro Glu His Val Gln
    50                  55                  60

Glu Glu Glu Glu Glu Glu Thr Cys Pro Tyr Ser Glu Ser Pro Ala
65                  70                  75                  80

Glu Leu Ser Leu Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
                100                 105                 110

```
Val Asp Ala Val Leu Val Asp Gly Gly Asp Ala Ala Gln Gly Arg Pro
            115                 120                 125

Ala Leu Ser Thr Ser Phe Leu Pro Ser Glu Phe Leu Val Arg Arg Gln
130                 135                 140

Ala Asp Asp Gln Glu Ala Ala Glu Asp Glu Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
        195                 200                 205

Val Trp Phe Gln Asn Arg Arg Ala Arg Ser Lys Leu Lys Gln Thr Glu
    210                 215                 220

Val Asp Cys Glu Tyr Leu Lys Arg Trp Cys Glu Lys Leu Ala Gln Glu
225                 230                 235                 240

Asn Arg Arg Leu Gln Arg Glu Val Ala Glu Leu Arg Arg Leu Cys Ser
                245                 250                 255

Ala Ala Tyr Pro Phe Tyr Gly Ala Ala Gly Phe Gly Val Ala Thr
            260                 265                 270

Ala Arg Val Cys Pro Ser Ser Cys Asp Asn Asp Val Ser Glu Ala Ala
        275                 280                 285

Ile Ser Gly Ala Pro Ser Ala Ala Pro Pro Ser Thr Leu Phe
    290                 295                 300

Ala Ser Trp Pro Pro His Phe Gly Pro Phe Thr Val Val Val Pro Pro
305                 310                 315                 320

Leu Leu Arg Arg Gln Pro Ser Ala Thr Thr Ser
                325                 330

<210> SEQ ID NO 29
<211> LENGTH: 221
<212> TYPE: PRT
<213> ORGANISM: Zea mays

<400> SEQUENCE: 29

Met Tyr Ser Thr Arg Glu Glu Glu Gly Val Gly Lys Ser Trp Leu Gly
1               5                   10                  15

Leu Gly Ile Gly Gly Ser Gly Gly Cys Asp Leu Met Gln Arg Asn
                20                  25                  30

Asn Arg Pro Pro Val Gln Phe Asp Leu Leu Phe Pro Pro Gln Gly Val
            35                  40                  45

Val Glu Gly Val Ala Ala Ser Lys Lys Ala Glu Lys Gly Gly Gly Gly
        50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Val Trp Phe Gln Asn Arg Arg Ala Arg Thr Lys Leu Lys Gln Thr
    130                 135                 140

Glu Ala Asp Cys Glu Ile Leu Lys Arg Cys Cys Glu Ser Leu Thr Gly
```

```
                145                 150                 155                 160
Glu Asn Gln Arg Leu Arg Leu Glu Leu Ala Gln Leu Gln Gly Ser Glu
                    165                 170                 175

Ala Gly Leu Tyr Leu Gln Ser Ser Phe Pro Leu Ala Ala Ala Met
                180                 185                 190

Ala Ser Val Cys Pro Ser Cys Asp Lys Val Ile Thr Val Ala Ser Gly
                195                 200                 205

Gly Glu Thr Ser Gly Arg Ser Ser Thr Ser Tyr Ser Ser
210                 215                 220

<210> SEQ ID NO 30
<211> LENGTH: 272
<212> TYPE: PRT
<213> ORGANISM: Zea mays

<400> SEQUENCE: 30

Met Ala Pro Gln Ser Leu Asp Leu Gly Leu Ser Leu Gly Leu Gly Val
1               5                   10                  15

Ala Ala Phe Gln Pro Ser Ser Phe Cys His Pro Gly Asn Ala Val Val
                20                  25                  30

Val Pro Ala Ala Ala Glu Arg Glu Ala Ser Pro Ala Ala Ala Glu Glu
                35                  40                  45

Arg Glu Arg Arg Cys Ser Pro Ala Gly Ser Pro Val Ser Ser Gly Ser
50                  55                  60

Gly Ser Gly Asn Lys Arg Ala Ala Glu Arg Ser Ala Gly Ala Gly
65                  70                  75                  80

Ala Gly Ser Gly Asp Glu Asp Asp Gly Ala Ala Arg Lys Lys Leu
                85                  90                  95

Arg Leu Ser Lys Asp Gln Ala Ala Val Leu Glu Glu Cys Phe Lys Thr
                100                 105                 110

His His Thr Leu Thr Pro Lys Gln Lys Val Ala Leu Ala Ser Ser Leu
                115                 120                 125

Gly Leu Arg Pro Arg Gln Val Glu Val Trp Phe Gln Asn Arg Arg Ala
                130                 135                 140

Arg Thr Lys Leu Lys Gln Thr Glu Val Asp Cys Glu Tyr Leu Lys Arg
145                 150                 155                 160

Trp Cys Glu Gln Leu Ala Glu Glu Asn Arg Arg Leu Gly Lys Glu Val
                165                 170                 175

Ala Glu Leu Arg Ala Leu Ser Ala Ala Pro Ala Ala Pro Leu Thr Thr
                180                 185                 190

Leu Thr Met Cys Leu Ser Cys Arg Val Ala Ser Ser Pro Ser
                195                 200                 205

Ser Ser Ser Ser Pro Arg Pro Ser Ile Pro Gly Ala Ala Ala Ala Ser
210                 215                 220

Gly Gly Ser Met Ala Ser Pro Ala Ala Ala Thr Leu Pro Ala His
225                 230                 235                 240

Arg Gln Phe Phe Cys Gly Phe Arg Asp Ala Gly Ala Ala Ala Ala Ala
                245                 250                 255

Tyr Gly Thr Ala Ser Ala Gly Leu Ala Lys Pro Val Arg Ala Ala Arg
                260                 265                 270

<210> SEQ ID NO 31
<211> LENGTH: 245
<212> TYPE: PRT
<213> ORGANISM: Zea mays
```

```
<400> SEQUENCE: 31

Met Ala Gln Glu Asp Val His Leu Asp Asp Ala Gly Leu Ala Leu Cys
1               5                   10                  15

Leu Ser Leu His Gly Thr Ser Ser Arg Leu Ser Thr Glu Ala Pro
            20                  25                  30

Arg Thr Leu Glu Pro Pro Ser Leu Thr Leu Ser Met Pro Asp Glu Ala
            35                  40                  45

Thr Ala Thr Ala Thr Gly Gly Ser Gly Gly Ser Gly Gly Ala Ala Arg
        50                  55                  60

Ser Val Ser Ser Arg Ser Val Glu Gly Val Lys Arg Glu Arg Val Asp
65                  70                  75                  80

Asp Ala Glu Gly Glu Arg Ala Ser Ser Thr Ala Ala Ala Arg Val
                85                  90                  95

Cys Ala Gly Ala Glu Asp Asp Asp Gly Ser Thr Arg Lys Lys Leu
                100                 105                 110

Arg Leu Thr Lys Glu Gln Ser Lys Leu Leu Glu Asp Arg Phe Lys Asp
            115                 120                 125

His Ser Thr Leu Asn Pro Lys Gln Lys Ile Ala Leu Ala Lys Gln Leu
        130                 135                 140

Lys Leu Arg Pro Arg Gln Val Glu Val Trp Phe Gln Asn Arg Arg Ala
145                 150                 155                 160

Arg Thr Lys Leu Lys Gln Thr Glu Val Asp Cys Glu Leu Leu Lys Arg
                165                 170                 175

Cys Cys Glu Ser Leu Ser Glu Glu Asn Arg Arg Leu Gln Arg Glu Leu
                180                 185                 190

Gln Glu Leu Arg Ala Leu Lys Leu Ala Gly Pro His Pro Gln Ala Pro
            195                 200                 205

Ser Ser Ser Pro Ala Ala Ala Thr Gln Gly Val Pro Val Pro Val Pro
        210                 215                 220

Pro Pro Leu Tyr Val Gln Met Gln Met Gln Leu Ser Ser Cys Arg Cys
225                 230                 235                 240

Cys Arg Pro Pro Arg
                245

<210> SEQ ID NO 32
<211> LENGTH: 254
<212> TYPE: PRT
<213> ORGANISM: Zea mays

<400> SEQUENCE: 32

Met Tyr Thr Thr Thr Arg Ala Met Glu Lys Glu Gly Phe Gly Lys
1               5                   10                  15

Ser Trp Leu Gly Leu Gly Ile Gly Gly Gly Arg Asp Leu Asn Leu
            20                  25                  30

Met Lys Arg Ser Arg Pro Leu Arg Pro Val Arg Leu Asp Leu Leu Phe
            35                  40                  45

Pro Pro Ser Val Glu Gly Gly Glu Ala Ala Ala Arg Ser Arg Lys Ala
        50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
                85                  90                  95

Asp Asp Gly Ala Gly Ala Arg Lys Lys Leu Arg Leu Thr Thr Glu Gln
                100                 105                 110
```

```
Ser Lys Leu Leu Glu Asp Thr Phe Arg Ala His Asn Ile Leu Ser His
            115                 120                 125

Ala Gln Lys His Glu Val Ala Arg Gln Val Asp Leu Ser Ala Arg Gln
        130                 135                 140

Val Glu Val Trp Phe Gln Asn Arg Arg Ala Arg Thr Lys Leu Lys Gln
145                 150                 155                 160

Thr Glu Val Asp Cys Glu Thr Leu Arg Arg Trp Arg Glu Ser Leu Ala
                165                 170                 175

Asp Glu Asn Leu Arg Leu Arg Leu Glu Leu Gln Leu Gln Arg Trp
            180                 185                 190

Ala Thr Ala Ala Ala Gly Gln Ser Ser Ala Ser Pro Ser Pro Ala Thr
        195                 200                 205

Ala Thr Ala Ser Val Cys Pro Ser Cys Asp Lys Val Val Val Thr
        210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250

<210> SEQ ID NO 33
<211> LENGTH: 262
<212> TYPE: PRT
<213> ORGANISM: Zea mays

<400> SEQUENCE: 33

Met Glu Gln Glu Glu Val Gly Leu Ala Leu Gly Leu Ser Leu Gly Ser
1               5                   10                  15

Gly His His His Gln Glu Leu Lys Pro Gln His Pro Ser His Pro Cys
            20                  25                  30

Ala Ala Leu Leu Glu Pro Ser Leu Ser Leu Ser Gly Pro Ala Thr Lys
        35                  40                  45

Asp Asp Gly Pro Thr Ala Pro Val Arg Arg Phe Ala Ala Val Lys Arg
    50                  55                  60

Glu Leu Gln Thr Met Glu Gly Asn Asp Asp Glu Ala Thr Gly Arg Val
65                  70                  75                  80

Leu Val Tyr Ser Val Ala Ser Ser Ala Val Val Thr Ala Asp Asp Asp
                85                  90                  95

Glu Gly Cys Asn Ser Ser Arg Lys Lys Leu Arg Leu Ser Lys Glu Gln
            100                 105                 110

Ser Ala Leu Leu Glu Asp His Phe Lys Glu His Ser Thr Leu Asn Pro
        115                 120                 125

Lys Gln Lys Ala Ala Leu Ala Arg Gln Leu Asn Leu Ser Pro Arg Gln
    130                 135                 140

Val Glu Val Trp Phe Gln Asn Arg Arg Ala Arg Thr Lys Leu Lys Gln
145                 150                 155                 160

Thr Glu Val Asp Cys Glu Ile Leu Lys Arg Cys Cys Glu Thr Leu Thr
                165                 170                 175

Glu Glu Asn Arg Arg Leu His Arg Glu Leu Gln Gln Leu Arg Ala Leu
            180                 185                 190

Ser His Pro His Pro His Pro Ala Ala Phe Phe Met Pro Thr Ala Ala
        195                 200                 205

Ala Ala Ala Leu Ser Ile Cys Pro Ser Cys Gln Arg Leu Val Ala Thr
        210                 215                 220

Gly Ala Ser Ala Ala Ala Ala Thr Thr Ala Gly Ala Asp Asn Lys Pro
225                 230                 235                 240
```

Lys Ala Gly Gly Pro Gly Gly Arg Ala Pro His Val Phe Ser Pro Phe
            245                 250                 255

Thr Asn Ser Ala Ala Cys
            260

<210> SEQ ID NO 34
<211> LENGTH: 335
<212> TYPE: PRT
<213> ORGANISM: Zea mays

<400> SEQUENCE: 34

Met Glu Leu Ala Leu Ser Leu Gly Glu Thr Met Ala Asp Ala Gly Arg
1               5                   10                  15

Asp Leu Met Leu Gly Leu Gly Met Gly Val Gly Val Arg Arg Glu Glu
            20                  25                  30

Glu Ala Gln Arg Gly Arg Arg Asp Arg Glu Val Arg Arg Glu Leu Glu
        35                  40                  45

Phe Thr Ala Arg Ser Ala Arg Ser Ser Pro Glu Pro Ala Val Arg Leu
    50                  55                  60

Thr Leu Leu His Gly Leu Gly Leu Pro Trp Pro Pro Pro Ser Ser
65                  70                  75                  80

Glu Thr Asn Arg His Leu Glu Ala Ser Ala Arg Gly Phe Asp Val Asn
                85                  90                  95

Arg Ala Pro Ser Leu Ser Ala Ala Gly Ala Ala Ala Glu Glu Asp Glu
            100                 105                 110

Glu Gln Asp Glu Ala Gly Ala Ala Ala Ala Ala Ser Ser Ser Pro
        115                 120                 125

Asn Asn Ser Ala Ser Ser Phe Pro Thr Asp Phe Ser Ala His Gly Gln
    130                 135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
        195                 200                 205

Glu Val Trp Phe Gln Asn Arg Arg Ala Arg Thr Lys Leu Lys Gln Thr
    210                 215                 220

Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
                245                 250                 255

Thr Val His Pro Phe Tyr Met His Leu Pro Ala Thr Thr Leu Ser Met
            260                 265                 270

Cys Pro Ser Cys Glu Arg Val Ala Ser Asn Ser Ala Pro Ala Pro Ala
        275                 280                 285

Ser Ser Pro Ser Pro Ala Thr Gly Ile Ala Ala Pro Ala Pro Glu Gln
    290                 295                 300

Arg Pro Ser Ser Phe Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 35
<211> LENGTH: 227
<212> TYPE: PRT
<213> ORGANISM: Zea mays

<400> SEQUENCE: 35

```
Met Met Glu Arg Val Glu Asp Leu Gly Leu Ser Leu Ser Leu Ser Ser
1               5                   10                  15
Ser Leu Ala Ser Pro Arg Thr His His Val Ala Thr Met Leu Leu Arg
                20                  25                  30
Ala Pro Glu Lys Arg Phe Leu Glu Met Pro Leu Leu Leu Pro Ala Lys
            35                  40                  45
Arg Thr Thr Glu Val Thr Gly Glu Asp Gly Leu Arg Gly Gly Ser Asp
        50                  55                  60
Glu Glu Asp Gly Gly Cys Gly Ile Asp Gly Ser Arg Lys Lys Leu Arg
65                  70                  75                  80
Leu Ser Lys Asp Gln Ser Ala Val Leu Glu Asp Ser Phe Arg Glu His
                85                  90                  95
Pro Thr Leu Asn Pro Arg Gln Lys Ala Ala Leu Ala Gln Gln Leu Gly
            100                 105                 110
Leu Arg Pro Arg Gln Val Glu Val Trp Phe Gln Asn Arg Arg Ala Arg
        115                 120                 125
Thr Lys Leu Lys Gln Thr Glu Val Asp Cys Glu Tyr Leu Lys Arg Cys
130                 135                 140
Cys Glu Thr Leu Thr Glu Glu Asn Arg Arg Leu Gln Lys Glu Val Gln
145                 150                 155                 160
Glu Leu Arg Ala Leu Lys Leu Val Ser Pro His Leu Tyr Met His Met
                165                 170                 175
Ser Pro Pro Thr Thr Leu Thr Met Cys Pro Ser Cys Glu Arg Val Ser
            180                 185                 190
Ser Ser Asn Gly Asn Ser Ala Ala Thr Ala Ala Arg Ala Arg
        195                 200                 205
Ala Gly Ala Gly Ala Gly Ala Ile Val Cys His Pro Ile Asp Arg Ala
    210                 215                 220
Thr Ser Thr
225
```

<210> SEQ ID NO 36
<211> LENGTH: 292
<212> TYPE: PRT
<213> ORGANISM: Zea mays

<400> SEQUENCE: 36

```
Met Ala Gln Glu Asp Val His Leu Asp Asp Ala Gly Leu Ala Leu Gly
1               5                   10                  15
Leu Ser Leu Gly Ser Gly Ser Gly Gly Ala Ser Gly Ala Ala Arg His
                20                  25                  30
Gly Gly Ile Ser Arg Arg Leu Ser Arg Glu Val Arg Leu Pro Ser Pro
            35                  40                  45
His Pro Leu Glu Pro Ser Leu Thr Leu Ser Leu Pro Asp Glu Ala Thr
        50                  55                  60
Ala Thr Gly Ser Gly Gly Gly Ala Ala His Ser Val Ser Ser Leu
65                  70                  75                  80
Ser Val Ala Gly Val Lys Arg Glu Arg Val Asp Asp Ala Glu Gly Glu
                85                  90                  95
Arg Ala Ser Ser Thr Ala Ala Leu Pro Arg Ala Cys Ala Gly Ala Glu
```

```
                100                 105                 110
Asp Asp Asp Asp Asp Gly Ser Thr Arg Lys Lys Leu Arg Leu Thr Lys
        115                 120                 125

Glu Gln Ser Ala Leu Leu Glu Asp Arg Phe Lys Glu His Ser Thr Leu
130                 135                 140

Asn Pro Lys Gln Lys Val Ala Leu Ala Lys Gln Leu Lys Leu Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
        195                 200                 205

Ala Leu Lys Phe Ala Pro His Pro Gln Ala Pro Ser Ser Ala Thr
    210                 215                 220

Gln Ala Gly Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Ala Lys Ala Glu Pro
            260                 265                 270

Arg Pro Lys Ala Ala Ala Thr His His Phe Phe Asn Pro Phe Thr His
        275                 280                 285

Ser Ala Ala Cys
    290

<210> SEQ ID NO 37
<211> LENGTH: 2846
<212> TYPE: DNA
<213> ORGANISM: Zea mays

<400> SEQUENCE: 37
ctgatgctag agcagagcgg ctttacactt ctcggcaact actcgtgtga tcgtgtctga      60
tcagtatact agtgaggcaa gaggaatgca aaattgcgct gctatagtaa ttccttagaa     120
gaataaaatg actacttact actatggtaa tttatgaata attttattaa gaataggtag     180
ttttagtcaa tgtcatcctt aacataaaac aagagcacta agccgcttta attcttgcat     240
ggaaccgtca cccgtgaccg tgactcgcga agaactccat gaccaccacc tccaaagact     300
ggcacgtgac gaggatttgc tgctgtgtct gtagtagtct ccaaaatccg aaccagtgtg     360
tgcccctgaa gatagcatgt ataattgacg atataggttt atgattaaac accacatcat     420
tacgacaaag ccaaattgac caaaacaaca ccgtaacgcc aataagaagc aatttttat      480
gcgtgcaacc tttgttggat tctcaatccc ctacaatatg attaatatta acgggttggt     540
ctaagcaaag taataattg tccaaacagt tttacctagg taacagtcaa agaaaaggtg     600
ttgtatgccc tcgttctggt tacaaaagcc acacttcaaa cttccttgcc atctacgatt     660
agctaagttg tctttggtga gggccacacc cctacctaga aaccaaagaa agatttctac     720
cttaaggggt agtttagct tccaaagcac acaattacga ttataattgg ggttatttat     780
taaaatatag tacatggatc acgttgagaa agccctgccc ctatgagctt cccacacgaa     840
agtgtccctc actggattca ggttaaccgg agccagcaag tgtaccatgt tctgccattc     900
cacgagttta aatccaacaa tgggtctccg gaaagaaaga tttatatttg catgtgacaa     960
cacttctgcg accagcaagg tcttattgca tattatatta ataagattcg ggaattgctc    1020
```

```
tctaagagga gtactgttaa gtcatttatc ctaccaaaat cttgttgctt gaccatgccc    1080
cacctgaaaa cgtccccacc taaggaattg atccttgatg ttcattaggc cagcccagaa    1140
atgagaatca cccgcttttc tggaaacttg ggtgagggat ttgcctccca ggtatttatt    1200
tcttaggagt cgtggccaca taccaccttc attgagtaat ttatagagcc aattgctgag    1260
taaacaaatg ttctttatgg ccagaatggt gactcccagc ccacctaact ctttaggttg    1320
gcaaataatc tgccatttgg ctactctata tttctattta tgatgtccac cttgctggaa    1380
gaatctggac cgaatagcat ctagcttcgc taagaagaag atcatgaaaa taggtagtct    1440
acttagaaca taattaatca aaacaagcct ccccttggag acaggaattt ggatttccaa    1500
ttactgagtc tcttctcaaa ccggttgata aaacaacacc actcgatgtt tctcaatctt    1560
cgatgggtca taggaatccc aaggtacttg aaagacattt tgcttattcc gcaaccaaag    1620
agccatgagt actaagtctc acatgcctta gctggcccat aataggaaat tcctcaatct    1680
tcgatgctat gatctaggaa caccaccgtg tcatctacat attgaaggat agacaaatct    1740
cctttaatca agtgtggtac gatcccagga aattgattct cctctattgc tctagcaaag    1800
agcactacca acatatcagc aacaatgttg aagagtatcg gtgagagagg ccccccttg     1860 tcaaaggccc ttgtgtgtcg agaaaaaggg tcctatacca tcattaactc taaccccccac   1920 gtgacctccc gagacgatat tttggatcca agcgcaccac tttggtgaga aacccttcat    1980
gcgcatagct tgcaggagaa aattccactt tagcttatta taagctttct cgaagtccaa    2040
cttaagaata attccatctc attttaacc tatgtagctc atgtacagac tcatgtaata    2100
caattacccc ttcaagaata ttacgatcgg gcataaacac agtctaagag ggtttaataa    2160
ttcgatggac aacccacacct attctgtttg tgagcacttt aataataatg ttaaaagtaa    2220
cactaagcaa acaaatagat ctatatttct ggattttcag attaatctct atcttaggaa    2280
ttaacataat ggctccgaag tttagtctat acaccgagag cgagttatta tggaagtccg    2340
cgaacaaagg cattaaatca tttttgttag gatagtggaa tgaagttcta gcattgtcct    2400
tgtgatgtta catgacacat ggcaaaaaaa aaactagcag atggttcgca tactcgttac    2460
tactaaagct aaatcatcaa tgcaatcaag aatcaaaccg ttcccaatgt gctgtaacct    2520
cagtcaaagg aagaagaaaa ccaccatcat atatgtctcc aacagtgtgg ctctaataat    2580
ttccctgcag acaaagtaca ttacacctgc tggcaggact actagtacca cgccacagtg    2640
tttccagcat tattattatt attattatta ttatttttac ctatgggtac tgccacactg    2700
tatccatctt tctctgcccg gcgcttatat aacgcctccc catgcttcta ctcctttcca    2760
atctgtgttt gtctttgctt gcccccttc tccccctca tctcccccct tttcttgttc      2820
ctgtgcctgt gcattggctg gcgatg                                         2846
```

<210> SEQ ID NO 38
<211> LENGTH: 3003
<212> TYPE: DNA
<213> ORGANISM: Zea mays

<400> SEQUENCE: 38

```
tgttgttgca tgtgtgatat ctgtccctat gatgtgatat cctgacagct aatagaatag      60
agtactcata cacaggtgca tcttcttttt cgaaggctat atcgaaatac ctccaagtta    120 agtgttttt ctattaggtc tacaaagggc acgaagtgta gaagaggcta ccataccgac     180
ggtggtggca gtgagaagat gcactttcca tctttcttta atttggtaag atatgaactt    240
```

-continued

```
tatatggtta taatgtttgg acctcttatg gttcaaaata tgtgggcaag acttaggctg      300 acacagtcg atgaaggttc ggcgtacttt cgagtcagat cgagtcaccg tttttatatt       360
tttgaatggg ttcaaatatt ttttaggcct tctcggtccg aaactatgat ccgaagcacg      420
atagacctga cctggcctaa ttcccagtac tacttttag accaatcatc cgttttccgc       480
gagagtcgtc gtcgaattaa tcaaaacttc agattggccg accaacagcc gaacgcacgc     540
acgcacgcac caagttttttt agattgagcc taccgtatga tgtcctatgc ctacctaatt    600
gcctattcct atgcacgcac caagttttgt aatggtattt agatggatat acttgacatt    660
tgtataatat aaatgtttaa tctttgtggg tacggttgac ccgacgggtg agccataccc    720
acatgtgtat gagtatggag gtaaattcat acccactgtg gatatgagtg atccgacggg    780
gctatttttt ttgtcgtggg tatgggtata ggatagtaat actcggtggg tatttaccca    840
ttgcatctct agtcaagcta gtatgacccg aaggcagggt tggagtgagc cttaattttc    900
ggcacgccgt gcccttgtca tggcacgggc ttaggccgac ctgacccaat gaagcatgta    960
gtgtttagtt ttcttttaatt tagtaagctg catactttat gtggttgtaa tgtcaggacc   1020
ttttgtggtt caaatatgtg ggccatgctt aggctggcac aacctatgaa agtttggcgt    1080
tctttagaga tgtgggccac tgtttctacc ttttgggttg acccgcctaa aagtttttta    1140
ggccttctcg gcccgagcct atttggccca aaacacgata ggcccaaccg aaccctattc    1200
ccaacactag tgtaagtgta aaaaacagac tggggagggga gaaacaaccc tcccggtatt   1260
attattccca tgtagcaatc atggaggcat gggagttgga tctagatgga gtggattgtg    1320
atggaattgg atatttccat gagacaaatt ggaggaaatc aagagatgag ggtatattga   1380
gagtgaaagg aattgaggac cgagagtggt gtgtgtgatg tatgtgggag ggtggagctc    1440
gttgttgctt acactatgtt atttgatggt gggcagaatg gtcttagagt caagtctttc    1500
gtttgggttt tccaagtttt ttattatatt ctagcaatac tatataaaga aattaaacta    1560
aggtgtatgt gttatatggc atactagctc gatggattat taaactatat tcacctgtag    1620
acaatagtaa aaacaatcta atttgtatgc atttgatgtg taagccgtgc tagcaacatg    1680
ggtcgtgctt tttgtccagc acgagcacga cccaaaatca ggagcccaaa gcatggccca    1740
acccaaagtc tatgggttga gctagcatga cctgaaggca cggctgaccg ggccttaatt    1800
tttggtctat cgtaccctca acatggcgca agcttaggcc ggcttgacac aatgaagcac    1860
acaatgttta attttcttta atttggtaag atatagattt atgtggttat actgtttgga    1920
acttttgtgg ttcaaatatg tggagcagac ttaggccggt acgacccgat aaaagtttgg    1980
tgtgctttag agttaggcta aaccactgtt tttatatttt agaatgacac gacacgatca    2040
aaagttttta gggcatgtgc aatgggtatc ttaagttgtg tcttagagtg tgtctagagg    2100
ggtgaatgta aaaaaactta agacatgtat cttgacgaag acacaatatc ttggttctat    2160
gtttgagaca agagactagc tgattggtca ctttaatttta ttaaatgctc tgattggtac    2220
aatgaatatt gtaagaaaca tgttttagac atgaccactg tattatgttg tgttttagtt    2280
gtgtcttata cttggagtac cgtgcagcag tatctaggtt gtacatgccc ttaggccttt    2340
tcggtcagaa cctatttgat ccgaagcatg atagacaccg catacatggc ctaattccca    2400
atactacttt ttagatcaat catccgtttt ccgcaagagt cgtcatcgaa ttaatcaaaa    2460
cgtaagattg gccgaccaat agccgaacgc acgcacgcac caagttttttt agattgagcc    2520 taccgtatga tgtcctatgc ctacctaatt gcctattcct acccacacga acaatcgagc    2580
caatccaaac caaactcccc gcgacaaagc ccgagacatg cacgcatgag accggctgag    2640
```

```
ccgatggatt ggagccgaga gccgagggga gagggtcaaa aaggcaggag tagatcgctc    2700
atggccgcga tgatgagcgc cccacgaggc agtcccttcg tcccttccct tccattaata    2760
attgcggtgc acaggagcgg agatccactt cacccgcacc gcacagctca tgatttgcac    2820
agccaccctc gtccgtcccc gcccagctgc tagcgcaagg aagcagctgg ctggctccaa    2880
tcccccgcca ccccgcctat ttataacacc accacttccc ttgcccccct cgccgtcgcc    2940
gccaccgcca ccaccaccac cgttgccgag ccctcgcctc accctcacag tcgtctcagg    3000
atg                                                                  3003
```

<210> SEQ ID NO 39
<211> LENGTH: 3003
<212> TYPE: DNA
<213> ORGANISM: Zea mays

<400> SEQUENCE: 39

```
cacacatttt tcctatgtgc ctcaaagcac aatacaacca gtgaatgtct ttgtgagcgt      60
tagaccctga tggtcatttt acttgttgat ctgaagtcaa ctaatggatc aaaacgacga     120
atggtattca tgagccctga agatgcctta tggattaaat aagtgttgtg catgttagtc     180
taaatcttaa tgattgactg tgcatttggt aataataaca ataagtttgc agaattgtaa     240
ccatgaagca acttgttgtt gcgtgtctcg ctgaatgttg agactaaccc ttcatgatga     300
aggacaaata tgtagtattc atgtcactac attaatctaa gtccaaagct cactgcataa     360
aaccactatc tgtaatgtgc gtaaaatttc ccaaataaat caccacaata gcatacattg     420
gccacaactg gatgattgtg gttggagatt ttatctgtat gcttttagaa catctcggca     480
ttagggggat gaatgcccat atagtgtaat gcctcaatat tctattaaac gcacaaaagc     540
caaactgaac ccgtcgttta gagtgtactc ctgtgtatat ggagtttgcc agaaattgtt     600
gaggagtaac catattggtt tgaatgcttc tacctgacgt agatgtggat atacccggga     660
ttaatatcat atccacattt gacttattgg catttgatct attctcgggg acgcctgcga     720
atatggtaca ttggccttag tcaaagcata tgtcctgatt gcagattcat gtggtctgta     780
ataactctcc tctgatgaac tcgccctgct ggtgatttgc ctcacgaaga ggttcatctt     840
gatgatgaag ttcctagcaa tgcgcgcaat atcattgtgc tgggaatatg aacaataaa      900 tctttcattt tgggaaatga tggagatcat tattaaatgt aggagacaaa tgtatcgaca     960
cctatcttga ctctatagat tgcaagggga tccagaacaa agtcctaggc atgagtgctt    1020
gaagctctct tatcgggtca atgataaatg caatcgaggt tgaaccaata atcgcaaaat    1080
ggaagtcgcg agcttgaaat tcggacattt atgggcacta ttgaaataat gtgtggtgaa    1140
tgcgatggtt caagtggtct agtgagagac ccatcccacg tatgtgttga ataaacactg    1200
ttccgctatg taatatatct ggcaaatggc atgaattaaa atatgcaggt actaggattc    1260
tgaagatctg tcatgagatc ctaggaggac ttatatcttt gaattataaa tatgcaacat    1320
ataaatctca taccgaataa tacattcctg atgaatgatc actctcctat gtaaggagaa    1380
tatctcctag ttgagactat cgttcccaga tggaacctat ccagaagaaa caaagtctgt    1440
gttgaacacc aaagtttgat aatcccaata aagggataaa gacccataca gacccgaaaa    1500
agaataagat gaggtaccaa aggacttgaa gttcaccgaa taagcacatg tgtattccat    1560 gagtttact catggtaatt tccactagat gtggaattac ggtatcctct aaagccctga    1620
tggcagaaat atataaggtt taggtgttac tggcaaaata tccccattgt gccagaatga    1680
```

| | |
|---|---|
| tagactgtaa cgatgtatct gatcgatgaa aaatccctga tggattacga tcttttgatgg | 1740 |
| acttttgtta caccatcata gatgttgcaa tggatgaaca cctcgagcga tgtgtcatat | 1800 |
| ttagaatatg tactattgca actatattat ccccctaagtc ctattgaagg acatgttatt | 1860 |
| tgctttgcac aactatgtat aaattgtggt gtaagataga aaatgatagc accccaacct | 1920 |
| catccattct cgttgttcca gatgaacaat gagacatata tcttgaagaa tatgcttgag | 1980 |
| ttatgaggga taacgactttt gacagatgtc atcgtcaggg ggagcgaatg cttatattga | 2040 |
| tcacaatcgt gagacaataa atgtcatatt ctatgccctg aaggcgtgag cttgatgatc | 2100 |
| aatatgtgaa cctttatgga actttctatc aaatatatag atccagtcga tcgaacacca | 2160 |
| tcagtcaaag tggcttattt aaattgatac gtgcacttat ttcgtatatc ctagaagtga | 2220 |
| gtagaggtaa agttcctgaa atagtccttg caaggatatg caatccgttt gctaaatcta | 2280 |
| tatgtgcata tacttccaga agaaaatatt ttgccatatt gatacagttt tgcaaggatc | 2340 |
| aggggagca catttctaaa gttagccttt gtagaagatt cggtagaatc tagatcccag | 2400 |
| aggatcgaaa tctgtcccga tgacagctgt tgtactcttt ttcccttggt gagttttctt | 2460 |
| gaagtttctc acatgaggtt tttaacgagg caacaaagtg caaatgcaat ttgtatcacc | 2520 |
| atgcactctt tctccatatt ttttccactg gttttttttgg agttttaacg aggcatgtgt | 2580 |
| tggtcgcggt attcgcccaa gggggagtgt tgagaaaccc taatgaaggg ttatgtgggc | 2640 |
| aaataccgaa tatagccctg agggctatcg cgtctctata catagaacct gtaccctca | 2700 |
| tatggaatag agaagagaaa gaggccagag gtccaaccct acatcgtgtc tattgtgttt | 2760 |
| cctctgtcgt gctaatggga agggagacgg gtcttctaca acttctcgcg cctctactgc | 2820 |
| tgacgggagg gaagagagcg gatctggtga tccgtggtaa cgtagttctc aacagtataa | 2880 |
| acagagaaac agagggatga tttgcatcct gatgctgtgc gctccaaaca tccattctgt | 2940 |
| ccatgacgta cgcatcacca caaccgccgc aggcaatcct cacagtcaca gctagccatc | 3000 |
| atg | 3003 |

<210> SEQ ID NO 40
<211> LENGTH: 3002
<212> TYPE: DNA
<213> ORGANISM: Zea mays
<220> FEATURE:
<221> NAME/KEY: misc_feature
<222> LOCATION: (786)..(835)
<223> OTHER INFORMATION: n is a, c, g, or t

<400> SEQUENCE: 40

| | |
|---|---|
| tcaggaaaac ttgtttagcc ccctgtcacc tctgttccga tcgctctgct tccttttcct | 60 |
| tgacctctcg gtggttgtct cggtcgattc cggtgcgcct tgggtcggtt ccggtgcgcc | 120 |
| ttggatcggt tccggtgcgt cttggtattg tgccgcagct ttttcgagca tcgcacgaaa | 180 |
| ttcagacaag acctcctatt catgtaataa aatgcataag aaatcatgca tgtttaatag | 240 |
| acattgtgaa atcagctgat taattaggta cacacacgaa attaaggatg tgtaatttac | 300 |
| ctcatgttct tgtggatcat aagtagggtc acgttgcaac tcacgcgcag cggccctatc | 360 |
| tatcctagtg gtaggaaaag ggtcgctagg cgtttcatat ccttccctgc tggattcttc | 420 |
| ttgagcaaca ctcttgtcca tgtggtcggg ccctaatcct tggtccttgg ttggagaact | 480 |
| cattgagcta catattaaca taagcaataa ttaaatttgt attaacaaat accctaaccc | 540 |
| ttatcgagga ggagtcgtat agaacgtata gagagagaga gagggagaga gaggaggagt | 600 |
| cgtataggac gtatagagag ggagagaggg agatggagag tcgtatagaa cgtatagaga | 660 |

```
gagagaggga gagaggagga gtcgtatagg acgtatagag tcgtatagaa cgtatctttt    720
gggagaggag tcgtatagaa cgtatagaga gagagaggga gagaggacga atctctagaa    780
tcgcannnnn nnnnnnnnnn nnnnnnnnnn nnnnnnnnnn nnnnnnnnnn nnnnntagtg    840
ttggagaaaa aaccctcggt aaaggactct ttgtcgagtg ttgtatttgt gacactacgg    900
caaagagcct ctttgccgag tgtcaaaaaa cgacactagg caaagaagct ctttgccgag    960
tgtcaaaaat aaacactcg gcaaagagtt cttcgccga gtgttttctt ttaccgaggg     1020
ttttttgcgt agcactcggc aaagagctct tgccgagtgc cagaaataaa cactcggcaa    1080
agaatatgac actcgggcaa agagccaaat tccggtagtg cctttccata tttcgtacag    1140
cttcatctcg agtccgaaat gttcctgtac atatactatg cttaggaaac attgtcaatc    1200
atgtttttta ggacattcgg aaagatgaag acctccaaca ctttgtatac taaacattgt    1260
ttgttttgtt agttagatta tcaaaaccaa taccgaaacc acatacacct ttgctgagtt    1320
taatacgtat cggcttctat tgtttctaca gtgtttttgt ctctatagat tgcagctgca    1380
acagtttaaa acaaactgac tttatttaat cagaacagaa caacccggcg tttcttaggc    1440
acagcaaaaa tgcaaaaaat gggagacgca aacaactaac gtaagataga tagccaacca    1500
cttgaacggc cacaatcact agctaagaca acgcattctc gagcagatcg cggtagtagt    1560
aggcgtatat cttgtacctt ctgccacaaa ccggcactcc accgcattat tgcatactcc    1620
ctccgtccca taagaaagt cgttctagcc tagcaggtga aaaacaagtc aagtgagaga    1680
ttacaacaat accccctagag gcgtgggctg cgccaatcgc tccctgctcc catgtctgct    1740
ctgatctcgt tgtctagaca ccagaacgac aatcttcaag ggacaaatgc caatgcccaa    1800
gacgacttct tttgtgggac ggagggagta tttgatatac ccctgttgca accgcaataa    1860
atcgatcgta ctagctagtg cgccccctgc agaaaaatac tctctcccgg ccgccactag    1920
atgccacacg tacgtagacg tgtatggagc acctgtacta tgtaaatggt agttcctatt    1980
gaaattcgat ccgtctaata gcttgttgga ttaggaatgt attaagagga ttagagagga    2040
ttaaatctca atatcctatc cgtctcggaa ttcgaacagg ccctaagagt gttgtgattc    2100
gatccctatt caagtccggt tactcaatat cctattcgta tccgattttt atccacatcc    2160
gtattctcaa agctgaatat ttaagatgtc gatatgctat tcaaatctta tccgacataa    2220
cttacaaata ttcgtatcca aatccgaaaa gaaaatagaa aaacaaatat agaacaagta    2280
atatttgttc gtatccaatc taattacacc actaaacaca tggatggagt ctatctagcg    2340
taatctcatc tggggacctg gattaccaag caaattaacc aacccggttg aatacataaa    2400
tactccggcg atgctcccac tgagtcaaag acgtttggtt cagttttttt accagctttt    2460
ttgaaaatct ggttgtgaga agaatctgag tattgtgggg attacgtgtg gaggaagatg    2520
aactgatcta aaggtttcga gatctagaaa aagcggattc ctactatcgt gatgattcga    2580
ctgattatgt gttcatatta attttagata gtctttaaca aaatatctta taaaagcgat    2640
ctgaaaagct aagacgttta tcataccgta gtagctttta gtgagcataa gctaaaataa    2700
gctcaaacaa acagggcgag cccgctaatc aaagaaatct cccccataga ctggagatcc    2760
accccacgag cgcccagctc atcattgtcg accacttgca tcagctacag acgtcgtctc    2820
tctctcctcc acttcaacaa acacttgatc tcgcgcgaat gcgcgatccc tctatttata    2880
ccccgcttct ctcacattcc gtcttcaaca actctggcga gcagcagtga acgtacttac    2940
gtcttccccc agctagctag ctatctacct tggtggtggc gattgatata tagattaaac    3000
``` at                                                                                 3002

<210> SEQ ID NO 41
<211> LENGTH: 3003
<212> TYPE: DNA
<213> ORGANISM: Zea mays

<400> SEQUENCE: 41

| | | | | | |
|---|---|---|---|---|---|
| cataaacgtg | cctcacaatc | gcgcggacgc | acgcgccccc | actggcccga | cctgaccacg | 60 |
| cgtgtgacca | ctaccttggc | tggggcttcc | catgcctatt | gaaaatcctg | gacttccatt | 120 |
| accaatagcc | tatatatata | tatatggaga | aagccctagt | taggtatacc | cacgtgacat | 180 |
| acatgtgtgc | gtctgatcgt | atgttgattc | tggcttgggc | agattttagt | gtaaaacatg | 240 |
| aaccaaaaca | gcgtaaatga | gtacaaattt | tagcataaat | tctagatctg | cttcggaacg | 300 |
| acgaatgtgg | ccggaaatta | cggcgcgaaa | atcgcgcgcg | tccgaccgtg | cgcgagtttt | 360 |
| ggatcggaca | gattttagtg | taaaacgtga | accagaacaa | cgtaaatgag | cacgaatttt | 420 |
| tgcataaatc | gtcgtttcgt | tttgtaacaa | caaatgcggt | ccgaattacg | acgtgaaaat | 480 |
| cgcgcgtatg | atagtatatg | ggttatggct | cgaacggatt | tcagcgtaaa | acatgaacca | 540 |
| aaacagcata | atgtggtatg | accgatcgag | tgaagtcctt | ttacgtaagt | gatacacgaa | 600 |
| aaatgatgat | tgcccgtgtg | tcttcaccaa | aagatccaaa | gtgtaatatt | gtgtcatatc | 660 |
| agttcatgtt | gatgatctta | acatcataga | aaataaactt | gatattgaag | cgcgtcatca | 720 |
| tttgacgaca | gaatttgaga | tgaaaggttt | gggtaaaacc | aaattttgct | taggtcttca | 780 |
| acttgagcat | ttaccttctg | gaacccttgt | atatcaaagt | acatataccc | aaaaggtatt | 840 |
| agaaaaattc | aatatgaata | tgtcttaacc | ttcaaagact | cctatggtgg | tcaaatgatg | 900 |
| aagaacggat | attgggacca | gagttcccat | atcttaatgt | cgttagtgca | ttaatgtacc | 960 |
| ttgctagtca | tacccggctg | atattgctt | ttgtagtaaa | tttgctagca | agatacagtt | 1020 |
| ctgctcctac | caaacgacat | tgggttggaa | ttaagaatat | cttccgatat | ctaaatgaca | 1080 |
| caaaggaatg | agattacatg | catattttct | tttggaaatc | agtgtgagtt | ttactcataa | 1140 |
| tccaaaagca | tggtgtactc | cttatttttcc | ccgcagtgtt | tttgaggaga | ataatatctt | 1200 |
| ggaagaacag | ccgaaggacg | atcaaacgaa | gttagattga | tcaaagggga | gtgctagaaa | 1260 |
| atgtgacatt | ttgtatgtaa | tcaatccaag | gggtgctgca | gttatctcgc | caaggaacac | 1320 |
| atcacttggc | ttgcaccggc | cttcataaat | atacatgaac | tcgtttccac | taatttacag | 1380 |
| cagaacgaac | cagctagcta | gctagctagc | catctaacgg | aataatacaa | tacactatca | 1440 |
| ttaccaaaaa | catcatcaac | atgtatgtat | attattacca | cgagaaattc | aaagcagtag | 1500 |
| agctagcttg | tccgtcatgc | atggcgggtt | actttatata | tattagtaca | cttgagctac | 1560 |
| ttgctgttct | gctggtttat | tgcgtgattg | gtttcgggtg | catgatgtac | acgtgtgctg | 1620 |
| gcgtctgctc | atatcagatt | tcagcaaat | gcgtgctgcg | gtcatatact | atctgccgca | 1680 |
| gcgcagtcgg | aaaataatgg | cttgtgtgtg | cgtgtatgtg | tgtcttgcta | aaggtcgacg | 1740 |
| atgcagagct | cacttagctt | gtttggttgc | agactactct | ctctctgact | ctctctatct | 1800 |
| gtatctgtat | atatccagat | actatacgga | caagtacagc | agtacgaatg | tcggcggaac | 1860 |
| aagtgtgtgg | tgcgaaaatt | gtctcatctc | ggcagctttt | tcctgacttg | tgtgttctgg | 1920 |
| agagccctga | cttccgttcc | gttacattgt | tcctgcttta | atttacaaat | atgcgtaccg | 1980 |
| atgcgtgtat | ataccatcta | tatatgtgtc | tatagaccag | gcgcgcgtac | gtggattgtt | 2040 |
| caccgtcatg | cacgcacgta | cacctgagca | gagcttataa | tgcatgcatg | cgctgaactt | 2100 |

```
tgcctccatg ggaggacggc ggggcgggcc aaccaatgca agagacgacc catcagagca    2160
agagggaagg gggccggagc ttacatgcat gatgcatgca cgtcatggag tgcgttgcac    2220
ttgagcaaaa cgctcaccac ccagctttcg tgttttttcc ccagtgtacg gttcatacaa    2280
ggcctttcgt acgtacgttc gtagccaatt aatgggctag ctcgtttccc acggagatag    2340
atttcttgtt gcacgccgtc agcgcgatat gatgatgatc ctcttaaagt gcacgtgtcg    2400
tcgtcagttt caggaccgac catcgatctg atcgattcgc gggggaccag gaaacggccc    2460
tccgatcctg cctatagcgc agctagctgg tctcttcttc accgcctttc cattcgtcgt    2520
cgtctcaaac aaaacagtag tacgtccaat cggggacatt accttcctgc taatccgtct    2580
ttgcgttcaa ataaaaacgt cagcctcgct ttgattagga ggattaacat ctctaacccc    2640
accctgcgcc gtgtcttctt cttcaatcca cacacgaaac tgacttcgtc ctccatccgg    2700
cctctgccgt tttcgcttcg cgagatagtt gtagtcgccc gccacctgct gcgcctataa    2760
agcaacaagg ctgagccttc atacgccggc tacttgctta cttaccacca ctagtcaatc    2820
tactgcgtcg tcttctcttc ccgtagtccc gagtcccgcc ggcccatctt cattcctctc    2880
catcgcgcgc ggtggcgcat gcaatctatg tactagggct gggccgctag gtagatagct    2940
gctgtgtgca cgtacatctc aggctctcag ctctctccct accgtcgtcg tacgtactcc    3000
atg                                                                  3003

<210> SEQ ID NO 42
<211> LENGTH: 3003
<212> TYPE: DNA
<213> ORGANISM: Zea mays

<400> SEQUENCE: 42
ttgattcgtt agctcagttc tagccacttg aggatcatat tcccagttgg gaccccatca      60
gggttcaaag caagtctagt ttgaaccaca gcagcatgat cagacttctt tttacatgat     120
ttctggtgcc taagcaaatg tccagtgcca gcattagaat tagcactcaa cctagctttg     180
caaaatttgc aaatacctgc aatgcgcacc ttcttaccat tacggttttc tgtgacttca     240
gtgaagtcat cccaaacagc agatccacgt ttaccagtgc tagaagaagt caatgaatca     300
agttcattag agccagcagc atcacttacc ggcccgggat taggagtggt atcgacaccg     360
aacaaggcag cagcagcatc tcccatgtca tcgacgtcat cgggaagctg ccctaactca     420
acgagctcct cgttgatggt tctagggtac cgaccgttgt cgtcgtcgtc atccataacc     480
gacttctatc tcggcaccgt acctcgacgg cagtggcggc actagcacga ctccgtagtc     540
ggccggcgac ctaccaaagt ccacaagcaa gcagcgaggg ttagggttag ggattggaat     600
ggtcaactgg cgaggaagcg aggaagagtg acatacctgc caagccggag cccggagccg     660
agacgagggt aaagtgcac gacgacggac gacgcgagag ggagagccgg agaagaggag     720
attagggtta gggattggga tggccgactg gagaggaaga gccggagagg gacttatctc     780
tgccaagccg cagcccggag ccggagacga tgacggggga cggtgggagg gagagcccgg     840
agcggagatt agggttaggg atttgtgatt agggttaggg atttcaccga tcaaccgatg     900
cagagccgga gtctggagag gggcgccgca cggaagggg ccgatgacga agatccgaca     960
gagactacgg cgatgggccg acggtgaggc ggtgagcagc agagcaggag gagagacgga    1020
gaggccgagg gcgagagcga aaccgcgagc gcgagagagt gactgagtga gagagaggag    1080
acggagagtc gggtcgggag ccgaagccga ggctatgcgc ttatgcggtg ccgctccccg    1140
```

| | |
|---|---:|
| taccgggccg gtccgtgcct gccgttctct ggcgggccgg gccgtgccgc ccggcgggcg | 1200 |
| cacccagcag cccagacacg gcctggtaaa atgggccggg ctggcccggg cacgaagcca | 1260 |
| accgggccgg gccgtgcttg ggccgggcca aaaaaacggg cctcgtgccg ggctcccgtg | 1320 |
| ctctgggctg catgctcatc tatatgtgtg actgtgctgc tgtctgctca tcgtattttt | 1380 |
| tcagcaaatg cgtgcggcca tacaccacca tctgccgcag cgcagtcgga aaataatggt | 1440 |
| tttgtgtgcg tgtatctgta catgtgcgtg gacgctaaag gtcgatgatg cagagctcac | 1500 |
| tttagcttgt ttgcttgctg cttgcatact ctctctctct ctctctccac catatccagc | 1560 |
| tacggacaag tacagaagta cgaatgtcac cggaacccgt gcaaagaatt gccatctcga | 1620 |
| cagcctttgt ctgaccactt atatatatca tgcatgcatg cgctgaactc atcagagcaa | 1680 |
| gagggaggag ggaccgaggg aggctgggag gggcatgcat gcacgtcatg cagtgcgttg | 1740 |
| cacttgagcc agccaatggg actccttact ttactagtta gtcaaacgag tactagctat | 1800 |
| agacggcctt tcgtagccaa tgggctagct cgttttccac ggagataata gatttatctc | 1860 |
| ttgtttagta ctcgtcgtca gcgctgtatg atgatgatcc tcttaaaagt gtcgtcagtt | 1920 |
| tcaggaccca tcgcggtgcc ggccgggctg catctgattc gcgggagacc aggaaacggc | 1980 |
| actcctcctc gtcccttctt caccgcgcgc gtgctccctg gcgcgggaaa aaatctgga | 2040 |
| tgtaaaccca ttcatttacg gtccctcgca tctaccacgt gaagacccag accaaaatct | 2100 |
| gtaatttaat caattagtaa ttattttttt tccgttctgt ttatgtgggc tctaggtgt | 2160 |
| gaggagctgc aagcgagtga gtttatattc cggaaaaaat ttctttgcat ccgagatgta | 2220 |
| aaaaatctct ttcacatcct cttacatgta ctacccggtg gtctatacaa atagaagaaa | 2280 |
| aataaataac taaagattaa agttgcaaat tttgatttgt ttttgtagat cttaaaagtg | 2340 |
| gtggatgtga gaggtcgtaa aagaggttgt ttgtatacat attttttcct tatattcggc | 2400 |
| aattttttcc ttatatttgt ttatgtagag aatttctctc cgcgcacgcg ccttttcctt | 2460 |
| tccattcatc gtctcagaca gacagtcgcc agcaacactc caatcgggga cattaccttc | 2520 |
| cctgctaatc cgtcttagct ttccaataaa aacgtccacc tcgctttgat tagcaggatt | 2580 |
| aaacctcccc ccatcctgcg cgcgtgtctt cttcaatcca cacacgaaac tgacctcgtc | 2640 |
| ctctgccgtt ttatttcgct tcgcgatcgc gggtaggagc aggagcagga gcgagcgaga | 2700 |
| tagctgtggt cgcccgccac ctgcgctgcg cctataaagc gacaaggctg agccttcata | 2760 |
| cgccggctac ttgcttacta ctactagtca atctactgcg tcgtcttccc ttcgtctccg | 2820 |
| accaacgcgc gcgcgcccat ctccattcct ctccatcgcg cgcggcgtgg cgcatgcgat | 2880 |
| ctatgtacta gggctgggct agctagctgc tgtgctgggt gcacgtacga ctcatctctc | 2940 |
| tctctctctc tctttctcta ccgtcgttgt actacgtact ccatgcacag cactcgtgcc | 3000 |
| atg | 3003 |

<210> SEQ ID NO 43
<211> LENGTH: 3003
<212> TYPE: DNA
<213> ORGANISM: Zea mays

<400> SEQUENCE: 43

| | |
|---|---:|
| attcccgtcg gttctgctgg ccgacgggag ttattaatta attcccgtcg gttccctagg | 60 |
| ccgacgggag ttattaatta attcccgtcg gccccacggc tggccggcgt cggtggtgag | 120 |
| cggcggcggc gtcaaaccga gagagacaag cgagaaaatg agccgcgcgg cggcggcgtc | 180 |
| gggcacataa agaattaatt cccgtcggct ggcgtcaggg ccgacgggaa ttagttaact | 240 |

```
cccgtcggct ggcggctggg ccgacgggag ttaaactaaa gcccgtcggc tggcggctgg      300
ccgacgggag ttaagataaa gcccgtgggc tagaatggag ccgacgggag ttatttaatt      360
cccgtcggcc cgagctcggg tcgacgagaa ttaaaatggc cgacgggaat cttcctgatt      420
cctgtagtgt ggatgcacgt cgttttcgtc gtgcgcaatt cgcatccgcg tcgtcgtcgg      480
atcggatcgg agctttgact gttttgtcga tcgcgagtga cgttcgtagc tagtagtaag      540
cttaccaagg ttgacgtgtt ccacgacgac gacgatccgt gtatacggtg caggacacat      600
gtgcatgcat gcatatgatg gtaggcttcg aacgggcggt ctagtaggga atcataccat      660
atgcaaataa acgtcggttg atgtacagga gagagagaga gagagagaga gagagagaga      720
gagagagaga gagagagaga gagagagaga gagagagaga gagagagaga gagagagaga      780
gagagagaga gagaggagac aagatctctc ctctgcaagc aataatcaga tggattagac      840
gccgtgcatg ctcaacaagc agattgatgg attcaagatt cattccagga agaaggtata      900
cggaagaatg ttgtcaagat gatcgagaag cagtggagat ctccttgcac gtactatata      960
cgagctagat ggggacaggg acattgacca gcgcgtcgtg gcacgtgtgg gaggggaag     1020 cagagcagag ccgccgcaca cacacgcata tggactttgt acggccgtgt cgacgacagc     1080
ggaaagcggc ggtaggtcgt ggacgttgac ccagctgtgc tgccgcaaca cacatgcagt     1140
ttccacatgt gtgaggtcag gcgcggagcg tttgtcgtca cgtataatcc atcgatcagc     1200
ggccgccgtg tgtacgtgga cgagacgacg acgagtcggc gtcggttgca cggcgtgcgt     1260
gcgtgcgtgc atgcatattc gcttcctata tacatacgta tcgatctagc agtgacgatg     1320
cgtatacatg catgtgtgtg aacaatgtgt gccggcaatc agggcagggg gagaccgacc     1380
ggatcaccgg accggcgacg atgtattctc gctccctgct tggtactcta ctcatctact     1440
gctagtacgt gtccttcgcc cgggtccacg tggacagcag caggcagggc gcgtggctcc     1500
gacacgtacg tacgagtacg acgactactc tgcatgcatg acaggttggt caagctagct     1560
agccgcgcaa gaaaaccccc ccgtcgtcgt cgtcgctcgc ccctagcagc ctgccgatat     1620
agcgtcgtgt ggaatggaac cagtcgtcgc ttggaagatc cgatcgatga gcaagcaagc     1680
aggcgcatgc agccgagccg ccggcagcgc tccccacccc acctaccgta ccgtaccgtg     1740
cgcgctccat gcttgcgctt gcctgcacgg ctgcaccgct gcacggtcta cgcgcgcgcg     1800
acactctact gagcgcgcga gctacacaca ctgcgctgct gctcgctccc gcgctcgagc     1860
cgctgttgtt gcatgcaaca agagtcaaga gacgacaagt caatcgcgct cgctcgctcg     1920
cccgatcatt gcgtccgtcg cttgcgtgcg tgtcaagtgt cagccagtat taataatcac     1980
ttaactaacc tatagccagc tagctagctt acttacatgt gcgtttaatt attcgtatgc     2040
ccgtgcgtca cactctgtgc atgtataatg catgtatcct tgacgacacc gactgcctag     2100
ccaggctcta gctcgttcgc acgcatgttt gcccctcgag attattcgga atccacactg     2160
cttttgaccg ttcacgcacg cgcataacta tcaactagac atgtatgtgg agcattgata     2220
tggtcatcac atcatcgatc gacatcacgc caaagaattt gttttttttt ttgacacttt     2280
tgctatattt cccagtgacg acattaattt ggcagtgcag agtacaacac aggactgaga     2340
tgtcccattc gtttgaaagt ttgattttc ttttttcttt tggagacgag tagtcatctg     2400
tctacagaga gatacaaaaa aaaacttcaa tacttaaatc aaactatgta aagaaaaac     2460 aggaaaataa tgagggatat atatatatat ataccagt aatttttttg atctaacgac     2520
gtcgagctaa tcgcacctgg agtagtttgt tatagattta cgccaaataa gtaatcacaa     2580
```

```
cactatctta aattgtcgtc atcggtttcc caatcgtgag acagacacct gatcttgacc      2640
gtccgagaaa ccgacgactt gtctgcctgc ctgcctgcct gccctgcag cagctgtttc       2700 ctgttcttgg catttattcc aacccaacca cgcacgcatc aacgcgtacg tactaaaact      2760
cccgccatta ccccccaca ttcattagca accttaattg cccttcatta accccccac        2820 cacacgaaac cgtactacga ccttgtcccc tggctccaat ccgccaccat cagctggttc      2880
ttggtgtgga agtggaacgc tgctcgtgtg ccactctgcc actgccacct atataagcgg      2940
acgcaccagc accaccagca cagcagcacc ctgtgcactg atcgagcctc catcttcgcc      3000
atg                                                                    3003
```

<210> SEQ ID NO 44
<211> LENGTH: 3003
<212> TYPE: DNA
<213> ORGANISM: Zea mays

<400> SEQUENCE: 44

```
actcttttaa tgtagtatat aattataaag acaacattca aaaggagttt cccacgcaac       60
catgtttggt tcccacgccg tcgtgtgcta gtgttttttt cgttttggat tacaataata      120
acgctgcagt gtagttgttt tgttctagga cgcggcggca cgtggagcag tggagtgagc      180
aagggcggcg acgtgtggga ggaacagtgc gtccgagagg agatagtgtt cagcggcatg      240
ggcgacttat gcagcagtga gctaacaact agttagaaat ttagttaaac ttaatcgtac      300
acattagtct ctctatttag attttttagg actaaaatct agcaactaat tgttaactac      360
aaataacagt tttgttattt attttttgaaa tctaatagtc atgtgtacca atttatctta     420
aaaaagtagt tttagaaaac tataaatata ttaagagttc atgtgtattt taataaaaac     480
accttgatca acactatatt ttagagatcg tgtcggcgtc ctaaacgact tgtaatttag     540
aaccgaacag agtatgtaga agttgaatca aaccagcagg catgtaaaaa gactaatata     600
accgtaaatg agtttgtcct taagtattgc cgatggagcg acaagaaca aactgtcgct      660 tacggatacg gactatacac gaaataactt gtgtatatgc aaagcttcgt aaaatcgata     720
tatatcttac tttaatacag catatttatg tgatgaaaat taaaaaatag tttacttta     780 aaaaacgagg atgataatta ttttagaacg gagggaaatg ttgtggacat tagcacgtga     840
tctggctctg tctgttggct gttgcacact tgctgcctgc gggtcgagct cagccacgcc     900
cggctcaggt ccaccgctca cgcatgcgct cggattggct gtggcagtgg caggactcgt     960
atgacggtat gagtacctca tggcaggtca ggaccgcagg agacgatggc agtacaatga    1020
cacgcatggc cgaatgcgtt ccgatggttc ctctttcttc ttttctgttg gagataaaag    1080
tgaaatacgc ctatcagctg agcgagcaat catcaatcgt tcgaaccagg gccgtgctga    1140
gaaccaatca tgaactcatt cccggatcat gattgagtcg atgatgatgg cagcagcaaa    1200
caggagcacc aggccatcta cgcccagcac agtgtaaaaa aaagaaaag aaaagtgaca    1260 gtcgcgtcga cgatgattgt aagctggtcc ccgggccacc tccggcaccg catcacaccg    1320
cgtgggtggg ggtggggcag ctgcagcccc gcgcggcgca gacaaccagg gagcgggtgc    1380
cggtgccggt tgcgcgcgag gggacagcgc gatggctgac gaggcccgcg cggcgtcggc    1440
atgcgtccgg gggcggggc acacctcata attgcccgaa acccacggc ccaatcacgt      1500 ctggcgtgcc gtgcatccca atccgcattc ataccactgc gccattccgt ggcagcgcac    1560
aaacgtttcc agatactcgt actgtagctt tgcaacgttc cggccgtgtg ccggtccgca    1620
ctctggtctg gatcgacgta cgtagcccga caccttaaaa ctagggctgg gcattcggtc    1680
```

| | |
|---|---|
| tattagggta attcggttcg gtctattcgg gttttgaaa tttcgggtta tgaaaatga | 1740 |
| gaaccgaaat ttccaaaata attttaggaa ccgaacccga atagacccat aatttcggtt | 1800 |
| cggtctattc ggtccaccga atagactcga atagtagaga gactattatc ttttgttaaa | 1860 |
| atatatacaa tttataatta attggaagta ctattattac ataagtgac tatagaaaat | 1920 |
| agcatactga gatatatata ctatcgttaa gatgatatca taattttag ctaataaact | 1980 |
| cataaatcat ataataatat catcatatat taagaggttt tttatatttc gggttattcg | 2040 |
| gtctattcgg gttttaaagc ttaggaaccg agcccgaacc cataatccga aatatatcac | 2100 |
| atataggaac cgaacccgaa cccgaaaacc cgaatagacc gataattcgg tctattcggg | 2160 |
| ttcgggttcg ggtttcggtt ttaaaatgcc caccccctact taaaaccttc actaaaacta | 2220 |
| ctagaacgga ttaagggcct attcgatcat atatatttga ctttcaggaa agacacgtcc | 2280 |
| acggaatgta cggtagacaa catctttgac cagattactg tcacccccta ctaattgtag | 2340 |
| aaaacttgtg gcacgcatgc gcgacagcag gagcgaagac cgagttttct gcgttctgtc | 2400 |
| ttaaggacga gcagcgacag tagccgcagc atccgtccag cgcagcgccg ggatcccggc | 2460 |
| ggcaccgata gacgacccgg ttgcgatcga tgcccggcgt cgtacggttt ccgagcagcc | 2520 |
| gcgcgcgcgt cgcgggagcg ggagcaacgg ggaatccgcg aagggacaca cggatcgcca | 2580 |
| tcgccgaggc atcggtgatc cacccatccc gcgcgagccc gtgccgtggg gggacatgtc | 2640 |
| aagcaagaga gaggcgccag cgccaccgct acgtgccgcc tggaccccc aggttcagct | 2700 |
| gatgattggg ctgcgccggc gagggtgacg cggctgccca cctcacct cacctcaccg | 2760 |
| atactattat gataccttga cctttcgtcc ctccctgcac tccacgtctc cacccccaca | 2820 |
| gagtatcccc ggccgtgcgc gtcctcttta aaagcaagac cctcccttc ctcctcactg | 2880 |
| ccacaccaca tcgacagctc catcgattca tccaccgcta tctctctctc tctctctctc | 2940 |
| tctctctctc tctctctctt tcaactgtaa gggaaaccga gctcaaagtg gcaaccatca | 3000 |
| atg | 3003 |

<210> SEQ ID NO 45
<211> LENGTH: 3003
<212> TYPE: DNA
<213> ORGANISM: Zea mays

<400> SEQUENCE: 45

| | |
|---|---|
| gtcgtcgctt cccggccacc cgcagcatcg tcgccggccg gttgcgcgac actaccagta | 60 |
| ccaccacacg caggagacac gcacacagcg cgcaccatgc tgtgagcctg tgaccatgat | 120 |
| ggcctcggac cagggaagga aaggattgat gggcgtaatc atcacatgca caaatgcgtc | 180 |
| ctcctgccgt gtggtccgtc tatccaatag aaccgttgt ggctcccccg gtccccgaac | 240 |
| cagtcctaat gcacccttac tcctactact agctaggatt ttgcttgttt gtttagggca | 300 |
| tgtacaacct agatacagct gcacggtact ccaagtataa gacacagcta aaacacaaca | 360 |
| taatacagtg gtcgtgtcta aaacgtgtgt cttaccatat tcattgtacc aatcagagca | 420 |
| ttcaataaat taaagtgacc aatcagctag cctcgtgtct cgaacataga gctaagacac | 480 |
| tgtgtcttcg tcaagataca tgtcttgagt ttttttacat tcacctccct agacacactc | 540 |
| taagacacaa cttaagacac tcattatacg tgcccttaaa catgcacgca tggcttaggt | 600 |
| aggtaggtag gggtagggcg acatgctcgc ccgcagaatc attgtgtgct caaaggtgag | 660 |
| cctgggcgag ccagcgaggg tatcaagtat catgtattcg tgtcgtggtt tactcctcct | 720 |

```
actatactcg aacaaggagg acatacgtca tcatgccgtc tacgatcggc tttggagttt      780
agaagacttt tcttccataa agttacacac atgattcctc atccgtgctc gttcgtaggg      840
tgcgtcacgt gctgtgtctg attccacttc cacgatcgct ctgctgtcgc taccctcttt      900
atttattgta catatatata acagaagaat actgctattt gtatagatga ttttttttatt     960 ccttgtatgg ttgcaatgcc gaccactcta tatatggttt tcagtcttac tctctgtgat     1020
atgtttaggt cttattgatt gagtactctc gtattcacct gtatccatcc atgtgtattg     1080
aggtgaatac gagagtatcc aaataagacc ttaaatgcaa ggtcgtcttt gagaagatct     1140
atctatctct cgacactagt tttttttttt gtgaagtcaa tatattcgag acacaaagag     1200
caccgtacca ccatttttatc tcatttagat tgttatccta atgttttaat tgcttatcga     1260
atattattta ctatatctat dacggttgca ttggccgaga aaatcttttc aaaattaaaa     1320
ttattaagga actatttgag atctacaatg gattaagaga ggttaaatgg tttggtgatt     1380
ctatgcattg agaaaagttg ttggatgaga ttaatcttga ttgtataatc gtcgacttta     1440
tatcacaaaa tgttaaaata catttttagt gtgatatcaa gtaacaaata aatgttatga     1500
ctatatttta tatttgtcat cttataaact tttaagcatt gaataaaagt tttcaataca     1560
tatgtggatg gttgccccaa aagtcaggaa cgaccctgac ttaacgggcc tctacgcact     1620
agtatttcat gagacgttct acccaaaaaa aaagtaaggc aaatcatatg aatggtacca     1680 aaagaagaa aagaaagata aggtactcaa ttttgtagac attaaaatatc ctccgcaata     1740 atagtcattg gattaatatg acttaatcta acctaacaag ggtctgtttg gatcttagga     1800
actaaaacaa aagtgactta gggagtaaaa ttcaaacaaa aagaactaaa agttatcaaa     1860
atagtaaaaa aatgtattct ttttagtcac ttttagctta tacgaagaag ctaagggtgt     1920
gtttggttga gaagcgaagg gaatgaaatg gctccattct tatttttttta tgtttggttt     1980 ctatggagga gagcagagca gttcttggag tctataaata gcaaatattt gggatgctct     2040
cgctgcacca aaacgaccag atgcgagcgc tctcatccct ctcatccact caatagtcac     2100
atgtctctcc aaccaaacaa taaacggagt ggattcactc tattatactc ttcaaccaaa     2160
caaaaactgt aaggttctgt ttgtcaaaca cagaatgaaa tgattcaatt attagaaacc     2220
ggaatgaagc cgttccatgc tatttggctc cctaccaaac gcaccctaaa ggtcgcaaag     2280
ccaacgccat tggtgtattt taattttata agaaattaca cgtgttctga aaagatgtag     2340
ccgtctgtca tggtttgctg catctaataa gccagtatac gacacacttc tgccgttgtc     2400
caattaggaa atcttaataa gagcatttcg tctgtctgtc tacgggagta ccggacgatt     2460
catcctggtt gttctgggta atgctttgtc tcggggacaa atggccgata gcaaggatac     2520
aaatagtgaa aaggaaggtc tgctgcaagt tgctcatggc agcacctggg acaaaaacaa     2580
tacgctcccc aagaaatacg cacatccccc ggccgggcgg agccggaggt cgcccggagc     2640
cggccgagct gtgagcacgg tggcatctgc atctgcgcct cccagctttc tgataaagat     2700
cgtgggcgct actaacgaaa ggggaaagat acgtcgcccg ccccgccacc ggtggtgatg     2760
attaacataa ttattagtgg ccgctgctgc cgctggccca tgctgctgcc gccactgctg     2820
cgactgcgac gctgcgcacc agtgctgtgc tgcatctgca tgcccgtccg ccgtgccgtg     2880
ccatccgaaa aagagagcag caccagcacg gccacggccc acggagcgca gcgctcctcc     2940
catgcggcca tgccatcggc catcgccatg cggtttttt aatcctgccc tcatgattcg     3000
atg                                                                   3003
```

```
<210> SEQ ID NO 46
<211> LENGTH: 3003
<212> TYPE: DNA
<213> ORGANISM: Zea mays

<400> SEQUENCE: 46
agcgtcctct aaattctatc ccctaaatga atattccgtg tcctttacat cacactctaa        60
aaaattttgt catttatatc ttttcagtct ccagcagcgt cccctaaatt cggtcctcta       120
aagctacaat gttaacatat ttccttttt catttttttc ctgttttctt cccatttaac        180
gcaatacaaa ggatgcgcaa aatagtgtat ttcattaatt tgcaaataat aatctctgaa       240
ataatgtttg attaataatt tcgaattgta aatattaatt aacattcgat gtgatattgt       300
gtttaattgt tgtcgataaa acgtcgaata gtattttatt gatataaaaa tatgttttca       360
aatttacatg tttccaccat aagcacgaca cttcttcaat aagccatcga caaagccacc       420
ataaatatgg aggctcccac catacactat agtttagggg acaatgtaga ggactttgtt       480
ggacgtgtag ggaatctgac tgaacctacg tttagagtac atgaccatat agtggttctt       540
gttggagcca gtctaacaac aatcacgata aaatttagac tcttgttgga gccagtctaa       600
caacaatcgc ggtaaaattt agattgtctt tctcctctgt ttgtggcgca ctcgctgccg       660
ctcgctatcc atagttgttg actcacgcat cgtctctttc cattcactca cgcgcttgct       720
ctcgtgcctg accagcgacc tcaggaacct ccctatgggc accgtctcct ccatcggcct       780
ctctgtcttc gccaccttca gcgccgacga ggtggccatg ctcgagacgc ttgtcctgct       840
ccccggccag gacgccgaaa ttgcacggga atcctccagg cgcagagcaa ggtcttcatg       900
ctgcctagtt ccgcttccgc gggcgcaccg tcaccaccgc ctggttctgt ctccgtcgtc       960
ggtcagggtc tgcgttcgtg gccctgggac taggagcaca tggtgcagac aacaagtgag      1020
aacattgctg aagccgacgc gtgcaaggta tttgaggaaa tgccaagctg atgcgagaac      1080
actactaaac gcaagcatcc acgcgtttta attgatttgt catcagttcg tcattatatt      1140
cttaatattt aagtagtgtg gcttagaaaa atggcataga caaaatgata gtatatctaa      1200
aagctactta tacaatttca gaacgagtta aagaatttaa attttaacta atatgtctaa      1260
aatatttgtt ggcataatgt ttatacgttc caaaatatct attattgaat aattattaat      1320
ttcttcattt tgtattgcag tacgttgaat ccaagtgcaa tataaaaaat gaataaataa      1380
ggtagtttgt gtattttgtt atcatggtag atttaaaaaa ccgaatttag aggtcgttgc      1440
tgtacatgaa gaagatatag aaaacataat cttttaaaat gtgttgtaaa cagtgttatt      1500
aaaaaggcgc ttgagcgcct tttaagcgct actgaggtag taaagcgtcg tacgtttcat      1560
aaatcaactt aaaagttctc gttttaagcg ctaaagcgcc acttttagc gttggccata       1620 ctcgcttctt gtcatgctca gttcggcac cgccacaacc tccctatgct actcggcgct       1680
cgcctccacc gctccgtatc tgactatctg ccctctgctc agcgtcgtg ctcgccactc        1740 cagtgctcca gctcgctatc cctttgctgc tcatgctcgc cactacctcc ttgctctcat      1800
ccttctcccc ccttccctgc tgatctgctc atattctcct ctgattttgg ttatgatgat      1860
gaagcaacaa acaatctcct ctgatttggg ttataatgat gaagcaacaa acaatagtgt      1920
tggctttggt gatgagtaag acaaagacaa gaatgatggt ggtatagatg atttggatga      1980
tggttattga gatatgatag agcgagattg agtaacgctt gtgtgcttgc aactgcggac      2040
attgcattcc cttcagttgc ttttgtgcta tatttgtgtc tttgtggttg tggacattgc      2100
attctacttt agttgctttt gtgctatgat tgtgattgtg gactattgca catttcattc      2160
```

```
tactttgttt atggttgttt acttgatagt tgctattagt tgaacacttg aacttgtgtt   2220
atcgtggatt tgcagtagtg tggttacaga catgttacat tattatgtga aattttgtta   2280
tattcatatt tttccatgtt gtttaaaaat acgttttaaa gctcacttaa acgttttaaa   2340
gtttaaaagt tctcatgagc gcttcagcgc tttatcgctt taataatctt ggctttaaag   2400
gatatggaat ttttctttag agaacaaaat ttagaggacg ttgctggaga ctttctagag   2460
ctctatatcg ttagcatgct caatggggtg tttggatgac tctagattct agctatagtt   2520
tataatatca atttaactag ttttaaaaat attttttaatc taaataataa ataaaatgac   2580
ttatctaaat atcttttaaa tgtttacaac tccacgattt tctggacatc taataatcca   2640
ccaaaatttc tagagctgga cctgttctaa acaggacctt agtagacctt tttaggtaga   2700
atttctattc aacttgtata tagaacgtgc ccatggaaat cctctgcgca acaaccctta   2760
cagaactata ataaacaaat gacaaggtgg tcataaaact ttagtgccga taatgattag   2820
ccagattgcg cccttacaaa ttaaagcatt atagtaacca aatctttttat ttgcctggta   2880 ctgtgttctg ttggtcaact ctatgataag atgattaccc acaccgtact atatatattg   2940
cctgatgctt tgtttccctt tagcccatta ctcgtatcgt atccttcctc tattcttgac   3000
atg                                                                 3003

<210> SEQ ID NO 47
<211> LENGTH: 3003
<212> TYPE: DNA
<213> ORGANISM: Zea mays

<400> SEQUENCE: 47
ccatatttgc aaaggtgtcc cgacagagtt ctcttgtctt gacatctaca aatccgacac     60
atactacatg gacaacgcac atccgtgccg gttcttgata tagcaaaagc acgatcaata    120
aaatcctctg tctttcttat ccaatccacc gagggatcat tcatacgcca accttcatac    180
atccatcgac ggtcctcacc caccatattt gatgctaaaa tagtaaaaca catcattcat    240
aaatttattc cgtatagagc aacaatttat tacgagcaac gagtcagaac gaattttagc    300
agcataaccc cgttgttctc tatttgcatg cccataaatg gtgtaataga gaacaacatg    360
gttatgtcac cgaaatctcg tttggacccg tcatcgtcat aaatccatag ctctatcatc    420
cactaacagg ctatccaaaa aagggacaat tccggactaa tacaagtcat atgtgtatta    480
gtagcacgca acaaataaga gactaacata attaaattat atgcaccacc tagcttatta    540
agttaattaa ccctattaac ataactttct acggtttaaa aacagttaac tctcggaagt    600
tagtatattt aatataaaaa actatagtac aaacactcgg aagttacctg tagcgatgcg    660
aagctcgatg gcgaagatgg tgctgcgtgg aggagaggcg gcgctcggcg cagggagcga    720
tgagccacac gggacgggta gcggccggcg cagtgagcag cgagccccga gcagggcggt    780
gttgccgcgg tggccggcga gaccgtgcga gcggccggca cggcggggcg cacggcgggg    840
gcagcggcct gtacggccgg ctgggcgggg caggcgggg cggggcggtg cagggtgggg    900
ccgggcacgg cggtgcaggg cggcggggca ggcagcggca gcgcggggcg gccgccgggg    960
aacggcgggc agcgccgggc ggccgccggg gaacggcggg cggcagcgcg gggcgagagg   1020
agcagcgagc aacgtcaatg gcgagaggag atgcgaggcg cctgttggga aaaacccga    1080 cggcgccgtt actttacaaa attagcttcc gagagctttg agtcagcccg tcggaagtta   1140
acagggcggg gcccggtccg tagccgtaag gaaccctacg cccggtccgc agtctaactt   1200
ccgagagccc ggtccgtagc cgtcggaagt taagggcctt ccgagagccc gtcggaagtt   1260
```

```
aaataaactg ccgagaggct acagttacaa ccgtcggaag ttgaataaac tgccgagagg    1320
caactagggc ttctaggaag ttattaactt cctacggttc tcgatagaaa ccgtaggaag    1380
ttataaagcc gtaggaagtt caaagttttg gtgtagtgga ttgcaacttc tatataacta    1440
tgtccaaaaa tctgttaaac aaacaatgat tgcaactgct gtctggtgta attgcaactg    1500
ctggtctggt gtgattgcaa cttctatata actatgtcca aaaatctgtt aaacaaaaca    1560
atgattgcaa ctgctgtctg gtgtaattgt aactgctggt ctggtgtgat tgcaacttct    1620
atataactat gtccaaaaat ctgttataca aacaatgat cgcaactgct ggtcttggtg    1680
cagactgaag ttgtcagggc cttcgcgttg gttcggcctg ggtggggcgg ttggctcgga    1740
cgaggtgctc ctggcgcgta ggttcggcct gggtgtattc tcaatattga atgcacccag    1800
gtgtaatata taaatacagt atatatatat atatatat atatatatac acacgaccga    1860
ttgtagtcac catcaattga accaatcaat cagtttatca attttcttta ctttctactc    1920
ttaggagtag ccaataacgt agtcttcttc gtcttgatct ttacttctct gtagctctac    1980
atcatctaga ggcattttag gtgtcctgtc gattacaaga caaactctag aatctcttct    2040
ctctaacggg gtctctcccg cgagtccgcc cggaggtgag atccaggtac cgttggtaaa    2100
tgccgccatc tctgctctac gcacacgtgg accgttcgac cagtccgacg tgaaccgtca    2160
gactctatac agggaacccg ctcctgctgt cagttcgcgc ggatcgtcca accacgccgc    2220
cgtagagagc ccatcgaacg aaacgtttcc ccagtgattg gcgtcgcgtc cagatcgacg    2280
cgtacgcgta tccaatgggc tagctagcta gctcgttttc cacggagata tagatttcgt    2340
gctacccgtc agcgatatga tgatgatcct cttaaagtgt cgtcagtttc agaaccatcg    2400
atgccgggcg ttaaattgca tctgattcgc gggagaccag gaaacggccc tgcttcctgg    2460
tctcttcttc accgcctgcc ttgctcgagc gcctttattt ccattcgtcg tcgtctcaaa    2520
caaaacagta gtacgtccaa tcggggacat taccttcctg ctaatccgtc tttgctttca    2580
aataaaaacg tccacctcgc tttgattagg aggattaacc tctctaaccc caccctgccc    2640
cgtgtcttct tcaatccaca cacgaaactg acttcgtcct ccatccggcc tctgccgttt    2700
tcgcttcgcc agatagttgt agtcgcccgc cacctgcgcc tataaagcaa cacggctgag    2760
cattcatacg ccggctactt gcttactact agtcaatcta ctgcgtcgtc gtcctctgtt    2820
ctcgacccct ccccgaccca cgcggccacg cccatcttca tttcctctc catcacgcgc     2880 ggtggtgcat gcgatctatg tatgtactag ggctaggcta ggcgagcttc tgggtgcacg    2940
taccgtacgt cgactcatct ccctctcttt ctctaccgtc gttgtactac gtactactcc    3000
atg                                                                 3003
```

<210> SEQ ID NO 48
<211> LENGTH: 1163
<212> TYPE: DNA
<213> ORGANISM: Zea mays

<400> SEQUENCE: 48

```
gcgaggcgac aggcacgctg tcgccgggcg acgcggccat cgcccgctcc cgctctcccg     60
ccctctcccc gtcccactct cgccccgta cgctcctctc gcccgtgctt cccgcctgca    120
ctggcaccag ccttatacta acttcttcgt acatgcccga atagctatgc agacgatcgc    180
acacgtttag gaaccacata aaactaccat gattctcccc tcaaacacct tcggagggga    240
gaagagtact ataatgtttt aatcatattg tccccttgt tgttctttct ataatttcga    300
```

| | |
|---|---|
| tgtaccttt tatactagcag aagacaatgt ttttttttcta tgggttatgt tatcagtcaa | 360 |
| tacccaaatg actaaacgtt tgcaaggctc aaggaaagtg caagcaacga gagatgcaaa | 420 |
| caactaatat aaggtagcaa ccacaacacc ggcccactac acaacgacaa ggaaatgaaa | 480 |
| ggggtggcaa gacaacgcat tcttgagcag aggccagagg tagtatagga gtatatgtgt | 540 |
| atattagtat cttgtacctt gtgctgccag aaaccggcac tcctgggcag tgcaatcacg | 600 |
| caaccgcatt atcacgcaca tcgaatgatc tgcggcgacc ccgctgcaat atttatcgat | 660 |
| cgtatagtac tagtagctac tagtgcgacc tgcattgcat taaaaatatt ctctctcgct | 720 |
| ctcggtcgcc agacgtagac gtagcacatg gagtctatct agcgtaatct cacctgggga | 780 |
| cctggattag ccagcaaatt aacccggcca tttgattaca taatactccg gcgatggctg | 840 |
| atgcccgccc ccgtgcgcg ctcaaggtc aatgccttcc gccctgccat ctccagcccg | 900 |
| ctaatcaaag aaatctcccc cccatggaga tccaccccac gagcgcccag ctcatcattg | 960 |
| tcgaccactt gcatatctct ctcctccact ccaactggtc tcgatccctc tatttatacc | 1020 |
| ccgcctcccg cacattcctt cttcaccaac tccggcggcc ggtgcagcag ctagcagtgg | 1080 |
| acgtacttat acgtctcccc ccagctagct ctaccttagg tagcatagtg gtgcggccgc | 1140 |
| gcttggttta aactagacac atg | 1163 |

<210> SEQ ID NO 49
<211> LENGTH: 3006
<212> TYPE: DNA
<213> ORGANISM: Zea mays

<400> SEQUENCE: 49

| | |
|---|---|
| aggcatgaaa agtagttaaa actactacta catcagacca atatattctg cttcacgggc | 60 |
| tggtggtttt aagcgaccta agtgtacaat ttattggtaa attttggctc catcaataca | 120 |
| gtactaataa ttttcccaac attttttttt tgacaaatgt gtaacaattt ctagtatata | 180 |
| tatgtttgga taactaaccg ctataattgt ggataactat tttgttgggg gttttatggg | 240 |
| aaaatgtaag tttatactca aagaaccgtt tgggcacact tgaggaggaa aataaaactc | 300 |
| acaaaaatat tggccactga taaaaacaac ttttattata aactatgttt accgtagaga | 360 |
| tgcaagcccg caaaattaat atcaagaggt gcacatgatg cacatattaa accgccatga | 420 |
| atatagagca gtatggtttt catgtgtata tctgctacta ttgtgcgtaa ttacaccata | 480 |
| tacatacatg tatctgttag aatctttggt gcttagcatc gattcctaag tccctataat | 540 |
| accaattcaa gtctaaaata tctcgatgat gagtagatct attctactga ggggtatagg | 600 |
| tatacatatc gttgttgttg ttcctagcca tcattgtggc ggcgtcttgc agcgaggacc | 660 |
| cgcctcctcc tccttatcga tctccctgcg ggtgtcgagg agattggttc ccatcgttga | 720 |
| tcggcggtgg ataagctcct ccaatattgc ctgcagggga atctcatatc ccgatagcat | 780 |
| gatagggatc tgagacatag tcacaacgat tctagtcact ccgagcgcct aggagatcgg | 840 |
| ttcctctcaa agtattgatt aaggttttgt ggtcgagcga ttagcgttag ctaaactcgt | 900 |
| cggcccctta atctattttt atggcgttgt gtgaccgtgg gatgcaacca acggttagga | 960 |
| tagcccccga tcagggcgcg gttagacggt taagattaat cctacccggt tactgttaac | 1020 |
| ctgctagtgt gtagatgaca catcctaaca gtatcgtcat aaatttagtg tgcttttctt | 1080 |
| agattaataa atctaaacat aaaaatatat aaatttctaa ccgttaaaca ttgcaaggga | 1140 |
| gccgtgttta accggcatcc aaactgtact gtgttccgta cgtttggcag aaagtaggtt | 1200 |
| acaagctgcg tgatgcccac tttcatcatc atcatacaaa atacatataa cgcacacacg | 1260 |

| | |
|---|---|
| cggtttgatg acaaaacacc gttccgttac tctgcctccg cctgttcatc cctggcaggc | 1320 |
| catatggtga gcagggcggc gcgcaacgca aaaggacccc ctgcagacca accgaatcag | 1380 |
| gacacagcgg ctgacgaaaa catgcatggc gccggccggt agctaatcca ccgccttgca | 1440 |
| ttatgcacgc cccggcccct cattagcacg gagccgagag taattagcgc cagtcaagag | 1500 |
| gattcgtgta atcggcactc cagacctgtc tcattggaaa ggtgtcacag tcacaggatg | 1560 |
| gagcaacacg cccggcccta agttttttcc ctctcatttt ccagagacag tgttgggtgt | 1620 |
| ccgatgtgga aagctcaaag ctgtgaggtg gtatgggaag agggcaaggc caagtccaac | 1680 |
| ccgttggatt ttgtgtcacg aaggtgccgc agctacgcga attgactgga cgatcttctg | 1740 |
| gattttgtgc aatatactaa aaagctagtt ttatataagt ttcattaaat ggacgtactg | 1800 |
| tcgaatagat atgttcaata tgataaagta atatttttaa aaggagggaa aaatagttc | 1860 |
| catcaacgat actatatatc tgaagtgtgt tttgttaatt agggtaaaaa aactagaggc | 1920 |
| gattgcttcc aaaggttagg gtcagaaaag agagagaagc tctctgctgg atggagaagg | 1980 |
| aaagtaactg gatattgcac ctaggaaatg agcacgcatc acaatcacag ccatgcatgc | 2040 |
| atggttggtt gaatgagtga tgggtaatgc tgccacagtc tcacagatag gaataggagt | 2100 |
| aatcctatag tgcacgcgtc aatcgttatt ttgcattttt ttgtgctacc ttattagctt | 2160 |
| gttcaaagta agagaaaaga acccacacat gctagataat ctggctaggg atcgaattta | 2220 |
| cataaacata tgtatagttg catacacgta cgtacgccgg ccgtacctaa ctgctccaga | 2280 |
| acgttctcct tcacatatat gtgcacgtca tgcatctttt cctctctttg gtcgatcgat | 2340 |
| ttgcatagta tatatatacg gttcgccttt tgcacgacac atgaatacat ggtattggaa | 2400 |
| gaaatggcgc aaattaaagt ggtacgtact gttgctccct gtccctgggg catttgagag | 2460 |
| cggatgaacg agaacgatgt gtgcgtttct actattctgc agcctgcccc tctgcacagg | 2520 |
| cgcgtccacg tggccgcgcc tcatcatcat gcatcccgct gacggctgaa ctgcctcctc | 2580 |
| cgctccgcag caagtgtcga agcgtgggct cgtgcgcgtg catccgcttg tcccttgccg | 2640 |
| gctcccccgc tcctcaaata ttctcgcccg cccggcctcc cctttcctcc atcctcatca | 2700 |
| accatttcat tccttcctga cttcctcctc ccgcacgcag cgcagcttgc aacccgcaac | 2760 |
| gaaccaaggc cgcgccgcgc gcgccctgcc ggccgtcaga gggaaaccca gctctaactg | 2820 |
| aagtgccggc tacatatact gctgtgctag ctagctagct agctactctt ctggtcctga | 2880 |
| gcgcacgtac gccatggctc aggaggacgt ccacctggac gatgccggcc tggcgctggg | 2940 |
| cctgtccctc ggcggcggcg gcggcggcgg agcctccgcc gcggcgcgcc acggtaccag | 3000 |
| cagatg | 3006 |

<210> SEQ ID NO 50
<211> LENGTH: 3003
<212> TYPE: DNA
<213> ORGANISM: Zea mays

<400> SEQUENCE: 50

| | |
|---|---|
| ccgtgcgttc aatatttttt gtctttgtca cattttttttt ctgcagttcc tagattatgt | 60 |
| gttgtgtctc tgtcgtcatg catgcttact catctgcact ggctggctgc agaaaccttta | 120 |
| attattagct tttttttttct ctggatgcat ggatcgacga cactgcaggg ctaacacaca | 180 |
| aatcatgcat atgcacagta cactgatgga tatgcatgga tcggatggag agtgatgcta | 240 |
| ctaactagtt gatggaatgg aagagctatc aaccgatcag tgatggtcta attttgcagc | 300 |

```
agtagttcat cagaattcat tcaattcaaa agggagggaa aaaggatgaa catctagctt    360
acaaataata cactagtatg tagctagcta gtgcaccaat tagtggagtc tgaggcggga    420
agcatcgaat taaaaagcac ggacaaatca gcggcataaa caaaaaaatc tggacaataa    480
aaaataaatc agtgacaaag acaaaaaata ttgaacgcac ggacaaatca gcggcataaa    540
caaaaaaatc tggacaataa aaaacaaatc agtgacaaag acaaaaaaat atgttcacag    600
tggggctcga acccacgacc ttaaggttaa aagccttgcg ctctgccaac tgagctagac    660
aagctttgtg gttatatatt cgagctcggc gccatagatc ttggcgccga gctcggtgcc    720
acgtcgacgc cgcttcagct cgtggacgac agcgcggcag gtagctcggc gccaagatct    780
atggcgccga gatgtgtaaa ctcggcgcca tagctcatgg cgccgagaaa tgggtccaaa    840
attgcattta agttttctgg gggtctaatt ggaaattttt gacacaaaaa ggactcaaaa    900
acaaaaaatt cggtcgtttt ccatggtgtt ttctttctgc cacatgcgac tgtcgtttcg    960
aactttagct cataaaacct acgtacggtt tgctcgtaa aacccgcacg tacagctgct    1020
atgtacttag gctagtcaca gtgatgattt catgtccctg ttttcaaaaa tgccacatca    1080
gctttatgga cgaatgaaac accatttctc aatagagagt ttcgtccac tatttcatat    1140
atcaacatat ttcttaaatg ctgcatataa ataaccaata gaatttactc aattatatga    1200
agatggaaca aaacactctc tgtagaggtt tcacacagtt tccaaaacat tggaaacgag    1260
tcaatatggt ttcatcccca taaaactcta tgaaactctt tcttcttaaa tgatgtgaca    1320
tatcatctaa atagctgatg tgtcaggcta attaatacat gaaacaactc atgaaacctt    1380
tattgtgatt agccttatac ccgaatttca ctactactag atataccttt tacagaaact    1440
acgaacggtt ttgctcggtt ggatctagga gctaaagcaa aatgatccat aaagtttagc    1500
tcccttttg gtatttttag tcacttttag ctcttatcgt ttagaacttt agctcgtaaa     1560
atggttaaat tttgaacact tttgctttat tagctcctgt gatctaggct tcgtttggtt    1620
tgggttgact aaagtttagt cacttttgt ccataaagag caaacatggt aactagaatg     1680
gggcgattaa actttagttc tttaggcacc aagaggtgac taaaagggac taagatatta    1740
tttttacctt atttgtcctc tccactttat ttcttatttc agtaagcatt cactaattaa    1800
gaggggtaac acaataatta ttcacaataa ttaatgctct ttagtccggt ttagtcactg    1860
gaaccaaact gagtaattta gcgagtaaat tagtgactaa acttcagtct agtgactaaa    1920
ggaaccaaac agggtcttag atgtccgctg atgaagcctc tagttaggac ccgtttggtt    1980
tggggtgact aaaatttagt caattttagt ccctaaaata ccaaacatgg tgactaaagt    2040
gggatgacta aatttaagtt ctttatagga gcgtaccac gttgggttga gtgggggcac     2100
gggcctccat tcaattttct ggttctagtg gaatttttat cttattcact gtagttataa    2160
aagtccatta ataagtagcc ttttatttag gcccttactc aggttttggg cccacactca    2220
aacttttggt tgagaccacc tctagttctt tagtcatcaa ggaggtgact aaatgaacta    2280
atgtaggatt tttacctcat ttgccctttt atctttctta gtgcaacagt catccactaa    2340
ttaataaggg taatatagtc attattcaca tcaattaata ttttttttatt ttttagttgg    2400
tgtagtcact gatggagtaa tttagtgact aaagtttatt caggtgacta aagtaaccaa    2460
aagggaccct aaacaggccc tgaaacatga agtagcccgg gattattaat cattcatcag    2520
tgatatgcat gcgacgatgg ccctcttaaa atgccgtcgg tttcaggaac cggccgggcg    2580
ggcggggca tcgagtggga gaccggaaaa cggcccctc gtggtcgtca gataaaaacg      2640
tccgagatcg atggctttaa ttgggggattc acctctcagt aaccccgtgt cttcttcaaa    2700
```

```
cccacacatg aaactgatct ctctgccgtt tccgaccgct tcgatcgcag gtagggagca    2760
agcgaggcag tcgtagtccc ccgcgcgccg ccaccaccac cgtctactac tagtctacta    2820
gtatactcgt gccttgacga ccccgccagg cgtcttctct tctcttctct cctatccgtc    2880
gtccatagct agcgatcgac cgacccatct tcctcttcat cgcgcgcccg gtggtgttgg    2940
gctaggctag ctactggtag ctaggtgcgg cgtgcagtag tgtctcagct cttgtgctcc    3000
atg                                                                  3003
```

<210> SEQ ID NO 51
<211> LENGTH: 3003
<212> TYPE: DNA
<213> ORGANISM: Zea mays

<400> SEQUENCE: 51

```
atctggtatc caaaggggtc aacctttgac ttgattgggt actcagactc cgattatgct      60
ggatgcaagg ttgataggaa gagtacatca gggacgtgcc aattcttagg aaggtccctg     120
gtgtcttgga gttctaagaa acaaacttct gttgccctat ccaccgctga ggccgagtat     180
gttgccgcag acagtgttg cgcgcaacta ctttggatga ggcaaaccct ccgggacttt     240
ggatacaatc tgagcaaagt cccactccta tgtgataatg agagtgaaat ccgcatggcg     300
gataatcctg ttgaacacag cccgcactaa gcacatagac atccggcatc acttttgag     360 agaccaccag caaaagggag atatcgaagt gttttatgtt agcaccgaga accagctagc     420
cgatatcttt accaagcctc tagatgagtc aacctttgt aggctgcata gtgagctaaa     480
tgtcttagat tcgcgtaact tggattgact tatagcatac atgtgtttta tgcatttgat     540
caagttcctt tatgcattta tgagatttgt tgtttaatgt atggtgctca agttgtacac     600
atgatccccg gacctcacaa gtccatgtgc aagtgatgca cttatttacg aggaggcatg     660
ccacaacttg acactttgag actaaccttg tgtttgagtt tacttgtttt agtctcaaaa     720
gtggattgaa agggaaatgt ggacttggac catgcaagat ttccactgca ctccgatgag     780
agggtaactt actccaagtt catctccatg ctcttttttgc cttttttactc ttaattgaag     840 attttggtga ggcaatgggg ttaaagggcc aataatgatc ccgttttggt gcttaatgcc     900 aaaggggag aaattaaggc caaagcaagc aatggatcag ctaccacttg agaattttga     960
aaatagtaga gttagagttt tggttttgtc aaaatactct tattgtctct tattgtcaaa    1020
agttggtctc ttgtgggaga atggttgatt atggaaaaag ggggaatttt tgaattcttg    1080
atcaatttct cttggaatac ctctctttat gtctcaacaa gtgggtttga cttagagata    1140
ggaaattgaa gttgatttgc aaaaacaaac caagtggtgg caaagaatga tcctaatatg    1200
ccaaatttga atcaaaaaca attcttcttc ttatttgcat tgatgttgca cttctatgtg    1260 ttgcttttg ttgtgttggc ataaatcacc aaaaggggg agattgaaag ggaaatgtgc    1320
ccttggccca tttctaaata ttttggtgat taagtgccaa cacaaatgtt taagtgttaa    1380
acagtgccaa atggtggatg aagtgcgaat caacacaaag gtatgattct agacttagta    1440
tattggtttt tgtgtactaa catatttgtc taagtgctag aatcagagaa aagacaaaaa    1500
gaaaatgact tggctaaagc agccaagact ctgctcagtc taggtgcacc ggactgtccg    1560
gtggtgcacc ggacagtgtc cggtgcgcca ggctggcttt ggtcaaactg gccactctcg    1620
ggatttcgtc ggcggtgtac ggctaaaaat caccggactg tccggtggtg caccggactg    1680
tccggtgagc caacggtcgg tcgagccaac agtcggccgc acaatccacg cgtgacgcgt    1740
```

```
ggccgggcca acggtcggat gggggcaccg gattgtccgg tgtgcaccgg acagtgtccg    1800
gtgcgccaac ggctctgaat cttcaacggt cggttgcacc tattttggaa ggcgatctgc    1860
accggacagt gaacagtgct tgtccggtgg tgcaccggac tgtccggtgt gccacccgac    1920
agaagacaag aatttccttc ctggattgct ttcaacggct cctagctgcc ttggggctat    1980
aaaagggacc cctaggcgca tggaggagga caccaagcat tcttgatcat tcacactctg    2040
tctttgcgca ctcgattggc attcttagtg atttgagctc cgttctagtg gtgaaccttg    2100
tgttattcat ttgagcttaa gtcttggatg tgtgtgtgag tattgctgtg gatttgtgtg    2160
tgttgcttac ctcccttact ctagttcttt cactttgatc cttattgtaa gggcgagaga    2220
ctccaagttg tggagatttc tcgcaaacgg gaaagagtaa agaaagaaga cacccctagt    2280
attcaagtgg atctttggat cacttgaaag gggttgagtg caaccctcgt ccattgggac    2340
gccacaacgt ggactaggca agtgttggac ttggccgaac cacgggataa accattgtgt    2400
ctatctgtgt tgatttcttt gtggttatca tgttttgcaa gaactcctct ctagccactt    2460
ggctttattg gtctaacact taatcaagtt tgtgacttta agtttcaagt ttttacagga    2520
tcatctattc acccccctct aggtgctctc aagccttcca tgtaaaaaaa ttaatacaat    2580
attttgcaat gaatatttgt gtggggatta ttttttgctta tacatgtgag aatgggaaaa    2640
agggtgttgg tcgtacacgt agaataatat gtacaattca attcctacct tttcattttt    2700
gtcaaccttt gcaagtgtga agtgcattat tgtgttttgg attgcctgtt tgggctcaag    2760
tggacatcct gctgtctgtt gccacccoct ctatatgtat gggtgtccat cctcctcatc    2820
tctctccccc tctcctcctc tagcttctcc ttctctctct ctccttcctg gaccattctc    2880
tctatctcct ttctctctct acacatactc agacgagcag aagcagctag ggacaccata    2940
ggcaaactac ttcagcaaga aattaaacta tctcctacgc aagatcagaa gaaactgtgt    3000
atg                                                                 3003

<210> SEQ ID NO 52
<211> LENGTH: 3003
<212> TYPE: DNA
<213> ORGANISM: Zea mays

<400> SEQUENCE: 52
acatattcta aagaatatat aagtatatat atatatatat cttatattat tgttagtgta      60
gcttttccct tcttctcttc taatagatca cctgcatttg agaaagagga gtgtagttta     120
agcaattact aaaatatgta ggtattattg atagaatgag taatgtgtta gagcaaccag     180
aatctcttgt atggtagtat aattttagta ttggagatga gacaagttgt ttgagatagt     240
ctaacaaccg gccaagagcc caagagttta gaaaaaacaa gtctatcact tacctaataa     300
tccttctatt cagataacta atactctctc cttttttat ttgccacatt ttagtttaaa     360
aatgaactag cggatcataa atattcgaaa accgagatac taacaaaatc aaaacagacc     420
ctacgccatt gattattacc cagtcgccac taaattattc tgaatgtcat tcatgttcct     480
acacctcgga ttcttggcgt ctcatgataa catagctaaa aaacgatttt atagaacatc     540
atttctttgg aatgttaaaa ttacctcaat aatgattgga ccatgccgca atcgagaaca     600
taacaaacag gacaaaatac tatatctgcg atccatggca aaaggtcgc ttcgtaaaaa      660 gtcaagaaaa catgaatttt actatatcta tattaatata tgtaatatca acatttagat     720 cttttaaacca gtctattata atatatctag cggtatttaa tacatactat aaatgttaat    780
gttttaaata ttttatcata aaaatatat tgttccattt ttttttgaga ctaggagcgt       840
```

```
acaaaattaa gttagaagtc ataaatgcat aagcgaaaga aagggttgtg cttgtatttc      900
ccctaaaaca caattgcacc gtgtcactga ttgtcgtgtt ttagttcaaa aaataaacta      960
gcgaacagac aaatactcga gaacgaagga agtacatttt taagtttaaa atctgtcctg     1020
aaataagaac acttcaagct ttgagacaat tcaattttag taatcctttc ctaatttctc     1080
tcttcccaaa gtgcaatagt tatatttgta tagaggcaca tatctaattt ctcattaatg     1140
ctaacctctt tttgccaaga ttctagtttt aggaatagac ggagtacttt tcaaagtcgc     1200
gggaaacaaa aaatgtgtta ctttccgagg agaaaggaac ccgacccggc cccgggtacg     1260
gtgctgtccg cgtacaaaca ggaatgattg catcctgatg tgcgcctcca atgcaagcat     1320
ccattccatt gcagccatca cgcgtcacca ttcacccaac cgcaggccat ccatgatggc     1380
aggcaggcag gagcgacgag caagcggtca gggtcaggcg ctccgctcgg ctcggcggcc     1440
tgctcgcccc ctcggccaca ccacacgctg cacgcgccgg ctgcccccgg ccggccgtat     1500
gccgccatca tgcggcatga ttgcggcgag agaacggccc atcgccttgt ccccattgta     1560
cacatcgaca ggattgcttc atatcacgca ggtaggcatg cagctagctg gctctcacca     1620
tacatgatga ggatggatga ggaattgatg gccgtaatca tgcctgcgtt cacaagacaa     1680
ttctcgccta tccttctagc tagcccagtg cttgctctca gtacactact agcgcatggg     1740
ggggcatggg cattgcattg cccctcgctc tcagtcaagc ctagctagct tgttcattcc     1800
atgcaattat actaggatct gccaactatc atgagcttcc atgcaggccg atcgagagag     1860
aaatactcct gcgacttgct acgagatagg aacaaaaatg aaggacataa aagttctgtt     1920
ctatatttct atacgtacgt tctagcacat cacacttgat cattccacat ttccacttgt     1980
ccagaaagct ttttctgccc ggcaaatcga tccggagtat acatgaaatg catcattaac     2040
ttttacgtaa atggactttt taactataca tgcacgcatc gtctgctgcc tactagtcct     2100
tcagtcctcc taaaaattac tccctacgtc ccaaaacaga attcattta tattaaatat     2160
acactcatta attaacatat acatgtagtt actacatgta tgtctatatt tgttatcatc     2220
tattttgagg ttgacgaaaa aagagagaac tagaaataac tatatttttt aagacggatc     2280
aagaataatt ctaacttatc cctaagtcaa tcaattttaa atctactaaa ttcacaaaaa     2340
aaatgctata agtatatatg ataaaaataa gtatcactac attttacaaa atatttttca     2400
tagcatatgt gtatatgttg ttataagtga catgttcttc actccccgat atatatactc     2460
caccagttgc aaacaaataa tacaagtata caacaattcc attacgcact gcacgacccc     2520
gggctgtaaa ctacatacat acacgcctac gctacgaccc gcaaaagaaa ggaaccaaaa     2580
aaaaagcaga cagcagcaac agtagcttct gcatgggcag ctttcgtgta aagattgcgg     2640
gtgccattta caaaggggga aagatacgta cccagtgata caataatgat taagctcatt     2700
attacctccc tcctgccaat gccaccccag ctctttactc attttataaa acacccctg      2760
agaagactcc caactgcgtc cagctccccc cacccagctc tccttttccg ggtcacgtgc     2820
ggaagcgtca actggtcaaa cccaccatta tcactcaggc ggaaacgcgc cggagggagg     2880
gagagaggag gggcgtgggt ggctgggccg agcgactcct ccttccagtc caccgctata     2940
aagccccgca ggcctggcga gtcccgacgg ttccattact ggtccctagc aggaagcagg     3000
atg                                                                  3003
```

<210> SEQ ID NO 53
<211> LENGTH: 3003
<212> TYPE: DNA

<213> ORGANISM: Zea mays

<400> SEQUENCE: 53

```
acacagttat gtcgttccac cattaattag acgagtatgt tttaaggatt ctgctacata      60
tcttattata tatgacgcat ttctcggagg aatctgtata gttccccacc tcacaagagc     120
tagacctgtg cttcgtcttt gctaactttc agtgaactca tataaataaa tccaccagag     180
ggtttagagt tagttaggtc cattgattt  atgcatgccc catggctata tcaagtgtgt     240
tcttgtccat gaggtgagga cgcagagtag agatggcaat aggtgggtgt gcatggtgat     300
ttcagatctg ttgtaatggt cccactgtgc gcaaaacagc ttgttgttgt tgttgttgca     360
atgtctactt cagtccttaa ggctaaaaac aggacctcaa actagccatt tgagagctaa     420
tgaatcttat aaatattaca agtgagttgg tacccattca tgatagctct agagacactt     480
aaatgctcaa aaatcactca atgattagcg tagatacttt gtgagtgctt agattaatta     540
gactacttcc attagcgctt gctctaagtt taggccggtg attagaaatg aggtatagac     600
gcctcttatt ccttggtgtt tgcgcgcacc gttgtattgg ttgtactgag aggagttgta     660
agttttacac gatcacagaa ctacatttgt ggtgcggtcg ccatcatata ctaaagggaa     720
ggagacccat aacattttag ccgaaaactc gatatttagt acagcaaata gtatctaggg     780
gaggccacaa cacaaaccga cttgcaagtg gttaaggacc agggctatcc atagacttac     840
ccgacctgag cttggccctc gtgtgtgggg aaccaacgag gactagagga aaacacttca     900
atatatctca gtaaaattat cgaagtcgtc aactagagtt tgtatctcta ttacacttaa     960
gctttcgtaa tttatattat gtactttggt cgtgtgttgt acctattagc tgctaatatt    1020
atctgatttg gtcttacggt ccaactagtg aggtgcaata cgcgttatct aagaattcaa    1080
gtaataatta gctagtctat tatctaaaaa tgtttggata aaaagataaa ccattaacat    1140
aacctgtaca aatccaaacg gggggccttg ataactccca aacacacatg cacgggtcat    1200
gcatgtaggt gagaagcaat accgagtagt atgagtactg tgtacgcaac tcgtatgagc    1260
cgctagctcc aagcaagtat aaatgtggat cgagtagatg aagacaagc gcgttgccat     1320
gtcaaaagga tggatggatg ggcggcaggc acgcaatgat gggatgatga taggtgagga    1380
ggtgagataa gcgccggcgg ggcccccgtg tgggggctag ccggcaaggt gcgtgccggc    1440
gcaaagcggg acacgatgat ttggggcatg gtggggaaag ggcatgcgcc ccggcccgcc    1500
cgcgctcgct ctcgcaccgc atgaatgggc acttgaactc gcctcgtatc gtcgtcctgt    1560
ggaggctagt gctagctgct gccatgccct accgcctacc gtaccaatgg gagcacgccc    1620
tctgcaacca tgtcgcccgt cgtccatcct cgaaccggcc ggtccggggc agccttatta    1680
gcgttttggt tggtaccaac tcgaaaagcc aatcattcct tcatgcactg ctcctacgtg    1740
ctgcgatcat tgcatgctat gcatggtagt attataacca gagcatgcag tagttctggt    1800
ggtcttagcg cgcgggccca aagctagaaa caaattaatt caatttgtag ccaagtgcta    1860
gctagctgct agtagctaat tcatatgtca tgaaatgtgc actgacatat acatcccagg    1920
ttagctagcc agctacaaac gtccgtattt gtccactgca ctgcatgcaa aagtagcact    1980
tcgatcaaaa gtacagtttt ttttaaaaaa atttgacagc gactccaatt tctgccgcac    2040
aattccaaag gagggcctag gagcctagct agctagctgt cgaaataatg cagaataaag    2100
gtaagtatta ggcggacaca cgttcttaaa tatacatctc ttcctatagt agatatatag    2160
tattacatgg agtacttagc atatctaaaa tcgatctaag catttcgaac cagacaagtg    2220
gtcaaaaatc tgcaacttt  agagaacgta tgtagtacta ttttatatta ctctgcagtg    2280
```

```
catatgcggc gaaattaatc tattttgcac cacgctgggc agcatatata tatagtatgc   2340
ccaggaacca tgcatataca gatcaagata aaaggcatac cacacccggt cacccgctat   2400
actatagttt ttttttatat atgcattatt ccagtggtca ggtgcatgga ttacaaaaac   2460
actatatagc aaccactagg tcgtcaacca agggggaaata tcatggtcgc cttagctttt   2520
ggtggaaaag aaaaaaaaaa gtcctaaatc tgggtgggga atagctgaag ttagctaggc   2580
cagcaatttt gagcggagag gctgcctttta ggcgggggag ggaggtgggg aagttatgat   2640
tgcaccaatt aaggagcccg cccccacaag ttaatgattg ctgtcccaga aactacgtac   2700
gtatgtgtga agtgagatcc aacattcctc ccgcccctgc tcccaccatg tctttaaaac   2760
cctcgctctc cccccccac ttcttttatc accttcatcg tctatcagcc agctccattc   2820
tatctactgc tactctcagt actatatatc tatccgcagt tccatagttc ttccagctgc   2880
tctacacata cacatacacg ctagctctag ctctcacatc gattgagatc atcagagagg   2940
tggaagaaga agaagctaag ataccagatc gaggaagaga ggcggtgcgg tggttggtag   3000
atg                                                                3003

<210> SEQ ID NO 54
<211> LENGTH: 1808
<212> TYPE: DNA
<213> ORGANISM: Zea mays

<400> SEQUENCE: 54
acgccagtgc acactgattc ttctaattat tgtaacgtca gtggaggctt catgggcagg     60
atgatcctgt aagttatgac ataggcgtag ctagcgggtg tatatgtaca gttcaactgt    120
aatgctgaca gggcaagatt tattcgacgg aattgcccct ttatagcatt tgccattgtt    180
agattcattt ctaatccaat aaactaacac gacgccaagt ttgttgtaaa ctggtgccta    240
gctgtatcga tgccttccgc aatttgagat ttatatatta cacaaaaaaa aactatttca    300
gaaaatccat ttatgtaagt tcatgaatag gatgatactg ggtgacattt tcactcgttt    360 ttctgttttgg tactggtatg tgatactaac aagagctgat gatttgttag aacataaaag    420
gcagttaatc caagacatgt gaggacgttt aaggtttggg gttaactcag cgacttcact    480
cttatgtcta atccaataca tcaagccgat gattctcaca cctaccacac aaaacaatca    540
caaaccaact gcagcaacag aacttagaag atcctggtta cctaggaagg ttttcgacaa    600
accaactcca gttacatgaa aaccttctta gactaaatta ttgtacaaca aaacgtcaga    660
ttagcctttc tagctatgct gccgacgcgt taagtaccac tggtgaggat atgatagagt    720
gtggcggcct cccgaagccg ccgcaggttg gtcgagtcaa ttggaattgt gcccagttga    780
tagttttagt tgatccaatt ctcatgtcta cagaacattc gactagcaaa agacccagtg    840
atctatcaaa atatttaatt gttttactaa gtcatatgat caataacact tacaaataca    900
tctggatgtg aataatttgt aggtatcatt ggaattcaat cttcagtttg acaaataacg    960
gcttagtagc accagaaaaa gagggggtta tgattccaca gtctgtgtag tgtgctggtt   1020
cagggacatg gaaccaccat gcggttgctc tggacagttt gaagactaaa tatctccagt   1080
catgtatata ataatcttac agtcactgag aggaatcacc acatggattt tacatatcat   1140
agtgatattt gtcgttccgt ttatatattt catacaaatt ttttacttcc gtcgcaacgc   1200
acgggcactc agcattgtat tcacgccgcc cgttgccagg gctctaagtc cattggaggc   1260
tcgcaattta tgtttcgtgg catcgcacgg gcacctacct agttagagaa ataagtgaca   1320
```

```
tgcttccttc atatttaaat aaattaaata ttctagttaa tcaatataaa gatcttaaag     1380
ataaattcaa tgaacgctac aataaatact ggtgcatgga cgacggtgtc accgaaaaca     1440
gcctgcttgc ggtttactct tccgtttaca tttaaactct cctgtgcagc aagtgtcaaa     1500
gcgtgggctc gcgtacgtac gtgcacgtga tgtgcgcgtg catccgcgcg cttgtccgtt     1560
gccggctccg ctcctcctca aatattctcg cctgccctcc tcatttcctc ctcaaccatt     1620
tcattccttc cttccttccc ctcgctcgcc ttcctggctt cttcctcccc agcacgcaca     1680
cgcacacgca cacacccagc cttttggctg ccctgccggc cgtcagagag agaaaccgag     1740
ctctaactaa ctgaagtggc ggccacatag ctagctactc ttctgatcct gagcgcgcac     1800
gcgccatg                                                             1808

<210> SEQ ID NO 55
<211> LENGTH: 9
<212> TYPE: DNA
<213> ORGANISM: artificial
<220> FEATURE:
<223> OTHER INFORMATION: consensus

<400> SEQUENCE: 55 caatsattg                                                               9

<210> SEQ ID NO 56
<211> LENGTH: 9
<212> TYPE: DNA
<213> ORGANISM: artificial
<220> FEATURE:
<223> OTHER INFORMATION: consensus

<400> SEQUENCE: 56 caatwattg                                                               9

<210> SEQ ID NO 57
<211> LENGTH: 828
<212> TYPE: DNA
<213> ORGANISM: Arabidopsis thaliana

<400> SEQUENCE: 57
atgataaaac tactatttac gtacatatgc acatacacat ataaactata tgctctatat       60
catatggatt acgcatgcgt gtgtatgtat aaatataaag gcatcgtcac gcttcaagtt      120
tgtctctttt atattaaact gagagttttc ctctcaaact ttacctttc ttcttcgatc       180 ctagctctta agaaccctaa taattcattg atcaaaataa tggcgatttt gccggaaaac      240
tcttcaaact tggatcttac tatctccgtt ccaggcttct cttcatcccc tctctccgat      300
gaaggaagtg gcggaggaag agaccagcta aggctagaca tgaatcggtt accgtcgtct      360
gaagacggag acgatgaaga attcagtcac gatgatggct ctgctcctcc gcgaaagaaa      420
ctccgtctaa ccagagaaca gtcacgtctt cttgaagata gtttcagaca gaatcatacc      480
cttaatccca aacaaaagga agtacttgcc aagcatttga tgctacggcc aagacaaatt      540
gaagtttggt ttcaaaaccg tagagcaagg agcaaattga agcaaaccga gatggaatgc      600
gagtatctca aaaggtggtt tggttcatta acggaagaaa accacaggct ccatagagaa      660
gtagaagagc ttagagccat aaaggttggc ccaacaacgg tgaactctgc ctcgagcctt      720
actatgtgtc ctcgctgcga gcgagttacc cctgccgcga gcccttcgag ggcggtggtg      780
ccggttccgg ctaagaaaac gtttccgccg caagagcgtg atcgttga                   828
```

<210> SEQ ID NO 58
<211> LENGTH: 275
<212> TYPE: PRT
<213> ORGANISM: Arabidopsis thaliana

<400> SEQUENCE: 58

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
        115                 120                 125

Ser His Asp Asp Gly Ser Ala Pro Pro Arg Lys Lys Leu Arg Leu Thr
    130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275

<210> SEQ ID NO 59
<211> LENGTH: 162
<212> TYPE: PRT
<213> ORGANISM: Arabidopsis thaliana

<400> SEQUENCE: 59

Met Asn Arg Leu Pro Ser Ser Glu Asp Gly Asp Glu Glu Phe Ser
1               5                   10                  15

His Asp Asp Gly Ser Ala Pro Pro Arg Lys Lys Leu Arg Leu Thr Arg
            20                  25                  30

Glu Gln Ser Arg Leu Leu Glu Asp Ser Phe Arg Gln Asn His Thr Leu
        35                  40                  45

Asn Pro Lys Gln Lys Glu Val Leu Ala Lys His Leu Met Leu Arg Pro

```
            50                  55                  60
Arg Gln Ile Glu Val Trp Phe Gln Asn Arg Arg Ala Arg Ser Lys Leu
 65                  70                  75                  80

Lys Gln Thr Glu Met Glu Cys Glu Tyr Leu Lys Arg Trp Phe Gly Ser
                 85                  90                  95

Leu Thr Glu Glu Asn His Arg Leu His Arg Glu Val Glu Glu Leu Arg
                100                 105                 110

Ala Ile Lys Val Gly Pro Thr Thr Val Asn Ser Ala Ser Ser Leu Thr
                115                 120                 125

Met Cys Pro Arg Cys Glu Arg Val Thr Pro Ala Ala Ser Pro Ser Arg
                130                 135                 140

Ala Val Val Pro Val Pro Ala Lys Lys Thr Phe Pro Pro Gln Glu Arg
145                 150                 155                 160

Asp Arg

<210> SEQ ID NO 60
<211> LENGTH: 162
<212> TYPE: PRT
<213> ORGANISM: Arabidopsis thaliana

<400> SEQUENCE: 60

Met Asn Arg Leu Pro Ser Ser Glu Asp Gly Asp Glu Glu Phe Ser
 1               5                  10                  15

His Asp Asp Gly Ser Ala Pro Pro Arg Lys Lys Leu Arg Leu Thr Arg
                 20                  25                  30

Glu Gln Ser Arg Leu Leu Glu Asp Ser Phe Arg Gln Asn His Thr Leu
                 35                  40                  45

Asn Pro Lys Gln Lys Glu Val Leu Ala Lys His Leu Met Leu Arg Pro
 50                  55                  60

Arg Gln Ile Glu Ala Trp Phe Ala Ala Arg Arg Ala Arg Ser Lys Leu
 65                  70                  75                  80

Lys Gln Thr Glu Met Glu Cys Glu Tyr Leu Lys Arg Trp Phe Gly Ser
                 85                  90                  95

Leu Thr Glu Glu Asn His Arg Leu His Arg Glu Val Glu Glu Leu Arg
                100                 105                 110

Ala Ile Lys Val Gly Pro Thr Thr Val Asn Ser Ala Ser Ser Leu Thr
                115                 120                 125

Met Cys Pro Arg Cys Glu Arg Val Thr Pro Ala Ala Ser Pro Ser Arg
                130                 135                 140

Ala Val Val Pro Val Pro Ala Lys Lys Thr Phe Pro Pro Gln Glu Arg
145                 150                 155                 160

Asp Arg

<210> SEQ ID NO 61
<211> LENGTH: 104
<212> TYPE: PRT
<213> ORGANISM: Arabidopsis thaliana

<400> SEQUENCE: 61

Met Asn Arg Leu Pro Ser Ser Glu Asp Gly Asp Glu Glu Phe Ser
 1               5                  10                  15

His Asp Asp Gly Ser Ala Pro Pro Thr Glu Met Glu Cys Glu Tyr Leu
                 20                  25                  30

Lys Arg Trp Phe Gly Ser Leu Thr Glu Glu Asn His Arg Leu His Arg
                 35                  40                  45
```

```
Glu Val Glu Glu Leu Arg Ala Ile Lys Val Gly Pro Thr Thr Val Asn
 50                  55                  60
Ser Ala Ser Ser Leu Thr Met Cys Pro Arg Cys Glu Arg Val Thr Pro
 65                  70                  75                  80
Ala Ala Ser Pro Ser Arg Ala Val Val Pro Val Pro Ala Lys Lys Thr
                 85                  90                  95
Phe Pro Pro Gln Glu Arg Asp Arg
                100
```

<210> SEQ ID NO 62
<211> LENGTH: 162
<212> TYPE: PRT
<213> ORGANISM: Arabidopsis thaliana

<400> SEQUENCE: 62

```
Met Asn Arg Leu Pro Ser Ser Glu Asp Gly Asp Glu Glu Phe Ser
 1                   5                  10                  15
His Asp Asp Gly Ser Ala Pro Pro Arg Lys Lys Leu Arg Leu Thr Arg
                 20                  25                  30
Glu Gln Ser Arg Leu Leu Glu Asp Ser Phe Arg Gln Asn His Thr Leu
                 35                  40                  45
Asn Pro Lys Gln Lys Glu Val Leu Ala Lys His Leu Met Leu Arg Pro
 50                  55                  60
Arg Gln Ile Glu Val Phe Phe Gln Asn Arg Arg Ala Arg Ser Lys Leu
 65                  70                  75                  80
Lys Gln Thr Glu Met Glu Cys Glu Tyr Leu Lys Arg Trp Phe Gly Ser
                 85                  90                  95
Leu Thr Glu Glu Asn His Arg Leu His Arg Glu Val Glu Glu Leu Arg
                100                 105                 110
Ala Ile Lys Val Gly Pro Thr Thr Val Asn Ser Ala Ser Ser Leu Thr
                115                 120                 125
Met Cys Pro Arg Cys Glu Arg Val Thr Pro Ala Ala Ser Pro Ser Arg
130                 135                 140
Ala Val Val Pro Val Pro Ala Lys Lys Thr Phe Pro Pro Gln Glu Arg
145                 150                 155                 160
Asp Arg
```

<210> SEQ ID NO 63
<211> LENGTH: 162
<212> TYPE: PRT
<213> ORGANISM: Arabidopsis thaliana

<400> SEQUENCE: 63

```
Met Asn Arg Leu Pro Ser Ser Glu Asp Gly Asp Glu Glu Phe Ser
 1                   5                  10                  15
His Asp Asp Gly Ser Ala Pro Pro Arg Lys Lys Leu Arg Leu Thr Arg
                 20                  25                  30
Glu Gln Ser Arg Leu Leu Glu Asp Ser Phe Arg Gln Asn His Thr Leu
                 35                  40                  45
Asn Pro Lys Gln Lys Glu Val Leu Ala Lys His Leu Met Leu Arg Pro
 50                  55                  60
Arg Gln Ile Glu Val Phe Phe Gln Asn Arg Arg Ala Arg Ser Lys Leu
 65                  70                  75                  80
Lys Gln Thr Glu Met Glu Cys Glu Tyr Leu Lys Arg Trp Phe Gly Ser
                 85                  90                  95
Leu Thr Glu Glu Asn His Arg Leu His Arg Glu Val Glu Glu Leu Arg
```

```
            100                 105                 110
Ala Ile Lys Val Gly Pro Thr Thr Val Asn Ser Ala Ser Ser Leu Thr
        115                 120                 125

Met Cys Pro Arg Cys Glu Arg Val Thr Pro Ala Ala Ser Pro Ser Arg
130                 135                 140

Ala Val Val Pro Val Pro Ala Lys Lys Thr Phe Pro Pro Gln Glu Arg
145                 150                 155                 160

Asp Arg

<210> SEQ ID NO 64
<211> LENGTH: 131
<212> TYPE: PRT
<213> ORGANISM: Arabidopsis thaliana

<400> SEQUENCE: 64

Met Asn Arg Leu Pro Ser Ser Glu Asp Gly Asp Glu Glu Phe Ser
1               5                   10                  15

His Asp Asp Gly Ser Ala Pro Pro Arg Lys Lys Leu Arg Leu Thr Arg
                20                  25                  30

Glu Gln Ser Arg Leu Leu Glu Asp Ser Phe Arg Gln Asn His Thr Leu
            35                  40                  45

Asn Pro Lys Gln Lys Glu Val Leu Ala Lys His Leu Met Leu Arg Pro
50                  55                  60

Arg Gln Ile Glu Val Trp Phe Gln Asn Arg Arg Ala Arg Ser Lys Leu
65                  70                  75                  80

Arg Ala Ile Lys Val Gly Pro Thr Thr Val Asn Ser Ala Ser Ser Leu
                85                  90                  95

Thr Met Cys Pro Arg Cys Glu Arg Val Thr Pro Ala Ala Ser Pro Ser
            100                 105                 110

Arg Ala Val Val Pro Val Pro Ala Lys Lys Thr Phe Pro Pro Gln Glu
        115                 120                 125

Arg Asp Arg
    130

<210> SEQ ID NO 65
<211> LENGTH: 162
<212> TYPE: PRT
<213> ORGANISM: Arabidopsis thaliana

<400> SEQUENCE: 65

Met Asn Arg Leu Pro Ser Ser Glu Asp Gly Asp Glu Glu Phe Ser
1               5                   10                  15

His Asp Asp Gly Ser Ala Pro Pro Arg Lys Lys Leu Arg Leu Thr Arg
                20                  25                  30

Glu Gln Ser Arg Leu Leu Glu Asp Ser Phe Arg Gln Asn His Thr Leu
            35                  40                  45

Asn Pro Lys Gln Lys Glu Val Leu Ala Lys His Leu Met Leu Arg Pro
50                  55                  60

Arg Gln Ile Glu Val Trp Phe Gln Asn Arg Arg Ala Arg Ser Lys Leu
65                  70                  75                  80

Lys Gln Ala Glu Met Glu Cys Glu Tyr Ala Lys Arg Trp Phe Gly Ser
                85                  90                  95

Ala Thr Glu Glu Asn His Arg Ala His Arg Glu Val Glu Glu Ala Arg
            100                 105                 110

Ala Ile Lys Val Gly Pro Thr Thr Val Asn Ser Ala Ser Ser Leu Thr
        115                 120                 125
```

```
Met Cys Pro Arg Cys Glu Arg Val Thr Pro Ala Ala Ser Pro Ser Arg
    130                 135                 140

Ala Val Val Pro Val Pro Ala Lys Lys Thr Phe Pro Pro Gln Glu Arg
145                 150                 155                 160

Asp Arg

<210> SEQ ID NO 66
<211> LENGTH: 162
<212> TYPE: PRT
<213> ORGANISM: Arabidopsis thaliana

<400> SEQUENCE: 66

Met Asn Arg Leu Pro Ser Ser Glu Asp Gly Asp Glu Glu Phe Ser
1               5                   10                  15

His Asp Asp Gly Ser Ala Pro Pro Arg Lys Lys Leu Arg Leu Thr Arg
                20                  25                  30

Glu Gln Ser Arg Leu Leu Glu Asp Ser Phe Arg Gln Asn His Thr Leu
            35                  40                  45

Asn Pro Lys Gln Lys Glu Val Leu Ala Lys His Leu Met Leu Arg Pro
    50                  55                  60

Arg Gln Ile Glu Val Trp Phe Gln Asn Arg Arg Ala Arg Ser Lys Leu
65                  70                  75                  80

Lys Gln Thr Glu Met Glu Ala Glu Tyr Leu Lys Arg Trp Phe Gly Ser
                85                  90                  95

Leu Thr Glu Glu Asn His Arg Leu His Arg Glu Val Glu Glu Leu Arg
            100                 105                 110

Ala Ile Lys Val Gly Pro Thr Thr Val Asn Ser Ala Ser Ser Leu Thr
        115                 120                 125

Met Ser Pro Arg Ser Glu Arg Val Thr Pro Ala Ala Ser Pro Ser Arg
    130                 135                 140

Ala Val Val Pro Val Pro Ala Lys Lys Thr Phe Pro Pro Gln Glu Arg
145                 150                 155                 160

Asp Arg

<210> SEQ ID NO 67
<211> LENGTH: 162
<212> TYPE: PRT
<213> ORGANISM: Arabidopsis thaliana

<400> SEQUENCE: 67

Met Asn Arg Leu Pro Ser Ser Glu Asp Gly Asp Glu Glu Phe Ser
1               5                   10                  15

His Asp Asp Gly Ser Ala Pro Pro Arg Lys Lys Leu Arg Leu Thr Arg
                20                  25                  30

Glu Gln Ser Arg Leu Leu Glu Asp Ser Phe Arg Gln Asn His Thr Leu
            35                  40                  45

Asn Pro Lys Gln Lys Glu Val Leu Ala Lys His Leu Met Leu Arg Pro
    50                  55                  60

Arg Gln Ile Glu Val Trp Phe Gln Asn Arg Arg Ala Arg Ser Lys Leu
65                  70                  75                  80

Lys Gln Thr Glu Met Glu Cys Glu Tyr Leu Lys Arg Trp Phe Gly Ser
                85                  90                  95

Leu Thr Glu Glu Asn His Arg Leu His Arg Glu Val Glu Glu Leu Arg
            100                 105                 110

Ala Ile Lys Val Gly Pro Thr Thr Val Asn Ser Ala Ser Ser Leu Thr
```

```
              115                 120                 125
Met Ser Pro Arg Ser Glu Arg Val Thr Pro Ala Ala Ser Pro Ser Arg
    130                 135                 140

Ala Val Val Pro Val Pro Ala Lys Lys Thr Phe Pro Pro Gln Glu Arg
145                 150                 155                 160

Asp Arg

<210> SEQ ID NO 68
<211> LENGTH: 162
<212> TYPE: PRT
<213> ORGANISM: Arabidopsis thaliana

<400> SEQUENCE: 68

Met Asn Arg Leu Pro Ser Ser Glu Asp Gly Asp Glu Glu Phe Ser
1               5                   10                  15

His Asp Asp Gly Ser Ala Pro Pro Arg Lys Lys Leu Arg Leu Thr Arg
                20                  25                  30

Glu Gln Ser Arg Leu Leu Glu Asp Ser Phe Arg Gln Asn His Thr Leu
            35                  40                  45

Asn Pro Lys Gln Lys Glu Val Leu Ala Lys His Leu Met Leu Arg Pro
    50                  55                  60

Arg Gln Ile Glu Val Trp Phe Gln Asn Arg Arg Ala Arg Ser Lys Leu
65                  70                  75                  80

Lys Gln Thr Glu Met Glu Cys Glu Tyr Leu Lys Arg Trp Phe Gly Ser
                85                  90                  95

Leu Thr Glu Glu Asn His Arg Leu His Arg Glu Val Glu Glu Leu Arg
            100                 105                 110

Ala Ile Lys Val Gly Pro Thr Thr Val Asn Ser Ala Ser Ser Leu Thr
    115                 120                 125

Met Cys Pro Arg Ser Glu Arg Val Thr Pro Ala Ala Ser Pro Ser Arg
    130                 135                 140

Ala Val Val Pro Val Pro Ala Lys Lys Thr Phe Pro Pro Gln Glu Arg
145                 150                 155                 160

Asp Arg

<210> SEQ ID NO 69
<211> LENGTH: 162
<212> TYPE: PRT
<213> ORGANISM: Arabidopsis thaliana

<400> SEQUENCE: 69

Met Asn Arg Leu Pro Ser Ser Glu Asp Gly Asp Glu Glu Phe Ser
1               5                   10                  15

His Asp Asp Gly Ser Ala Pro Pro Arg Lys Lys Leu Arg Leu Thr Arg
                20                  25                  30

Glu Gln Ser Arg Leu Leu Glu Asp Ser Phe Arg Gln Asn His Thr Leu
            35                  40                  45

Asn Pro Lys Gln Lys Glu Val Leu Ala Lys His Leu Met Leu Arg Pro
    50                  55                  60

Arg Gln Ile Glu Val Trp Phe Gln Asn Arg Arg Ala Arg Ser Lys Leu
65                  70                  75                  80

Lys Gln Thr Glu Met Glu Cys Glu Tyr Leu Lys Arg Trp Phe Gly Ser
                85                  90                  95

Leu Thr Glu Glu Asn His Arg Leu His Arg Glu Val Glu Glu Leu Arg
            100                 105                 110
```

```
Ala Ile Lys Val Gly Pro Thr Thr Val Asn Ser Ala Ser Ser Leu Thr
            115                 120                 125

Met Ser Pro Arg Cys Glu Arg Val Thr Pro Ala Ala Ser Pro Ser Arg
    130                 135                 140

Ala Val Val Pro Val Pro Ala Lys Lys Thr Phe Pro Pro Gln Glu Arg
145                 150                 155                 160

Asp Arg

<210> SEQ ID NO 70
<211> LENGTH: 275
<212> TYPE: PRT
<213> ORGANISM: Arabidopsis thaliana

<400> SEQUENCE: 70

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
            115                 120                 125

Ser His Asp Asp Gly Ser Ala Pro Pro Arg Lys Lys Leu Arg Leu Thr
        130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Ser Pro Arg Ser Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275

<210> SEQ ID NO 71
<211> LENGTH: 275
<212> TYPE: PRT
<213> ORGANISM: Arabidopsis thaliana
```

<400> SEQUENCE: 71

```
Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
            115                 120                 125

Ser His Asp Asp Gly Ser Ala Pro Pro Arg Lys Lys Leu Arg Leu Thr
130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Lys Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275
```

<210> SEQ ID NO 72
<211> LENGTH: 217
<212> TYPE: PRT
<213> ORGANISM: Arabidopsis thaliana

<400> SEQUENCE: 72

```
Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80
```

-continued

```
Ser Ser Asn Leu Asp Leu Thr Ile Ser Val Pro Gly Phe Ser Ser Ser
                85                  90                  95

Pro Leu Ser Asp Glu Gly Ser Gly Gly Gly Arg Asp Gln Leu Arg Leu
            100                 105                 110

Asp Met Asn Arg Leu Pro Ser Ser Glu Asp Gly Asp Asp Glu Glu Phe
            115                 120                 125

Ser His Asp Asp Gly Ser Ala Pro Pro Thr Glu Met Glu Cys Glu Tyr
            130                 135                 140

Leu Lys Arg Trp Phe Gly Ser Leu Thr Glu Glu Asn His Arg Leu His
145                 150                 155                 160

Arg Glu Val Glu Glu Leu Arg Ala Ile Lys Val Gly Pro Thr Thr Val
                165                 170                 175

Asn Ser Ala Ser Ser Leu Thr Met Cys Pro Arg Cys Glu Arg Val Thr
            180                 185                 190

Pro Ala Ala Ser Pro Ser Arg Ala Val Val Pro Val Pro Ala Lys Lys
            195                 200                 205

Thr Phe Pro Pro Gln Glu Arg Asp Arg
            210                 215

<210> SEQ ID NO 73
<211> LENGTH: 275
<212> TYPE: PRT
<213> ORGANISM: Arabidopsis thaliana

<400> SEQUENCE: 73

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
                20                  25                  30

Lys Gly Ile Val Thr Leu Gln Val Cys Leu Phe Tyr Ile Lys Leu Arg
            35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65              70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Gly Arg Asp Gln Leu Arg Leu
            100                 105                 110

Asp Met Asn Arg Leu Pro Ser Ser Glu Asp Gly Asp Asp Glu Glu Phe
            115                 120                 125

Ser His Asp Asp Gly Ser Ala Pro Pro Arg Lys Lys Leu Arg Leu Thr
            130                 135                 140

Arg Glu Gln Ser Arg Leu Leu Glu Asp Ser Leu Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
            195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240
```

```
Thr Met Cys Pro Arg Cys Glu Arg Val Thr Pro Ala Ala Ser Pro Ser
            245                 250                 255

Arg Ala Val Val Pro Val Pro Ala Lys Lys Thr Phe Pro Pro Gln Glu
        260                 265                 270

Arg Asp Arg
    275

<210> SEQ ID NO 74
<211> LENGTH: 202
<212> TYPE: PRT
<213> ORGANISM: Arabidopsis thaliana

<400> SEQUENCE: 74

Met Ala Ile Leu Pro Glu Asn Ser Ser Asn Leu Asp Leu Thr Ile Ser
1               5                   10                  15

Val Pro Gly Phe Ser Ser Pro Leu Ser Asp Glu Gly Ser Gly Gly
            20                  25                  30

Gly Arg Asp Gln Leu Arg Leu Asp Met Asn Arg Leu Pro Ser Ser Glu
        35                  40                  45

Asp Gly Asp Asp Glu Glu Phe Ser His Asp Asp Gly Ser Ala Pro Pro
    50                  55                  60

Arg Lys Lys Leu Arg Leu Thr Arg Glu Gln Ser Arg Leu Leu Glu Asp
65                  70                  75                  80

Ser Phe Arg Gln Asn His Thr Leu Asn Pro Lys Gln Lys Glu Val Leu
                85                  90                  95

Ala Lys His Leu Met Leu Arg Pro Arg Gln Ile Glu Val Trp Phe Gln
            100                 105                 110

Asn Arg Arg Ala Arg Ser Lys Leu Lys Gln Thr Glu Met Glu Cys Glu
        115                 120                 125

Tyr Leu Lys Arg Trp Phe Gly Ser Leu Thr Glu Glu Asn His Arg Leu
    130                 135                 140

His Arg Glu Val Glu Glu Leu Arg Ala Ile Lys Val Gly Pro Thr Thr
145                 150                 155                 160

Val Asn Ser Ala Ser Ser Leu Thr Met Ser Pro Arg Ser Glu Arg Val
                165                 170                 175

Thr Pro Ala Ala Ser Pro Ser Arg Ala Val Val Pro Val Pro Ala Lys
            180                 185                 190

Lys Thr Phe Pro Pro Gln Glu Arg Asp Arg
        195                 200

<210> SEQ ID NO 75
<211> LENGTH: 486
<212> TYPE: DNA
<213> ORGANISM: Zea mays

<400> SEQUENCE: 75
gcatctgctg ttctttattt ctatacatac atatatacta tcatcggtta tttgcttctc      60
tattctgtcc gagtacttta cggtgttccg cacatagatc tcgtggccgg ctgttttgcg     120
ctttcgcttg cgtttcttgg ccctgctggt gttgaccggt ccgaacgggg gcagatcgat     180
gctttgggtt tgaagcggag ctcctatcat tccaatgaag ggtcgttccg aagggctggt     240
tccgctgctc gttcatggtt cccactatcc tatctcatca tgtgtatata tgtaatccat     300
gggggagggt ttctctcgtc tttgagatag gcttgtggtt tgcatgaccg aggagctgca     360
ccgccccctt gctggccgct ctttggattg aagggagctc tgcatcctga tccacccctc     420
```

```
cattttttttt gcttgttgtg tccttcctgg gacctgagat ctgaggctcg tggtggctca    480
ctgtag                                                                486

<210> SEQ ID NO 76
<211> LENGTH: 21
<212> TYPE: DNA
<213> ORGANISM: Zea mays

<400> SEQUENCE: 76
tttggattga agggagctct g                                               21

<210> SEQ ID NO 77
<211> LENGTH: 486
<212> TYPE: DNA
<213> ORGANISM: artificial
<220> FEATURE:
<223> OTHER INFORMATION: engineered miRNA precursor

<400> SEQUENCE: 77
gcatctgctg ttctttattt ctatacatac atatatacta tcatcggtta tttgcttctc    60
tattctgtcc gagtacttta cggtgttccg cacatagatc tcgtggccgg ctgttttgcg    120
ctttcgcttg cgtttcttgg ccctgctggt gttgaccggt ccgaacgggg gcagatcgat    180
gctttgggtt tgaagactgg aggagcgctg caaggcgaag ggtcgttccg aagggctggt    240
tccgctgctc gttcatggtt cccactatcc tatctcatca tgtgtatata tgtaatccat    300
gggggagggt ttctctcgtc tttgagatag gcttgtggtt tgcatgaccg aggagctgca    360 ccgcccccctt gctggccgct ctccttgaag ctctcctcca gtcatcctga tccacccctc    420 cattttttttt gcttgttgtg tccttcctgg gacctgagat ctgaggctcg tggtggctca    480
ctgtag                                                                486

<210> SEQ ID NO 78
<211> LENGTH: 21
<212> TYPE: DNA
<213> ORGANISM: artificial
<220> FEATURE:
<223> OTHER INFORMATION: engineered miRNA

<400> SEQUENCE: 78
tccttgaagc tctcctccag t                                               21

<210> SEQ ID NO 79
<211> LENGTH: 21
<212> TYPE: DNA
<213> ORGANISM: Artificial sequence
<220> FEATURE:
<223> OTHER INFORMATION: engineered miRNA recognition site

<400> SEQUENCE: 79
cctggaggag agcttcaagg a                                               21

<210> SEQ ID NO 80
<211> LENGTH: 25
<212> TYPE: DNA
<213> ORGANISM: artificial
<220> FEATURE:
<223> OTHER INFORMATION: DNA binding sequence

<400> SEQUENCE: 80
tagagacact taaatgctca aaaat                                           25
```

```
<210> SEQ ID NO 81
<211> LENGTH: 21
<212> TYPE: DNA
<213> ORGANISM: artificial
<220> FEATURE:
<223> OTHER INFORMATION: synthetic oligo sequence

<400> SEQUENCE: 81
cactcaatga ttagcgtaga t                                            21

<210> SEQ ID NO 82
<211> LENGTH: 25
<212> TYPE: DNA
<213> ORGANISM: artificial
<220> FEATURE:
<223> OTHER INFORMATION: synthetic oligo sequence

<400> SEQUENCE: 82
taattaatct aagcactcac aaagt                                        25

<210> SEQ ID NO 83
<211> LENGTH: 25
<212> TYPE: DNA
<213> ORGANISM: artificial
<220> FEATURE:
<223> OTHER INFORMATION: synthetic oligo sequence

<400> SEQUENCE: 83
tgaggtgcaa tacgcgttat ctaag                                        25

<210> SEQ ID NO 84
<211> LENGTH: 20
<212> TYPE: DNA
<213> ORGANISM: artificial
<220> FEATURE:
<223> OTHER INFORMATION: synthetic oligo sequence

<400> SEQUENCE: 84
ttcaagtaat aattagctag                                              20

<210> SEQ ID NO 85
<211> LENGTH: 25
<212> TYPE: DNA
<213> ORGANISM: artificial
<220> FEATURE:
<223> OTHER INFORMATION: synthetic oligo sequence

<400> SEQUENCE: 85
tatccaaaca tttttagata ataga                                        25

<210> SEQ ID NO 86
<211> LENGTH: 19
<212> TYPE: DNA
<213> ORGANISM: artificial
<220> FEATURE:
<223> OTHER INFORMATION: synthetic oligo sequence

<400> SEQUENCE: 86
ttggttggta ccaactcga                                               19

<210> SEQ ID NO 87
<211> LENGTH: 21
<212> TYPE: DNA
<213> ORGANISM: artificial
<220> FEATURE:
<223> OTHER INFORMATION: synthetic oligo sequence
```

-continued

<400> SEQUENCE: 87
aaagccaatc attccttcat g    21

<210> SEQ ID NO 88
<211> LENGTH: 21
<212> TYPE: DNA
<213> ORGANISM: artificial
<220> FEATURE:
<223> OTHER INFORMATION: synthetic oligo sequence

<400> SEQUENCE: 88
tcgcagcacg taggagcagt g    21

<210> SEQ ID NO 89
<211> LENGTH: 25
<212> TYPE: DNA
<213> ORGANISM: artificial
<220> FEATURE:
<223> OTHER INFORMATION: synthetic oligo sequence

<400> SEQUENCE: 89
tgcaccaatt aaggagcccg ccccc    25

<210> SEQ ID NO 90
<211> LENGTH: 22
<212> TYPE: DNA
<213> ORGANISM: artificial
<220> FEATURE:
<223> OTHER INFORMATION: synthetic oligo sequence

<400> SEQUENCE: 90
acaagttaat gattgctgtc cc    22

<210> SEQ ID NO 91
<211> LENGTH: 25
<212> TYPE: DNA
<213> ORGANISM: artificial
<220> FEATURE:
<223> OTHER INFORMATION: synthetic oligo sequence

<400> SEQUENCE: 91
ttcacacata cgtacgtagt ttctg    25

<210> SEQ ID NO 92
<211> LENGTH: 253
<212> TYPE: PRT
<213> ORGANISM: Zea mays

<400> SEQUENCE: 92

Met Val Ala Gly Ser Ala Leu Ala Leu Glu Asp Asp Glu Glu Pro
1               5                   10                  15

Gly Ala Ala Ala Leu Ser Ser Ser Pro Asn Asp Ser Ala Gly Ser Phe
                20                  25                  30

Pro Leu Asp Leu Gly Gly Pro Arg Ala His Ala Glu Gly Ala Ala Ala
            35                  40                  45

Arg Ala Gly Gly Glu Arg Ser Ser Ser Arg Ala Ser Asp Glu Asp Glu
        50                  55                  60

Gly Ala Ser Ala Arg Lys Lys Leu Arg Leu Ser Lys Glu Gln Ser Ala
65                  70                  75                  80

Phe Leu Glu Glu Ser Phe Lys Glu His Ser Thr Leu Asn Pro Lys Gln
                85                  90                  95

Lys Ala Ala Leu Ala Lys Gln Leu Asn Leu Arg Pro Arg Gln Val Glu

```
            100                 105                 110
Val Trp Phe Gln Asn Arg Arg Ala Arg Thr Lys Leu Lys Gln Thr Glu
        115                 120                 125

Val Asp Cys Glu Tyr Leu Lys Arg Cys Cys Glu Thr Leu Thr Glu Glu
130                 135                 140

Asn Arg Arg Leu His Lys Glu Leu Ala Glu Leu Arg Ala Leu Lys Thr
145                 150                 155                 160

Ala Pro Pro Phe Phe Met Arg Leu Pro Ala Thr Thr Leu Ser Met Cys
                165                 170                 175

Pro Ser Cys Glu Arg Val Ala Ser Gly Pro Ser Pro Ala Ser Thr Ser
            180                 185                 190

Ala Pro Ala Ser Ser Thr Pro Pro Ala Thr Ala Ala Thr Thr Ala Ile
        195                 200                 205

Ser Tyr Ala Ala Ala Ala Ala Pro Val Arg Ala Asp His Arg Pro
        210                 215                 220

Ser Ser Phe Ala Ala Leu Phe Ala Ala Thr Arg Ser Phe Pro Leu Ala
225                 230                 235                 240

Ser Gln Pro Arg Pro Pro Ala Pro Ala Ser Asn Cys Leu
                245                 250

<210> SEQ ID NO 93
<211> LENGTH: 213
<212> TYPE: PRT
<213> ORGANISM: Zea mays

<400> SEQUENCE: 93

Met Ala Val Pro Gly Leu Ser Ser Ser Gly Ser Glu Gly Phe Gly
1               5                   10                  15

Cys Asn Asn Asn Gly Ser Gly Asn Gly Asn Asn Met Arg Asp Leu
            20                  25                  30

Asp Met Asn Gln Pro Ala Ser Gly Gly Glu Glu Glu Phe Pro Met
        35                  40                  45

Gly Ser Val Glu Glu Glu Glu Asp Glu Arg Gly Gly Ala Gly Gly Pro
    50                  55                  60

His Arg Ala Lys Lys Leu Arg Leu Ser Lys Glu Gln Ser Arg Leu Leu
65                  70                  75                  80

Glu Glu Ser Phe Arg Leu Asn His Thr Leu Thr Pro Lys Gln Lys Glu
                85                  90                  95

Ala Leu Ala Val Lys Leu Lys Leu Arg Pro Arg Gln Val Glu Val Trp
            100                 105                 110

Phe Gln Asn Arg Arg Ala Arg Thr Lys Leu Lys Gln Thr Glu Leu Glu
        115                 120                 125

Cys Glu Tyr Leu Lys Arg Cys Phe Gly Ser Leu Thr Glu Glu Asn Arg
    130                 135                 140

Arg Leu Gln Arg Glu Val Glu Glu Leu Arg Ala Met Arg Val Ala Pro
145                 150                 155                 160

Pro Thr Val Leu Ser Pro His Thr Arg Gln Pro Leu Pro Ala Ser Ala
                165                 170                 175

Leu Thr Met Cys Pro Arg Cys Glu Arg Ile Thr Ala Ala Thr Ala Ala
            180                 185                 190

Arg Thr Pro Arg Pro Pro Ala Ser Pro Phe His Pro Arg Arg
        195                 200                 205

Pro Ser Ala Ala Phe
    210
```

<210> SEQ ID NO 94
<211> LENGTH: 191
<212> TYPE: PRT
<213> ORGANISM: Zea mays

<400> SEQUENCE: 94

Met Asp Ile Ser Ala Gln Gly Gln Gly Gln Gly Gln Asp Gln Ala Ala
1               5                   10                  15

Pro Ala Ala Asp Arg Ala Cys Ser Arg Ala Ser Asp Glu Asp Asp Gly
            20                  25                  30

Gly Ser Ala Arg Lys Lys Leu Arg Leu Ser Lys Glu Gln Ser Ala Phe
        35                  40                  45

Leu Glu Glu Ser Phe Lys Val Arg Ala Thr Pro Asn Pro Lys Gln Lys
    50                  55                  60

Leu Ala Leu Ala Arg Gln Leu Asn Leu Arg Ala Arg Gln Val Glu Val
65                  70                  75                  80

Trp Phe Gln Asn Arg Arg Ala Arg Thr Lys Leu Lys Gln Thr Glu Val
                85                  90                  95

Asp Cys Glu His Leu Lys Arg Cys Cys Glu Thr Leu Thr Gly Glu Asn
            100                 105                 110

Arg Arg Leu His Lys Glu Leu Ala Glu Leu Arg Ala Leu Lys Ala Val
        115                 120                 125

Arg Pro Leu Leu His Met His Leu Pro Ala Thr Thr Leu Ser Met Cys
    130                 135                 140

Pro Ser Cys Glu Arg Val Ala Ser Thr Ser Ser Ala Ala Pro Ala Ala
145                 150                 155                 160

Pro Ala Pro Ala Ser Pro Ser Pro Ala Ala Gly Ala Gly Ile Ala Ala
                165                 170                 175

Ser Ala Pro Asp Pro Asp Gln Arg Pro Ser Ser Ser Phe Ala Ala
            180                 185                 190

<210> SEQ ID NO 95
<211> LENGTH: 247
<212> TYPE: PRT
<213> ORGANISM: Zea mays

<400> SEQUENCE: 95

Met Val Ala Ala Phe Gln Pro Ser Phe Cys His Pro Ala Gly Asn Asp
1               5                   10                  15

Ala Ala Glu Arg Glu Ala Ser Pro Thr Ala Asp Glu Arg Glu Arg Arg
            20                  25                  30

Cys Ser Pro Ala Gly Ser Pro Thr Ser Ser Gly Ser Gly Lys Arg Val
        35                  40                  45

Ala Ala Glu Arg Ser Ala Gly Ser Gly Ser Gly Asp Glu Asp Asp Asp
    50                  55                  60

Gly Gly Ala Arg Lys Lys Leu Arg Leu Ser Lys Asp Gln Ala Ala Val
65                  70                  75                  80

Leu Glu Glu Cys Phe Lys Thr His His Thr Leu Thr Pro Lys Gln Lys
                85                  90                  95

Ala Ala Leu Ala Ser Arg Leu Gly Leu Arg Ala Arg Gln Val Glu Val
            100                 105                 110

Trp Phe Gln Asn Arg Arg Ala Arg Thr Lys Leu Lys Gln Thr Glu Val
        115                 120                 125

Asp Cys Glu Tyr Leu Arg Arg Trp Cys Glu Gln Leu Ala Glu Glu Asn
    130                 135                 140

```
Arg Arg Leu Gly Lys Glu Val Ala Glu Leu Arg Ala Leu Ser Ala Ala
145                 150                 155                 160

Pro Ala Pro Ala Ala Pro Leu Thr Ala Leu Thr Met Cys Leu Ser Cys
                165                 170                 175

Arg Arg Val Ser Ser Ser Cys Ser Ser Ser Pro Pro Asn Thr His
            180                 185                 190

Ala His Ala Ala Ala Gly Thr Gly Arg Ser Val Ala Ala Ala Ala
            195                 200                 205

Ala Thr Thr Leu Pro Ala His Arg Gln Phe Leu Cys Gly Phe Arg Asp
        210                 215                 220

Gly Gly Ala Ala Ala Ala Val Tyr Gly Thr Ser Ser Ala Leu Ala
225                 230                 235                 240

Lys Ala Leu Arg Ala Ala Arg
                245
```

<210> SEQ ID NO 96
<211> LENGTH: 175
<212> TYPE: PRT
<213> ORGANISM: Zea mays

<400> SEQUENCE: 96

```
Met Ser Gly Val Gly Gly Gly Ala Arg Lys Lys Leu Arg Leu Ser Lys
1               5                   10                  15

Glu Gln Ser Ala Phe Leu Glu Asp Ser Phe Lys Ala His Ser Thr Leu
                20                  25                  30

Thr Pro Lys Gln Lys Ser Asp Leu Ala Lys Arg Leu Lys Leu Arg Pro
            35                  40                  45

Arg Gln Val Glu Val Trp Phe Gln Asn Arg Arg Ala Arg Ser Lys Leu
50                  55                  60

Lys Gln Thr Glu Val Asp Cys Glu Tyr Leu Lys Arg Trp Cys Glu Lys
65                  70                  75                  80

Leu Ala Gln Glu Asn Arg Arg Leu Gln Arg Glu Val Ala Glu Leu Arg
                85                  90                  95

Arg Leu Cys Ser Ala Ala Tyr Pro Phe Tyr Gly Ala Ala Gly Phe
                100                 105                 110

Gly Val Ala Thr Ala Arg Val Cys Pro Ser Ser Cys Asp Asn Asp Val
            115                 120                 125

Ser Glu Ala Ala Ile Ser Gly Ala Pro Ser Ala Ala Pro Pro Pro
        130                 135                 140

Ser Thr Leu Phe Ala Ser Trp Pro Pro His Phe Gly Pro Phe Thr Val
145                 150                 155                 160

Val Val Pro Pro Leu Leu Arg Arg Gln Pro Ser Ala Thr Thr Ser
                165                 170                 175
```

<210> SEQ ID NO 97
<211> LENGTH: 221
<212> TYPE: PRT
<213> ORGANISM: Zea mays

<400> SEQUENCE: 97

```
Met Lys Arg Asn Asn Arg Pro Pro Val Gln Phe Asp Leu Leu Phe Pro
1               5                   10                  15

Pro Gln Ser Val Lys Glu Glu Gly Ala Ala Ser Lys Lys Ala Glu Lys
                20                  25                  30

Gly Gly Gly Arg Lys Arg Leu Lys Val Val Thr Ala Asp Glu Asp Gly
            35                  40                  45
```

-continued

```
Arg Gln Ser Pro His Gly Gly Pro Gly Pro Ser Asp Gly Ser Gly Ala
 50                  55                  60
Gly Ala Arg Lys Lys Leu Arg Leu Thr Asn Glu Gln Ser Thr Leu Leu
 65                  70                  75                  80
Glu Asp Thr Phe Arg Ala His Asn Ile Leu Ser Asn Ala Gln Lys Gln
                 85                  90                  95
Glu Leu Ala Arg Gln Val Asp Leu Ser Ala Arg Gln Val Glu Val Trp
            100                 105                 110
Phe Gln Asn Arg Arg Ala Arg Thr Lys Leu Lys Gln Thr Glu Val Asp
            115                 120                 125
Cys Glu Ile Leu Lys Arg Cys Cys Glu Ser Leu Thr Gly Glu Asn Gln
130                 135                 140
Arg Leu Arg Leu Glu Leu Ala Gln Leu Gln Arg Ser Ala Ala Ala Ala
145                 150                 155                 160
Ala Glu Ala Gly Leu Tyr Val Gln Ser Ser Phe Pro Pro Leu Ala Thr
                165                 170                 175
Ala Thr Ala Thr Ala Ser Val Cys Pro Ser Cys Asp Lys Val Ile Ala
            180                 185                 190
Val Ser Ser Gly Gly Glu Thr Ser Gly Lys Ser Ser Thr Ser Tyr Ser
195                 200                 205
Ser Arg Arg Ala Gly Phe Pro Ser Ile Met Gly Ser Arg
210                 215                 220

<210> SEQ ID NO 98
<211> LENGTH: 312
<212> TYPE: PRT
<213> ORGANISM: Zea mays

<400> SEQUENCE: 98

Met Gly Val Gly Val Arg Arg Glu Glu Ala Gln Arg Gly Arg Arg
 1               5                  10                  15
Asp Arg Glu Val Arg Arg Glu Leu Glu Phe Thr Ala Arg Ser Ala Arg
             20                  25                  30
Ser Ser Pro Glu Pro Ala Val Arg Leu Thr Leu Leu His Gly Leu Gly
         35                  40                  45
Leu Pro Trp Pro Pro Pro Ser Ser Glu Thr Asn Arg His Leu Glu
 50                  55                  60
Ala Ser Ala Arg Gly Phe Asp Val Asn Arg Ala Pro Ser Leu Ser Ala
 65                  70                  75                  80
Ala Gly Ala Ala Ala Glu Glu Asp Glu Glu Gln Asp Glu Ala Gly Ala
                 85                  90                  95
Ala Ala Ala Ala Ala Ser Ser Ser Pro Asn Asn Ser Ala Ser Ser Phe
            100                 105                 110
Pro Thr Asp Phe Ser Ala His Gly Gln Val Ala Pro Gly Ala Asp Arg
            115                 120                 125
Ala Cys Ser Arg Ala Ser Asp Glu Asp Gly Gly Ser Ala Arg Lys
130                 135                 140
Lys Leu Arg Leu Ser Lys Glu Gln Ser Ala Phe Leu Glu Asp Ser Phe
145                 150                 155                 160
Lys Glu His Ala Thr Leu Asn Pro Lys Gln Lys Leu Ala Leu Ala Lys
                165                 170                 175
Gln Leu Asn Leu Arg Pro Arg Gln Val Glu Val Trp Phe Gln Asn Arg
            180                 185                 190
Arg Ala Arg Thr Lys Leu Lys Gln Thr Glu Val Asp Cys Glu Tyr Leu
            195                 200                 205
```

```
Lys Arg Cys Cys Glu Thr Leu Thr Glu Glu Asn Arg Leu Gln Lys
210                 215                 220

Glu Leu Ser Glu Leu Arg Ala Leu Lys Thr Val His Pro Phe Tyr Met
225                 230                 235                 240

His Leu Pro Ala Thr Thr Leu Ser Met Cys Pro Ser Cys Glu Arg Val
                245                 250                 255

Ala Ser Asn Ser Ala Pro Ala Pro Ala Ser Ser Pro Ser Pro Ala Thr
            260                 265                 270

Gly Ile Ala Ala Pro Ala Pro Glu Gln Arg Pro Ser Ser Phe Ala Ala
                275                 280                 285

Leu Phe Ser Ser Pro Leu Asn Arg Pro Leu Ala Ala Gln Ala Gln Pro
            290                 295                 300

Gln Pro Gln Ala Pro Ala Asn Ser
305                 310

<210> SEQ ID NO 99
<211> LENGTH: 195
<212> TYPE: PRT
<213> ORGANISM: Zea mays

<400> SEQUENCE: 99

Met Lys Arg Asn Asn Arg Pro Pro Val Gln Leu Asp Asp Leu Leu Ser
1               5                   10                  15

Phe Pro Pro Gln Ser Val Ala Ala Ser Lys Lys Gln Ala Glu Lys
            20                  25                  30

Gly Gly Gly Gly Arg Lys Arg His Lys Ile Val Val Thr Ala Asp Glu
                35                  40                  45

Asp Gly Arg Gln Ser Pro His Gly Gly Ala Arg Lys Lys Leu Arg Leu
            50                  55                  60

Thr Lys Ala Gln Ser Thr Leu Leu Glu Asp Thr Phe Arg Ala His Asn
65                  70                  75                  80

Ile Leu Ser His Ala Gln Lys Gln Glu Leu Ala Arg Gln Val Asn Leu
                85                  90                  95

Ser Ala Arg Gln Val Glu Val Trp Phe Gln Asn Arg Arg Ala Arg Thr
            100                 105                 110

Lys Leu Lys Gln Thr Glu Ala Asp Cys Glu Val Leu Lys Arg Tyr Cys
        115                 120                 125

Glu Arg Leu Thr Gly Glu Asn Gln Arg Leu Arg Leu Glu Leu Ala Gln
    130                 135                 140

Leu Gln Arg Ser Pro Ala Ala Glu Glu Ala Gly Phe Tyr Val Gln Ser
145                 150                 155                 160

Ser Phe Pro Phe Pro Pro Leu Ala Thr Ala Met Ala Ser Val Cys Pro
                165                 170                 175

Ser Cys Asp Lys Val Val Ala Val Thr Ser Gly Lys Ser Ser Thr Ser
            180                 185                 190

Tyr Ser Ser
        195

<210> SEQ ID NO 100
<211> LENGTH: 193
<212> TYPE: PRT
<213> ORGANISM: Zea mays

<400> SEQUENCE: 100

Met Gln Arg Asn Asn Arg Pro Pro Val Gln Phe Asp Leu Leu Phe Pro
1               5                   10                  15
```

```
Pro Gln Gly Val Val Glu Gly Val Ala Ala Ser Lys Lys Ala Glu Lys
            20                  25                  30

Gly Gly Gly Gly Arg Lys Arg Leu Lys Val Val Thr Gly Thr Ala Asp
        35                  40                  45

Glu Asp Gly Gln Gln Pro Pro Gly Ala Arg Lys Lys Leu Arg Leu Thr
 50                  55                  60

Lys Ala Gln Ser Thr Leu Leu Glu Asp Thr Phe Arg Ala His Ser Ile
 65                  70                  75                  80

Leu Ser Asn Ala Gln Lys Gln Glu Leu Ala Arg Gln Val Asp Leu Ser
                85                  90                  95

Ala Arg Gln Val Glu Val Trp Phe Gln Asn Arg Arg Ala Arg Thr Lys
            100                 105                 110

Leu Lys Gln Thr Glu Ala Asp Cys Glu Ile Leu Lys Arg Cys Cys Glu
        115                 120                 125

Ser Leu Thr Gly Glu Asn Gln Arg Leu Arg Leu Glu Leu Ala Gln Leu
130                 135                 140

Gln Gly Ser Glu Ala Gly Leu Tyr Leu Gln Ser Ser Phe Pro Pro Leu
145                 150                 155                 160

Ala Ala Ala Met Ala Ser Val Cys Pro Ser Cys Asp Lys Val Ile Thr
                165                 170                 175

Val Ala Ser Gly Gly Glu Thr Ser Gly Arg Ser Ser Thr Ser Tyr Ser
            180                 185                 190

Ser

<210> SEQ ID NO 101
<211> LENGTH: 199
<212> TYPE: PRT
<213> ORGANISM: Zea mays

<400> SEQUENCE: 101

Met Leu Leu Arg Ala Pro Glu Lys Arg Phe Leu Glu Met Pro Leu Leu
 1               5                  10                  15

Leu Pro Ala Lys Arg Thr Thr Glu Val Thr Gly Glu Asp Gly Leu Arg
            20                  25                  30

Gly Gly Ser Asp Glu Glu Asp Gly Cys Gly Ile Asp Gly Ser Arg
        35                  40                  45

Lys Lys Leu Arg Leu Ser Lys Asp Gln Ser Ala Val Leu Glu Asp Ser
 50                  55                  60

Phe Arg Glu His Pro Thr Leu Asn Pro Arg Gln Lys Ala Ala Leu Ala
 65                  70                  75                  80

Gln Gln Leu Gly Leu Arg Pro Arg Gln Val Glu Val Trp Phe Gln Asn
                85                  90                  95

Arg Arg Ala Arg Thr Lys Leu Lys Gln Thr Glu Val Asp Cys Glu Tyr
            100                 105                 110

Leu Lys Arg Cys Cys Glu Thr Leu Thr Glu Glu Asn Arg Arg Leu Gln
        115                 120                 125

Lys Glu Val Gln Glu Leu Arg Ala Leu Lys Leu Val Ser Pro His Leu
130                 135                 140

Tyr Met His Met Ser Pro Pro Thr Thr Leu Thr Met Cys Pro Ser Cys
145                 150                 155                 160

Glu Arg Val Ser Ser Asn Gly Asn Ser Ala Ala Ala Thr Ala Ala
                165                 170                 175

Ala Arg Ala Arg Ala Gly Ala Gly Ala Gly Ala Ile Val Cys His Pro
            180                 185                 190
```

```
Ile Asp Arg Ala Thr Ser Thr
        195

<210> SEQ ID NO 102
<211> LENGTH: 243
<212> TYPE: PRT
<213> ORGANISM: Zea mays

<400> SEQUENCE: 102

Met Val Val Val Pro Ala Ala Glu Arg Glu Ala Ser Pro Ala Ala
1               5                   10                  15

Ala Glu Glu Arg Glu Arg Arg Cys Ser Pro Ala Gly Ser Pro Val Ser
            20                  25                  30

Ser Gly Ser Gly Ser Gly Asn Lys Arg Ala Ala Ala Glu Arg Ser Ala
        35                  40                  45

Gly Ala Gly Ala Gly Ser Gly Asp Glu Asp Asp Gly Ala Ala Arg
    50                  55                  60

Lys Lys Leu Arg Leu Ser Lys Asp Gln Ala Ala Val Leu Glu Glu Cys
65                  70                  75                  80

Phe Lys Thr His His Thr Leu Thr Pro Lys Gln Lys Val Ala Leu Ala
                85                  90                  95

Ser Ser Leu Gly Leu Arg Pro Arg Gln Val Glu Val Trp Phe Gln Asn
            100                 105                 110

Arg Arg Ala Arg Thr Lys Leu Lys Gln Thr Glu Val Asp Cys Glu Tyr
        115                 120                 125

Leu Lys Arg Trp Cys Glu Gln Leu Ala Glu Glu Asn Arg Arg Leu Gly
    130                 135                 140

Lys Glu Val Ala Glu Leu Arg Ala Leu Ser Ala Ala Pro Ala Ala Pro
145                 150                 155                 160

Leu Thr Thr Leu Thr Met Cys Leu Ser Cys Arg Arg Val Ala Ser Ser
                165                 170                 175

Ser Pro Ser Ser Ser Ser Pro Arg Pro Ser Ile Pro Gly Ala Ala
            180                 185                 190

Ala Ala Ser Gly Gly Ser Met Ala Ser Pro Ala Ala Ala Thr Leu
        195                 200                 205

Pro Ala His Arg Gln Phe Phe Cys Gly Phe Arg Asp Ala Gly Ala Ala
    210                 215                 220

Ala Ala Ala Tyr Gly Thr Ala Ser Ala Gly Leu Ala Lys Pro Val Arg
225                 230                 235                 240

Ala Ala Arg

<210> SEQ ID NO 103
<211> LENGTH: 222
<212> TYPE: PRT
<213> ORGANISM: Zea mays

<400> SEQUENCE: 103

Met Lys Arg Ser Arg Pro Leu Arg Pro Val Arg Leu Asp Leu Leu Phe
1               5                   10                  15

Pro Pro Ser Val Glu Gly Gly Glu Ala Ala Arg Ser Arg Lys Ala
            20                  25                  30

Gly Ala Gly Ala Leu Arg Asn Met Ser Leu Lys Gln Val Ala Gly Asp
        35                  40                  45

Asp Asp Gly Gly Gln Ser Ser His Gly Gly Pro Ser Pro Ser Asp Asp
    50                  55                  60
```

```
Asp Asp Gly Ala Gly Ala Arg Lys Lys Leu Arg Leu Thr Thr Glu Gln
 65                  70                  75                  80

Ser Lys Leu Leu Glu Asp Thr Phe Arg Ala His Asn Ile Leu Ser His
                 85                  90                  95

Ala Gln Lys His Glu Val Ala Arg Gln Val Asp Leu Ser Ala Arg Gln
            100                 105                 110

Val Glu Val Trp Phe Gln Asn Arg Arg Ala Arg Thr Lys Leu Lys Gln
        115                 120                 125

Thr Glu Val Asp Cys Glu Thr Leu Arg Arg Trp Arg Glu Ser Leu Ala
    130                 135                 140

Asp Glu Asn Leu Arg Leu Arg Leu Glu Leu Glu Gln Leu Gln Arg Trp
145                 150                 155                 160

Ala Thr Ala Ala Ala Gly Gln Ser Ser Ala Ser Pro Ser Pro Ala Thr
                165                 170                 175

Ala Thr Ala Ser Val Cys Pro Ser Cys Asp Lys Val Val Val Val Thr
            180                 185                 190

Val Thr Ser Cys Gly Glu Thr Ser Gly Lys Ser Ser Thr Ser Ser Tyr
        195                 200                 205

Ser Ser Ser Pro Pro Leu Asp Met Leu Asp Arg Ser Val Gln
210                 215                 220

<210> SEQ ID NO 104
<211> LENGTH: 185
<212> TYPE: PRT
<213> ORGANISM: Zea mays

<400> SEQUENCE: 104

Met Arg Asp Leu Asp Met Asn Gln Pro Ala Ser Gly Gly Glu Glu Glu
  1               5                  10                  15

Glu Phe Pro Met Gly Ser Val Glu Glu Glu Asp Glu Arg Gly Gly Gly
                 20                  25                  30

Ala Gly Gly Pro His Arg Ala Lys Lys Leu Arg Leu Ser Lys Glu Gln
             35                  40                  45

Ser Arg Leu Leu Glu Glu Ser Phe Arg Leu Asn His Thr Leu Thr Pro
 50                  55                  60

Lys Gln Lys Glu Ala Leu Ala Val Lys Leu Lys Leu Arg Pro Arg Gln
 65                  70                  75                  80

Val Glu Val Trp Phe Gln Asn Arg Arg Ala Arg Thr Lys Leu Lys Gln
                 85                  90                  95

Thr Glu Leu Glu Cys Glu Tyr Leu Lys Arg Cys Phe Gly Ser Leu Thr
            100                 105                 110

Glu Glu Asn Arg Arg Leu Gln Arg Glu Val Glu Glu Leu Arg Ala Met
        115                 120                 125

Arg Val Ala Pro Pro Thr Val Leu Ser Pro His Thr Arg Gln Pro Leu
    130                 135                 140

Pro Ala Ser Ala Leu Thr Met Cys Pro Arg Cys Glu Arg Ile Thr Ala
145                 150                 155                 160

Ala Thr Ala Ala Arg Thr Pro Arg Pro Pro Ala Ala Ser Pro Phe
                165                 170                 175

His Pro Arg Arg Pro Ser Ala Ala Phe
            180                 185

<210> SEQ ID NO 105
<211> LENGTH: 187
<212> TYPE: PRT
<213> ORGANISM: Zea mays
```

<400> SEQUENCE: 105

```
Met Pro Leu Leu Leu Pro Ala Lys Arg Thr Thr Glu Val Thr Gly Glu
1               5                   10                  15

Asp Gly Leu Arg Gly Gly Ser Asp Glu Glu Asp Gly Gly Cys Gly Ile
            20                  25                  30

Asp Gly Ser Arg Lys Lys Leu Arg Leu Ser Lys Asp Gln Ser Ala Val
        35                  40                  45

Leu Glu Asp Ser Phe Arg Glu His Pro Thr Leu Asn Pro Arg Gln Lys
    50                  55                  60

Ala Ala Leu Ala Gln Gln Leu Gly Leu Arg Pro Arg Gln Val Glu Val
65                  70                  75                  80

Trp Phe Gln Asn Arg Arg Ala Arg Thr Lys Leu Lys Gln Thr Glu Val
                85                  90                  95

Asp Cys Glu Tyr Leu Lys Arg Cys Cys Glu Thr Leu Thr Glu Glu Asn
            100                 105                 110

Arg Arg Leu Gln Lys Glu Val Gln Glu Leu Arg Ala Leu Lys Leu Val
        115                 120                 125

Ser Pro His Leu Tyr Met His Met Ser Pro Thr Thr Leu Thr Met
    130                 135                 140

Cys Pro Ser Cys Glu Arg Val Ser Ser Ser Asn Gly Asn Ser Ala Ala
145                 150                 155                 160

Ala Thr Ala Ala Ala Arg Ala Arg Ala Gly Ala Gly Ala Gly Ala Ile
                165                 170                 175

Val Cys His Pro Ile Asp Arg Ala Thr Ser Thr
            180                 185
```

<210> SEQ ID NO 106
<211> LENGTH: 202
<212> TYPE: PRT
<213> ORGANISM: Zea mays

<400> SEQUENCE: 106

```
Met Pro Asp Glu Ala Thr Ala Thr Ala Thr Gly Gly Ser Gly Gly Ser
1               5                   10                  15

Gly Gly Ala Ala Arg Ser Val Ser Ser Arg Ser Val Glu Gly Val Lys
            20                  25                  30

Arg Glu Arg Val Asp Asp Ala Glu Gly Glu Arg Ala Ser Ser Thr Ala
        35                  40                  45

Ala Ala Ala Arg Val Cys Ala Gly Ala Glu Asp Asp Asp Asp Gly Ser
    50                  55                  60

Thr Arg Lys Lys Leu Arg Leu Thr Lys Glu Gln Ser Lys Leu Leu Glu
65                  70                  75                  80

Asp Arg Phe Lys Asp His Ser Thr Leu Asn Pro Lys Gln Lys Ile Ala
                85                  90                  95

Leu Ala Lys Gln Leu Lys Leu Arg Pro Arg Gln Val Glu Val Trp Phe
            100                 105                 110

Gln Asn Arg Arg Ala Arg Thr Lys Leu Lys Gln Thr Glu Val Asp Cys
        115                 120                 125

Glu Leu Leu Lys Arg Cys Cys Glu Ser Leu Ser Glu Glu Asn Arg Arg
    130                 135                 140

Leu Gln Arg Glu Leu Gln Glu Leu Arg Ala Leu Lys Leu Ala Gly Pro
145                 150                 155                 160

His Pro Gln Ala Pro Ser Ser Ser Pro Ala Ala Ala Thr Gln Gly Val
                165                 170                 175
```

```
Pro Val Pro Val Pro Pro Pro Leu Tyr Val Gln Met Gln Met Gln Leu
            180                 185                 190

Ser Ser Cys Arg Cys Cys Arg Pro Pro Arg
        195                 200

<210> SEQ ID NO 107
<211> LENGTH: 180
<212> TYPE: PRT
<213> ORGANISM: Zea mays

<400> SEQUENCE: 107

Met Asn Gln Pro Ala Ser Gly Gly Glu Glu Glu Phe Pro Met Gly
1               5                   10                  15

Ser Val Glu Glu Glu Asp Glu Arg Gly Gly Ala Gly Gly Pro His
            20                  25                  30

Arg Ala Lys Lys Leu Arg Leu Ser Lys Glu Gln Ser Arg Leu Leu Glu
            35                  40                  45

Glu Ser Phe Arg Leu Asn His Thr Leu Thr Pro Lys Gln Lys Glu Ala
    50                  55                  60

Leu Ala Val Lys Leu Lys Leu Arg Pro Arg Gln Val Glu Val Trp Phe
65                  70                  75                  80

Gln Asn Arg Arg Ala Arg Thr Lys Leu Lys Gln Thr Glu Leu Glu Cys
                85                  90                  95

Glu Tyr Leu Lys Arg Cys Phe Gly Ser Leu Thr Glu Glu Asn Arg Arg
            100                 105                 110

Leu Gln Arg Glu Val Glu Glu Leu Arg Ala Met Arg Val Ala Pro Pro
        115                 120                 125

Thr Val Leu Ser Pro His Thr Arg Gln Pro Leu Pro Ala Ser Ala Leu
    130                 135                 140

Thr Met Cys Pro Arg Cys Glu Arg Ile Thr Ala Ala Thr Ala Ala Arg
145                 150                 155                 160

Thr Pro Arg Pro Pro Ala Ala Ser Pro Phe His Pro Arg Arg Pro
                165                 170                 175

Ser Ala Ala Phe
            180

<210> SEQ ID NO 108
<211> LENGTH: 220
<212> TYPE: PRT
<213> ORGANISM: Zea mays

<400> SEQUENCE: 108

Met Leu Thr Leu Pro Pro Ser Arg Thr Val Gln Leu Phe Gly Glu Val
1               5                   10                  15

Leu Ser Val Gln Asp Gly Asp Gly Thr Gln Ala Leu Arg His His His
            20                  25                  30

Thr Gly Arg Pro Pro Ala Ala Ser Ser Arg Lys Lys Lys Arg Lys Asp
        35                  40                  45

Ala Ala Ala Ala Gly Gly Ala Ser Ala Thr Asp Ala Ala Ala Asn Gly
    50                  55                  60

His His His Gln Ser Lys Lys Thr Lys Thr Thr Ala Ala Arg Arg Asp
65                  70                  75                  80

Asp Gly Gly Gly Gly Arg Lys Lys Leu Arg Leu Thr Ser Ala Gln Ala
                85                  90                  95

Thr Leu Leu Glu Asp Ser Phe Arg Ala His Asn Ile Leu Ser His Gly
            100                 105                 110
```

```
Glu Lys Gln Glu Leu Ala Arg Gln Ala Gly Leu Ser Ala Arg Gln Val
            115                 120                 125

Glu Val Trp Phe Gln Asn Arg Ala Arg Thr Lys Leu Lys Gln Thr
    130                 135                 140

Glu Val Asp Cys Asp Leu Leu Arg Arg Trp Cys Ala Arg Leu Ser Asp
145                 150                 155                 160

Asp Asn Asp Arg Leu Arg Arg Asp Leu Ala Asp Leu Arg Arg Ala Ala
                165                 170                 175

Ser Ser Ser Ala Gly Leu Gly Ala Val Val Cys Cys Ala Ser Cys Gly
            180                 185                 190

Ala Asp Arg Gln Leu Ala Leu Ala Ala Ala Asp Asn Val Leu Pro
        195                 200                 205

Ser Val Ala Ser Pro Ser His Ser Pro His Leu Thr
    210                 215                 220

<210> SEQ ID NO 109
<211> LENGTH: 208
<212> TYPE: PRT
<213> ORGANISM: Zea mays

<400> SEQUENCE: 109

Met Ser Ser Gly Ser Gly Lys Arg Val Ala Ala Glu Arg Ser Ala Gly
1               5                   10                  15

Ser Gly Ser Gly Asp Glu Asp Asp Gly Gly Ala Arg Lys Lys Leu
            20                  25                  30

Arg Leu Ser Lys Asp Gln Ala Ala Val Leu Glu Glu Cys Phe Lys Thr
            35                  40                  45

His His Thr Leu Thr Pro Lys Gln Lys Ala Ala Leu Ala Ser Arg Leu
        50                  55                  60

Gly Leu Arg Ala Arg Gln Val Glu Val Trp Phe Gln Asn Arg Arg Ala
65                  70                  75                  80

Arg Thr Lys Leu Lys Gln Thr Glu Val Asp Cys Glu Tyr Leu Arg Arg
                85                  90                  95

Trp Cys Glu Gln Leu Ala Glu Glu Asn Arg Arg Leu Gly Lys Glu Val
            100                 105                 110

Ala Glu Leu Arg Ala Leu Ser Ala Ala Pro Ala Pro Ala Ala Pro Leu
            115                 120                 125

Thr Ala Leu Thr Met Cys Leu Ser Cys Arg Arg Val Ser Ser Ser Ser
        130                 135                 140

Cys Ser Ser Ser Pro Pro Asn Thr His Ala His Ala Ala Ala Ala Gly
145                 150                 155                 160

Thr Gly Arg Ser Val Ala Ala Ala Ala Thr Thr Leu Pro Ala His
                165                 170                 175

Arg Gln Phe Leu Cys Gly Phe Arg Asp Gly Ala Ala Ala Ala
            180                 185                 190

Val Tyr Gly Thr Ser Ser Ala Leu Ala Lys Ala Leu Arg Ala Ala Arg
        195                 200                 205

<210> SEQ ID NO 110
<211> LENGTH: 166
<212> TYPE: PRT
<213> ORGANISM: Zea mays

<400> SEQUENCE: 110

Met Gly Ser Val Glu Glu Glu Asp Glu Arg Gly Gly Ala Gly Gly
1               5                   10                  15
```

Pro His Arg Ala Lys Lys Leu Arg Leu Ser Lys Glu Gln Ser Arg Leu
            20                  25                  30

Leu Glu Glu Ser Phe Arg Leu Asn His Thr Leu Thr Pro Lys Gln Lys
 35                  40                  45

Glu Ala Leu Ala Val Lys Leu Lys Leu Arg Pro Arg Gln Val Glu Val
 50                  55                  60

Trp Phe Gln Asn Arg Arg Ala Arg Thr Lys Leu Lys Gln Thr Glu Leu
 65                  70                  75                  80

Glu Cys Glu Tyr Leu Lys Arg Cys Phe Gly Ser Leu Thr Glu Glu Asn
                 85                  90                  95

Arg Arg Leu Gln Arg Glu Val Glu Glu Leu Arg Ala Met Arg Val Ala
            100                 105                 110

Pro Pro Thr Val Leu Ser Pro His Thr Arg Gln Pro Leu Pro Ala Ser
            115                 120                 125

Ala Leu Thr Met Cys Pro Arg Cys Glu Arg Ile Thr Ala Ala Thr Ala
130                 135                 140

Ala Arg Thr Pro Arg Pro Pro Ala Ala Ser Pro Phe His Pro Arg
145                 150                 155                 160

Arg Pro Ser Ala Ala Phe
                165

<210> SEQ ID NO 111
<211> LENGTH: 237
<212> TYPE: PRT
<213> ORGANISM: Zea mays

<400> SEQUENCE: 111

Met His His Ala Gly Ala Ala Met Thr Met Arg Ala Ser Thr Ser Pro
1               5                   10                  15

Asp Ser Gly Asp Thr Thr Ala Lys Arg Glu Arg Glu Gly Glu Leu
            20                  25                  30

Glu Arg Thr Gly Ser Ala Gly Gly Val Arg Ser Asp Glu Glu Asp Gly
 35                  40                  45

Ala Asp Gly Gly Ala Gly Gly Arg Lys Lys Leu Arg Leu Ser Lys Asp
 50                  55                  60

Gln Ala Ala Val Leu Glu Glu Cys Phe Lys Thr His Ser Thr Leu Asn
 65                  70                  75                  80

Pro Lys Gln Lys Val Gln Leu Ala Asn Arg Leu Gly Leu Arg Pro Arg
                 85                  90                  95

Gln Val Glu Val Trp Phe Gln Asn Arg Arg Ala Arg Thr Lys Leu Lys
            100                 105                 110

Gln Thr Glu Val Asp Cys Glu Tyr Leu Lys Arg Trp Cys Asp Arg Leu
            115                 120                 125

Ala Asp Glu Asn Lys Arg Leu Glu Lys Glu Leu Ala Asp Leu Arg Ala
130                 135                 140

Leu Lys Ala Ala Pro Pro Ser Ser Ala Ala Gln Pro Ala Ser Ala
145                 150                 155                 160

Ala Ala Thr Leu Thr Met Cys Pro Ser Cys Arg Arg Val Ala Ala Ala
                165                 170                 175

Ala Ser His His His Gln Pro Pro Pro Gln Cys His Pro Lys Pro
            180                 185                 190

Thr Val Ala Ala Gly Gly Ser Val Val Pro Arg Pro Ser His Cys
            195                 200                 205

Gln Phe Phe Pro Ala Ala Ala Val Asp Arg Thr Ser Gln Gly Thr Trp

```
                210               215                  220
Asn Thr Ala Ala Pro Pro Leu Val Thr Arg Glu Leu Phe
225                 230                 235
```

<210> SEQ ID NO 112
<211> LENGTH: 183
<212> TYPE: PRT
<213> ORGANISM: Zea mays

<400> SEQUENCE: 112

```
Met Lys Val Val Thr Ala Asp Glu Asp Gly Arg Gln Ser Pro His Gly
1               5                   10                  15

Gly Pro Gly Pro Ser Asp Gly Ser Gly Ala Gly Ala Arg Lys Lys Leu
            20                  25                  30

Arg Leu Thr Asn Glu Gln Ser Thr Leu Leu Glu Asp Thr Phe Arg Ala
        35                  40                  45

His Asn Ile Leu Ser Asn Ala Gln Lys Gln Glu Leu Ala Arg Gln Val
    50                  55                  60

Asp Leu Ser Ala Arg Gln Val Glu Val Trp Phe Gln Asn Arg Arg Ala
65                  70                  75                  80

Arg Thr Lys Leu Lys Gln Thr Glu Val Asp Cys Glu Ile Leu Lys Arg
                85                  90                  95

Cys Cys Glu Ser Leu Thr Gly Glu Asn Gln Arg Leu Arg Leu Glu Leu
            100                 105                 110

Ala Gln Leu Gln Arg Ser Ala Ala Ala Ala Glu Ala Gly Leu Tyr
        115                 120                 125

Val Gln Ser Ser Phe Pro Pro Leu Ala Thr Ala Thr Ala Thr Ala Ser
    130                 135                 140

Val Cys Pro Ser Cys Asp Lys Val Ile Ala Val Ser Ser Gly Gly Glu
145                 150                 155                 160

Thr Ser Gly Lys Ser Ser Thr Ser Tyr Ser Arg Arg Ala Gly Phe
                165                 170                 175

Pro Ser Ile Met Gly Ser Arg
            180
```

<210> SEQ ID NO 113
<211> LENGTH: 261
<212> TYPE: PRT
<213> ORGANISM: Zea mays

<400> SEQUENCE: 113

```
Met Ser Leu Pro Ala Pro Gln Trp Trp Lys Trp Asn Gly Pro Gly Leu
1               5                   10                  15

Phe Phe Gly Thr Thr Met Asp Gln Gln Gln Gln Pro Ala Ala Ala Arg
            20                  25                  30

His Gly His Glu Met Pro Phe Leu Arg Gly Val Asp Val Asn Arg Ala
        35                  40                  45

Pro Ala Gly Asp Thr Arg Arg Gly Ser Cys Ser Glu Asp Asp Glu Glu
    50                  55                  60

Pro Gly Gly Ala Ser Ser Ser Pro Asn Ser Thr Leu Ser Ser Ser Leu
65                  70                  75                  80

Ser Gly Lys Arg Ala Ala Pro Ala Arg Ser Gly Gly Glu Val Ala Asp
                85                  90                  95

His Thr Pro Arg Ala Gly Gly Gly Ser Asp Asp Glu Asp Ser Gly Gly
            100                 105                 110

Gly Ser Arg Lys Lys Leu Arg Leu Ser Lys Asp Gln Ala Ala Val Leu
```

```
            115                 120                 125
Glu Glu Ser Phe Lys Glu His Asn Thr Leu Asn Pro Lys Gln Lys Ala
130                 135                 140

Ala Leu Ala Lys Gln Leu Asn Leu Lys Pro Arg Gln Val Glu Val Trp
145                 150                 155                 160

Phe Gln Asn Arg Arg Ala Arg Thr Lys Leu Lys Gln Thr Glu Val Asp
                165                 170                 175

Cys Glu Phe Leu Lys Arg Cys Cys Glu Thr Leu Thr Glu Glu Asn Arg
                180                 185                 190

Arg Leu Gln Arg Glu Val Ala Glu Leu Arg Val Leu Lys Leu Val Ala
                195                 200                 205

Pro His His Tyr Ala Arg Met Pro Pro Thr Thr Leu Thr Met Cys
        210                 215                 220

Pro Ser Cys Glu Arg Leu Ala Ser Ala Ser Ala Asp Gln Ala
225                 230                 235                 240

Gly Arg Ala Gly Pro Cys Trp Gly Pro Leu Pro Val Phe Val Asp Gly
                245                 250                 255

Pro Ala Arg Arg Pro
            260

<210> SEQ ID NO 114
<211> LENGTH: 214
<212> TYPE: PRT
<213> ORGANISM: Zea mays

<400> SEQUENCE: 114

Met Val Ser Ser Gly Ser Gly Ser Gly Asn Lys Arg Ala Ala Ala Glu
1               5                   10                  15

Arg Ser Ala Gly Ala Gly Ala Gly Ser Gly Asp Glu Asp Asp Asp Gly
                20                  25                  30

Ala Ala Arg Lys Lys Leu Arg Leu Ser Lys Asp Gln Ala Ala Val Leu
                35                  40                  45

Glu Glu Cys Phe Lys Thr His His Thr Leu Thr Pro Lys Gln Lys Val
50                  55                  60

Ala Leu Ala Ser Ser Leu Gly Leu Arg Pro Arg Gln Val Glu Val Trp
65                  70                  75                  80

Phe Gln Asn Arg Arg Ala Arg Thr Lys Leu Lys Gln Thr Glu Val Asp
                85                  90                  95

Cys Glu Tyr Leu Lys Arg Trp Cys Glu Gln Leu Ala Glu Glu Asn Arg
                100                 105                 110

Arg Leu Gly Lys Glu Val Ala Glu Leu Arg Ala Leu Ser Ala Ala Pro
                115                 120                 125

Ala Ala Pro Leu Thr Thr Leu Thr Met Cys Leu Ser Cys Arg Arg Val
                130                 135                 140

Ala Ser Ser Ser Pro Ser Ser Ser Ser Pro Arg Pro Ser Ile Pro
145                 150                 155                 160

Gly Ala Ala Ala Ala Ser Gly Gly Ser Met Ala Ser Pro Ala Ala Ala
                165                 170                 175

Ala Thr Leu Pro Ala His Arg Gln Phe Phe Cys Gly Phe Arg Asp Ala
                180                 185                 190

Gly Ala Ala Ala Ala Tyr Gly Thr Ala Ser Ala Gly Leu Ala Lys
                195                 200                 205

Pro Val Arg Ala Ala Arg
            210
```

<210> SEQ ID NO 115
<211> LENGTH: 191
<212> TYPE: PRT
<213> ORGANISM: Zea mays

<400> SEQUENCE: 115

Met Gly Ala Gly Ala Leu Arg Asn Met Ser Leu Lys Gln Val Ala Gly
1               5                   10                  15

Asp Asp Asp Gly Gly Gln Ser Ser His Gly Gly Pro Ser Pro Ser Asp
            20                  25                  30

Asp Asp Asp Gly Ala Gly Ala Arg Lys Lys Leu Arg Leu Thr Thr Glu
        35                  40                  45

Gln Ser Lys Leu Leu Glu Asp Thr Phe Arg Ala His Asn Ile Leu Ser
50                  55                  60

His Ala Gln Lys His Glu Val Ala Arg Gln Val Asp Leu Ser Ala Arg
65                  70                  75                  80

Gln Val Glu Val Trp Phe Gln Asn Arg Arg Ala Arg Thr Lys Leu Lys
                85                  90                  95

Gln Thr Glu Val Asp Cys Glu Thr Leu Arg Arg Trp Arg Glu Ser Leu
            100                 105                 110

Ala Asp Glu Asn Leu Arg Leu Arg Leu Glu Leu Glu Gln Leu Gln Arg
        115                 120                 125

Trp Ala Thr Ala Ala Gly Gln Ser Ser Ala Ser Pro Ser Pro Ala
130                 135                 140

Thr Ala Thr Ala Ser Val Cys Pro Ser Cys Asp Lys Val Val Val
145                 150                 155                 160

Thr Val Thr Ser Cys Gly Glu Thr Ser Gly Lys Ser Ser Thr Ser Ser
                165                 170                 175

Tyr Ser Ser Pro Pro Leu Asp Met Leu Asp Arg Ser Val Gln
            180                 185                 190

<210> SEQ ID NO 116
<211> LENGTH: 230
<212> TYPE: PRT
<213> ORGANISM: Zea mays

<400> SEQUENCE: 116

Met Thr Met Arg Ala Ser Thr Ser Pro Asp Ser Gly Asp Thr Thr Thr
1               5                   10                  15

Ala Lys Arg Glu Arg Glu Gly Glu Leu Glu Arg Thr Gly Ser Ala Gly
            20                  25                  30

Gly Val Arg Ser Asp Glu Glu Asp Gly Ala Asp Gly Ala Gly Gly
        35                  40                  45

Arg Lys Lys Leu Arg Leu Ser Lys Asp Gln Ala Ala Val Leu Glu Glu
50                  55                  60

Cys Phe Lys Thr His Ser Thr Leu Asn Pro Lys Gln Lys Val Gln Leu
65                  70                  75                  80

Ala Asn Arg Leu Gly Leu Arg Pro Arg Gln Val Glu Val Trp Phe Gln
                85                  90                  95

Asn Arg Arg Ala Arg Thr Lys Leu Lys Gln Thr Glu Val Asp Cys Glu
            100                 105                 110

Tyr Leu Lys Arg Trp Cys Asp Arg Leu Ala Asp Glu Asn Lys Arg Leu
        115                 120                 125

Glu Lys Glu Leu Ala Asp Leu Arg Ala Leu Lys Ala Ala Pro Pro Ser
    130                 135                 140

Ser Ala Ala Ala Gln Pro Ala Ser Ala Ala Thr Leu Thr Met Cys
145                 150                 155                 160

Pro Ser Cys Arg Arg Val Ala Ala Ala Ser His His His Gln Pro
            165                 170                 175

Pro Pro Pro Gln Cys His Pro Lys Pro Thr Val Ala Ala Gly Gly Gly
            180                 185                 190

Ser Val Val Pro Arg Pro Ser His Cys Gln Phe Phe Pro Ala Ala Ala
            195                 200                 205

Val Asp Arg Thr Ser Gln Gly Thr Trp Asn Thr Ala Ala Pro Pro Leu
    210                 215                 220

Val Thr Arg Glu Leu Phe
225                 230

<210> SEQ ID NO 117
<211> LENGTH: 181
<212> TYPE: PRT
<213> ORGANISM: Zea mays

<400> SEQUENCE: 117

Met Val Ser Ser Arg Ser Val Glu Gly Val Lys Arg Glu Arg Val Asp
1               5                   10                  15

Asp Ala Glu Gly Glu Arg Ala Ser Ser Thr Ala Ala Ala Arg Val
            20                  25                  30

Cys Ala Gly Ala Glu Asp Asp Asp Gly Ser Thr Arg Lys Lys Leu
            35                  40                  45

Arg Leu Thr Lys Glu Gln Ser Lys Leu Leu Glu Asp Arg Phe Lys Asp
    50                  55                  60

His Ser Thr Leu Asn Pro Lys Gln Lys Ile Ala Leu Ala Lys Gln Leu
65                  70                  75                  80

Lys Leu Arg Pro Arg Gln Val Glu Val Trp Phe Gln Asn Arg Arg Ala
                85                  90                  95

Arg Thr Lys Leu Lys Gln Thr Glu Val Asp Cys Glu Leu Leu Lys Arg
            100                 105                 110

Cys Cys Glu Ser Leu Ser Glu Glu Asn Arg Arg Leu Gln Arg Glu Leu
            115                 120                 125

Gln Glu Leu Arg Ala Leu Lys Leu Ala Gly Pro His Pro Gln Ala Pro
130                 135                 140

Ser Ser Ser Pro Ala Ala Ala Thr Gln Gly Val Pro Val Pro Val Pro
145                 150                 155                 160

Pro Pro Leu Tyr Val Gln Met Gln Met Gln Leu Ser Ser Cys Arg Cys
            165                 170                 175

Cys Arg Pro Pro Arg
            180

<210> SEQ ID NO 118
<211> LENGTH: 228
<212> TYPE: PRT
<213> ORGANISM: Zea mays

<400> SEQUENCE: 118

Met Arg Ala Ser Thr Ser Pro Asp Ser Gly Asp Thr Thr Ala Lys
1               5                   10                  15

Arg Glu Arg Glu Gly Glu Leu Glu Arg Thr Gly Ser Ala Gly Gly Val
            20                  25                  30

Arg Ser Asp Glu Glu Asp Gly Ala Asp Gly Gly Ala Gly Gly Arg Lys
            35                  40                  45

```
Lys Leu Arg Leu Ser Lys Asp Gln Ala Ala Val Leu Glu Glu Cys Phe
 50                  55                  60

Lys Thr His Ser Thr Leu Asn Pro Lys Gln Lys Val Gln Leu Ala Asn
 65                  70                  75                  80

Arg Leu Gly Leu Arg Pro Arg Gln Val Glu Val Trp Phe Gln Asn Arg
                 85                  90                  95

Arg Ala Arg Thr Lys Leu Lys Gln Thr Glu Val Asp Cys Glu Tyr Leu
            100                 105                 110

Lys Arg Trp Cys Asp Arg Leu Ala Asp Glu Asn Lys Arg Leu Glu Lys
        115                 120                 125

Glu Leu Ala Asp Leu Arg Ala Leu Lys Ala Ala Pro Pro Ser Ser Ala
130                 135                 140

Ala Ala Gln Pro Ala Ser Ala Ala Ala Thr Leu Thr Met Cys Pro Ser
145                 150                 155                 160

Cys Arg Arg Val Ala Ala Ala Ser His His Gln Pro Pro
                165                 170                 175

Pro Gln Cys His Pro Lys Pro Thr Val Ala Ala Gly Gly Ser Val
            180                 185                 190

Val Pro Arg Pro Ser His Cys Gln Phe Phe Pro Ala Ala Val Asp
        195                 200                 205

Arg Thr Ser Gln Gly Thr Trp Asn Thr Ala Ala Pro Pro Leu Val Thr
210                 215                 220

Arg Glu Leu Phe
225

<210> SEQ ID NO 119
<211> LENGTH: 156
<212> TYPE: PRT
<213> ORGANISM: Zea mays

<400> SEQUENCE: 119

Met Lys Ile Val Val Thr Ala Asp Glu Asp Gly Arg Gln Ser Pro His
  1               5                  10                  15

Gly Gly Ala Arg Lys Lys Leu Arg Leu Thr Lys Ala Gln Ser Thr Leu
             20                  25                  30

Leu Glu Asp Thr Phe Arg Ala His Asn Ile Leu Ser His Ala Gln Lys
         35                  40                  45

Gln Glu Leu Ala Arg Gln Val Asn Leu Ser Ala Arg Gln Val Glu Val
     50                  55                  60

Trp Phe Gln Asn Arg Arg Ala Arg Thr Lys Leu Lys Gln Thr Glu Ala
 65                  70                  75                  80

Asp Cys Glu Val Leu Lys Arg Tyr Cys Glu Arg Leu Thr Gly Glu Asn
                 85                  90                  95

Gln Arg Leu Arg Leu Glu Leu Ala Gln Leu Gln Arg Ser Pro Ala Ala
            100                 105                 110

Glu Glu Ala Gly Phe Tyr Val Gln Ser Ser Phe Pro Phe Pro Pro Leu
        115                 120                 125

Ala Thr Ala Met Ala Ser Val Cys Pro Ser Cys Asp Lys Val Val Ala
130                 135                 140

Val Thr Ser Gly Lys Ser Ser Thr Ser Tyr Ser Ser
145                 150                 155

<210> SEQ ID NO 120
<211> LENGTH: 154
<212> TYPE: PRT
<213> ORGANISM: Zea mays
```

<400> SEQUENCE: 120

Met Lys Val Val Thr Gly Thr Ala Asp Glu Asp Gly Gln Gln Pro Pro
1               5                   10                  15

Gly Ala Arg Lys Lys Leu Arg Leu Thr Lys Ala Gln Ser Thr Leu Leu
            20                  25                  30

Glu Asp Thr Phe Arg Ala His Ser Ile Leu Ser Asn Ala Gln Lys Gln
        35                  40                  45

Glu Leu Ala Arg Gln Val Asp Leu Ser Ala Arg Gln Val Glu Val Trp
    50                  55                  60

Phe Gln Asn Arg Arg Ala Arg Thr Lys Leu Lys Gln Thr Glu Ala Asp
65                  70                  75                  80

Cys Glu Ile Leu Lys Arg Cys Cys Glu Ser Leu Thr Gly Glu Asn Gln
                85                  90                  95

Arg Leu Arg Leu Glu Leu Ala Gln Leu Gln Gly Ser Glu Ala Gly Leu
            100                 105                 110

Tyr Leu Gln Ser Ser Phe Pro Pro Leu Ala Ala Ala Met Ala Ser Val
        115                 120                 125

Cys Pro Ser Cys Asp Lys Val Ile Thr Val Ala Ser Gly Gly Glu Thr
    130                 135                 140

Ser Gly Arg Ser Ser Thr Ser Tyr Ser Ser
145                 150

<210> SEQ ID NO 121
<211> LENGTH: 194
<212> TYPE: PRT
<213> ORGANISM: Zea mays

<400> SEQUENCE: 121

Met Glu Gly Asn Asp Asp Glu Ala Thr Gly Arg Val Leu Val Tyr Ser
1               5                   10                  15

Val Ala Ser Ser Ala Val Val Thr Ala Asp Asp Asp Glu Gly Cys Asn
            20                  25                  30

Ser Ser Arg Lys Lys Leu Arg Leu Ser Lys Glu Gln Ser Ala Leu Leu
        35                  40                  45

Glu Asp His Phe Lys Glu His Ser Thr Leu Asn Pro Lys Gln Lys Ala
    50                  55                  60

Ala Leu Ala Arg Gln Leu Asn Leu Ser Pro Arg Gln Val Glu Val Trp
65                  70                  75                  80

Phe Gln Asn Arg Arg Ala Arg Thr Lys Leu Lys Gln Thr Glu Val Asp
                85                  90                  95

Cys Glu Ile Leu Lys Arg Cys Cys Glu Thr Leu Thr Glu Glu Asn Arg
            100                 105                 110

Arg Leu His Arg Glu Leu Gln Gln Leu Arg Ala Leu Ser His Pro His
        115                 120                 125

Pro His Pro Ala Ala Phe Phe Met Pro Thr Ala Ala Ala Ala Ala Leu
    130                 135                 140

Ser Ile Cys Pro Ser Cys Gln Arg Leu Val Ala Thr Gly Ala Ser Ala
145                 150                 155                 160

Ala Ala Ala Thr Thr Ala Gly Ala Asp Asn Lys Pro Lys Ala Gly Gly
                165                 170                 175

Pro Gly Gly Arg Ala Pro His Val Phe Ser Pro Phe Thr Asn Ser Ala
            180                 185                 190

Ala Cys

```
<210> SEQ ID NO 122
<211> LENGTH: 183
<212> TYPE: PRT
<213> ORGANISM: Zea mays

<400> SEQUENCE: 122

Met Ser Leu Lys Gln Val Ala Gly Asp Asp Gly Gly Gln Ser Ser
1               5                   10                  15

His Gly Gly Pro Ser Pro Ser Asp Asp Asp Gly Ala Gly Ala Arg
            20                  25                  30

Lys Lys Leu Arg Leu Thr Thr Glu Gln Ser Lys Leu Leu Glu Asp Thr
        35                  40                  45

Phe Arg Ala His Asn Ile Leu Ser His Ala Gln Lys His Glu Val Ala
    50                  55                  60

Arg Gln Val Asp Leu Ser Ala Arg Gln Val Glu Val Trp Phe Gln Asn
65                  70                  75                  80

Arg Arg Ala Arg Thr Lys Leu Lys Gln Thr Glu Val Asp Cys Glu Thr
                85                  90                  95

Leu Arg Arg Trp Arg Glu Ser Leu Ala Asp Glu Asn Leu Arg Leu Arg
            100                 105                 110

Leu Glu Leu Glu Gln Leu Gln Arg Trp Ala Thr Ala Ala Ala Gly Gln
        115                 120                 125

Ser Ser Ala Ser Pro Ser Pro Ala Thr Ala Thr Ala Ser Val Cys Pro
    130                 135                 140

Ser Cys Asp Lys Val Val Val Thr Val Thr Ser Cys Gly Glu Thr
145                 150                 155                 160

Ser Gly Lys Ser Ser Thr Ser Ser Tyr Ser Ser Pro Pro Leu Asp
                165                 170                 175

Met Leu Asp Arg Ser Val Gln
            180

<210> SEQ ID NO 123
<211> LENGTH: 217
<212> TYPE: PRT
<213> ORGANISM: Zea mays

<400> SEQUENCE: 123

Met Val Ser Ser Leu Ser Val Ala Gly Val Lys Arg Glu Arg Val Asp
1               5                   10                  15

Asp Ala Glu Gly Glu Arg Ala Ser Ser Thr Ala Ala Leu Pro Arg Ala
            20                  25                  30

Cys Ala Gly Ala Glu Asp Asp Asp Asp Gly Ser Thr Arg Lys Lys
        35                  40                  45

Leu Arg Leu Thr Lys Glu Gln Ser Ala Leu Leu Glu Asp Arg Phe Lys
    50                  55                  60

Glu His Ser Thr Leu Asn Pro Lys Gln Lys Val Ala Leu Ala Lys Gln
65                  70                  75                  80

Leu Lys Leu Arg Pro Arg Gln Val Glu Val Trp Phe Gln Asn Arg Arg
                85                  90                  95

Ala Arg Thr Lys Leu Lys Gln Thr Glu Val Asp Cys Glu Leu Leu Lys
            100                 105                 110

Arg Cys Cys Glu Ser Leu Thr Glu Glu Asn Arg Arg Leu Gln Arg Glu
        115                 120                 125

Leu Gln Glu Leu Arg Ala Leu Lys Phe Ala Pro His Pro Gln Ala Pro
    130                 135                 140
```

```
Pro Ser Ser Ala Thr Gln Ala Gly Ala Ala Gly Val Val Pro Ala
145                 150                 155                 160

Pro Pro Pro Leu Tyr Met Gln Met Gln Met Pro Ala Ala Thr
            165                 170                 175

Leu Ser Leu Cys Pro Ser Cys Asp Arg Leu Ala Gly Pro Gly Ala Ala
            180                 185                 190

Ala Lys Ala Glu Pro Arg Pro Lys Ala Ala Thr His His Phe Phe
        195                 200                 205

Asn Pro Phe Thr His Ser Ala Ala Cys
    210                 215

<210> SEQ ID NO 124
<211> LENGTH: 240
<212> TYPE: PRT
<213> ORGANISM: Zea mays

<400> SEQUENCE: 124

Met Asp Gln Gln Gln Pro Ala Ala Ala Arg His Gly His Glu Met
1               5                   10                  15

Pro Phe Leu Arg Gly Val Asp Val Asn Arg Ala Pro Ala Gly Asp Thr
            20                  25                  30

Arg Arg Gly Ser Cys Ser Glu Asp Glu Glu Pro Gly Gly Ala Ser
        35                  40                  45

Ser Ser Pro Asn Ser Thr Leu Ser Ser Ser Leu Ser Gly Lys Arg Ala
    50                  55                  60

Ala Pro Ala Arg Ser Gly Gly Glu Val Ala Asp His Thr Pro Arg Ala
65                  70                  75                  80

Gly Gly Gly Ser Asp Asp Glu Asp Ser Gly Gly Gly Ser Arg Lys Lys
                85                  90                  95

Leu Arg Leu Ser Lys Asp Gln Ala Ala Val Leu Glu Glu Ser Phe Lys
            100                 105                 110

Glu His Asn Thr Leu Asn Pro Lys Gln Lys Ala Ala Leu Ala Lys Gln
        115                 120                 125

Leu Asn Leu Lys Pro Arg Gln Val Glu Val Trp Phe Gln Asn Arg Arg
    130                 135                 140

Ala Arg Thr Lys Leu Lys Gln Thr Glu Val Asp Cys Glu Phe Leu Lys
145                 150                 155                 160

Arg Cys Cys Glu Thr Leu Thr Glu Glu Asn Arg Arg Leu Gln Arg Glu
                165                 170                 175

Val Ala Glu Leu Arg Val Leu Lys Leu Val Ala Pro His His Tyr Ala
            180                 185                 190

Arg Met Pro Pro Pro Thr Thr Leu Thr Met Cys Pro Ser Cys Glu Arg
        195                 200                 205

Leu Ala Ser Ala Ser Ala Ser Ala Asp Gln Ala Gly Arg Ala Gly Pro
    210                 215                 220

Cys Trp Gly Pro Leu Pro Val Phe Val Asp Gly Pro Ala Arg Arg Pro
225                 230                 235                 240

<210> SEQ ID NO 125
<211> LENGTH: 182
<212> TYPE: PRT
<213> ORGANISM: Zea mays

<400> SEQUENCE: 125

Met Ser Ser Arg Lys Lys Lys Arg Lys Asp Ala Ala Ala Gly Gly
1               5                   10                  15
```

```
Ala Ser Ala Thr Asp Ala Ala Asn Gly His His His Gln Ser Lys
            20                  25                  30

Lys Thr Lys Thr Thr Ala Ala Arg Arg Asp Asp Gly Gly Gly Arg
            35                  40                  45

Lys Lys Leu Arg Leu Thr Ser Ala Gln Ala Thr Leu Leu Glu Asp Ser
 50                      55                  60

Phe Arg Ala His Asn Ile Leu Ser His Gly Glu Lys Gln Glu Leu Ala
 65                  70                  75                  80

Arg Gln Ala Gly Leu Ser Ala Arg Gln Val Glu Val Trp Phe Gln Asn
                 85                  90                  95

Arg Arg Ala Arg Thr Lys Leu Lys Gln Thr Glu Val Asp Cys Asp Leu
                100                 105                 110

Leu Arg Arg Trp Cys Ala Arg Leu Ser Asp Asp Asn Asp Arg Leu Arg
            115                 120                 125

Arg Asp Leu Ala Asp Leu Arg Arg Ala Ala Ser Ser Ser Ala Gly Leu
130                 135                 140

Gly Ala Val Val Cys Cys Ala Ser Cys Gly Ala Asp Arg Gln Leu Ala
145                 150                 155                 160

Leu Ala Ala Ala Ala Asp Asn Val Leu Pro Ser Val Ala Ser Pro Ser
                165                 170                 175

His Ser Pro His Leu Thr
            180

<210> SEQ ID NO 126
<211> LENGTH: 234
<212> TYPE: PRT
<213> ORGANISM: Zea mays

<400> SEQUENCE: 126

Met Ala Ala Ala Arg His Gly His Glu Met Pro Phe Leu Arg Gly Val
 1               5                  10                  15

Asp Val Asn Arg Ala Pro Ala Gly Asp Thr Arg Arg Gly Ser Cys Ser
            20                  25                  30

Glu Asp Asp Glu Glu Pro Gly Gly Ala Ser Ser Ser Pro Asn Ser Thr
        35                  40                  45

Leu Ser Ser Ser Leu Ser Gly Lys Arg Ala Ala Pro Ala Arg Ser Gly
 50                  55                  60

Gly Glu Val Ala Asp His Thr Pro Arg Ala Gly Gly Gly Ser Asp Asp
 65                  70                  75                  80

Glu Asp Ser Gly Gly Gly Ser Arg Lys Lys Leu Arg Leu Ser Lys Asp
                 85                  90                  95

Gln Ala Ala Val Leu Glu Glu Ser Phe Lys Glu His Asn Thr Leu Asn
                100                 105                 110

Pro Lys Gln Lys Ala Ala Leu Ala Lys Gln Leu Asn Leu Lys Pro Arg
            115                 120                 125

Gln Val Glu Val Trp Phe Gln Asn Arg Arg Ala Arg Thr Lys Leu Lys
        130                 135                 140

Gln Thr Glu Val Asp Cys Glu Phe Leu Lys Arg Cys Cys Glu Thr Leu
145                 150                 155                 160

Thr Glu Glu Asn Arg Arg Leu Gln Arg Glu Val Ala Glu Leu Arg Val
                165                 170                 175

Leu Lys Leu Val Ala Pro His His Tyr Ala Arg Met Pro Pro Pro Thr
            180                 185                 190

Thr Leu Thr Met Cys Pro Ser Cys Glu Arg Leu Ala Ser Ala Ser Ala
        195                 200                 205
```

Ser Ala Asp Gln Ala Gly Arg Ala Gly Pro Cys Trp Gly Pro Leu Pro
    210                 215                 220

Val Phe Val Asp Gly Pro Ala Arg Arg Pro
225                 230

<210> SEQ ID NO 127
<211> LENGTH: 229
<212> TYPE: PRT
<213> ORGANISM: Zea mays

<400> SEQUENCE: 127

Met Asn Arg Ala Leu Ser Val Ala Gly Ala Gly Ala Glu Glu Asp Glu
1               5                   10                  15

Ala Ala Val Ala Ala Ala Thr Ala Ala Ala Ser Ser Ser Pro Asn Asn
            20                  25                  30

Ser Ser Gly Ser Phe Ala Met Asp Ile Ser Ala Gln Gly Gln Gly Gln
        35                  40                  45

Gly Gln Asp Gln Ala Ala Pro Ala Ala Asp Arg Ala Cys Ser Arg Ala
    50                  55                  60

Ser Asp Glu Asp Asp Gly Gly Ser Ala Arg Lys Lys Leu Arg Leu Ser
65                  70                  75                  80

Lys Glu Gln Ser Ala Phe Leu Glu Glu Ser Phe Lys Val Arg Ala Thr
                85                  90                  95

Pro Asn Pro Lys Gln Lys Leu Ala Leu Ala Arg Gln Leu Asn Leu Arg
            100                 105                 110

Ala Arg Gln Val Glu Val Trp Phe Gln Asn Arg Arg Ala Arg Thr Lys
        115                 120                 125

Leu Lys Gln Thr Glu Val Asp Cys Glu His Leu Lys Arg Cys Cys Glu
    130                 135                 140

Thr Leu Thr Gly Glu Asn Arg Arg Leu His Lys Glu Leu Ala Glu Leu
145                 150                 155                 160

Arg Ala Leu Lys Ala Val Arg Pro Leu Leu His Met His Leu Pro Ala
                165                 170                 175

Thr Thr Leu Ser Met Cys Pro Ser Cys Glu Arg Val Ala Ser Thr Ser
            180                 185                 190

Ser Ala Ala Pro Ala Ala Pro Ala Pro Ala Ser Pro Ser Pro Ala Ala
        195                 200                 205

Gly Ala Gly Ile Ala Ala Ser Ala Pro Asp Pro Asp Gln Arg Pro Ser
    210                 215                 220

Ser Ser Phe Ala Ala
225

<210> SEQ ID NO 128
<211> LENGTH: 225
<212> TYPE: PRT
<213> ORGANISM: Zea mays

<400> SEQUENCE: 128

Met Pro Phe Leu Arg Gly Val Asp Val Asn Arg Ala Pro Ala Gly Asp
1               5                   10                  15

Thr Arg Arg Gly Ser Cys Ser Glu Asp Asp Glu Glu Pro Gly Gly Ala
            20                  25                  30

Ser Ser Ser Pro Asn Ser Thr Leu Ser Ser Ser Leu Ser Gly Lys Arg
        35                  40                  45

Ala Ala Pro Ala Arg Ser Gly Gly Glu Val Ala Asp His Thr Pro Arg
    50                  55                  60

```
Ala Gly Gly Gly Ser Asp Glu Asp Ser Gly Gly Ser Arg Lys
 65                  70                  75                  80

Lys Leu Arg Leu Ser Lys Asp Gln Ala Ala Val Leu Glu Glu Ser Phe
                 85                  90                  95

Lys Glu His Asn Thr Leu Asn Pro Lys Gln Lys Ala Ala Leu Ala Lys
            100                 105                 110

Gln Leu Asn Leu Lys Pro Arg Gln Val Glu Val Trp Phe Gln Asn Arg
        115                 120                 125

Arg Ala Arg Thr Lys Leu Lys Gln Thr Glu Val Asp Cys Glu Phe Leu
130                 135                 140

Lys Arg Cys Cys Glu Thr Leu Thr Glu Glu Asn Arg Arg Leu Gln Arg
145                 150                 155                 160

Glu Val Ala Glu Leu Arg Val Leu Lys Leu Val Ala Pro His His Tyr
                165                 170                 175

Ala Arg Met Pro Pro Thr Thr Leu Thr Met Cys Pro Ser Cys Glu
            180                 185                 190

Arg Leu Ala Ser Ala Ser Ala Ser Ala Asp Gln Ala Gly Arg Ala Gly
        195                 200                 205

Pro Cys Trp Gly Pro Leu Pro Val Phe Val Asp Gly Pro Ala Arg Arg
    210                 215                 220

Pro
225

<210> SEQ ID NO 129
<211> LENGTH: 242
<212> TYPE: PRT
<213> ORGANISM: Zea mays

<400> SEQUENCE: 129

Met Val Asn Arg Ala Pro Ser Leu Ser Ala Ala Gly Ala Ala Ala Glu
  1               5                  10                  15

Glu Asp Glu Gln Asp Glu Ala Gly Ala Ala Ala Ala Ala Ala Ala Ser
                 20                  25                  30

Ser Ser Pro Asn Asn Ser Ala Ser Ser Phe Pro Thr Asp Phe Ser Ala
             35                  40                  45

His Gly Gln Val Ala Pro Gly Ala Asp Arg Ala Cys Ser Arg Ala Ser
 50                  55                  60

Asp Glu Asp Asp Gly Gly Ser Ala Arg Lys Lys Leu Arg Leu Ser Lys
 65                  70                  75                  80

Glu Gln Ser Ala Phe Leu Glu Asp Ser Phe Lys Glu His Ala Thr Leu
                 85                  90                  95

Asn Pro Lys Gln Lys Leu Ala Leu Ala Lys Gln Leu Asn Leu Arg Pro
            100                 105                 110

Arg Gln Val Glu Val Trp Phe Gln Asn Arg Arg Ala Arg Thr Lys Leu
        115                 120                 125

Lys Gln Thr Glu Val Asp Cys Glu Tyr Leu Lys Arg Cys Cys Glu Thr
130                 135                 140

Leu Thr Glu Glu Asn Arg Arg Leu Gln Lys Glu Leu Ser Glu Leu Arg
145                 150                 155                 160

Ala Leu Lys Thr Val His Pro Phe Tyr Met His Leu Pro Ala Thr Thr
                165                 170                 175

Leu Ser Met Cys Pro Ser Cys Glu Arg Val Ala Ser Asn Ser Ala Pro
            180                 185                 190

Ala Pro Ala Ser Ser Pro Ser Pro Ala Thr Gly Ile Ala Ala Pro Ala
```

```
                195                 200                 205
Pro Glu Gln Arg Pro Ser Ser Phe Ala Ala Leu Phe Ser Ser Pro Leu
210                 215                 220

Asn Arg Pro Leu Ala Ala Gln Ala Gln Pro Gln Pro Gln Ala Pro Ala
225                 230                 235                 240

Asn Ser

<210> SEQ ID NO 130
<211> LENGTH: 259
<212> TYPE: PRT
<213> ORGANISM: Zea mays

<400> SEQUENCE: 130

Met Val Asn Arg Ala Pro Ser Val Ala Gly Ser Ala Leu Ala Leu Glu
1               5                   10                  15

Asp Asp Glu Glu Glu Pro Gly Ala Ala Ala Leu Ser Ser Ser Pro Asn
                20                  25                  30

Asp Ser Ala Gly Ser Phe Pro Leu Asp Leu Gly Gly Pro Arg Ala His
            35                  40                  45

Ala Glu Gly Ala Ala Ala Arg Ala Gly Gly Glu Arg Ser Ser Ser Arg
50                  55                  60

Ala Ser Asp Glu Asp Glu Gly Ala Ser Ala Arg Lys Lys Leu Arg Leu
65                  70                  75                  80

Ser Lys Glu Gln Ser Ala Phe Leu Glu Glu Ser Phe Lys Glu His Ser
                85                  90                  95

Thr Leu Asn Pro Lys Gln Lys Ala Ala Leu Ala Lys Gln Leu Asn Leu
            100                 105                 110

Arg Pro Arg Gln Val Glu Val Trp Phe Gln Asn Arg Arg Ala Arg Thr
        115                 120                 125

Lys Leu Lys Gln Thr Glu Val Asp Cys Glu Tyr Leu Lys Arg Cys Cys
130                 135                 140

Glu Thr Leu Thr Glu Glu Asn Arg Arg Leu His Lys Glu Leu Ala Glu
145                 150                 155                 160

Leu Arg Ala Leu Lys Thr Ala Pro Pro Phe Phe Met Arg Leu Pro Ala
                165                 170                 175

Thr Thr Leu Ser Met Cys Pro Ser Cys Glu Arg Val Ala Ser Gly Pro
            180                 185                 190

Ser Pro Ala Ser Thr Ser Ala Pro Ala Ser Ser Thr Pro Pro Ala Thr
        195                 200                 205

Ala Ala Thr Thr Ala Ile Ser Tyr Ala Ala Ala Ala Ala Ala Pro Val
210                 215                 220

Arg Ala Asp His Arg Pro Ser Ser Phe Ala Ala Leu Phe Ala Ala Thr
225                 230                 235                 240

Arg Ser Phe Pro Leu Ala Ser Gln Pro Arg Pro Pro Ala Pro Ala Ser
                245                 250                 255

Asn Cys Leu

<210> SEQ ID NO 131
<211> LENGTH: 227
<212> TYPE: PRT
<213> ORGANISM: Zea mays

<400> SEQUENCE: 131

Met Met Glu Arg Val Glu Asp Leu Gly Leu Ser Leu Ser Leu Ser Ser
1               5                   10                  15
```

```
Ser Leu Ala Ser Pro Arg Thr His His Val Ala Thr Met Leu Leu Arg
            20                  25                  30

Ala Pro Glu Lys Arg Phe Leu Glu Met Pro Leu Leu Leu Pro Ala Lys
        35                  40                  45

Arg Thr Thr Glu Val Thr Gly Glu Asp Gly Leu Arg Gly Gly Ser Asp
 50                  55                  60

Glu Glu Asp Gly Gly Cys Gly Ile Asp Gly Ser Arg Lys Lys Leu Arg
 65                  70                  75                  80

Leu Ser Lys Asp Gln Ser Ala Val Leu Glu Asp Ser Phe Arg Glu His
                85                  90                  95

Pro Thr Leu Asn Pro Arg Gln Lys Ala Ala Leu Ala Gln Gln Leu Gly
            100                 105                 110

Leu Arg Pro Arg Gln Val Glu Val Trp Phe Gln Asn Arg Arg Ala Arg
        115                 120                 125

Thr Lys Leu Lys Gln Thr Glu Val Asp Cys Glu Tyr Leu Lys Arg Cys
130                 135                 140

Cys Glu Thr Leu Thr Glu Glu Asn Arg Arg Leu Gln Lys Glu Val Gln
145                 150                 155                 160

Glu Leu Arg Ala Leu Lys Leu Val Ser Pro His Leu Tyr Met His Met
                165                 170                 175

Ser Pro Pro Thr Thr Leu Thr Met Ser Pro Ser Glu Arg Val Ser
            180                 185                 190

Ser Ser Asn Gly Asn Ser Ala Ala Ala Thr Ala Ala Ala Arg Ala Arg
        195                 200                 205

Ala Gly Ala Gly Ala Gly Ala Ile Val Cys His Pro Ile Asp Arg Ala
210                 215                 220

Thr Ser Thr
225

<210> SEQ ID NO 132
<211> LENGTH: 261
<212> TYPE: PRT
<213> ORGANISM: Zea mays

<400> SEQUENCE: 132

Met Ala Pro Gln Ser Leu Asp Leu Gly Leu Ser Leu Gly Leu Gly Val
 1               5                  10                  15

Ala Ala Phe Gln Pro Ser Phe Cys His Pro Ala Gly Asn Asp Ala Ala
            20                  25                  30

Glu Arg Glu Ala Ser Pro Thr Ala Asp Glu Arg Glu Arg Arg Cys Ser
        35                  40                  45

Pro Ala Gly Ser Pro Thr Ser Ser Gly Ser Gly Lys Arg Val Ala Ala
 50                  55                  60

Glu Arg Ser Ala Gly Ser Gly Ser Gly Asp Glu Asp Asp Gly Gly
 65                  70                  75                  80

Ala Arg Lys Lys Leu Arg Leu Ser Lys Asp Gln Ala Ala Val Leu Glu
                85                  90                  95

Glu Cys Phe Lys Thr His His Thr Leu Thr Pro Lys Gln Lys Ala Ala
            100                 105                 110

Leu Ala Ser Arg Leu Gly Leu Arg Ala Arg Gln Val Glu Val Trp Phe
        115                 120                 125

Gln Asn Arg Arg Ala Arg Thr Lys Leu Lys Gln Thr Glu Val Asp Cys
130                 135                 140

Glu Tyr Leu Arg Arg Trp Cys Glu Gln Leu Ala Glu Glu Asn Arg Arg
145                 150                 155                 160
```

-continued

```
Leu Gly Lys Glu Val Ala Glu Leu Arg Ala Leu Ser Ala Ala Pro Ala
                165                 170                 175

Pro Ala Ala Pro Leu Thr Ala Leu Thr Met Ser Leu Ser Ser Arg Arg
            180                 185                 190

Val Ser Ser Ser Cys Ser Ser Pro Pro Asn Thr His Ala His
        195                 200                 205

Ala Ala Ala Ala Gly Thr Gly Arg Ser Val Ala Ala Ala Ala Ala Thr
    210                 215                 220

Thr Leu Pro Ala His Arg Gln Phe Leu Cys Gly Phe Arg Asp Gly Gly
225                 230                 235                 240

Ala Ala Ala Ala Val Tyr Gly Thr Ser Ser Ala Leu Ala Lys Ala
                245                 250                 255

Leu Arg Ala Ala Arg
            260

<210> SEQ ID NO 133
<211> LENGTH: 225
<212> TYPE: PRT
<213> ORGANISM: Zea mays

<400> SEQUENCE: 133

Met Gly Ser Thr Ser Pro Ser Gly Leu Glu Leu Thr Met Ala Val Pro
1               5                   10                  15

Gly Leu Ser Ser Ser Gly Ser Glu Gly Phe Gly Cys Asn Asn Asn
                20                  25                  30

Asn Gly Ser Gly Asn Gly Asn Asn Met Arg Asp Leu Asp Met Asn Gln
            35                  40                  45

Pro Ala Ser Gly Gly Glu Glu Glu Phe Pro Met Gly Ser Val Glu
    50                  55                  60

Glu Glu Glu Asp Glu Arg Gly Gly Ala Gly Gly Pro His Arg Ala Lys
65                  70                  75                  80

Lys Leu Arg Leu Ser Lys Glu Gln Ser Arg Leu Leu Glu Glu Ser Phe
                85                  90                  95

Arg Leu Asn His Thr Leu Thr Pro Lys Gln Lys Glu Ala Leu Ala Val
                100                 105                 110

Lys Leu Lys Leu Arg Pro Arg Gln Val Glu Val Trp Phe Gln Asn Arg
            115                 120                 125

Arg Ala Arg Thr Lys Leu Lys Gln Thr Glu Leu Glu Cys Glu Tyr Leu
    130                 135                 140

Lys Arg Cys Phe Gly Ser Leu Thr Glu Glu Asn Arg Arg Leu Gln Arg
145                 150                 155                 160

Glu Val Glu Glu Leu Arg Ala Met Arg Val Ala Pro Pro Thr Val Leu
                165                 170                 175

Ser Pro His Thr Arg Gln Pro Leu Pro Ala Ser Ala Leu Thr Met Ser
            180                 185                 190

Pro Arg Ser Glu Arg Ile Thr Ala Ala Thr Ala Ala Arg Thr Pro Arg
        195                 200                 205

Pro Pro Pro Ala Ala Ser Pro Phe His Pro Arg Pro Ser Ala Ala
    210                 215                 220

Phe
225

<210> SEQ ID NO 134
<211> LENGTH: 221
<212> TYPE: PRT
```

<213> ORGANISM: Zea mays

<400> SEQUENCE: 134

```
Met Tyr Ser Thr Arg Glu Glu Glu Gly Val Gly Lys Ser Trp Leu Gly
1               5                   10                  15

Leu Gly Ile Gly Gly Gly Ser Gly Gly Cys Asp Leu Met Gln Arg Asn
            20                  25                  30

Asn Arg Pro Pro Val Gln Phe Asp Leu Leu Phe Pro Pro Gln Gly Val
        35                  40                  45

Val Glu Gly Val Ala Ala Ser Lys Lys Ala Glu Lys Gly Gly Gly Gly
    50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Val Trp Phe Gln Asn Arg Arg Ala Arg Thr Lys Leu Lys Gln Thr
130                 135                 140

Glu Ala Asp Cys Glu Ile Leu Lys Arg Cys Cys Glu Ser Leu Thr Gly
145                 150                 155                 160

Glu Asn Gln Arg Leu Arg Leu Glu Leu Ala Gln Leu Gln Gly Ser Glu
                165                 170                 175

Ala Gly Leu Tyr Leu Gln Ser Ser Phe Pro Pro Leu Ala Ala Ala Met
            180                 185                 190

Ala Ser Val Ser Pro Ser Ser Asp Lys Val Ile Thr Val Ala Ser Gly
        195                 200                 205

Gly Glu Thr Ser Gly Arg Ser Ser Thr Ser Tyr Ser Ser
    210                 215                 220
```

<210> SEQ ID NO 135
<211> LENGTH: 272
<212> TYPE: PRT
<213> ORGANISM: Zea mays

<400> SEQUENCE: 135

```
Met Ala Pro Gln Ser Leu Asp Leu Gly Leu Ser Leu Gly Leu Gly Val
1               5                   10                  15

Ala Ala Phe Gln Pro Ser Ser Phe Cys His Pro Gly Asn Ala Val Val
            20                  25                  30

Val Pro Ala Ala Ala Glu Arg Glu Ala Ser Pro Ala Ala Ala Glu Glu
        35                  40                  45

Arg Glu Arg Arg Cys Ser Pro Ala Gly Ser Pro Val Ser Ser Gly Ser
    50                  55                  60

Gly Ser Gly Asn Lys Arg Ala Ala Ala Glu Arg Ser Ala Gly Ala Gly
65                  70                  75                  80

Ala Gly Ser Gly Asp Glu Asp Asp Gly Ala Ala Arg Lys Lys Leu
                85                  90                  95

Arg Leu Ser Lys Asp Gln Ala Ala Val Leu Glu Glu Cys Phe Lys Thr
            100                 105                 110

His His Thr Leu Thr Pro Lys Gln Lys Val Ala Leu Ala Ser Ser Leu
        115                 120                 125

Gly Leu Arg Pro Arg Gln Val Glu Val Trp Phe Gln Asn Arg Arg Ala
```

-continued

```
                130                 135                 140
Arg Thr Lys Leu Lys Gln Thr Glu Val Asp Cys Glu Tyr Leu Lys Arg
145                 150                 155                 160

Trp Cys Glu Gln Leu Ala Glu Asn Arg Arg Leu Gly Lys Glu Val
                165                 170                 175

Ala Glu Leu Arg Ala Leu Ser Ala Ala Pro Ala Ala Pro Leu Thr Thr
                180                 185                 190

Leu Thr Met Ser Leu Ser Ser Arg Arg Val Ala Ser Ser Ser Pro Ser
                195                 200                 205

Ser Ser Ser Ser Pro Arg Pro Ser Ile Pro Gly Ala Ala Ala Ser
    210                 215                 220

Gly Gly Ser Met Ala Ser Pro Ala Ala Ala Thr Leu Pro Ala His
225                 230                 235                 240

Arg Gln Phe Phe Cys Gly Phe Arg Asp Ala Gly Ala Ala Ala Ala
                245                 250                 255

Tyr Gly Thr Ala Ser Ala Gly Leu Ala Lys Pro Val Arg Ala Ala Arg
                260                 265                 270

<210> SEQ ID NO 136
<211> LENGTH: 223
<212> TYPE: PRT
<213> ORGANISM: Zea mays

<400> SEQUENCE: 136

Met Tyr Ser Cys Thr Arg Ala Met Glu Glu Glu Gly Val Gly Lys Ser
1               5                   10                  15

Trp Leu Gly Leu Gly Ile Gly Gly Gly Asp Leu Met Lys Arg Asn
                20                  25                  30

Asn Arg Pro Pro Val Gln Leu Asp Asp Leu Leu Ser Phe Pro Pro Gln
                35                  40                  45

Ser Val Ala Ala Ser Lys Lys Gln Ala Glu Lys Gly Gly Gly Gly
                50                  55                  60

Arg Lys Arg His Lys Ile Val Val Thr Ala Asp Glu Asp Gly Arg Gln
65                  70                  75                  80

Ser Pro His Gly Gly Ala Arg Lys Lys Leu Arg Leu Thr Lys Ala Gln
                85                  90                  95

Ser Thr Leu Leu Glu Asp Thr Phe Arg Ala His Asn Ile Leu Ser His
                100                 105                 110

Ala Gln Lys Gln Glu Leu Ala Arg Gln Val Asn Leu Ser Ala Arg Gln
                115                 120                 125

Val Glu Val Trp Phe Gln Asn Arg Arg Ala Arg Thr Lys Leu Lys Gln
                130                 135                 140

Thr Glu Ala Asp Cys Glu Val Leu Lys Arg Tyr Cys Glu Arg Leu Thr
145                 150                 155                 160

Gly Glu Asn Gln Arg Leu Arg Leu Glu Leu Ala Gln Leu Gln Arg Ser
                165                 170                 175

Pro Ala Ala Glu Glu Ala Gly Phe Tyr Val Gln Ser Ser Phe Pro Phe
                180                 185                 190

Pro Pro Leu Ala Thr Ala Met Ala Ser Val Ser Pro Ser Ser Asp Lys
                195                 200                 205

Val Val Ala Val Thr Ser Gly Lys Ser Ser Thr Ser Tyr Ser Ser
    210                 215                 220

<210> SEQ ID NO 137
<211> LENGTH: 241
```

```
<212> TYPE: PRT
<213> ORGANISM: Zea mays

<400> SEQUENCE: 137

Met Glu Glu Glu Gly Val Gly Lys Ser Trp Leu Ala Leu Gly Ile Gly
1               5                   10                  15

Gly Gly Asp Leu Met Lys Arg Asn Asn Arg Pro Val Gln Phe Asp
            20                  25                  30

Leu Leu Phe Pro Pro Gln Ser Val Lys Glu Glu Gly Ala Ala Ser Lys
            35                  40                  45

Lys Ala Glu Lys Gly Gly Arg Lys Arg Leu Lys Val Val Thr Ala
50                  55                  60

Asp Glu Asp Gly Arg Gln Ser Pro His Gly Gly Pro Gly Pro Ser Asp
65                  70                  75                  80

Gly Ser Gly Ala Gly Ala Arg Lys Lys Leu Arg Leu Thr Asn Glu Gln
                85                  90                  95

Ser Thr Leu Leu Glu Asp Thr Phe Arg Ala His Asn Ile Leu Ser Asn
                100                 105                 110

Ala Gln Lys Gln Glu Leu Ala Arg Gln Val Asp Leu Ser Ala Arg Gln
        115                 120                 125

Val Glu Val Trp Phe Gln Asn Arg Arg Ala Arg Thr Lys Leu Lys Gln
    130                 135                 140

Thr Glu Val Asp Cys Glu Ile Leu Lys Arg Cys Cys Glu Ser Leu Thr
145                 150                 155                 160

Gly Glu Asn Gln Arg Leu Arg Leu Glu Leu Ala Gln Leu Gln Arg Ser
                165                 170                 175

Ala Ala Ala Ala Ala Glu Ala Gly Leu Tyr Val Gln Ser Ser Phe Pro
            180                 185                 190

Pro Leu Ala Thr Ala Thr Ala Thr Ala Ser Val Ser Pro Ser Ser Asp
        195                 200                 205

Lys Val Ile Ala Val Ser Ser Gly Gly Glu Thr Ser Gly Lys Ser Ser
    210                 215                 220

Thr Ser Tyr Ser Ser Arg Arg Ala Gly Phe Pro Ser Ile Met Gly Ser
225                 230                 235                 240

Arg

<210> SEQ ID NO 138
<211> LENGTH: 262
<212> TYPE: PRT
<213> ORGANISM: Zea mays

<400> SEQUENCE: 138

Met Glu Gln Glu Glu Val Gly Leu Ala Leu Gly Leu Ser Leu Gly Ser
1               5                   10                  15

Gly His His His Gln Glu Leu Lys Pro Gln His Pro Ser His Pro Cys
            20                  25                  30

Ala Ala Leu Leu Glu Pro Ser Leu Ser Leu Ser Gly Pro Ala Thr Lys
            35                  40                  45

Asp Asp Gly Pro Thr Ala Pro Val Arg Arg Phe Ala Ala Val Lys Arg
50                  55                  60

Glu Leu Gln Thr Met Glu Gly Asn Asp Asp Glu Ala Thr Gly Arg Val
65                  70                  75                  80

Leu Val Tyr Ser Val Ala Ser Ser Ala Val Val Thr Ala Asp Asp Asp
                85                  90                  95

Glu Gly Cys Asn Ser Ser Arg Lys Lys Leu Arg Leu Ser Lys Glu Gln
```

```
                100             105             110
Ser Ala Leu Leu Glu Asp His Phe Lys Glu His Ser Thr Leu Asn Pro
            115                 120                 125
Lys Gln Lys Ala Ala Leu Ala Arg Gln Leu Asn Leu Ser Pro Arg Gln
        130                 135                 140
Val Glu Val Trp Phe Gln Asn Arg Arg Ala Arg Thr Lys Leu Lys Gln
145                 150                 155                 160
Thr Glu Val Asp Cys Glu Ile Leu Lys Arg Cys Cys Glu Thr Leu Thr
                165                 170                 175
Glu Glu Asn Arg Arg Leu His Arg Glu Leu Gln Gln Leu Arg Ala Leu
            180                 185                 190
Ser His Pro His Pro His Pro Ala Ala Phe Phe Met Pro Thr Ala Ala
        195                 200                 205
Ala Ala Ala Leu Ser Ile Ser Pro Ser Ser Gln Arg Leu Val Ala Thr
        210                 215                 220
Gly Ala Ser Ala Ala Ala Thr Thr Ala Gly Ala Asp Asn Lys Pro
225                 230                 235                 240
Lys Ala Gly Gly Pro Gly Gly Arg Ala Pro His Val Phe Ser Pro Phe
                245                 250                 255
Thr Asn Ser Ala Ala Cys
            260

<210> SEQ ID NO 139
<211> LENGTH: 295
<212> TYPE: PRT
<213> ORGANISM: Zea mays

<400> SEQUENCE: 139

Met Met Pro Gln Ala Ser Ala Ser Leu Asp Leu Gly Leu Ser Leu Gly
1               5                   10                  15
Leu Thr Leu Thr Ser Gln Gly Ser Leu Ser Ser Ser Thr Thr Thr Ala
            20                  25                  30
Gly Ser Ser Ser Pro Trp Ala Ala Ala Leu Ser Ser Val Val Ala Asp
        35                  40                  45
Val Ala Arg Ala Arg Gly Asp Ala Tyr Ala Gln His His Ala Gly Ala
    50                  55                  60
Ala Met Thr Met Arg Ala Ser Thr Ser Pro Asp Ser Gly Asp Thr Thr
65                  70                  75                  80
Thr Ala Lys Arg Glu Arg Glu Gly Leu Glu Arg Thr Gly Ser Ala
                85                  90                  95
Gly Gly Val Arg Ser Asp Glu Glu Asp Gly Ala Asp Gly Gly Ala Gly
                100                 105                 110
Gly Arg Lys Lys Leu Arg Leu Ser Lys Asp Gln Ala Ala Val Leu Glu
            115                 120                 125
Glu Cys Phe Lys Thr His Ser Thr Leu Asn Pro Lys Gln Lys Val Gln
        130                 135                 140
Leu Ala Asn Arg Leu Gly Leu Arg Pro Arg Gln Val Glu Val Trp Phe
145                 150                 155                 160
Gln Asn Arg Arg Ala Arg Thr Lys Leu Lys Gln Thr Glu Val Asp Cys
                165                 170                 175
Glu Tyr Leu Lys Arg Trp Cys Asp Arg Leu Ala Asp Glu Asn Lys Arg
            180                 185                 190
Leu Glu Lys Glu Leu Ala Asp Leu Arg Ala Leu Lys Ala Ala Pro Pro
        195                 200                 205
```

```
Ser Ser Ala Ala Ala Gln Pro Ala Ser Ala Ala Thr Leu Thr Met
    210                 215                 220

Ser Pro Ser Ser Arg Arg Val Ala Ala Ala Ser His His His Gln
225                 230                 235                 240

Pro Pro Pro Pro Gln Cys His Pro Lys Pro Thr Val Ala Ala Gly Gly
                245                 250                 255

Gly Ser Val Val Pro Arg Pro Ser His Cys Gln Phe Phe Pro Ala Ala
                260                 265                 270

Ala Val Asp Arg Thr Ser Gln Gly Thr Trp Asn Thr Ala Ala Pro Pro
            275                 280                 285

Leu Val Thr Arg Glu Leu Phe
        290             295
```

<210> SEQ ID NO 140
<211> LENGTH: 267
<212> TYPE: PRT
<213> ORGANISM: Zea mays

<400> SEQUENCE: 140

```
Met Ser Ser Leu Thr Thr Ala Ala Ser Ser Ser Ser Met Glu Glu
1               5                   10                  15

His Cys Tyr Ser Val Ser Ala Glu Glu Val Val Gly Thr His Leu Ser
            20                  25                  30

Leu Gly Ile Gly Gly Gly Gly Gly Gly Asp Lys Arg Thr Met
        35                  40                  45

Leu Thr Leu Pro Pro Ser Arg Thr Val Gln Leu Phe Gly Glu Val Leu
    50                  55                  60

Ser Val Gln Asp Gly Asp Gly Thr Gln Ala Leu Arg His His His Thr
65                  70                  75                  80

Gly Arg Pro Pro Ala Ala Ser Ser Arg Lys Lys Arg Lys Asp Ala
                85                  90                  95

Ala Ala Ala Gly Gly Ala Ser Ala Thr Asp Ala Ala Ala Asn Gly His
            100                 105                 110

His His Gln Ser Lys Lys Thr Lys Thr Thr Ala Ala Arg Arg Asp Asp
        115                 120                 125

Gly Gly Gly Gly Arg Lys Lys Leu Arg Leu Thr Ser Ala Gln Ala Thr
    130                 135                 140

Leu Leu Glu Asp Ser Phe Arg Ala His Asn Ile Leu Ser His Gly Glu
145                 150                 155                 160

Lys Gln Glu Leu Ala Arg Gln Ala Gly Leu Ser Ala Arg Gln Val Glu
                165                 170                 175

Val Trp Phe Gln Asn Arg Arg Ala Arg Thr Lys Leu Lys Gln Thr Glu
            180                 185                 190

Val Asp Cys Asp Leu Leu Arg Arg Trp Cys Ala Arg Leu Ser Asp Asp
        195                 200                 205

Asn Asp Arg Leu Arg Arg Asp Leu Ala Asp Leu Arg Arg Ala Ala Ser
    210                 215                 220

Ser Ser Ala Gly Leu Gly Ala Val Val Cys Ser Ala Ser Gly Ala
225                 230                 235                 240

Asp Arg Gln Leu Ala Leu Ala Ala Ala Asp Asn Val Leu Pro Ser
                245                 250                 255

Val Ala Ser Pro Ser His Ser Pro His Leu Thr
            260                 265
```

<210> SEQ ID NO 141

<211> LENGTH: 245
<212> TYPE: PRT
<213> ORGANISM: Zea mays

<400> SEQUENCE: 141

Met Ala Gln Glu Asp Val His Leu Asp Asp Ala Gly Leu Ala Leu Cys
1               5                   10                  15

Leu Ser Leu His Gly Thr Ser Ser Arg Leu Ser Thr Glu Ala Pro
            20                  25                  30

Arg Thr Leu Glu Pro Pro Ser Leu Thr Leu Ser Met Pro Asp Glu Ala
            35                  40                  45

Thr Ala Thr Ala Thr Gly Gly Ser Gly Gly Ser Gly Gly Ala Ala Arg
50                  55                  60

Ser Val Ser Ser Arg Ser Val Glu Gly Val Lys Arg Glu Arg Val Asp
65                  70                  75                  80

Asp Ala Glu Gly Glu Arg Ala Ser Ser Thr Ala Ala Ala Arg Val
                85                  90                  95

Cys Ala Gly Ala Glu Asp Asp Asp Gly Ser Thr Arg Lys Lys Leu
            100                 105                 110

Arg Leu Thr Lys Glu Gln Ser Lys Leu Leu Glu Asp Arg Phe Lys Asp
            115                 120                 125

His Ser Thr Leu Asn Pro Lys Gln Lys Ile Ala Leu Ala Lys Gln Leu
130                 135                 140

Lys Leu Arg Pro Arg Gln Val Glu Val Trp Phe Gln Asn Arg Arg Ala
145                 150                 155                 160

Arg Thr Lys Leu Lys Gln Thr Glu Val Asp Cys Glu Leu Leu Lys Arg
                165                 170                 175

Cys Cys Glu Ser Leu Ser Glu Glu Asn Arg Arg Leu Gln Arg Glu Leu
            180                 185                 190

Gln Glu Leu Arg Ala Leu Lys Leu Ala Gly Pro His Pro Gln Ala Pro
            195                 200                 205

Ser Ser Ser Pro Ala Ala Ala Thr Gln Gly Val Pro Val Pro Val Pro
            210                 215                 220

Pro Pro Leu Tyr Val Gln Met Gln Met Gln Leu Ser Ser Ser Arg Cys
225                 230                 235                 240

Ser Arg Pro Pro Arg
                245

<210> SEQ ID NO 142
<211> LENGTH: 292
<212> TYPE: PRT
<213> ORGANISM: Zea mays

<400> SEQUENCE: 142

Met Ala Gln Glu Asp Val His Leu Asp Asp Ala Gly Leu Ala Leu Gly
1               5                   10                  15

Leu Ser Leu Gly Ser Gly Ser Gly Gly Ala Ser Gly Ala Ala Arg His
            20                  25                  30

Gly Gly Ile Ser Arg Arg Leu Ser Arg Glu Val Arg Leu Pro Ser Pro
            35                  40                  45

His Pro Leu Glu Pro Ser Leu Thr Leu Ser Leu Pro Asp Glu Ala Thr
50                  55                  60

Ala Thr Gly Ser Gly Gly Gly Ala Ala His Ser Val Ser Ser Leu
65                  70                  75                  80

Ser Val Ala Gly Val Lys Arg Glu Arg Val Asp Asp Ala Glu Gly Glu
                85                  90                  95

-continued

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
            115                 120                 125

Glu Gln Ser Ala Leu Leu Glu Asp Arg Phe Lys Glu His Ser Thr Leu
    130                 135                 140

Asn Pro Lys Gln Lys Val Ala Leu Ala Lys Gln Leu Lys Leu Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
            195                 200                 205

Ala Leu Lys Phe Ala Pro His Pro Gln Ala Pro Pro Ser Ser Ala Thr
    210                 215                 220

Gln Ala Gly Ala Ala Gly Val Val Pro Ala Pro Pro Pro Leu
225                 230                 235                 240

Tyr Met Gln Met Gln Met Pro Ala Ala Ala Thr Leu Ser Leu Ser Pro
                245                 250                 255

Ser Ser Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
            275                 280                 285

Ser Ala Ala Cys
    290

<210> SEQ ID NO 143
<211> LENGTH: 315
<212> TYPE: PRT
<213> ORGANISM: Zea mays

<400> SEQUENCE: 143

Met Ala Asp Ser Gly Ser Asp Leu Val Leu Gly Leu Gly Met Gly Val
1               5                   10                  15

Gly Val Arg Arg Glu Glu Glu Thr Gln Arg Gly Arg Arg Asp Arg Glu
            20                  25                  30

Ala Arg Arg Glu Leu Glu Phe Glu Thr Gly Arg Cys Ala Arg Pro Ser
            35                  40                  45

Pro Glu Pro Ala Val Arg Leu Thr Leu Leu Pro Gly Leu Val Pro Ser
    50                  55                  60

Leu Gly Leu Pro Trp Pro Leu Ser Ser Glu Thr Asn Arg Glu Val Ser
65                  70                  75                  80

Thr Arg Gly Phe Asp Asp Val Asn Arg Ala Leu Ser Val Ala Gly Ala
                85                  90                  95

Gly Ala Glu Glu Asp Glu Ala Ala Val Ala Ala Thr Ala Ala Ala
            100                 105                 110

Ser Ser Ser Pro Asn Asn Ser Ser Gly Ser Phe Ala Met Asp Ile Ser
            115                 120                 125

Ala Gln Gly Gln Gly Gln Gly Gln Asp Gln Ala Ala Pro Ala Ala Asp
    130                 135                 140

Arg Ala Cys Ser Arg Ala Ser Asp Glu Asp Asp Gly Gly Ser Ala Arg
145                 150                 155                 160

Lys Lys Leu Arg Leu Ser Lys Glu Gln Ser Ala Phe Leu Glu Glu Ser

```
               165                 170                 175
Phe Lys Val Arg Ala Thr Pro Asn Pro Lys Gln Lys Leu Ala Leu Ala
            180                 185                 190

Arg Gln Leu Asn Leu Arg Ala Arg Gln Val Glu Val Trp Phe Gln Asn
        195                 200                 205

Arg Arg Ala Arg Thr Lys Leu Lys Gln Thr Glu Val Asp Cys Glu His
    210                 215                 220

Leu Lys Arg Cys Cys Glu Thr Leu Thr Gly Glu Asn Arg Arg Leu His
225                 230                 235                 240

Lys Glu Leu Ala Glu Leu Arg Ala Leu Lys Ala Val Arg Pro Leu Leu
            245                 250                 255

His Met His Leu Pro Ala Thr Thr Leu Ser Met Ser Pro Ser Ser Glu
        260                 265                 270

Arg Val Ala Ser Thr Ser Ser Ala Ala Pro Ala Ala Pro Ala Pro Ala
    275                 280                 285

Ser Pro Ser Pro Ala Ala Gly Ala Gly Ile Ala Ala Ser Ala Pro Asp
290                 295                 300

Pro Asp Gln Arg Pro Ser Ser Ser Phe Ala Ala
305                 310                 315

<210> SEQ ID NO 144
<211> LENGTH: 335
<212> TYPE: PRT
<213> ORGANISM: Zea mays

<400> SEQUENCE: 144

Met Glu Leu Ala Leu Ser Leu Gly Glu Thr Met Ala Asp Ala Gly Arg
1               5                   10                  15

Asp Leu Met Leu Gly Leu Gly Met Gly Val Gly Val Arg Arg Glu Glu
            20                  25                  30

Glu Ala Gln Arg Gly Arg Arg Asp Arg Glu Val Arg Arg Glu Leu Glu
        35                  40                  45

Phe Thr Ala Arg Ser Ala Arg Ser Ser Pro Glu Pro Ala Val Arg Leu
    50                  55                  60

Thr Leu Leu His Gly Leu Gly Leu Pro Trp Pro Pro Pro Pro Ser Ser
65                  70                  75                  80

Glu Thr Asn Arg His Leu Glu Ala Ser Ala Arg Gly Phe Asp Val Asn
            85                  90                  95

Arg Ala Pro Ser Leu Ser Ala Ala Gly Ala Ala Ala Glu Glu Asp Glu
        100                 105                 110

Glu Gln Asp Glu Ala Gly Ala Ala Ala Ala Ala Ser Ser Ser Pro
    115                 120                 125

Asn Asn Ser Ala Ser Ser Phe Pro Thr Asp Phe Ser Ala His Gly Gln
130                 135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
            165                 170                 175

Ala Phe Leu Glu Asp Ser Phe Lys Glu His Ala Thr Leu Asn Pro Lys
        180                 185                 190

Gln Lys Leu Ala Leu Ala Lys Gln Leu Asn Leu Arg Pro Arg Gln Val
    195                 200                 205

Glu Val Trp Phe Gln Asn Arg Arg Ala Arg Thr Lys Leu Lys Gln Thr
    210                 215                 220
```

```
Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
            245                 250                 255

Thr Val His Pro Phe Tyr Met His Leu Pro Ala Thr Thr Leu Ser Met
        260                 265                 270

Ser Pro Ser Ser Glu Arg Val Ala Ser Asn Ser Ala Pro Ala Pro Ala
    275                 280                 285

Ser Ser Pro Ser Pro Ala Thr Gly Ile Ala Ala Pro Ala Pro Glu Gln
290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
            325                 330                 335

<210> SEQ ID NO 145
<211> LENGTH: 354
<212> TYPE: PRT
<213> ORGANISM: Zea mays

<400> SEQUENCE: 145

Met Glu Leu Gly Leu Ser Leu Gly Asp Ala Ala Val Pro Asp Ala Gly
1               5                   10                  15

Arg Ala Ala Pro Glu Leu Gly Leu Gly Leu Gly Val Gly Ile Gly Ser
            20                  25                  30

Asn Ala Ala Gly Thr Gly Arg Gly Ser Lys Ala Ala Gly Thr Thr Gly
        35                  40                  45

Thr Thr Gly Trp Trp Ala Ala Pro Ala Thr Pro Glu Ser Ala Val Arg
    50                  55                  60

Leu Ser Leu Val Ser Ser Leu Gly Leu Gln Trp Pro Pro Pro Asp Gly
65                  70                  75                  80

Gly Ile Cys His Val Gly Arg Asp Glu Ala Pro Ala Arg Gly Phe Asp
                85                  90                  95

Val Asn Arg Ala Pro Ser Val Ala Gly Ser Ala Leu Ala Leu Glu Asp
            100                 105                 110

Asp Glu Glu Glu Pro Gly Ala Ala Ala Leu Ser Ser Ser Pro Asn Asp
        115                 120                 125

Ser Ala Gly Ser Phe Pro Leu Asp Leu Gly Gly Pro Arg Ala His Ala
    130                 135                 140

Glu Gly Ala Ala Ala Arg Ala Gly Gly Glu Arg Ser Ser Ser Arg Ala
145                 150                 155                 160

Ser Asp Glu Asp Glu Gly Ala Ser Ala Arg Lys Lys Leu Arg Leu Ser
                165                 170                 175

Lys Glu Gln Ser Ala Phe Leu Glu Glu Ser Phe Lys Glu His Ser Thr
            180                 185                 190

Leu Asn Pro Lys Gln Lys Ala Ala Leu Ala Lys Gln Leu Asn Leu Arg
        195                 200                 205

Pro Arg Gln Val Glu Val Trp Phe Gln Asn Arg Arg Ala Arg Thr Lys
    210                 215                 220

Leu Lys Gln Thr Glu Val Asp Cys Glu Tyr Leu Lys Arg Cys Cys Glu
225                 230                 235                 240

Thr Leu Thr Glu Glu Asn Arg Arg Leu His Lys Glu Leu Ala Glu Leu
                245                 250                 255

Arg Ala Leu Lys Thr Ala Pro Pro Phe Phe Met Arg Leu Pro Ala Thr
            260                 265                 270
```

Thr Leu Ser Met Ser Pro Ser Ser Glu Arg Val Ala Ser Gly Pro Ser
            275                 280                 285

Pro Ala Ser Thr Ser Ala Pro Ala Ser Ser Thr Pro Pro Ala Thr Ala
        290                 295                 300

Ala Thr Thr Ala Ile Ser Tyr Ala Ala Ala Ala Ala Ala Pro Val Arg
305                 310                 315                 320

Ala Asp His Arg Pro Ser Ser Phe Ala Ala Leu Phe Ala Ala Thr Arg
                325                 330                 335

Ser Phe Pro Leu Ala Ser Gln Pro Arg Pro Ala Pro Ala Ser Asn
            340                 345                 350

Cys Leu

<210> SEQ ID NO 146
<211> LENGTH: 319
<212> TYPE: PRT
<213> ORGANISM: Zea mays

<400> SEQUENCE: 146

Met Asp Ile Met Ala Leu Asn Ala Arg Asp Glu Glu Gln Tyr Gly Asn
1               5                   10                  15

Asn His Leu Gly Leu Gly Leu Ser Leu Ser Leu Gly Leu Gly Val Ala
            20                  25                  30

Thr Ala Ala Pro Val Glu Val Glu Pro Pro Pro Pro Arg Gln Gln
        35                  40                  45

Gln Gln Arg Ala Ile Ser Val Ala Pro Ile Thr Ser Leu Pro Ala Pro
    50                  55                  60

Gln Trp Trp Lys Trp Asn Gly Pro Gly Leu Phe Phe Gly Thr Thr Met
65                  70                  75                  80

Asp Gln Gln Gln Gln Pro Ala Ala Ala Arg His Gly His Glu Met Pro
                85                  90                  95

Phe Leu Arg Gly Val Asp Val Asn Arg Ala Pro Ala Gly Asp Thr Arg
            100                 105                 110

Arg Gly Ser Cys Ser Glu Asp Asp Glu Glu Pro Gly Gly Ala Ser Ser
        115                 120                 125

Ser Pro Asn Ser Thr Leu Ser Ser Ser Leu Ser Gly Lys Arg Ala Ala
130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
                165                 170                 175

Arg Leu Ser Lys Asp Gln Ala Ala Val Leu Glu Glu Ser Phe Lys Glu
            180                 185                 190

His Asn Thr Leu Asn Pro Lys Gln Lys Ala Ala Leu Ala Lys Gln Leu
        195                 200                 205

Asn Leu Lys Pro Arg Gln Val Glu Val Trp Phe Gln Asn Arg Arg Ala
    210                 215                 220

Arg Thr Lys Leu Lys Gln Thr Glu Val Asp Cys Glu Phe Leu Lys Arg
225                 230                 235                 240

Cys Cys Glu Thr Leu Thr Glu Glu Asn Arg Arg Leu Gln Arg Glu Val
                245                 250                 255

Ala Glu Leu Arg Val Leu Lys Leu Val Ala Pro His His Tyr Ala Arg
            260                 265                 270

Met Pro Pro Pro Thr Thr Leu Thr Met Ser Pro Ser Ser Glu Arg Leu
        275                 280                 285

Ala Ser Ala Ser Ala Ser Ala Asp Gln Ala Gly Arg Ala Gly Pro Cys
            290                 295                 300

Trp Gly Pro Leu Pro Val Phe Val Asp Gly Pro Ala Arg Arg Pro
305                 310                 315

<210> SEQ ID NO 147
<211> LENGTH: 331
<212> TYPE: PRT
<213> ORGANISM: Zea mays

<400> SEQUENCE: 147

Met Glu Leu Glu Leu Ser Leu Gly Asp Ser Arg Ala Pro Ala Lys Ser
1               5                   10                  15

Ala Ser Thr Pro Ala Ala Leu Thr Pro Ile His Ala Gly Ala Gly Gly
            20                  25                  30

Glu Gly His Glu Leu Ala Leu Glu Leu Gly Val Gly Ala Ala Lys Arg
        35                  40                  45

Ala Glu Gln Asp Asn Gln Lys Thr Pro Val Gln Pro Glu His Val Gln
    50                  55                  60

Glu Glu Glu Glu Glu Glu Thr Cys Pro Tyr Ser Glu Ser Pro Ala
65                  70                  75                  80

Glu Leu Ser Leu Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
            100                 105                 110

Val Asp Ala Val Leu Val Asp Gly Gly Asp Ala Ala Gln Gly Arg Pro
        115                 120                 125

Ala Leu Ser Thr Ser Phe Leu Pro Ser Glu Phe Leu Val Arg Arg Gln
    130                 135                 140

Ala Asp Asp Gln Glu Ala Ala Ala Glu Asp Glu Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
        195                 200                 205

Val Trp Phe Gln Asn Arg Arg Ala Arg Ser Lys Leu Lys Gln Thr Glu
    210                 215                 220

Val Asp Cys Glu Tyr Leu Lys Arg Trp Cys Glu Lys Leu Ala Gln Glu
225                 230                 235                 240

Asn Arg Arg Leu Gln Arg Glu Val Ala Glu Leu Arg Arg Leu Cys Ser
                245                 250                 255

Ala Ala Tyr Pro Phe Tyr Gly Ala Ala Gly Phe Gly Val Ala Thr
            260                 265                 270

Ala Arg Val Ser Pro Ser Ser Asp Asn Asp Val Ser Glu Ala Ala
        275                 280                 285

Ile Ser Gly Ala Pro Ser Ala Ala Pro Pro Ser Thr Leu Phe
    290                 295                 300

Ala Ser Trp Pro Pro His Phe Gly Pro Phe Thr Val Val Val Pro Pro
305                 310                 315                 320

Leu Leu Arg Arg Gln Pro Ser Ala Thr Thr Ser
                325                 330

<210> SEQ ID NO 148
<211> LENGTH: 241
<212> TYPE: PRT
<213> ORGANISM: Zea mays

<400> SEQUENCE: 148

```
Met Glu Glu Gly Val Gly Lys Ser Trp Ala Ala Gly Ile Gly
1               5                   10                  15

Gly Gly Asp Leu Met Lys Arg Asn Asn Arg Pro Pro Val Gln Phe Asp
                20                  25                  30

Leu Leu Phe Pro Pro Gln Ser Val Lys Glu Glu Gly Ala Ala Ser Lys
            35                  40                  45

Lys Ala Glu Lys Gly Gly Gly Arg Lys Arg Leu Lys Val Val Thr Ala
    50                  55                  60

Asp Glu Asp Gly Arg Gln Ser Pro His Gly Gly Pro Gly Pro Ser Asp
65                  70                  75                  80

Gly Ser Gly Ala Gly Ala Arg Lys Lys Leu Arg Leu Thr Asn Glu Gln
                85                  90                  95

Ser Thr Leu Leu Glu Asp Thr Phe Arg Ala His Asn Ile Leu Ser Asn
                100                 105                 110

Ala Gln Lys Gln Glu Leu Ala Arg Gln Val Asp Leu Ser Ala Arg Gln
            115                 120                 125

Val Glu Val Trp Phe Gln Asn Arg Arg Ala Arg Thr Lys Leu Lys Gln
    130                 135                 140

Thr Glu Val Asp Cys Glu Ile Leu Lys Arg Cys Cys Glu Ser Leu Thr
145                 150                 155                 160

Gly Glu Asn Gln Arg Leu Arg Leu Glu Leu Ala Gln Leu Gln Arg Ser
                165                 170                 175

Ala Ala Ala Ala Ala Glu Ala Gly Leu Tyr Val Gln Ser Ser Phe Pro
            180                 185                 190

Pro Leu Ala Thr Ala Thr Ala Thr Ala Ser Val Cys Pro Ser Cys Asp
    195                 200                 205

Lys Val Ile Ala Val Ser Ser Gly Glu Thr Ser Gly Lys Ser Ser
    210                 215                 220

Thr Ser Tyr Ser Ser Arg Arg Ala Gly Phe Pro Ser Ile Met Gly Ser
225                 230                 235                 240

Arg
```

<210> SEQ ID NO 149
<211> LENGTH: 241
<212> TYPE: PRT
<213> ORGANISM: Zea mays

<400> SEQUENCE: 149

```
Met Glu Glu Gly Val Gly Lys Ser Trp Ala Ala Gly Ile Gly
1               5                   10                  15

Gly Gly Asp Leu Met Lys Arg Asn Asn Arg Pro Pro Val Gln Phe Asp
                20                  25                  30

Leu Leu Phe Pro Pro Gln Ser Val Lys Glu Glu Gly Ala Ala Ser Lys
            35                  40                  45

Lys Ala Glu Lys Gly Gly Gly Arg Lys Arg Leu Lys Val Val Thr Ala
    50                  55                  60

Asp Glu Asp Gly Arg Gln Ser Pro His Gly Gly Pro Gly Pro Ser Asp
65                  70                  75                  80

Gly Ser Gly Ala Gly Ala Arg Lys Lys Leu Arg Leu Thr Asn Glu Gln
                85                  90                  95
```

```
Ser Thr Leu Leu Glu Asp Thr Phe Arg Ala His Asn Ile Leu Ser Asn
            100                 105                 110

Ala Gln Lys Gln Glu Leu Ala Arg Gln Val Asp Leu Ser Ala Arg Gln
            115                 120                 125

Val Glu Val Trp Phe Gln Asn Arg Arg Ala Arg Thr Lys Leu Lys Gln
            130                 135                 140

Thr Glu Val Asp Cys Glu Ile Leu Lys Arg Cys Cys Glu Ser Leu Thr
145                 150                 155                 160

Gly Glu Asn Gln Arg Ala Arg Ala Glu Ala Gln Leu Gln Arg Ser
                165                 170                 175

Ala Ala Ala Ala Ala Glu Ala Gly Leu Tyr Val Gln Ser Ser Phe Pro
            180                 185                 190

Pro Leu Ala Thr Ala Thr Ala Thr Ala Ser Val Cys Pro Ser Cys Asp
            195                 200                 205

Lys Val Ile Ala Val Ser Ser Gly Gly Glu Thr Ser Gly Lys Ser Ser
            210                 215                 220

Thr Ser Tyr Ser Ser Arg Arg Ala Gly Phe Pro Ser Ile Met Gly Ser
225                 230                 235                 240

Arg
```

<210> SEQ ID NO 150
<211> LENGTH: 245
<212> TYPE: PRT
<213> ORGANISM: Zea mays

<400> SEQUENCE: 150

```
Met Ala Gln Glu Asp Val His Leu Asp Asp Ala Gly Ala Ala Ala Cys
1               5                   10                  15

Ala Ser Ala His Gly Thr Ser Ser Ser Arg Leu Ser Thr Glu Ala Pro
            20                  25                  30

Arg Thr Leu Glu Pro Pro Ser Leu Thr Leu Ser Met Pro Asp Glu Ala
            35                  40                  45

Thr Ala Thr Ala Thr Gly Gly Ser Gly Gly Ser Gly Gly Ala Ala Arg
50                  55                  60

Ser Val Ser Ser Arg Ser Val Glu Gly Val Lys Arg Glu Arg Val Asp
65                  70                  75                  80

Asp Ala Glu Gly Glu Arg Ala Ser Thr Ala Ala Ala Arg Val
                85                  90                  95

Cys Ala Gly Ala Glu Asp Asp Asp Gly Ser Thr Arg Lys Lys Leu
            100                 105                 110

Arg Leu Thr Lys Glu Gln Ser Lys Leu Leu Glu Asp Arg Phe Lys Asp
            115                 120                 125

His Ser Thr Leu Asn Pro Lys Gln Lys Ile Ala Leu Ala Lys Gln Leu
            130                 135                 140

Lys Leu Arg Pro Arg Gln Val Glu Val Trp Phe Gln Asn Arg Arg Ala
145                 150                 155                 160

Arg Thr Lys Leu Lys Gln Thr Glu Val Asp Cys Glu Leu Leu Lys Arg
            165                 170                 175

Cys Cys Glu Ser Leu Ser Glu Gly Asn Arg Arg Leu Gln Arg Glu Leu
            180                 185                 190

Gln Glu Leu Arg Ala Leu Lys Leu Ala Gly Pro His Pro Gln Ala Pro
            195                 200                 205

Ser Ser Ser Pro Ala Ala Ala Thr Gln Gly Val Pro Val Pro Val Pro
            210                 215                 220
```

```
Pro Pro Leu Tyr Val Gln Met Gln Met Gln Leu Ser Ser Cys Arg Cys
225                 230                 235                 240

Cys Arg Pro Pro Arg
            245

<210> SEQ ID NO 151
<211> LENGTH: 292
<212> TYPE: PRT
<213> ORGANISM: Zea mays

<400> SEQUENCE: 151

Met Ala Gln Glu Asp Val His Leu Asp Asp Ala Gly Ala Ala Ala Gly
1               5                   10                  15

Ala Ser Ala Gly Ser Gly Ser Gly Ala Ser Gly Ala Ala Arg His
            20                  25                  30

Gly Gly Ile Ser Arg Arg Leu Ser Arg Glu Val Arg Leu Pro Ser Pro
        35                  40                  45

His Pro Leu Glu Pro Ser Leu Thr Leu Ser Leu Pro Asp Glu Ala Thr
    50                  55                  60

Ala Thr Gly Ser Gly Gly Gly Ala Ala His Ser Val Ser Ser Leu
65                  70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
        115                 120                 125

Glu Gln Ser Ala Leu Leu Glu Asp Arg Phe Lys Glu His Ser Thr Leu
    130                 135                 140

Asn Pro Lys Gln Lys Val Ala Leu Ala Lys Gln Leu Lys Leu Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
        195                 200                 205

Ala Leu Lys Phe Ala Pro His Pro Gln Ala Pro Ser Ser Ala Thr
    210                 215                 220

Gln Ala Gly Ala Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
        275                 280                 285

Ser Ala Ala Cys
    290

<210> SEQ ID NO 152
<211> LENGTH: 292
<212> TYPE: PRT
<213> ORGANISM: Zea mays

<400> SEQUENCE: 152
```

Met Ala Gln Glu Asp Val His Leu Asp Asp Ala Gly Ala Ala Ala Gly
1               5                   10                  15

Ala Ser Ala Gly Ser Gly Ser Gly Gly Ala Ser Gly Ala Ala Arg His
            20                  25                  30

Gly Gly Ile Ser Arg Arg Leu Ser Arg Glu Val Arg Leu Pro Ser Pro
            35                  40                  45

His Pro Leu Glu Pro Ser Leu Thr Leu Ser Leu Pro Asp Glu Ala Thr
    50                  55                  60

Ala Thr Gly Ser Gly Gly Gly Ala Ala His Ser Val Ser Ser Leu
65              70                  75                  80

Ser Val Ala Gly Val Lys Arg Glu Arg Val Asp Asp Ala Glu Gly Glu
            85                  90                  95

Arg Ala Ser Ser Thr Ala Ala Leu Pro Arg Ala Cys Ala Gly Ala Glu
            100                 105                 110

Asp Asp Asp Asp Asp Gly Ser Thr Arg Lys Lys Leu Arg Leu Thr Lys
            115                 120                 125

Glu Gln Ser Ala Leu Leu Glu Asp Arg Phe Lys Glu His Ser Thr Leu
130                 135                 140

Asn Pro Lys Gln Lys Val Ala Leu Ala Lys Gln Ala Lys Ala Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
        195                 200                 205

Ala Leu Lys Phe Ala Pro His Pro Gln Ala Pro Pro Ser Ser Ala Thr
210                 215                 220

Gln Ala Gly Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Ala Lys Ala Glu Pro
            260                 265                 270

Arg Pro Lys Ala Ala Ala Thr His His Phe Phe Asn Pro Phe Thr His
            275                 280                 285

Ser Ala Ala Cys
            290

<210> SEQ ID NO 153
<211> LENGTH: 245
<212> TYPE: PRT
<213> ORGANISM: Zea mays

<400> SEQUENCE: 153

Met Ala Gln Glu Asp Val His Leu Asp Asp Ala Gly Ala Ala Ala Cys
1               5                   10                  15

Ala Ser Ala His Gly Thr Ser Ser Arg Leu Ser Thr Glu Ala Pro
            20                  25                  30

Arg Thr Leu Glu Pro Pro Ser Ala Thr Ala Ser Met Pro Asp Glu Ala
            35                  40                  45

Thr Ala Thr Ala Thr Gly Gly Ser Gly Gly Ser Gly Gly Ala Ala Arg
        50                  55                  60

Ser Val Ser Ser Arg Ser Val Glu Gly Val Lys Arg Glu Arg Val Asp

```
                65                  70                  75                  80
Asp Ala Glu Gly Glu Arg Ala Ser Ser Thr Ala Ala Ala Arg Val
                    85                  90                  95

Cys Ala Gly Ala Glu Asp Asp Asp Gly Ser Thr Arg Lys Lys Leu
                    100                 105                 110

Arg Leu Thr Lys Glu Gln Ser Lys Leu Leu Glu Asp Arg Phe Lys Asp
                    115                 120                 125

His Ser Thr Leu Asn Pro Lys Gln Lys Ile Ala Leu Ala Lys Gln Leu
        130                 135                 140

Lys Leu Arg Pro Arg Gln Val Glu Val Trp Phe Gln Asn Arg Arg Ala
145                 150                 155                 160

Arg Thr Lys Leu Lys Gln Thr Glu Val Asp Cys Glu Leu Leu Lys Arg
                165                 170                 175

Cys Cys Glu Ser Leu Ser Glu Gly Asn Arg Arg Leu Gln Arg Glu Leu
                    180                 185                 190

Gln Glu Leu Arg Ala Leu Lys Leu Ala Gly Pro His Pro Gln Ala Pro
                195                 200                 205

Ser Ser Ser Pro Ala Ala Ala Thr Gln Gly Val Pro Val Pro Val Pro
        210                 215                 220

Pro Pro Leu Tyr Val Gln Met Gln Met Gln Leu Ser Ser Cys Arg Cys
225                 230                 235                 240

Cys Arg Pro Pro Arg
                245

<210> SEQ ID NO 154
<211> LENGTH: 292
<212> TYPE: PRT
<213> ORGANISM: Zea mays

<400> SEQUENCE: 154

Met Ala Gln Glu Asp Val His Leu Asp Asp Ala Gly Ala Ala Ala Gly
1               5                   10                  15

Ala Ser Ala Gly Ser Gly Ser Gly Gly Ala Ser Gly Ala Ala Arg His
                20                  25                  30

Gly Gly Ile Ser Arg Arg Leu Ser Arg Glu Val Arg Leu Pro Ser Pro
            35                  40                  45

His Pro Leu Glu Pro Ser Ala Thr Ala Ser Ala Pro Asp Glu Ala Thr
        50                  55                  60

Ala Thr Gly Ser Gly Gly Gly Ala Ala His Ser Val Ser Ser Leu
65                  70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
                100                 105                 110

Asp Asp Asp Asp Gly Ser Thr Arg Lys Lys Leu Arg Leu Thr Lys
            115                 120                 125

Glu Gln Ser Ala Leu Leu Glu Asp Arg Phe Lys Glu His Ser Thr Leu
        130                 135                 140

Asn Pro Lys Gln Lys Val Ala Leu Ala Lys Gln Leu Lys Leu Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
                180                 185                 190
```

```
Leu Thr Glu Glu Asn Arg Arg Leu Gln Arg Glu Leu Gln Glu Leu Arg
            195                 200                 205

Ala Leu Lys Phe Ala Pro His Pro Gln Ala Pro Pro Ser Ser Ala Thr
210                 215                 220

Gln Ala Gly Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
            275                 280                 285

Ser Ala Ala Cys
    290

<210> SEQ ID NO 155
<211> LENGTH: 292
<212> TYPE: PRT
<213> ORGANISM: Zea mays

<400> SEQUENCE: 155

Met Ala Gln Glu Asp Val His Leu Asp Asp Ala Gly Ala Ala Ala Gly
1               5                   10                  15

Ala Ser Ala Gly Ser Gly Ser Gly Gly Ala Ser Gly Ala Ala Arg His
            20                  25                  30

Gly Gly Ile Ser Arg Arg Leu Ser Arg Glu Val Arg Leu Pro Ser Pro
            35                  40                  45

His Pro Leu Glu Pro Ser Ala Thr Ala Ser Ala Pro Asp Glu Ala Thr
50                  55                  60

Ala Thr Gly Ser Gly Gly Gly Ala Ala His Ser Val Ser Ser Leu
65                  70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
            115                 120                 125

Glu Gln Ser Ala Leu Leu Glu Asp Arg Phe Lys Glu His Ser Thr Leu
    130                 135                 140

Asn Pro Lys Gln Lys Val Ala Leu Ala Lys Gln Ala Lys Ala Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
            195                 200                 205

Ala Leu Lys Phe Ala Pro His Pro Gln Ala Pro Pro Ser Ser Ala Thr
210                 215                 220

Gln Ala Gly Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Lys Ala Glu Pro
            260                 265                 270
```

```
Arg Pro Lys Ala Ala Ala Thr His His Phe Phe Asn Pro Phe Thr His
        275                 280                 285

Ser Ala Ala Cys
    290

<210> SEQ ID NO 156
<211> LENGTH: 292
<212> TYPE: PRT
<213> ORGANISM: Zea mays

<400> SEQUENCE: 156

Met Ala Gln Glu Asp Val His Leu Asp Asp Ala Gly Leu Ala Leu Gly
1               5                   10                  15

Leu Ser Leu Gly Ser Gly Ser Gly Ala Ser Gly Ala Ala Arg His
            20                  25                  30

Gly Gly Ile Ser Arg Arg Leu Ser Arg Glu Val Arg Leu Pro Ser Pro
        35                  40                  45

His Pro Leu Glu Pro Ser Leu Thr Leu Ser Leu Pro Asp Glu Ala Thr
    50                  55                  60

Ala Thr Gly Ser Gly Gly Gly Ala Ala His Ser Val Ser Ser Leu
65              70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
        115                 120                 125

Glu Gln Ser Ala Leu Leu Glu Asp Arg Phe Lys Glu His Ser Thr Leu
    130                 135                 140

Asn Pro Lys Gln Lys Val Ala Leu Ala Lys Gln Ala Lys Ala Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
        195                 200                 205

Ala Leu Lys Phe Ala Pro His Pro Gln Ala Pro Ser Ser Ala Thr
    210                 215                 220

Gln Ala Gly Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
        275                 280                 285

Ser Ala Ala Cys
    290

<210> SEQ ID NO 157
<211> LENGTH: 221
<212> TYPE: PRT
<213> ORGANISM: Zea mays

<400> SEQUENCE: 157
```

```
Met Tyr Ser Thr Arg Glu Glu Gly Val Gly Lys Ser Trp Ala Gly
1               5                   10                  15

Ala Gly Ile Gly Gly Ser Gly Gly Cys Asp Leu Met Gln Arg Asn
            20                  25                  30

Asn Arg Pro Pro Val Gln Phe Asp Leu Leu Phe Pro Gln Gly Val
        35                  40                  45

Val Glu Gly Val Ala Ala Ser Lys Lys Ala Glu Lys Gly Gly Gly
    50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
                100                 105                 110

Gln Lys Gln Glu Leu Ala Arg Gln Val Asp Leu Ser Ala Arg Gln Val
            115                 120                 125

Glu Val Trp Phe Gln Asn Arg Arg Ala Arg Thr Lys Leu Lys Gln Thr
    130                 135                 140

Glu Ala Asp Cys Glu Ile Leu Lys Arg Cys Cys Glu Ser Leu Thr Gly
145                 150                 155                 160

Glu Asn Gln Arg Leu Arg Leu Glu Leu Ala Gln Leu Gln Gly Ser Glu
                165                 170                 175

Ala Gly Leu Tyr Leu Gln Ser Ser Phe Pro Leu Ala Ala Ala Met
            180                 185                 190

Ala Ser Val Cys Pro Ser Cys Asp Lys Val Ile Thr Val Ala Ser Gly
            195                 200                 205

Gly Glu Thr Ser Gly Arg Ser Ser Thr Ser Tyr Ser Ser
210                 215                 220

<210> SEQ ID NO 158
<211> LENGTH: 221
<212> TYPE: PRT
<213> ORGANISM: Zea mays

<400> SEQUENCE: 158

Met Tyr Ser Thr Arg Glu Glu Gly Val Gly Lys Ser Trp Ala Gly
1               5                   10                  15

Ala Gly Ile Gly Gly Ser Gly Gly Cys Asp Leu Met Gln Arg Asn
            20                  25                  30

Asn Arg Pro Pro Val Gln Phe Asp Leu Leu Phe Pro Gln Gly Val
        35                  40                  45

Val Glu Gly Val Ala Ala Ser Lys Lys Ala Glu Lys Gly Gly Gly
    50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
                100                 105                 110

Gln Lys Gln Glu Leu Ala Arg Gln Val Asp Leu Ser Ala Arg Gln Val
            115                 120                 125

Glu Val Trp Phe Gln Asn Arg Arg Ala Arg Thr Lys Leu Lys Gln Thr
    130                 135                 140

Glu Ala Asp Cys Glu Ile Leu Lys Arg Cys Cys Glu Ser Leu Thr Gly
```

```
145                 150                 155                 160
Glu Asn Gln Arg Ala Arg Ala Glu Ala Ala Gln Leu Gln Gly Ser Glu
                165                 170                 175

Ala Gly Leu Tyr Leu Gln Ser Ser Phe Pro Leu Ala Ala Ala Met
            180                 185                 190

Ala Ser Val Cys Pro Ser Cys Asp Lys Val Ile Thr Val Ala Ser Gly
                195                 200                 205

Gly Glu Thr Ser Gly Arg Ser Ser Thr Ser Tyr Ser Ser
            210                 215                 220

<210> SEQ ID NO 159
<211> LENGTH: 221
<212> TYPE: PRT
<213> ORGANISM: Zea mays

<400> SEQUENCE: 159

Met Tyr Ser Thr Arg Glu Glu Glu Gly Val Gly Lys Ser Trp Ala Gly
1               5                   10                  15

Ala Gly Ile Gly Gly Gly Ser Gly Gly Cys Asp Leu Met Gln Arg Asn
                20                  25                  30

Asn Arg Pro Pro Val Gln Phe Asp Leu Leu Phe Pro Pro Gln Gly Val
            35                  40                  45

Val Glu Gly Val Ala Ala Ser Lys Lys Ala Glu Lys Gly Gly Gly Gly
        50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Val Trp Phe Gln Asn Arg Arg Ala Arg Thr Lys Leu Lys Gln Thr
130                 135                 140

Glu Ala Asp Cys Glu Ile Leu Lys Arg Cys Cys Glu Ser Leu Thr Gly
145                 150                 155                 160

Glu Asn Gln Arg Ala Arg Ala Glu Ala Ala Gln Leu Gln Gly Ser Glu
                165                 170                 175

Ala Gly Ala Tyr Ala Gln Ser Ser Phe Pro Leu Ala Ala Ala Met
            180                 185                 190

Ala Ser Val Cys Pro Ser Cys Asp Lys Val Ile Thr Val Ala Ser Gly
                195                 200                 205

Gly Glu Thr Ser Gly Arg Ser Ser Thr Ser Tyr Ser Ser
            210                 215                 220

<210> SEQ ID NO 160
<211> LENGTH: 221
<212> TYPE: PRT
<213> ORGANISM: Zea mays

<400> SEQUENCE: 160

Met Tyr Ser Thr Arg Glu Glu Glu Gly Val Gly Lys Ser Trp Ala Gly
1               5                   10                  15

Ala Gly Ile Gly Gly Gly Ser Gly Gly Cys Asp Leu Met Gln Arg Asn
                20                  25                  30

Asn Arg Pro Pro Val Gln Phe Asp Leu Leu Phe Pro Pro Gln Gly Val
```

```
            35                  40                  45
Val Glu Gly Val Ala Ser Lys Lys Ala Glu Lys Gly Gly Gly
 50                  55                  60

Arg Lys Arg Leu Lys Val Val Thr Gly Thr Ala Asp Glu Asp Gly Gln
 65                  70                  75                  80

Gln Pro Pro Gly Ala Arg Lys Lys Leu Arg Leu Thr Lys Ala Gln Ser
                 85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Val Trp Phe Gln Asn Arg Ala Arg Thr Lys Leu Lys Gln Thr
130                 135                 140

Glu Ala Asp Cys Glu Ile Leu Lys Arg Cys Cys Glu Ser Leu Thr Gly
145                 150                 155                 160

Glu Asn Gln Arg Leu Arg Leu Glu Leu Ala Gln Leu Gln Gly Ser Glu
                165                 170                 175

Ala Gly Ala Tyr Ala Gln Ser Ser Phe Pro Pro Leu Ala Ala Ala Met
            180                 185                 190

Ala Ser Val Cys Pro Ser Cys Asp Lys Val Ile Thr Val Ala Ser Gly
        195                 200                 205

Gly Glu Thr Ser Gly Arg Ser Ser Thr Ser Tyr Ser Ser
210                 215                 220

<210> SEQ ID NO 161
<211> LENGTH: 227
<212> TYPE: PRT
<213> ORGANISM: Zea mays

<400> SEQUENCE: 161

Met Met Glu Arg Val Glu Asp Leu Gly Leu Ser Leu Ser Leu Ser Ser
  1               5                  10                  15

Ser Leu Ala Ser Pro Arg Thr His His Val Ala Thr Met Leu Leu Arg
             20                  25                  30

Ala Pro Glu Lys Arg Phe Leu Glu Met Pro Leu Leu Leu Pro Ala Lys
         35                  40                  45

Arg Thr Thr Glu Val Thr Gly Glu Asp Gly Leu Arg Gly Gly Ser Asp
 50                  55                  60

Glu Glu Asp Gly Gly Cys Gly Ile Asp Gly Ser Arg Lys Lys Leu Arg
 65                  70                  75                  80

Leu Ser Lys Asp Gln Ser Ala Val Leu Glu Asp Ser Phe Arg Glu His
                 85                  90                  95

Pro Thr Leu Asn Pro Arg Gln Lys Ala Ala Leu Ala Gln Gln Leu Gly
            100                 105                 110

Leu Arg Pro Arg Gln Val Glu Val Trp Phe Gln Asn Arg Arg Ala Arg
        115                 120                 125

Thr Lys Leu Lys Gln Thr Glu Val Asp Cys Glu Tyr Leu Lys Arg Cys
130                 135                 140

Cys Glu Thr Leu Thr Glu Glu Asn Arg Arg Leu Gln Lys Glu Val Gln
145                 150                 155                 160

Glu Leu Arg Ala Ala Lys Ala Val Ser Pro His Leu Tyr Met His Met
                165                 170                 175

Ser Pro Pro Thr Thr Leu Thr Met Cys Pro Ser Cys Glu Arg Val Ser
            180                 185                 190
```

```
Ser Ser Asn Gly Asn Ser Ala Ala Ala Thr Ala Ala Arg Ala Arg
            195                 200                 205

Ala Gly Ala Gly Ala Gly Ala Ile Val Cys His Pro Ile Asp Arg Ala
210                 215                 220

Thr Ser Thr
225

<210> SEQ ID NO 162
<211> LENGTH: 221
<212> TYPE: PRT
<213> ORGANISM: Zea mays

<400> SEQUENCE: 162

Met Tyr Ser Thr Arg Glu Glu Gly Val Gly Lys Ser Trp Leu Gly
1               5                   10                  15

Leu Gly Ile Gly Gly Gly Ser Gly Gly Cys Asp Leu Met Gln Arg Asn
                20                  25                  30

Asn Arg Pro Pro Val Gln Phe Asp Leu Leu Phe Pro Pro Gln Gly Val
            35                  40                  45

Val Glu Gly Val Ala Ala Ser Lys Lys Ala Glu Lys Gly Gly Gly Gly
50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Val Trp Phe Gln Asn Arg Arg Ala Arg Thr Lys Leu Lys Gln Thr
130                 135                 140

Glu Ala Asp Cys Glu Ile Leu Lys Arg Cys Cys Glu Ser Leu Thr Gly
145                 150                 155                 160

Glu Asn Gln Arg Ala Arg Ala Glu Ala Ala Gln Leu Gln Gly Ser Glu
                165                 170                 175

Ala Gly Leu Tyr Leu Gln Ser Ser Phe Pro Pro Leu Ala Ala Ala Met
            180                 185                 190

Ala Ser Val Cys Pro Ser Cys Asp Lys Val Ile Thr Val Ala Ser Gly
        195                 200                 205

Gly Glu Thr Ser Gly Arg Ser Ser Thr Ser Tyr Ser Ser
210                 215                 220

<210> SEQ ID NO 163
<211> LENGTH: 221
<212> TYPE: PRT
<213> ORGANISM: Zea mays

<400> SEQUENCE: 163

Met Tyr Ser Thr Arg Glu Glu Gly Val Gly Lys Ser Trp Leu Gly
1               5                   10                  15

Leu Gly Ile Gly Gly Gly Ser Gly Gly Cys Asp Leu Met Gln Arg Asn
                20                  25                  30

Asn Arg Pro Pro Val Gln Phe Asp Leu Leu Phe Pro Pro Gln Gly Val
            35                  40                  45

Val Glu Gly Val Ala Ala Ser Lys Lys Ala Glu Lys Gly Gly Gly Gly
50                  55                  60
```

Arg Lys Arg Leu Lys Val Val Thr Gly Thr Ala Asp Glu Asp Gly Gln
 65                  70                  75                  80

Gln Pro Pro Gly Ala Arg Lys Lys Leu Arg Leu Thr Lys Ala Gln Ser
                 85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Val Trp Phe Gln Asn Arg Arg Ala Arg Thr Lys Leu Lys Gln Thr
130                 135                 140

Glu Ala Asp Cys Glu Ile Leu Lys Arg Cys Cys Glu Ser Leu Thr Gly
145                 150                 155                 160

Glu Asn Gln Arg Ala Arg Ala Glu Ala Ala Gln Leu Gln Gly Ser Glu
                165                 170                 175

Ala Gly Ala Tyr Ala Gln Ser Ser Phe Pro Pro Leu Ala Ala Ala Met
            180                 185                 190

Ala Ser Val Cys Pro Ser Cys Asp Lys Val Ile Thr Val Ala Ser Gly
        195                 200                 205

Gly Glu Thr Ser Gly Arg Ser Ser Thr Ser Tyr Ser Ser
210                 215                 220

<210> SEQ ID NO 164
<211> LENGTH: 241
<212> TYPE: PRT
<213> ORGANISM: Zea mays

<400> SEQUENCE: 164

Met Glu Glu Glu Gly Val Gly Lys Ser Trp Leu Ala Leu Gly Ile Gly
1               5                   10                  15

Gly Gly Asp Leu Met Lys Arg Asn Asn Arg Pro Val Gln Phe Asp
            20                  25                  30

Leu Leu Phe Pro Pro Gln Ser Val Lys Glu Glu Gly Ala Ala Ser Lys
        35                  40                  45

Lys Ala Glu Lys Gly Gly Arg Lys Arg Leu Lys Val Val Thr Ala
 50                  55                  60

Asp Glu Asp Gly Arg Gln Ser Pro His Gly Gly Pro Gly Pro Ser Asp
 65                  70                  75                  80

Gly Ser Gly Ala Gly Ala Arg Lys Lys Leu Arg Leu Thr Asn Glu Gln
                 85                  90                  95

Ser Thr Leu Leu Glu Asp Thr Phe Arg Ala His Asn Ile Leu Ser Asn
            100                 105                 110

Ala Gln Lys Gln Glu Leu Ala Arg Gln Val Asp Leu Ser Ala Arg Gln
        115                 120                 125

Val Glu Val Trp Phe Gln Asn Arg Arg Ala Arg Thr Lys Leu Lys Gln
130                 135                 140

Thr Glu Val Asp Cys Glu Ile Leu Lys Arg Cys Cys Glu Ser Leu Thr
145                 150                 155                 160

Gly Glu Asn Gln Arg Ala Arg Ala Glu Ala Ala Gln Leu Gln Arg Ser
                165                 170                 175

Ala Ala Ala Ala Glu Ala Gly Leu Tyr Val Gln Ser Ser Phe Pro
            180                 185                 190

Pro Leu Ala Thr Ala Thr Ala Thr Ala Ser Val Cys Pro Ser Cys Asp
        195                 200                 205

Lys Val Ile Ala Val Ser Ser Gly Gly Glu Thr Ser Gly Lys Ser Ser
210                 215                 220

```
Thr Ser Tyr Ser Ser Arg Arg Ala Gly Phe Pro Ser Ile Met Gly Ser
225                 230                 235                 240

Arg

<210> SEQ ID NO 165
<211> LENGTH: 221
<212> TYPE: PRT
<213> ORGANISM: Zea mays

<400> SEQUENCE: 165

Met Tyr Ser Thr Arg Glu Glu Gly Val Gly Lys Ser Trp Leu Gly
1               5                   10                  15

Leu Gly Ile Gly Gly Ser Gly Gly Cys Asp Leu Met Gln Arg Asn
                20                  25                  30

Asn Arg Pro Pro Val Gln Phe Asp Leu Leu Phe Pro Gln Gly Val
                35                  40                  45

Val Glu Gly Val Ala Ala Ser Lys Lys Ala Glu Lys Gly Gly Gly Gly
    50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                    85                  90                  95

Thr Leu Leu Glu Asp Thr Phe Arg Ala His Ser Ile Leu Ser Asn Ala
                100                 105                 110

Gln Lys Gln Glu Leu Ala Arg Gln Val Asp Leu Ser Ala Arg Gln Val
            115                 120                 125

Glu Val Trp Phe Gln Asn Arg Arg Ala Arg Thr Lys Leu Lys Gln Thr
    130                 135                 140

Glu Ala Asp Cys Glu Ile Leu Lys Arg Cys Cys Glu Ser Leu Thr Gly
145                 150                 155                 160

Glu Asn Gln Arg Leu Arg Leu Glu Leu Ala Gln Leu Gln Gly Ser Glu
                165                 170                 175

Ala Gly Ala Tyr Ala Gln Ser Ser Phe Pro Pro Leu Ala Ala Ala Met
            180                 185                 190

Ala Ser Val Cys Pro Ser Cys Asp Lys Val Ile Thr Val Ala Ser Gly
    195                 200                 205

Gly Glu Thr Ser Gly Arg Ser Thr Ser Tyr Ser Ser
    210                 215                 220

<210> SEQ ID NO 166
<211> LENGTH: 254
<212> TYPE: PRT
<213> ORGANISM: Zea mays

<400> SEQUENCE: 166

Met Tyr Thr Thr Thr Arg Ala Met Glu Lys Glu Glu Gly Phe Gly Lys
1               5                   10                  15

Ser Trp Leu Gly Leu Gly Ile Gly Gly Gly Arg Asp Leu Asn Leu
                20                  25                  30

Met Lys Arg Ser Arg Pro Leu Arg Pro Val Arg Leu Asp Leu Leu Phe
                35                  40                  45

Pro Pro Ser Val Glu Gly Gly Glu Ala Ala Ala Arg Ser Arg Lys Ala
        50                  55                  60

Gly Ala Gly Ala Leu Arg Asn Met Ser Leu Lys Gln Val Ala Gly Asp
65                  70                  75                  80
```

```
Asp Asp Gly Gly Gln Ser Ser His Gly Gly Pro Ser Pro Ser Asp
                85                  90                  95

Asp Asp Gly Ala Gly Ala Arg Lys Lys Leu Arg Leu Thr Thr Glu Gln
            100                 105                 110

Ser Lys Leu Leu Glu Asp Thr Phe Arg Ala His Asn Ile Leu Ser His
        115                 120                 125

Ala Gln Lys His Glu Val Ala Arg Gln Val Asp Leu Ser Ala Arg Gln
    130                 135                 140

Val Glu Val Trp Phe Gln Asn Arg Arg Ala Arg Thr Lys Leu Lys Gln
145                 150                 155                 160

Thr Glu Val Asp Cys Glu Thr Leu Arg Arg Trp Arg Glu Ser Leu Ala
                165                 170                 175

Asp Glu Asn Leu Arg Ala Arg Ala Glu Ala Glu Gln Leu Gln Arg Trp
            180                 185                 190

Ala Thr Ala Ala Ala Gly Gln Ser Ser Ala Ser Pro Ser Pro Ala Thr
        195                 200                 205

Ala Thr Ala Ser Val Cys Pro Ser Cys Asp Lys Val Val Val Thr
    210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250

<210> SEQ ID NO 167
<211> LENGTH: 223
<212> TYPE: PRT
<213> ORGANISM: Zea mays

<400> SEQUENCE: 167

Met Tyr Ser Cys Thr Arg Ala Met Glu Glu Gly Val Gly Lys Ser
1               5                   10                  15

Trp Ala Gly Ala Gly Ile Gly Gly Gly Asp Leu Met Lys Arg Asn
            20                  25                  30

Asn Arg Pro Pro Val Gln Leu Asp Asp Leu Leu Ser Phe Pro Pro Gln
            35                  40                  45

Ser Val Ala Ala Ala Ser Lys Lys Gln Ala Glu Lys Gly Gly Gly Gly
        50                  55                  60

Arg Lys Arg His Lys Ile Val Thr Ala Asp Glu Asp Gly Arg Gln
65                  70                  75                  80

Ser Pro His Gly Gly Ala Arg Lys Lys Leu Arg Leu Thr Lys Ala Gln
                85                  90                  95

Ser Thr Leu Leu Glu Asp Thr Phe Arg Ala His Asn Ile Leu Ser His
            100                 105                 110

Ala Gln Lys Gln Glu Leu Ala Arg Gln Val Asn Leu Ser Ala Arg Gln
        115                 120                 125

Val Glu Val Trp Phe Gln Asn Arg Arg Ala Arg Thr Lys Leu Lys Gln
    130                 135                 140

Thr Glu Ala Asp Cys Glu Val Leu Lys Arg Tyr Cys Glu Arg Leu Thr
145                 150                 155                 160

Gly Glu Asn Gln Arg Leu Arg Leu Glu Leu Ala Gln Leu Gln Arg Ser
                165                 170                 175

Pro Ala Ala Glu Glu Ala Gly Phe Tyr Val Gln Ser Ser Phe Pro Phe
            180                 185                 190

Pro Pro Leu Ala Thr Ala Met Ala Ser Val Cys Pro Ser Cys Asp Lys
        195                 200                 205
```

Val Val Ala Val Thr Ser Gly Lys Ser Ser Thr Ser Tyr Ser Ser
    210                 215                 220

<210> SEQ ID NO 168
<211> LENGTH: 223
<212> TYPE: PRT
<213> ORGANISM: Zea mays

<400> SEQUENCE: 168

Met Tyr Ser Cys Thr Arg Ala Met Glu Glu Gly Val Gly Lys Ser
1               5                   10                  15

Trp Ala Gly Ala Gly Ile Gly Gly Gly Asp Leu Met Lys Arg Asn
                20                  25                  30

Asn Arg Pro Pro Val Gln Leu Asp Asp Leu Leu Ser Phe Pro Pro Gln
                35                  40                  45

Ser Val Ala Ala Ala Ser Lys Lys Gln Ala Glu Lys Gly Gly Gly
    50                  55                  60

Arg Lys Arg His Lys Ile Val Val Thr Ala Asp Glu Asp Gly Arg Gln
65                  70                  75                  80

Ser Pro His Gly Gly Ala Arg Lys Lys Leu Arg Leu Thr Lys Ala Gln
                85                  90                  95

Ser Thr Leu Leu Glu Asp Thr Phe Arg Ala His Asn Ile Leu Ser His
                100                 105                 110

Ala Gln Lys Gln Glu Leu Ala Arg Gln Val Asn Leu Ser Ala Arg Gln
                115                 120                 125

Val Glu Val Trp Phe Gln Asn Arg Arg Ala Arg Thr Lys Leu Lys Gln
                130                 135                 140

Thr Glu Ala Asp Cys Glu Val Leu Lys Arg Tyr Cys Glu Arg Leu Thr
145                 150                 155                 160

Gly Glu Asn Gln Arg Ala Arg Ala Glu Ala Ala Gln Leu Gln Arg Ser
                165                 170                 175

Pro Ala Ala Glu Glu Ala Gly Phe Tyr Val Gln Ser Ser Phe Pro Phe
                180                 185                 190

Pro Pro Leu Ala Thr Ala Met Ala Ser Val Cys Pro Ser Cys Asp Lys
                195                 200                 205

Val Val Ala Val Thr Ser Gly Lys Ser Ser Thr Ser Tyr Ser Ser
    210                 215                 220

<210> SEQ ID NO 169
<211> LENGTH: 335
<212> TYPE: PRT
<213> ORGANISM: Zea mays

<400> SEQUENCE: 169

Met Glu Leu Ala Leu Ser Leu Gly Glu Thr Met Ala Asp Ala Gly Arg
1               5                   10                  15

Asp Ala Met Ala Gly Ala Gly Met Gly Val Gly Val Arg Arg Glu Glu
                20                  25                  30

Glu Ala Gln Arg Gly Arg Arg Asp Arg Glu Val Arg Arg Glu Leu Glu
                35                  40                  45

Phe Thr Ala Arg Ser Ala Arg Ser Ser Pro Glu Pro Ala Val Arg Leu
    50                  55                  60

Thr Leu Leu His Gly Leu Gly Leu Pro Trp Pro Pro Pro Ser Ser
65                  70                  75                  80

Glu Thr Asn Arg His Leu Glu Ala Ser Ala Arg Gly Phe Asp Val Asn
                85                  90                  95

```
Arg Ala Pro Ser Leu Ser Ala Ala Gly Ala Ala Ala Glu Glu Asp Glu
                100                 105                 110

Glu Gln Asp Glu Ala Gly Ala Ala Ala Ala Ala Ser Ser Ser Pro
        115                 120                 125

Asn Asn Ser Ala Ser Ser Phe Pro Thr Asp Phe Ser Ala His Gly Gln
130                 135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
        195                 200                 205

Glu Val Trp Phe Gln Asn Arg Arg Ala Arg Thr Lys Leu Lys Gln Thr
    210                 215                 220

Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
                245                 250                 255

Thr Val His Pro Phe Tyr Met His Leu Pro Ala Thr Thr Leu Ser Met
            260                 265                 270

Cys Pro Ser Cys Glu Arg Val Ala Ser Asn Ser Ala Pro Ala Pro Ala
        275                 280                 285

Ser Ser Pro Ser Pro Ala Thr Gly Ile Ala Ala Pro Ala Pro Glu Gln
    290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 170
<211> LENGTH: 335
<212> TYPE: PRT
<213> ORGANISM: Zea mays

<400> SEQUENCE: 170

Met Glu Leu Ala Leu Ser Leu Gly Glu Thr Met Ala Asp Ala Gly Arg
1               5                   10                  15

Asp Ala Met Ala Gly Ala Gly Met Gly Val Gly Val Arg Arg Glu Glu
                20                  25                  30

Glu Ala Gln Arg Gly Arg Arg Asp Arg Glu Val Arg Arg Glu Leu Glu
            35                  40                  45

Phe Thr Ala Arg Ser Ala Arg Ser Ser Pro Glu Pro Ala Val Arg Leu
    50                  55                  60

Thr Leu Leu His Gly Ala Gly Ala Pro Trp Pro Pro Pro Ser Ser
65                  70                  75                  80

Glu Thr Asn Arg His Leu Glu Ala Ser Ala Arg Gly Phe Asp Val Asn
                85                  90                  95

Arg Ala Pro Ser Leu Ser Ala Ala Gly Ala Ala Ala Glu Glu Asp Glu
                100                 105                 110

Glu Gln Asp Glu Ala Gly Ala Ala Ala Ala Ala Ser Ser Ser Pro
        115                 120                 125

Asn Asn Ser Ala Ser Ser Phe Pro Thr Asp Phe Ser Ala His Gly Gln
```

```
            130                 135                 140
Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
        195                 200                 205

Glu Val Trp Phe Gln Asn Arg Arg Ala Arg Thr Lys Leu Lys Gln Thr
    210                 215                 220

Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
                245                 250                 255

Thr Val His Pro Phe Tyr Met His Leu Pro Ala Thr Thr Leu Ser Met
            260                 265                 270

Cys Pro Ser Cys Glu Arg Val Ala Ser Asn Ser Ala Pro Ala Pro Ala
        275                 280                 285

Ser Ser Pro Ser Pro Ala Thr Gly Ile Ala Ala Pro Ala Pro Glu Gln
    290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 171
<211> LENGTH: 254
<212> TYPE: PRT
<213> ORGANISM: Zea mays

<400> SEQUENCE: 171

Met Tyr Thr Thr Thr Arg Ala Met Glu Lys Glu Gly Phe Gly Lys
1               5                   10                  15

Ser Trp Ala Gly Ala Gly Ile Gly Gly Gly Arg Asp Leu Asn Leu
                20                  25                  30

Met Lys Arg Ser Arg Pro Leu Arg Pro Val Arg Leu Asp Leu Leu Phe
            35                  40                  45

Pro Pro Ser Val Glu Gly Gly Glu Ala Ala Arg Ser Arg Lys Ala
50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
                85                  90                  95

Asp Asp Gly Ala Gly Ala Arg Lys Lys Leu Arg Leu Thr Thr Glu Gln
            100                 105                 110

Ser Lys Leu Leu Glu Asp Thr Phe Arg Ala His Asn Ile Leu Ser His
        115                 120                 125

Ala Gln Lys His Glu Val Ala Arg Gln Val Asp Leu Ser Ala Arg Gln
    130                 135                 140

Val Glu Val Trp Phe Gln Asn Arg Arg Ala Arg Thr Lys Leu Lys Gln
145                 150                 155                 160

Thr Glu Val Asp Cys Glu Thr Leu Arg Arg Trp Arg Glu Ser Leu Ala
                165                 170                 175
```

```
Asp Glu Asn Leu Arg Leu Arg Leu Glu Leu Gln Leu Gln Arg Trp
            180                 185                 190

Ala Thr Ala Ala Ala Gly Gln Ser Ser Ala Ser Pro Ser Pro Ala Thr
        195                 200                 205

Ala Thr Ala Ser Val Cys Pro Ser Cys Asp Lys Val Val Val Val Thr
        210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250
```

<210> SEQ ID NO 172
<211> LENGTH: 254
<212> TYPE: PRT
<213> ORGANISM: Zea mays

<400> SEQUENCE: 172

```
Met Tyr Thr Thr Thr Arg Ala Met Glu Lys Glu Glu Gly Phe Gly Lys
1               5                   10                  15

Ser Trp Ala Gly Ala Gly Ile Gly Gly Gly Arg Asp Leu Asn Leu
            20                  25                  30

Met Lys Arg Ser Arg Pro Leu Arg Pro Val Arg Leu Asp Leu Leu Phe
        35                  40                  45

Pro Pro Ser Val Glu Gly Gly Glu Ala Ala Arg Ser Arg Lys Ala
50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
            85                  90                  95

Asp Asp Gly Ala Gly Ala Arg Lys Lys Leu Arg Leu Thr Thr Glu Gln
        100                 105                 110

Ser Lys Leu Leu Glu Asp Thr Phe Arg Ala His Asn Ile Leu Ser His
        115                 120                 125

Ala Gln Lys His Glu Val Ala Arg Gln Val Asp Leu Ser Ala Arg Gln
    130                 135                 140

Val Glu Val Trp Phe Gln Asn Arg Arg Ala Arg Thr Lys Leu Lys Gln
145                 150                 155                 160

Thr Glu Val Asp Cys Glu Thr Leu Arg Arg Trp Arg Glu Ser Leu Ala
                165                 170                 175

Asp Glu Asn Leu Arg Ala Arg Ala Glu Ala Gln Leu Gln Arg Trp
            180                 185                 190

Ala Thr Ala Ala Ala Gly Gln Ser Ser Ala Ser Pro Ser Pro Ala Thr
        195                 200                 205

Ala Thr Ala Ser Val Cys Pro Ser Cys Asp Lys Val Val Val Val Thr
        210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250
```

<210> SEQ ID NO 173
<211> LENGTH: 319
<212> TYPE: PRT
<213> ORGANISM: Zea mays

<400> SEQUENCE: 173

Met Asp Ile Met Ala Leu Asn Ala Arg Asp Glu Glu Gln Tyr Gly Asn
1               5                   10                  15

Asn His Ala Gly Ala Gly Ala Ser Ala Ser Ala Gly Ala Gly Val Ala
            20                  25                  30

Thr Ala Ala Pro Val Glu Val Glu Pro Pro Pro Pro Arg Gln Gln
            35                  40                  45

Gln Gln Arg Ala Ile Ser Val Ala Pro Ile Thr Ser Leu Pro Ala Pro
50                  55                  60

Gln Trp Trp Lys Trp Asn Gly Pro Gly Leu Phe Gly Thr Thr Met
65                  70                  75                  80

Asp Gln Gln Gln Gln Pro Ala Ala Ala Arg His Gly His Glu Met Pro
                85                  90                  95

Phe Leu Arg Gly Val Asp Val Asn Arg Ala Pro Ala Gly Asp Thr Arg
                100                 105                 110

Arg Gly Ser Cys Ser Glu Asp Glu Glu Pro Gly Gly Ala Ser Ser
            115                 120                 125

Ser Pro Asn Ser Thr Leu Ser Ser Ser Leu Ser Gly Lys Arg Ala Ala
    130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
                165                 170                 175

Arg Leu Ser Lys Asp Gln Ala Ala Val Leu Glu Ser Phe Lys Glu
                180                 185                 190

His Asn Thr Leu Asn Pro Lys Gln Lys Ala Ala Leu Ala Lys Gln Leu
            195                 200                 205

Asn Leu Lys Pro Arg Gln Val Glu Val Trp Phe Gln Asn Arg Arg Ala
210                 215                 220

Arg Thr Lys Leu Lys Gln Thr Glu Val Asp Cys Glu Phe Leu Lys Arg
225                 230                 235                 240

Cys Cys Glu Thr Leu Thr Glu Glu Asn Arg Arg Leu Gln Arg Glu Val
                245                 250                 255

Ala Glu Leu Arg Val Leu Lys Leu Val Ala Pro His His Tyr Ala Arg
            260                 265                 270

Met Pro Pro Pro Thr Thr Leu Thr Met Cys Pro Ser Cys Glu Arg Leu
            275                 280                 285

Ala Ser Ala Ser Ala Ser Ala Asp Gln Ala Gly Arg Ala Gly Pro Cys
            290                 295                 300

Trp Gly Pro Leu Pro Val Phe Val Asp Gly Pro Ala Arg Arg Pro
305                 310                 315

<210> SEQ ID NO 174
<211> LENGTH: 319
<212> TYPE: PRT
<213> ORGANISM: Zea mays

<400> SEQUENCE: 174

Met Asp Ile Met Ala Leu Asn Ala Arg Asp Glu Glu Gln Tyr Gly Asn
1               5                   10                  15

Asn His Ala Gly Ala Gly Ala Ser Ala Ser Ala Gly Ala Gly Val Ala
            20                  25                  30

Thr Ala Ala Pro Val Glu Val Glu Pro Pro Pro Pro Arg Gln Gln
            35                  40                  45

Gln Gln Arg Ala Ile Ser Val Ala Pro Ile Thr Ser Leu Pro Ala Pro
50                  55                  60

```
Gln Trp Trp Lys Trp Asn Gly Pro Gly Leu Phe Phe Gly Thr Thr Met
 65                  70                  75                  80

Asp Gln Gln Gln Pro Ala Ala Arg His Gly His Glu Met Pro
             85                  90                  95

Phe Leu Arg Gly Val Asp Val Asn Arg Ala Pro Ala Gly Asp Thr Arg
            100                 105                 110

Arg Gly Ser Cys Ser Glu Asp Glu Glu Pro Gly Gly Ala Ser Ser
            115                 120                 125

Ser Pro Asn Ser Thr Leu Ser Ser Leu Ser Gly Lys Arg Ala Ala
130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
                165                 170                 175

Arg Leu Ser Lys Asp Gln Ala Ala Val Leu Glu Glu Ser Phe Lys Glu
                180                 185                 190

His Asn Thr Leu Asn Pro Lys Gln Lys Ala Ala Leu Ala Lys Gln Leu
            195                 200                 205

Asn Leu Lys Pro Arg Gln Val Glu Val Trp Phe Gln Asn Arg Arg Ala
210                 215                 220

Arg Thr Lys Leu Lys Gln Thr Glu Val Asp Cys Glu Phe Leu Lys Arg
225                 230                 235                 240

Cys Cys Glu Thr Leu Thr Glu Glu Asn Arg Arg Leu Gln Arg Glu Val
                245                 250                 255

Ala Glu Leu Arg Val Ala Lys Ala Val Ala Pro His His Tyr Ala Arg
                260                 265                 270

Met Pro Pro Pro Thr Thr Leu Thr Met Cys Pro Ser Cys Glu Arg Leu
            275                 280                 285

Ala Ser Ala Ser Ala Ser Ala Asp Gln Ala Gly Arg Ala Gly Pro Cys
290                 295                 300

Trp Gly Pro Leu Pro Val Phe Val Asp Gly Pro Ala Arg Arg Pro
305                 310                 315

<210> SEQ ID NO 175
<211> LENGTH: 254
<212> TYPE: PRT
<213> ORGANISM: Zea mays

<400> SEQUENCE: 175

Met Tyr Thr Thr Thr Arg Ala Met Glu Lys Glu Glu Gly Phe Gly Lys
1               5                   10                  15

Ser Trp Ala Gly Ala Gly Ile Gly Gly Gly Arg Asp Ala Asn Ala
            20                  25                  30

Met Lys Arg Ser Arg Pro Leu Arg Pro Val Arg Leu Asp Leu Leu Phe
            35                  40                  45

Pro Pro Ser Val Glu Gly Gly Glu Ala Ala Ala Arg Ser Arg Lys Ala
            50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
                85                  90                  95

Asp Asp Gly Ala Gly Ala Arg Lys Lys Leu Arg Leu Thr Thr Glu Gln
            100                 105                 110

Ser Lys Leu Leu Glu Asp Thr Phe Arg Ala His Asn Ile Leu Ser His
```

```
                115                 120                 125
Ala Gln Lys His Glu Val Ala Arg Gln Val Asp Leu Ser Ala Arg Gln
            130                 135                 140
Val Glu Val Trp Phe Gln Asn Arg Arg Ala Arg Thr Lys Leu Lys Gln
145                 150                 155                 160
Thr Glu Val Asp Cys Glu Thr Leu Arg Arg Trp Arg Glu Ser Leu Ala
                165                 170                 175
Asp Glu Asn Leu Arg Leu Arg Leu Glu Leu Glu Gln Leu Gln Arg Trp
            180                 185                 190
Ala Thr Ala Ala Ala Gly Gln Ser Ser Ala Ser Pro Ser Pro Ala Thr
                195                 200                 205
Ala Thr Ala Ser Val Cys Pro Ser Cys Asp Lys Val Val Val Val Thr
            210                 215                 220
Val Thr Ser Cys Gly Glu Thr Ser Gly Lys Ser Ser Thr Ser Ser Tyr
225                 230                 235                 240
Ser Ser Ser Pro Pro Leu Asp Met Leu Asp Arg Ser Val Gln
                245                 250

<210> SEQ ID NO 176
<211> LENGTH: 254
<212> TYPE: PRT
<213> ORGANISM: Zea mays

<400> SEQUENCE: 176

Met Tyr Thr Thr Thr Arg Ala Met Glu Lys Glu Glu Gly Phe Gly Lys
1               5                   10                  15
Ser Trp Ala Gly Ala Gly Ile Gly Gly Gly Arg Asp Ala Asn Ala
            20                  25                  30
Met Lys Arg Ser Arg Pro Leu Arg Pro Val Arg Leu Asp Leu Leu Phe
            35                  40                  45
Pro Pro Ser Val Glu Gly Gly Glu Ala Ala Arg Ser Arg Lys Ala
50                  55                  60
Gly Ala Gly Ala Leu Arg Asn Met Ser Leu Lys Gln Val Ala Gly Asp
65                  70                  75                  80
Asp Asp Gly Gly Gln Ser Ser His Gly Gly Pro Ser Pro Ser Asp Asp
                85                  90                  95
Asp Asp Gly Ala Gly Ala Arg Lys Lys Leu Arg Leu Thr Thr Glu Gln
            100                 105                 110
Ser Lys Leu Leu Glu Asp Thr Phe Arg Ala His Asn Ile Leu Ser His
            115                 120                 125
Ala Gln Lys His Glu Val Ala Arg Gln Val Asp Leu Ser Ala Arg Gln
            130                 135                 140
Val Glu Val Trp Phe Gln Asn Arg Arg Ala Arg Thr Lys Leu Lys Gln
145                 150                 155                 160
Thr Glu Val Asp Cys Glu Thr Leu Arg Arg Trp Arg Glu Ser Leu Ala
                165                 170                 175
Asp Glu Asn Leu Arg Ala Arg Ala Glu Ala Glu Gln Leu Gln Arg Trp
            180                 185                 190
Ala Thr Ala Ala Ala Gly Gln Ser Ser Ala Ser Pro Ser Pro Ala Thr
                195                 200                 205
Ala Thr Ala Ser Val Cys Pro Ser Cys Asp Lys Val Val Val Val Thr
            210                 215                 220
Val Thr Ser Cys Gly Glu Thr Ser Gly Lys Ser Ser Thr Ser Ser Tyr
225                 230                 235                 240
```

-continued

Ser Ser Ser Pro Pro Leu Asp Met Leu Asp Arg Ser Val Gln
            245                 250

<210> SEQ ID NO 177
<211> LENGTH: 331
<212> TYPE: PRT
<213> ORGANISM: Zea mays

<400> SEQUENCE: 177

Met Glu Leu Glu Ala Ser Ala Gly Asp Ser Arg Ala Pro Ala Lys Ser
1               5                   10                  15

Ala Ser Thr Pro Ala Ala Leu Thr Pro Ile His Ala Gly Ala Gly Gly
            20                  25                  30

Glu Gly His Glu Leu Ala Leu Glu Leu Gly Val Gly Ala Ala Lys Arg
        35                  40                  45

Ala Glu Gln Asp Asn Gln Lys Thr Pro Val Gln Pro Glu His Val Gln
    50                  55                  60

Glu Glu Glu Glu Glu Glu Thr Cys Pro Tyr Ser Glu Ser Pro Ala
65                  70                  75                  80

Glu Leu Ser Leu Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
            100                 105                 110

Val Asp Ala Val Leu Val Asp Gly Gly Asp Ala Ala Gln Gly Arg Pro
        115                 120                 125

Ala Leu Ser Thr Ser Phe Leu Pro Ser Glu Phe Leu Val Arg Arg Gln
    130                 135                 140

Ala Asp Asp Gln Glu Ala Ala Ala Glu Asp Glu Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
        195                 200                 205

Val Trp Phe Gln Asn Arg Arg Ala Arg Ser Lys Leu Lys Gln Thr Glu
    210                 215                 220

Val Asp Cys Glu Tyr Leu Lys Arg Trp Cys Glu Lys Leu Ala Gln Glu
225                 230                 235                 240

Asn Arg Arg Leu Gln Arg Glu Val Ala Glu Leu Arg Arg Leu Cys Ser
                245                 250                 255

Ala Ala Tyr Pro Phe Tyr Gly Ala Ala Ala Gly Phe Gly Val Ala Thr
            260                 265                 270

Ala Arg Val Cys Pro Ser Ser Cys Asp Asn Asp Val Ser Glu Ala Ala
        275                 280                 285

Ile Ser Gly Ala Pro Ser Ala Ala Ala Pro Pro Ser Thr Leu Phe
    290                 295                 300

Ala Ser Trp Pro Pro His Phe Gly Pro Phe Thr Val Val Pro Pro
305                 310                 315                 320

Leu Leu Arg Arg Gln Pro Ser Ala Thr Thr Ser
                325                 330

<210> SEQ ID NO 178
<211> LENGTH: 331
<212> TYPE: PRT
<213> ORGANISM: Zea mays

<400> SEQUENCE: 178

Met Glu Leu Glu Ala Ser Ala Gly Asp Ser Arg Ala Pro Ala Lys Ser
1               5                   10                  15

Ala Ser Thr Pro Ala Ala Leu Thr Pro Ile His Ala Gly Ala Gly Gly
            20                  25                  30

Glu Gly His Glu Ala Ala Glu Ala Gly Val Gly Ala Ala Lys Arg
        35                  40                  45

Ala Glu Gln Asp Asn Gln Lys Thr Pro Val Gln Pro Glu His Val Gln
    50                  55                  60

Glu Glu Glu Glu Glu Glu Thr Cys Pro Tyr Ser Glu Ser Pro Ala
65                  70                  75                  80

Glu Leu Ser Leu Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
            100                 105                 110

Val Asp Ala Val Leu Val Asp Gly Gly Asp Ala Ala Gln Gly Arg Pro
        115                 120                 125

Ala Leu Ser Thr Ser Phe Leu Pro Ser Glu Phe Leu Val Arg Arg Gln
    130                 135                 140

Ala Asp Asp Gln Glu Ala Ala Ala Glu Asp Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
        195                 200                 205

Val Trp Phe Gln Asn Arg Arg Ala Arg Ser Lys Leu Lys Gln Thr Glu
    210                 215                 220

Val Asp Cys Glu Tyr Leu Lys Arg Trp Cys Lys Leu Ala Gln Glu
225                 230                 235                 240

Asn Arg Arg Leu Gln Arg Glu Val Ala Glu Leu Arg Arg Leu Cys Ser
                245                 250                 255

Ala Ala Tyr Pro Phe Tyr Gly Ala Ala Ala Gly Phe Gly Val Ala Thr
            260                 265                 270

Ala Arg Val Cys Pro Ser Ser Cys Asp Asn Asp Val Ser Glu Ala Ala
        275                 280                 285

Ile Ser Gly Ala Pro Ser Ala Ala Pro Pro Ser Thr Leu Phe
    290                 295                 300

Ala Ser Trp Pro Pro His Phe Gly Pro Phe Thr Val Val Pro Pro
305                 310                 315                 320

Leu Leu Arg Arg Gln Pro Ser Ala Thr Thr Ser
                325                 330

<210> SEQ ID NO 179
<211> LENGTH: 331
<212> TYPE: PRT
<213> ORGANISM: Zea mays

<400> SEQUENCE: 179

Met Glu Leu Glu Ala Ser Ala Gly Asp Ser Arg Ala Pro Ala Lys Ser
1               5                   10                  15

Ala Ser Thr Pro Ala Ala Leu Thr Pro Ile His Ala Gly Ala Gly Gly
            20                  25                  30

```
Glu Gly His Glu Ala Ala Ala Glu Ala Gly Val Gly Ala Ala Lys Arg
            35                  40                  45

Ala Glu Gln Asp Asn Gln Lys Thr Pro Val Gln Pro Glu His Val Gln
 50                  55                  60

Glu Glu Glu Glu Glu Glu Glu Thr Cys Pro Tyr Ser Glu Ser Pro Ala
 65                  70                  75                  80

Glu Ala Ser Ala Ile Gly Cys Pro Leu Leu Pro Ala Ala Ser Ala Glu
                 85                  90                  95

Ile Gly Ser Val Asn Ser Ser Glu Val Cys Val Arg Arg Gly Phe Gly
                100                 105                 110

Val Asp Ala Val Leu Val Asp Gly Gly Asp Ala Ala Gln Gly Arg Pro
                115                 120                 125

Ala Leu Ser Thr Ser Phe Leu Pro Ser Glu Phe Leu Val Arg Arg Gln
            130                 135                 140

Ala Asp Asp Gln Glu Ala Ala Ala Glu Asp Glu Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
            195                 200                 205

Val Trp Phe Gln Asn Arg Arg Ala Arg Ser Lys Leu Lys Gln Thr Glu
            210                 215                 220

Val Asp Cys Glu Tyr Leu Lys Arg Trp Cys Lys Leu Ala Gln Glu
225                 230                 235                 240

Asn Arg Arg Leu Gln Arg Glu Val Ala Glu Leu Arg Arg Leu Cys Ser
                245                 250                 255

Ala Ala Tyr Pro Phe Tyr Gly Ala Ala Ala Gly Phe Gly Val Ala Thr
            260                 265                 270

Ala Arg Val Cys Pro Ser Ser Cys Asp Asn Asp Val Ser Glu Ala Ala
            275                 280                 285

Ile Ser Gly Ala Pro Ser Ala Ala Pro Pro Ser Thr Leu Phe
            290                 295                 300

Ala Ser Trp Pro Pro His Phe Gly Pro Phe Thr Val Val Pro Pro
305                 310                 315                 320

Leu Leu Arg Arg Gln Pro Ser Ala Thr Thr Ser
            325                 330

<210> SEQ ID NO 180
<211> LENGTH: 331
<212> TYPE: PRT
<213> ORGANISM: Zea mays

<400> SEQUENCE: 180

Met Glu Leu Glu Ala Ser Ala Gly Asp Ser Arg Ala Pro Ala Lys Ser
1               5                   10                  15

Ala Ser Thr Pro Ala Ala Leu Thr Pro Ile His Ala Gly Ala Gly Gly
                20                  25                  30

Glu Gly His Glu Leu Ala Leu Glu Leu Gly Val Gly Ala Ala Lys Arg
            35                  40                  45

Ala Glu Gln Asp Asn Gln Lys Thr Pro Val Gln Pro Glu His Val Gln
 50                  55                  60

Glu Glu Glu Glu Glu Glu Glu Thr Cys Pro Tyr Ser Glu Ser Pro Ala
```

```
            65                  70                  75                  80
Glu Ala Ser Ala Ile Gly Cys Pro Leu Leu Pro Ala Ala Ser Ala Glu
                85                  90                  95
Ile Gly Ser Val Asn Ser Ser Glu Val Cys Val Arg Arg Gly Phe Gly
            100                 105                 110
Val Asp Ala Val Leu Val Asp Gly Asp Ala Ala Gln Gly Arg Pro
        115                 120                 125
Ala Leu Ser Thr Ser Phe Leu Pro Ser Glu Phe Leu Val Arg Arg Gln
    130                 135                 140
Ala Asp Asp Gln Glu Ala Ala Glu Asp Glu Glu Met Ser Gly Val
145                 150                 155                 160
Gly Gly Gly Ala Arg Lys Lys Leu Arg Leu Ser Lys Glu Gln Ser Ala
                165                 170                 175
Phe Leu Glu Asp Ser Phe Lys Ala His Ser Thr Leu Thr Pro Lys Gln
            180                 185                 190
Lys Ser Asp Leu Ala Lys Arg Leu Lys Leu Arg Pro Arg Gln Val Glu
        195                 200                 205
Val Trp Phe Gln Asn Arg Arg Ala Arg Ser Lys Leu Lys Gln Thr Glu
    210                 215                 220
Val Asp Cys Glu Tyr Leu Lys Arg Trp Cys Glu Lys Leu Ala Gln Glu
225                 230                 235                 240
Asn Arg Arg Leu Gln Arg Glu Val Ala Glu Leu Arg Arg Leu Cys Ser
                245                 250                 255
Ala Ala Tyr Pro Phe Tyr Gly Ala Ala Ala Gly Phe Gly Val Ala Thr
            260                 265                 270
Ala Arg Val Cys Pro Ser Ser Cys Asp Asn Asp Val Ser Glu Ala Ala
        275                 280                 285
Ile Ser Gly Ala Pro Ser Ala Ala Pro Pro Ser Thr Leu Phe
    290                 295                 300
Ala Ser Trp Pro Pro His Phe Gly Pro Phe Thr Val Val Pro Pro
305                 310                 315                 320
Leu Leu Arg Arg Gln Pro Ser Ala Thr Thr Ser
                325                 330

<210> SEQ ID NO 181
<211> LENGTH: 354
<212> TYPE: PRT
<213> ORGANISM: Zea mays

<400> SEQUENCE: 181

Met Glu Leu Gly Leu Ser Leu Gly Asp Ala Ala Val Pro Asp Ala Gly
1               5                   10                  15
Arg Ala Ala Pro Glu Ala Gly Ala Gly Ala Gly Val Gly Ile Gly Ser
            20                  25                  30
Asn Ala Ala Gly Thr Gly Arg Gly Ser Lys Ala Ala Gly Thr Thr Gly
        35                  40                  45
Thr Thr Gly Trp Trp Ala Ala Pro Ala Thr Pro Glu Ser Ala Val Arg
    50                  55                  60
Leu Ser Leu Val Ser Ser Leu Gly Leu Gln Trp Pro Pro Pro Asp Gly
65                  70                  75                  80
Gly Ile Cys His Val Gly Arg Asp Glu Ala Pro Ala Arg Gly Phe Asp
                85                  90                  95
Val Asn Arg Ala Pro Ser Val Ala Gly Ser Ala Leu Ala Leu Glu Asp
            100                 105                 110
```

Asp Glu Glu Glu Pro Gly Ala Ala Ala Leu Ser Ser Ser Pro Asn Asp
            115                 120                 125

Ser Ala Gly Ser Phe Pro Leu Asp Leu Gly Pro Arg Ala His Ala
130                 135                 140

Glu Gly Ala Ala Ala Arg Ala Gly Glu Arg Ser Ser Ser Arg Ala
145                 150                 155                 160

Ser Asp Glu Asp Glu Gly Ala Ser Ala Arg Lys Lys Leu Arg Leu Ser
                165                 170                 175

Lys Glu Gln Ser Ala Phe Leu Glu Glu Ser Phe Lys Glu His Ser Thr
            180                 185                 190

Leu Asn Pro Lys Gln Lys Ala Ala Leu Ala Lys Gln Leu Asn Leu Arg
            195                 200                 205

Pro Arg Gln Val Glu Val Trp Phe Gln Asn Arg Arg Ala Arg Thr Lys
            210                 215                 220

Leu Lys Gln Thr Glu Val Asp Cys Glu Tyr Leu Lys Arg Cys Cys Glu
225                 230                 235                 240

Thr Leu Thr Glu Glu Asn Arg Arg Leu His Lys Glu Leu Ala Glu Leu
                245                 250                 255

Arg Ala Leu Lys Thr Ala Pro Pro Phe Phe Met Arg Leu Pro Ala Thr
            260                 265                 270

Thr Leu Ser Met Cys Pro Ser Cys Glu Arg Val Ala Ser Gly Pro Ser
            275                 280                 285

Pro Ala Ser Thr Ser Ala Pro Ala Ser Ser Thr Pro Pro Ala Thr Ala
            290                 295                 300

Ala Thr Thr Ala Ile Ser Tyr Ala Ala Ala Ala Ala Ala Pro Val Arg
305                 310                 315                 320

Ala Asp His Arg Pro Ser Ser Phe Ala Ala Leu Phe Ala Ala Thr Arg
                325                 330                 335

Ser Phe Pro Leu Ala Ser Gln Pro Arg Pro Ala Pro Ala Ser Asn
            340                 345                 350

Cys Leu

<210> SEQ ID NO 182
<211> LENGTH: 267
<212> TYPE: PRT
<213> ORGANISM: Zea mays

<400> SEQUENCE: 182

Met Ser Ser Leu Thr Thr Ala Ala Ser Ser Ser Ser Met Glu Glu
1               5                   10                  15

His Cys Tyr Ser Val Ser Ala Glu Glu Val Val Gly Thr His Leu Ser
            20                  25                  30

Leu Gly Ile Gly Gly Gly Gly Gly Gly Gly Asp Lys Arg Thr Met
            35                  40                  45

Leu Thr Leu Pro Pro Ser Arg Thr Val Gln Leu Phe Gly Glu Val Leu
50                  55                  60

Ser Val Gln Asp Gly Asp Gly Thr Gln Ala Leu Arg His His His Thr
65                  70                  75                  80

Gly Arg Pro Pro Ala Ala Ser Ser Arg Lys Lys Arg Lys Asp Ala
                85                  90                  95

Ala Ala Ala Gly Gly Ala Ser Ala Thr Asp Ala Ala Ala Asn Gly His
            100                 105                 110

His His Gln Ser Lys Lys Thr Lys Thr Thr Ala Ala Arg Arg Asp Asp
            115                 120                 125

```
Gly Gly Gly Gly Arg Lys Lys Leu Arg Leu Thr Ser Ala Gln Ala Thr
        130                 135                 140
Leu Leu Glu Asp Ser Phe Arg Ala His Asn Ile Leu Ser His Gly Glu
145                 150                 155                 160
Lys Gln Glu Leu Ala Arg Gln Ala Gly Leu Ser Ala Arg Gln Val Glu
                165                 170                 175
Val Trp Phe Gln Asn Arg Arg Ala Arg Thr Lys Leu Lys Gln Thr Glu
            180                 185                 190
Val Asp Cys Asp Leu Leu Arg Arg Trp Cys Ala Arg Leu Ser Asp Asp
        195                 200                 205
Asn Asp Arg Leu Arg Arg Asp Leu Ala Asp Leu Arg Arg Ala Ala Ser
210                 215                 220
Ser Ser Ala Gly Leu Gly Ala Val Val Cys Ala Ser Cys Gly Ala
225                 230                 235                 240
Asp Arg Gln Ala Ala Ala Ala Ala Ala Asp Asn Val Leu Pro Ser
                245                 250                 255
Val Ala Ser Pro Ser His Ser Pro His Leu Thr
            260                 265

<210> SEQ ID NO 183
<211> LENGTH: 319
<212> TYPE: PRT
<213> ORGANISM: Zea mays

<400> SEQUENCE: 183

Met Asp Ile Met Ala Leu Asn Ala Arg Asp Glu Glu Gln Tyr Gly Asn
1               5                   10                  15
Asn His Leu Gly Leu Gly Leu Ser Leu Ser Leu Gly Leu Gly Val Ala
                20                  25                  30
Thr Ala Ala Pro Val Glu Val Pro Pro Pro Pro Arg Gln Gln
            35                  40                  45
Gln Gln Arg Ala Ile Ser Val Ala Pro Ile Thr Ser Leu Pro Ala Pro
        50                  55                  60
Gln Trp Trp Lys Trp Asn Gly Pro Gly Leu Phe Phe Gly Thr Thr Met
65              70                  75                  80
Asp Gln Gln Gln Gln Pro Ala Ala Arg His Gly His Glu Met Pro
                85                  90                  95
Phe Leu Arg Gly Val Asp Val Asn Arg Ala Pro Ala Gly Asp Thr Arg
            100                 105                 110
Arg Gly Ser Cys Ser Glu Asp Asp Glu Glu Pro Gly Gly Ala Ser Ser
        115                 120                 125
Ser Pro Asn Ser Thr Leu Ser Ser Ser Leu Ser Gly Lys Arg Ala Ala
130                 135                 140
Pro Ala Arg Ser Gly Gly Glu Val Ala Asp His Thr Pro Arg Ala Gly
145                 150                 155                 160
Gly Gly Ser Asp Asp Glu Asp Ser Gly Gly Gly Ser Arg Lys Lys Leu
                165                 170                 175
Arg Leu Ser Lys Asp Gln Ala Ala Val Leu Glu Glu Ser Phe Lys Glu
            180                 185                 190
His Asn Thr Leu Asn Pro Lys Gln Lys Ala Ala Leu Ala Lys Gln Leu
        195                 200                 205
Asn Leu Lys Pro Arg Gln Val Glu Val Trp Phe Gln Asn Arg Arg Ala
210                 215                 220
Arg Thr Lys Leu Lys Gln Thr Glu Val Asp Cys Glu Phe Leu Lys Arg
225                 230                 235                 240
```

```
Cys Cys Glu Thr Leu Thr Glu Asn Arg Arg Leu Gln Arg Glu Val
            245                 250                 255

Ala Glu Leu Arg Val Ala Lys Ala Val Ala Pro His His Tyr Ala Arg
        260                 265                 270

Met Pro Pro Thr Thr Leu Thr Met Cys Pro Ser Cys Glu Arg Leu
        275                 280                 285

Ala Ser Ala Ser Ala Ser Ala Asp Gln Ala Gly Arg Ala Gly Pro Cys
290                 295                 300

Trp Gly Pro Leu Pro Val Phe Val Asp Gly Pro Ala Arg Arg Pro
305                 310                 315
```

<210> SEQ ID NO 184
<211> LENGTH: 254
<212> TYPE: PRT
<213> ORGANISM: Zea mays

<400> SEQUENCE: 184

```
Met Tyr Thr Thr Thr Arg Ala Met Glu Lys Glu Glu Gly Phe Gly Lys
1               5                   10                  15

Ser Trp Leu Gly Leu Gly Ile Gly Gly Gly Arg Asp Ala Asn Ala
            20                  25                  30

Met Lys Arg Ser Arg Pro Leu Arg Pro Val Arg Leu Asp Leu Leu Phe
        35                  40                  45

Pro Pro Ser Val Glu Gly Gly Glu Ala Ala Arg Ser Arg Lys Ala
50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
                85                  90                  95

Asp Asp Gly Ala Gly Ala Arg Lys Lys Leu Arg Leu Thr Thr Glu Gln
            100                 105                 110

Ser Lys Leu Leu Glu Asp Thr Phe Arg Ala His Asn Ile Leu Ser His
        115                 120                 125

Ala Gln Lys His Glu Val Ala Arg Gln Val Asp Leu Ser Ala Arg Gln
130                 135                 140

Val Glu Val Trp Phe Gln Asn Arg Arg Ala Arg Thr Lys Leu Lys Gln
145                 150                 155                 160

Thr Glu Val Asp Cys Glu Thr Leu Arg Arg Trp Arg Glu Ser Leu Ala
                165                 170                 175

Asp Glu Asn Leu Arg Leu Arg Leu Glu Leu Glu Gln Leu Gln Arg Trp
            180                 185                 190

Ala Thr Ala Ala Ala Gly Gln Ser Ser Ala Ser Pro Ser Pro Ala Thr
        195                 200                 205

Ala Thr Ala Ser Val Cys Pro Ser Cys Asp Lys Val Val Val Thr
210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250
```

<210> SEQ ID NO 185
<211> LENGTH: 254
<212> TYPE: PRT
<213> ORGANISM: Zea mays

<400> SEQUENCE: 185

```
Met Tyr Thr Thr Thr Arg Ala Met Glu Lys Glu Gly Phe Gly Lys
1               5                   10                  15

Ser Trp Leu Gly Leu Gly Ile Gly Gly Gly Arg Asp Ala Asn Ala
            20                  25                  30

Met Lys Arg Ser Arg Pro Leu Arg Pro Val Arg Leu Asp Leu Leu Phe
            35                  40                  45

Pro Pro Ser Val Glu Gly Gly Glu Ala Ala Arg Ser Arg Lys Ala
    50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
                85                  90                  95

Asp Asp Gly Ala Gly Ala Arg Lys Lys Leu Arg Leu Thr Thr Glu Gln
            100                 105                 110

Ser Lys Leu Leu Glu Asp Thr Phe Arg Ala His Asn Ile Leu Ser His
            115                 120                 125

Ala Gln Lys His Glu Val Ala Arg Gln Val Asp Leu Ser Ala Arg Gln
130                 135                 140

Val Glu Val Trp Phe Gln Asn Arg Arg Ala Arg Thr Lys Leu Lys Gln
145                 150                 155                 160

Thr Glu Val Asp Cys Glu Thr Leu Arg Arg Trp Arg Glu Ser Leu Ala
                165                 170                 175

Asp Glu Asn Leu Arg Ala Arg Ala Glu Ala Glu Gln Leu Gln Arg Trp
            180                 185                 190

Ala Thr Ala Ala Ala Gly Gln Ser Ser Ala Ser Pro Ser Pro Ala Thr
            195                 200                 205

Ala Thr Ala Ser Val Cys Pro Ser Cys Asp Lys Val Val Val Val Thr
            210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250
```

<210> SEQ ID NO 186
<211> LENGTH: 267
<212> TYPE: PRT
<213> ORGANISM: Zea mays

<400> SEQUENCE: 186

```
Met Ser Ser Leu Thr Thr Ala Ala Ser Ser Ser Ser Met Glu Glu
1               5                   10                  15

His Cys Tyr Ser Val Ser Ala Glu Glu Val Val Gly Thr His Ala Ser
            20                  25                  30

Ala Gly Ile Gly Gly Gly Gly Gly Gly Gly Asp Lys Arg Thr Met
            35                  40                  45

Leu Thr Leu Pro Pro Ser Arg Thr Val Gln Leu Phe Gly Glu Val Leu
    50                  55                  60

Ser Val Gln Asp Gly Asp Gly Thr Gln Ala Leu Arg His His His Thr
65                  70                  75                  80

Gly Arg Pro Pro Ala Ala Ser Ser Arg Lys Lys Lys Arg Lys Asp Ala
                85                  90                  95

Ala Ala Ala Gly Gly Ala Ser Ala Thr Asp Ala Ala Ala Asn Gly His
            100                 105                 110

His His Gln Ser Lys Lys Thr Lys Thr Thr Ala Ala Arg Arg Asp Asp
```

```
                115                 120                 125
Gly Gly Gly Gly Arg Lys Lys Leu Arg Leu Thr Ser Ala Gln Ala Thr
            130                 135                 140
Leu Leu Glu Asp Ser Phe Arg Ala His Asn Ile Leu Ser His Gly Glu
145                 150                 155                 160
Lys Gln Glu Leu Ala Arg Gln Ala Gly Leu Ser Ala Arg Gln Val Glu
                165                 170                 175
Val Trp Phe Gln Asn Arg Arg Ala Arg Thr Lys Leu Lys Gln Thr Glu
            180                 185                 190
Val Asp Cys Asp Leu Leu Arg Arg Trp Cys Ala Arg Leu Ser Asp Asp
                195                 200                 205
Asn Asp Arg Leu Arg Arg Asp Leu Ala Asp Leu Arg Arg Ala Ala Ser
            210                 215                 220
Ser Ser Ala Gly Leu Gly Ala Val Val Cys Cys Ala Ser Cys Gly Ala
225                 230                 235                 240
Asp Arg Gln Leu Ala Leu Ala Ala Ala Asp Asn Val Leu Pro Ser
                245                 250                 255
Val Ala Ser Pro Ser His Ser Pro His Leu Thr
                260                 265

<210> SEQ ID NO 187
<211> LENGTH: 267
<212> TYPE: PRT
<213> ORGANISM: Zea mays

<400> SEQUENCE: 187

Met Ser Ser Leu Thr Thr Ala Ala Ser Ser Ser Ser Met Glu Glu
1                   5                   10                  15
His Cys Tyr Ser Val Ser Ala Glu Glu Val Val Gly Thr His Ala Ser
                20                  25                  30
Ala Gly Ile Gly Gly Gly Gly Gly Gly Gly Asp Lys Arg Thr Met
            35                  40                  45
Leu Thr Leu Pro Pro Ser Arg Thr Val Gln Leu Phe Gly Glu Val Leu
50                  55                  60
Ser Val Gln Asp Gly Asp Gly Thr Gln Ala Leu Arg His His His Thr
65                  70                  75                  80
Gly Arg Pro Pro Ala Ala Ser Ser Arg Lys Lys Lys Arg Lys Asp Ala
                85                  90                  95
Ala Ala Ala Gly Gly Ala Ser Ala Thr Asp Ala Ala Ala Asn Gly His
            100                 105                 110
His His Gln Ser Lys Lys Thr Lys Thr Thr Ala Ala Arg Arg Asp Asp
        115                 120                 125
Gly Gly Gly Gly Arg Lys Lys Leu Arg Leu Thr Ser Ala Gln Ala Thr
            130                 135                 140
Leu Leu Glu Asp Ser Phe Arg Ala His Asn Ile Leu Ser His Gly Glu
145                 150                 155                 160
Lys Gln Glu Leu Ala Arg Gln Ala Gly Leu Ser Ala Arg Gln Val Glu
                165                 170                 175
Val Trp Phe Gln Asn Arg Arg Ala Arg Thr Lys Leu Lys Gln Thr Glu
            180                 185                 190
Val Asp Cys Asp Leu Leu Arg Arg Trp Cys Ala Arg Leu Ser Asp Asp
                195                 200                 205
Asn Asp Arg Leu Arg Arg Asp Leu Ala Asp Leu Arg Arg Ala Ala Ser
            210                 215                 220
```

Ser Ser Ala Gly Leu Gly Ala Val Val Cys Cys Ala Ser Cys Gly Ala
225                 230                 235                 240

Asp Arg Gln Ala Ala Ala Ala Ala Ala Asp Asn Val Leu Pro Ser
            245                 250                 255

Val Ala Ser Pro Ser His Ser Pro His Leu Thr
            260                 265

<210> SEQ ID NO 188
<211> LENGTH: 354
<212> TYPE: PRT
<213> ORGANISM: Zea mays

<400> SEQUENCE: 188

Met Glu Ala Gly Ala Ser Ala Gly Asp Ala Ala Val Pro Asp Ala Gly
1               5                   10                  15

Arg Ala Ala Pro Glu Leu Gly Leu Gly Leu Gly Val Gly Ile Gly Ser
                20                  25                  30

Asn Ala Ala Gly Thr Gly Arg Gly Ser Lys Ala Ala Gly Thr Thr Gly
            35                  40                  45

Thr Thr Gly Trp Trp Ala Ala Pro Ala Thr Pro Glu Ser Ala Val Arg
50                  55                  60

Leu Ser Leu Val Ser Ser Leu Gly Leu Gln Trp Pro Pro Asp Gly
65                  70                  75                  80

Gly Ile Cys His Val Gly Arg Asp Glu Ala Pro Ala Arg Gly Phe Asp
                85                  90                  95

Val Asn Arg Ala Pro Ser Val Ala Gly Ser Ala Leu Ala Leu Glu Asp
            100                 105                 110

Asp Glu Glu Glu Pro Gly Ala Ala Ala Leu Ser Ser Ser Pro Asn Asp
        115                 120                 125

Ser Ala Gly Ser Phe Pro Leu Asp Leu Gly Gly Pro Arg Ala His Ala
    130                 135                 140

Glu Gly Ala Ala Ala Arg Ala Gly Gly Glu Arg Ser Ser Ser Arg Ala
145                 150                 155                 160

Ser Asp Glu Asp Glu Gly Ala Ser Ala Arg Lys Lys Leu Arg Leu Ser
                165                 170                 175

Lys Glu Gln Ser Ala Phe Leu Glu Glu Ser Phe Lys Glu His Ser Thr
            180                 185                 190

Leu Asn Pro Lys Gln Lys Ala Ala Leu Ala Lys Gln Leu Asn Leu Arg
        195                 200                 205

Pro Arg Gln Val Glu Val Trp Phe Gln Asn Arg Arg Ala Arg Thr Lys
    210                 215                 220

Leu Lys Gln Thr Glu Val Asp Cys Glu Tyr Leu Lys Arg Cys Cys Glu
225                 230                 235                 240

Thr Leu Thr Glu Glu Asn Arg Arg Leu His Lys Glu Leu Ala Glu Leu
                245                 250                 255

Arg Ala Leu Lys Thr Ala Pro Pro Phe Phe Met Arg Leu Pro Ala Thr
            260                 265                 270

Thr Leu Ser Met Cys Pro Ser Cys Glu Arg Val Ala Ser Gly Pro Ser
        275                 280                 285

Pro Ala Ser Thr Ser Ala Pro Ala Ser Ser Thr Pro Pro Ala Thr Ala
    290                 295                 300

Ala Thr Thr Ala Ile Ser Tyr Ala Ala Ala Ala Ala Pro Val Arg
305                 310                 315                 320

Ala Asp His Arg Pro Ser Ser Phe Ala Ala Leu Phe Ala Ala Thr Arg
                325                 330                 335

```
Ser Phe Pro Leu Ala Ser Gln Pro Arg Pro Ala Pro Ala Ser Asn
                340                 345                 350

Cys Leu

<210> SEQ ID NO 189
<211> LENGTH: 335
<212> TYPE: PRT
<213> ORGANISM: Zea mays

<400> SEQUENCE: 189

Met Glu Ala Ala Ala Ser Ala Gly Glu Thr Met Ala Asp Ala Gly Arg
1               5                   10                  15

Asp Leu Met Leu Gly Leu Gly Met Gly Val Gly Val Arg Arg Glu Glu
                20                  25                  30

Glu Ala Gln Arg Gly Arg Arg Asp Arg Glu Val Arg Arg Glu Leu Glu
            35                  40                  45

Phe Thr Ala Arg Ser Ala Arg Ser Ser Pro Glu Pro Ala Val Arg Leu
    50                  55                  60

Thr Leu Leu His Gly Leu Gly Leu Pro Trp Pro Pro Pro Ser Ser
65                  70                  75                  80

Glu Thr Asn Arg His Leu Glu Ala Ser Ala Arg Gly Phe Asp Val Asn
                85                  90                  95

Arg Ala Pro Ser Leu Ser Ala Ala Gly Ala Ala Glu Glu Asp Glu
            100                 105                 110

Glu Gln Asp Glu Ala Gly Ala Ala Ala Ala Ala Ser Ser Ser Pro
        115                 120                 125

Asn Asn Ser Ala Ser Ser Phe Pro Thr Asp Phe Ser Ala His Gly Gln
    130                 135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
        195                 200                 205

Glu Val Trp Phe Gln Asn Arg Arg Ala Arg Thr Lys Leu Lys Gln Thr
    210                 215                 220

Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
                245                 250                 255

Thr Val His Pro Phe Tyr Met His Leu Pro Ala Thr Thr Leu Ser Met
            260                 265                 270

Cys Pro Ser Cys Glu Arg Val Ala Ser Asn Ser Ala Pro Ala Pro Ala
        275                 280                 285

Ser Ser Pro Ser Pro Ala Thr Gly Ile Ala Ala Pro Ala Pro Glu Gln
    290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 190
```

```
<211> LENGTH: 335
<212> TYPE: PRT
<213> ORGANISM: Zea mays

<400> SEQUENCE: 190

Met Glu Ala Ala Ala Ser Ala Gly Glu Thr Met Ala Asp Ala Gly Arg
1               5                   10                  15

Asp Ala Met Ala Gly Ala Gly Met Gly Val Gly Val Arg Arg Glu Glu
                20                  25                  30

Glu Ala Gln Arg Gly Arg Arg Asp Arg Glu Val Arg Arg Glu Leu Glu
            35                  40                  45

Phe Thr Ala Arg Ser Ala Arg Ser Ser Pro Glu Pro Ala Val Arg Leu
50                  55                  60

Thr Leu Leu His Gly Leu Gly Leu Pro Trp Pro Pro Pro Ser Ser
65                  70                  75                  80

Glu Thr Asn Arg His Leu Glu Ala Ser Ala Arg Gly Phe Asp Val Asn
                85                  90                  95

Arg Ala Pro Ser Leu Ser Ala Ala Gly Ala Ala Ala Glu Glu Asp Glu
            100                 105                 110

Glu Gln Asp Glu Ala Gly Ala Ala Ala Ala Ala Ser Ser Ser Pro
        115                 120                 125

Asn Asn Ser Ala Ser Ser Phe Pro Thr Asp Phe Ser Ala His Gly Gln
130                 135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
        195                 200                 205

Glu Val Trp Phe Gln Asn Arg Arg Ala Arg Thr Lys Leu Lys Gln Thr
210                 215                 220

Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
                245                 250                 255

Thr Val His Pro Phe Tyr Met His Leu Pro Ala Thr Thr Leu Ser Met
            260                 265                 270

Cys Pro Ser Cys Glu Arg Val Ala Ser Asn Ser Ala Pro Ala Pro Ala
        275                 280                 285

Ser Ser Pro Ser Pro Ala Thr Gly Ile Ala Ala Pro Ala Pro Glu Gln
290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 191
<211> LENGTH: 335
<212> TYPE: PRT
<213> ORGANISM: Zea mays

<400> SEQUENCE: 191

Met Glu Ala Ala Ala Ser Ala Gly Glu Thr Met Ala Asp Ala Gly Arg
1               5                   10                  15
```

Asp Ala Met Ala Gly Ala Gly Met Gly Val Gly Val Arg Arg Glu Glu
            20                  25                  30

Glu Ala Gln Arg Gly Arg Arg Asp Arg Glu Val Arg Arg Glu Leu Glu
            35                  40                  45

Phe Thr Ala Arg Ser Ala Arg Ser Ser Pro Glu Pro Ala Val Arg Leu
50                      55                  60

Thr Leu Leu His Gly Ala Gly Ala Pro Trp Pro Pro Pro Ser Ser
65                  70                  75                  80

Glu Thr Asn Arg His Leu Glu Ala Ser Ala Arg Gly Phe Asp Val Asn
                85                  90                  95

Arg Ala Pro Ser Leu Ser Ala Ala Gly Ala Ala Ala Glu Glu Asp Glu
            100                 105                 110

Glu Gln Asp Glu Ala Gly Ala Ala Ala Ala Ala Ser Ser Ser Pro
            115                 120                 125

Asn Asn Ser Ala Ser Ser Phe Pro Thr Asp Phe Ser Ala His Gly Gln
130                     135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
            195                 200                 205

Glu Val Trp Phe Gln Asn Arg Arg Ala Arg Thr Lys Leu Lys Gln Thr
            210                 215                 220

Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
                245                 250                 255

Thr Val His Pro Phe Tyr Met His Leu Pro Ala Thr Thr Leu Ser Met
            260                 265                 270

Cys Pro Ser Cys Glu Arg Val Ala Ser Asn Ser Ala Pro Ala Pro Ala
            275                 280                 285

Ser Ser Pro Ser Pro Ala Thr Gly Ile Ala Ala Pro Ala Pro Glu Gln
            290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
            325                 330                 335

<210> SEQ ID NO 192
<211> LENGTH: 335
<212> TYPE: PRT
<213> ORGANISM: Zea mays

<400> SEQUENCE: 192

Met Glu Ala Ala Ala Ser Ala Gly Glu Thr Met Ala Asp Ala Gly Arg
1               5                   10                  15

Asp Leu Met Leu Gly Leu Gly Met Gly Val Gly Val Arg Arg Glu Glu
            20                  25                  30

Glu Ala Gln Arg Gly Arg Arg Asp Arg Glu Val Arg Arg Glu Leu Glu
            35                  40                  45

Phe Thr Ala Arg Ser Ala Arg Ser Ser Pro Glu Pro Ala Val Arg Leu

```
            50                  55                  60
Thr Leu Leu His Gly Ala Gly Ala Pro Trp Pro Pro Pro Ser Ser
 65                  70                  75                  80

Glu Thr Asn Arg His Leu Glu Ala Ser Ala Arg Gly Phe Asp Val Asn
                 85                  90                  95

Arg Ala Pro Ser Leu Ser Ala Ala Gly Ala Ala Ala Glu Glu Asp Glu
                100                 105                 110

Glu Gln Asp Glu Ala Gly Ala Ala Ala Ala Ala Ser Ser Ser Pro
                115                 120                 125

Asn Asn Ser Ala Ser Ser Phe Pro Thr Asp Phe Ser Ala His Gly Gln
                130                 135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
                180                 185                 190

Gln Lys Leu Ala Leu Ala Lys Gln Leu Asn Leu Arg Pro Arg Gln Val
                195                 200                 205

Glu Val Trp Phe Gln Asn Arg Arg Ala Arg Thr Lys Leu Lys Gln Thr
                210                 215                 220

Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
                245                 250                 255

Thr Val His Pro Phe Tyr Met His Leu Pro Ala Thr Thr Leu Ser Met
                260                 265                 270

Cys Pro Ser Cys Glu Arg Val Ala Ser Asn Ser Ala Pro Ala Pro Ala
                275                 280                 285

Ser Ser Pro Ser Pro Ala Thr Gly Ile Ala Ala Pro Ala Pro Glu Gln
                290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 193
<211> LENGTH: 354
<212> TYPE: PRT
<213> ORGANISM: Zea mays

<400> SEQUENCE: 193

Met Glu Ala Gly Ala Ser Ala Gly Asp Ala Ala Val Pro Asp Ala Gly
 1               5                  10                  15

Arg Ala Ala Pro Glu Leu Gly Ala Gly Ala Gly Val Gly Ile Gly Ser
                20                  25                  30

Asn Ala Ala Gly Thr Gly Arg Gly Ser Lys Ala Ala Gly Thr Thr Gly
                35                  40                  45

Thr Thr Gly Trp Trp Ala Ala Pro Ala Thr Pro Glu Ser Ala Val Arg
            50                  55                  60

Leu Ser Leu Val Ser Ser Leu Gly Leu Gln Trp Pro Pro Pro Asp Gly
 65                  70                  75                  80

Gly Ile Cys His Val Gly Arg Asp Glu Ala Pro Ala Arg Gly Phe Asp
                85                  90                  95
```

Val Asn Arg Ala Pro Ser Val Ala Gly Ser Ala Leu Ala Leu Glu Asp
            100                 105                 110

Asp Glu Glu Glu Pro Gly Ala Ala Ala Leu Ser Ser Pro Asn Asp
            115                 120                 125

Ser Ala Gly Ser Phe Pro Leu Asp Leu Gly Gly Pro Arg Ala His Ala
    130                 135                 140

Glu Gly Ala Ala Ala Arg Ala Gly Gly Glu Arg Ser Ser Ser Arg Ala
145                 150                 155                 160

Ser Asp Glu Asp Glu Gly Ala Ser Ala Arg Lys Lys Leu Arg Leu Ser
                165                 170                 175

Lys Glu Gln Ser Ala Phe Leu Glu Glu Ser Phe Lys Glu His Ser Thr
            180                 185                 190

Leu Asn Pro Lys Gln Lys Ala Ala Leu Ala Lys Gln Leu Asn Leu Arg
        195                 200                 205

Pro Arg Gln Val Glu Val Trp Phe Gln Asn Arg Arg Ala Arg Thr Lys
    210                 215                 220

Leu Lys Gln Thr Glu Val Asp Cys Glu Tyr Leu Lys Arg Cys Cys Glu
225                 230                 235                 240

Thr Leu Thr Glu Glu Asn Arg Arg Leu His Lys Glu Leu Ala Glu Leu
                245                 250                 255

Arg Ala Leu Lys Thr Ala Pro Pro Phe Phe Met Arg Leu Pro Ala Thr
            260                 265                 270

Thr Leu Ser Met Cys Pro Ser Cys Glu Arg Val Ala Ser Gly Pro Ser
        275                 280                 285

Pro Ala Ser Thr Ser Ala Pro Ala Ser Ser Thr Pro Pro Ala Thr Ala
    290                 295                 300

Ala Thr Thr Ala Ile Ser Tyr Ala Ala Ala Ala Ala Ala Pro Val Arg
305                 310                 315                 320

Ala Asp His Arg Pro Ser Ser Phe Ala Ala Leu Phe Ala Ala Thr Arg
                325                 330                 335

Ser Phe Pro Leu Ala Ser Gln Pro Arg Pro Pro Ala Pro Ala Ser Asn
            340                 345                 350

Cys Leu

<210> SEQ ID NO 194
<211> LENGTH: 262
<212> TYPE: PRT
<213> ORGANISM: Zea mays

<400> SEQUENCE: 194

Met Glu Gln Glu Glu Val Gly Leu Ala Leu Gly Leu Ser Leu Gly Ser
1               5                   10                  15

Gly His His His Gln Glu Leu Lys Pro Gln His Pro Ser His Pro Cys
            20                  25                  30

Ala Ala Leu Leu Glu Pro Ser Ala Ser Ala Ser Gly Pro Ala Thr Lys
        35                  40                  45

Asp Asp Gly Pro Thr Ala Pro Val Arg Arg Phe Ala Ala Val Lys Arg
    50                  55                  60

Glu Leu Gln Thr Met Glu Gly Asn Asp Asp Glu Ala Thr Gly Arg Val
65                  70                  75                  80

Leu Val Tyr Ser Val Ala Ser Ser Ala Val Val Thr Ala Asp Asp Asp
                85                  90                  95

Glu Gly Cys Asn Ser Ser Arg Lys Lys Leu Arg Leu Ser Lys Glu Gln
            100                 105                 110

Ser Ala Leu Leu Glu Asp His Phe Lys Glu His Ser Thr Leu Asn Pro
            115                 120                 125

Lys Gln Lys Ala Ala Leu Ala Arg Gln Leu Asn Leu Ser Pro Arg Gln
130                 135                 140

Val Glu Val Trp Phe Gln Asn Arg Arg Ala Arg Thr Lys Leu Lys Gln
145                 150                 155                 160

Thr Glu Val Asp Cys Glu Ile Leu Lys Arg Cys Cys Glu Thr Leu Thr
                165                 170                 175

Glu Glu Asn Arg Arg Leu His Arg Glu Leu Gln Gln Leu Arg Ala Leu
            180                 185                 190

Ser His Pro His Pro His Pro Ala Ala Phe Phe Met Pro Thr Ala Ala
        195                 200                 205

Ala Ala Ala Leu Ser Ile Cys Pro Ser Cys Gln Arg Leu Val Ala Thr
    210                 215                 220

Gly Ala Ser Ala Ala Ala Thr Thr Ala Gly Ala Asp Asn Lys Pro
225                 230                 235                 240

Lys Ala Gly Gly Pro Gly Gly Arg Ala Pro His Val Phe Ser Pro Phe
                245                 250                 255

Thr Asn Ser Ala Ala Cys
            260

<210> SEQ ID NO 195
<211> LENGTH: 245
<212> TYPE: PRT
<213> ORGANISM: Zea mays

<400> SEQUENCE: 195

Met Ala Gln Glu Asp Val His Leu Asp Asp Ala Gly Leu Ala Leu Cys
1               5                   10                  15

Leu Ser Leu His Gly Thr Ser Ser Ser Arg Leu Ser Thr Glu Ala Pro
            20                  25                  30

Arg Thr Leu Glu Pro Pro Ser Ala Thr Ala Ser Met Pro Asp Glu Ala
        35                  40                  45

Thr Ala Thr Ala Thr Gly Gly Ser Gly Gly Ser Gly Gly Ala Ala Arg
    50                  55                  60

Ser Val Ser Ser Arg Ser Val Glu Gly Val Lys Arg Glu Arg Val Asp
65                  70                  75                  80

Asp Ala Glu Gly Glu Arg Ala Ser Ser Thr Ala Ala Ala Ala Arg Val
                85                  90                  95

Cys Ala Gly Ala Glu Asp Asp Asp Gly Ser Thr Arg Lys Lys Leu
            100                 105                 110

Arg Leu Thr Lys Glu Gln Ser Lys Leu Leu Glu Asp Arg Phe Lys Asp
        115                 120                 125

His Ser Thr Leu Asn Pro Lys Gln Lys Ile Ala Leu Ala Lys Gln Leu
    130                 135                 140

Lys Leu Arg Pro Arg Gln Val Glu Val Trp Phe Gln Asn Arg Arg Ala
145                 150                 155                 160

Arg Thr Lys Leu Lys Gln Thr Glu Val Asp Cys Glu Leu Leu Lys Arg
                165                 170                 175

Cys Cys Glu Ser Leu Ser Glu Glu Asn Arg Arg Leu Gln Arg Glu Leu
            180                 185                 190

Gln Glu Leu Arg Ala Leu Lys Leu Ala Gly Pro His Pro Gln Ala Pro
        195                 200                 205

Ser Ser Ser Pro Ala Ala Ala Thr Gln Gly Val Pro Val Pro Val Pro
    210                 215                 220

-continued

Pro Pro Leu Tyr Val Gln Met Gln Met Gln Leu Ser Ser Cys Arg Cys
225                 230                 235                 240

Cys Arg Pro Pro Arg
            245

<210> SEQ ID NO 196
<211> LENGTH: 227
<212> TYPE: PRT
<213> ORGANISM: Zea mays

<400> SEQUENCE: 196

Met Met Glu Arg Val Glu Asp Leu Gly Leu Ser Leu Ser Leu Ser Ser
1               5                   10                  15

Ser Leu Ala Ser Pro Arg Thr His His Val Ala Thr Met Leu Leu Arg
            20                  25                  30

Ala Pro Glu Lys Arg Phe Leu Glu Met Pro Ala Leu Ala Pro Ala Lys
        35                  40                  45

Arg Thr Thr Glu Val Thr Gly Glu Asp Gly Leu Arg Gly Gly Ser Asp
    50                  55                  60

Glu Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Leu Asn Pro Arg Gln Lys Ala Ala Leu Ala Gln Gln Leu Gly
            100                 105                 110

Leu Arg Pro Arg Gln Val Glu Val Trp Phe Gln Asn Arg Arg Ala Arg
        115                 120                 125

Thr Lys Leu Lys Gln Thr Glu Val Asp Cys Glu Tyr Leu Lys Arg Cys
    130                 135                 140

Cys Glu Thr Leu Thr Glu Glu Asn Arg Arg Leu Gln Lys Glu Val Gln
145                 150                 155                 160

Glu Leu Arg Ala Leu Lys Leu Val Ser Pro His Leu Tyr Met His Met
                165                 170                 175

Ser Pro Pro Thr Thr Leu Thr Met Cys Pro Ser Cys Glu Arg Val Ser
            180                 185                 190

Ser Ser Asn Gly Asn Ser Ala Ala Thr Ala Ala Ala Arg Ala Arg
        195                 200                 205

Ala Gly Ala Gly Ala Gly Ala Ile Val Cys His Pro Ile Asp Arg Ala
    210                 215                 220

Thr Ser Thr
225

<210> SEQ ID NO 197
<211> LENGTH: 227
<212> TYPE: PRT
<213> ORGANISM: Zea mays

<400> SEQUENCE: 197

Met Met Glu Arg Val Glu Asp Leu Gly Leu Ser Leu Ser Leu Ser Ser
1               5                   10                  15

Ser Leu Ala Ser Pro Arg Thr His His Val Ala Thr Met Leu Leu Arg
            20                  25                  30

Ala Pro Glu Lys Arg Phe Leu Glu Met Pro Ala Leu Ala Pro Ala Lys
        35                  40                  45

Arg Thr Thr Glu Val Thr Gly Glu Asp Gly Leu Arg Gly Gly Ser Asp
    50                  55                  60

```
Glu Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Leu Asn Pro Arg Gln Lys Ala Ala Leu Ala Gln Gln Leu Gly
            100                 105                 110

Leu Arg Pro Arg Gln Val Glu Val Trp Phe Gln Asn Arg Arg Ala Arg
        115                 120                 125

Thr Lys Leu Lys Gln Thr Glu Val Asp Cys Glu Tyr Leu Lys Arg Cys
    130                 135                 140

Cys Glu Thr Leu Thr Glu Asn Arg Arg Leu Gln Lys Glu Val Gln
145                 150                 155                 160

Glu Leu Arg Ala Ala Lys Ala Val Ser Pro His Leu Tyr Met His Met
                165                 170                 175

Ser Pro Pro Thr Thr Leu Thr Met Cys Pro Ser Cys Glu Arg Val Ser
            180                 185                 190

Ser Ser Asn Gly Asn Ser Ala Ala Ala Thr Ala Ala Ala Arg Ala Arg
        195                 200                 205

Ala Gly Ala Gly Ala Gly Ala Ile Val Cys His Pro Ile Asp Arg Ala
    210                 215                 220

Thr Ser Thr
225

<210> SEQ ID NO 198
<211> LENGTH: 331
<212> TYPE: PRT
<213> ORGANISM: Zea mays

<400> SEQUENCE: 198

Met Glu Leu Glu Leu Ser Leu Gly Asp Ser Arg Ala Pro Ala Lys Ser
1               5                   10                  15

Ala Ser Thr Pro Ala Ala Leu Thr Pro Ile His Ala Gly Ala Gly Gly
            20                  25                  30

Glu Gly His Glu Ala Ala Ala Glu Ala Gly Val Gly Ala Ala Lys Arg
        35                  40                  45

Ala Glu Gln Asp Asn Gln Lys Thr Pro Val Gln Pro Glu His Val Gln
    50                  55                  60

Glu Glu Glu Glu Glu Glu Thr Cys Pro Tyr Ser Glu Ser Pro Ala
65                  70                  75                  80

Glu Leu Ser Leu Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
            100                 105                 110

Val Asp Ala Val Leu Val Asp Gly Gly Asp Ala Ala Gln Gly Arg Pro
        115                 120                 125

Ala Leu Ser Thr Ser Phe Leu Pro Ser Glu Phe Leu Val Arg Arg Gln
    130                 135                 140

Ala Asp Asp Gln Glu Ala Ala Glu Asp Glu Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
```

```
                195                 200                 205
Val Trp Phe Gln Asn Arg Arg Ala Arg Ser Lys Leu Lys Gln Thr Glu
210                 215                 220

Val Asp Cys Glu Tyr Leu Lys Arg Trp Cys Glu Lys Leu Ala Gln Glu
225                 230                 235                 240

Asn Arg Arg Leu Gln Arg Glu Val Ala Glu Leu Arg Arg Leu Cys Ser
                245                 250                 255

Ala Ala Tyr Pro Phe Tyr Gly Ala Ala Gly Phe Gly Val Ala Thr
            260                 265                 270

Ala Arg Val Cys Pro Ser Ser Cys Asp Asn Asp Val Ser Glu Ala Ala
                275                 280                 285

Ile Ser Gly Ala Pro Ser Ala Ala Pro Pro Ser Thr Leu Phe
290                 295                 300

Ala Ser Trp Pro Pro His Phe Gly Pro Phe Thr Val Val Val Pro Pro
305                 310                 315                 320

Leu Leu Arg Arg Gln Pro Ser Ala Thr Thr Ser
                325                 330
```

<210> SEQ ID NO 199
<211> LENGTH: 331
<212> TYPE: PRT
<213> ORGANISM: Zea mays

<400> SEQUENCE: 199

```
Met Glu Leu Glu Leu Ser Leu Gly Asp Ser Arg Ala Pro Ala Lys Ser
1               5                   10                  15

Ala Ser Thr Pro Ala Ala Leu Thr Pro Ile His Ala Gly Ala Gly Gly
                20                  25                  30

Glu Gly His Glu Ala Ala Ala Glu Ala Gly Val Gly Ala Ala Lys Arg
            35                  40                  45

Ala Glu Gln Asp Asn Gln Lys Thr Pro Val Gln Pro Glu His Val Gln
50                  55                  60

Glu Glu Glu Glu Glu Glu Thr Cys Pro Tyr Ser Glu Ser Pro Ala
65                  70                  75                  80

Glu Ala Ser Ala Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
            100                 105                 110

Val Asp Ala Val Leu Val Asp Gly Gly Asp Ala Ala Gln Gly Arg Pro
        115                 120                 125

Ala Leu Ser Thr Ser Phe Leu Pro Ser Glu Phe Leu Val Arg Arg Gln
130                 135                 140

Ala Asp Asp Gln Glu Ala Ala Ala Glu Asp Glu Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
        195                 200                 205

Val Trp Phe Gln Asn Arg Arg Ala Arg Ser Lys Leu Lys Gln Thr Glu
210                 215                 220

Val Asp Cys Glu Tyr Leu Lys Arg Trp Cys Glu Lys Leu Ala Gln Glu
225                 230                 235                 240
```

```
Asn Arg Arg Leu Gln Arg Glu Val Ala Glu Leu Arg Leu Cys Ser
                245                 250                 255

Ala Ala Tyr Pro Phe Tyr Gly Ala Ala Gly Phe Gly Val Ala Thr
            260                 265                 270

Ala Arg Val Cys Pro Ser Ser Cys Asp Asn Asp Val Ser Glu Ala Ala
        275                 280                 285

Ile Ser Gly Ala Pro Ser Ala Ala Pro Pro Ser Thr Leu Phe
290                 295                 300

Ala Ser Trp Pro Pro His Phe Gly Pro Phe Thr Val Val Pro Pro
305                 310                 315                 320

Leu Leu Arg Arg Gln Pro Ser Ala Thr Thr Ser
                325                 330

<210> SEQ ID NO 200
<211> LENGTH: 292
<212> TYPE: PRT
<213> ORGANISM: Zea mays

<400> SEQUENCE: 200

Met Ala Gln Glu Asp Val His Leu Asp Asp Ala Gly Leu Ala Leu Gly
1               5                   10                  15

Leu Ser Leu Gly Ser Gly Ser Gly Ala Ser Gly Ala Ala Arg His
                20                  25                  30

Gly Gly Ile Ser Arg Arg Leu Ser Arg Glu Val Arg Leu Pro Ser Pro
            35                  40                  45

His Pro Leu Glu Pro Ser Ala Thr Ala Ser Ala Pro Asp Glu Ala Thr
    50                  55                  60

Ala Thr Gly Ser Gly Gly Gly Ala Ala His Ser Val Ser Ser Leu
65                  70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
        115                 120                 125

Glu Gln Ser Ala Leu Leu Glu Asp Arg Phe Lys Glu His Ser Thr Leu
    130                 135                 140

Asn Pro Lys Gln Lys Val Ala Leu Ala Lys Gln Leu Lys Leu Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
        195                 200                 205

Ala Leu Lys Phe Ala Pro His Pro Gln Ala Pro Ser Ser Ala Thr
    210                 215                 220

Gln Ala Gly Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
        275                 280                 285
```

```
Ser Ala Ala Cys
    290

<210> SEQ ID NO 201
<211> LENGTH: 292
<212> TYPE: PRT
<213> ORGANISM: Zea mays

<400> SEQUENCE: 201

Met Ala Gln Glu Asp Val His Leu Asp Asp Ala Gly Leu Ala Leu Gly
1               5                   10                  15

Leu Ser Leu Gly Ser Gly Ser Gly Ala Ser Gly Ala Ala Arg His
            20                  25                  30

Gly Gly Ile Ser Arg Arg Leu Ser Arg Glu Val Arg Leu Pro Ser Pro
        35                  40                  45

His Pro Leu Glu Pro Ser Ala Thr Ala Ser Ala Pro Asp Glu Ala Thr
    50                  55                  60

Ala Thr Gly Ser Gly Gly Gly Ala Ala His Ser Val Ser Ser Leu
65                  70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
        115                 120                 125

Glu Gln Ser Ala Leu Leu Glu Asp Arg Phe Lys Glu His Ser Thr Leu
130                 135                 140

Asn Pro Lys Gln Lys Val Ala Leu Ala Lys Gln Ala Lys Ala Arg Pro
145                 150                 155                 160

Arg Gln Val Glu Val Trp Phe Gln Asn Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
        195                 200                 205

Ala Leu Lys Phe Ala Pro His Pro Gln Ala Pro Pro Ser Ser Ala Thr
210                 215                 220

Gln Ala Gly Ala Ala Gly Val Val Pro Ala Pro Pro Pro Leu
225                 230                 235                 240

Tyr Met Gln Met Gln Met Pro Ala Ala Thr Leu Ser Leu Cys Pro
                245                 250                 255

Ser Cys Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
        275                 280                 285

Ser Ala Ala Cys
    290

<210> SEQ ID NO 202
<211> LENGTH: 261
<212> TYPE: PRT
<213> ORGANISM: Zea mays

<400> SEQUENCE: 202

Met Ala Pro Gln Ser Ala Asp Ala Gly Ala Ser Ala Gly Ala Gly Val
1               5                   10                  15
```

```
Ala Ala Phe Gln Pro Ser Phe Cys His Pro Gly Asn Asp Ala Ala
            20                  25                  30

Glu Arg Glu Ala Ser Pro Thr Ala Asp Glu Arg Glu Arg Cys Ser
        35                  40                  45

Pro Ala Gly Ser Pro Thr Ser Ser Gly Ser Gly Lys Arg Val Ala Ala
    50                  55                  60

Glu Arg Ser Ala Gly Ser Gly Ser Gly Asp Glu Asp Asp Gly Gly
65                  70                  75                  80

Ala Arg Lys Lys Leu Arg Leu Ser Lys Asp Gln Ala Ala Val Leu Glu
                85                  90                  95

Glu Cys Phe Lys Thr His His Thr Leu Thr Pro Lys Gln Lys Ala Ala
            100                 105                 110

Leu Ala Ser Arg Leu Gly Leu Arg Ala Arg Gln Val Glu Val Trp Phe
            115                 120                 125

Gln Asn Arg Arg Ala Arg Thr Lys Leu Lys Gln Thr Glu Val Asp Cys
130                 135                 140

Glu Tyr Leu Arg Arg Trp Cys Glu Gln Leu Ala Glu Glu Asn Arg Arg
145                 150                 155                 160

Leu Gly Lys Glu Val Ala Glu Leu Arg Ala Leu Ser Ala Ala Pro Ala
                165                 170                 175

Pro Ala Ala Pro Leu Thr Ala Leu Thr Met Cys Leu Ser Cys Arg Arg
            180                 185                 190

Val Ser Ser Ser Ser Cys Ser Ser Ser Pro Pro Asn Thr His Ala His
            195                 200                 205

Ala Ala Ala Ala Gly Thr Gly Arg Ser Val Ala Ala Ala Ala Ala Thr
            210                 215                 220

Thr Leu Pro Ala His Arg Gln Phe Leu Cys Gly Phe Arg Asp Gly Gly
225                 230                 235                 240

Ala Ala Ala Ala Ala Val Tyr Gly Thr Ser Ser Ala Leu Ala Lys Ala
                245                 250                 255

Leu Arg Ala Ala Arg
                260

<210> SEQ ID NO 203
<211> LENGTH: 272
<212> TYPE: PRT
<213> ORGANISM: Zea mays

<400> SEQUENCE: 203

Met Ala Pro Gln Ser Ala Asp Ala Gly Ala Ser Ala Gly Ala Gly Val
1               5                   10                  15

Ala Ala Phe Gln Pro Ser Ser Phe Cys His Pro Gly Asn Ala Val Val
            20                  25                  30

Val Pro Ala Ala Ala Glu Arg Glu Ala Ser Pro Ala Ala Ala Glu Glu
        35                  40                  45

Arg Glu Arg Arg Cys Ser Pro Ala Gly Ser Pro Val Ser Ser Gly Ser
    50                  55                  60

Gly Ser Gly Asn Lys Arg Ala Ala Ala Glu Arg Ser Ala Gly Ala Gly
65                  70                  75                  80

Ala Gly Ser Gly Asp Glu Asp Asp Gly Ala Ala Arg Lys Lys Leu
                85                  90                  95

Arg Leu Ser Lys Asp Gln Ala Ala Val Leu Glu Glu Cys Phe Lys Thr
            100                 105                 110

His His Thr Leu Thr Pro Lys Gln Lys Val Ala Leu Ala Ser Ser Leu
```

```
              115                 120                 125
Gly Leu Arg Pro Arg Gln Val Glu Val Trp Phe Gln Asn Arg Arg Ala
        130                 135                 140
Arg Thr Lys Leu Lys Gln Thr Glu Val Asp Cys Glu Tyr Leu Lys Arg
145                 150                 155                 160
Trp Cys Glu Gln Leu Ala Glu Asn Arg Arg Leu Gly Lys Glu Val
                165                 170                 175
Ala Glu Leu Arg Ala Leu Ser Ala Ala Pro Ala Pro Leu Thr Thr
            180                 185                 190
Leu Thr Met Cys Leu Ser Cys Arg Arg Val Ala Ser Ser Pro Ser
        195                 200                 205
Ser Ser Ser Ser Pro Arg Pro Ser Ile Pro Gly Ala Ala Ala Ser
        210                 215                 220
Gly Gly Ser Met Ala Ser Pro Ala Ala Ala Thr Leu Pro Ala His
225                 230                 235                 240
Arg Gln Phe Phe Cys Gly Phe Arg Asp Ala Gly Ala Ala Ala Ala
                245                 250                 255
Tyr Gly Thr Ala Ser Ala Gly Leu Ala Lys Pro Val Arg Ala Ala Arg
            260                 265                 270
```

<210> SEQ ID NO 204
<211> LENGTH: 335
<212> TYPE: PRT
<213> ORGANISM: Zea mays

<400> SEQUENCE: 204

```
Met Glu Leu Ala Leu Ser Leu Gly Glu Thr Met Ala Asp Ala Gly Arg
1               5                   10                  15
Asp Leu Met Leu Gly Leu Gly Met Gly Val Gly Val Arg Arg Glu Glu
            20                  25                  30
Glu Ala Gln Arg Gly Arg Arg Asp Arg Glu Val Arg Arg Glu Leu Glu
        35                  40                  45
Phe Thr Ala Arg Ser Ala Arg Ser Ser Pro Glu Pro Ala Val Arg Leu
50                  55                  60
Thr Leu Leu His Gly Ala Gly Ala Pro Trp Pro Pro Pro Ser Ser
65                  70                  75                  80
Glu Thr Asn Arg His Leu Glu Ala Ser Ala Arg Gly Phe Asp Val Asn
                85                  90                  95
Arg Ala Pro Ser Leu Ser Ala Ala Gly Ala Ala Ala Glu Glu Asp Glu
            100                 105                 110
Glu Gln Asp Glu Ala Gly Ala Ala Ala Ala Ala Ser Ser Ser Pro
        115                 120                 125
Asn Asn Ser Ala Ser Ser Phe Pro Thr Asp Phe Ser Ala His Gly Gln
        130                 135                 140
Val Ala Pro Gly Ala Asp Arg Ala Cys Ser Arg Ala Ser Asp Glu Asp
145                 150                 155                 160
Asp Gly Gly Ser Ala Arg Lys Lys Leu Arg Leu Ser Lys Glu Gln Ser
                165                 170                 175
Ala Phe Leu Glu Asp Ser Phe Lys Glu His Ala Thr Leu Asn Pro Lys
            180                 185                 190
Gln Lys Leu Ala Leu Ala Lys Gln Leu Asn Leu Arg Pro Arg Gln Val
        195                 200                 205
Glu Val Trp Phe Gln Asn Arg Arg Ala Arg Thr Lys Leu Lys Gln Thr
        210                 215                 220
```

```
Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
            245                 250                 255

Thr Val His Pro Phe Tyr Met His Leu Pro Ala Thr Thr Leu Ser Met
        260                 265                 270

Cys Pro Ser Cys Glu Arg Val Ala Ser Asn Ser Ala Pro Ala Pro Ala
    275                 280                 285

Ser Ser Pro Ser Pro Ala Thr Gly Ile Ala Ala Pro Ala Pro Glu Gln
290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 205
<211> LENGTH: 315
<212> TYPE: PRT
<213> ORGANISM: Zea mays

<400> SEQUENCE: 205

Met Ala Asp Ser Gly Ser Asp Ala Val Ala Gly Ala Gly Met Gly Val
1               5                   10                  15

Gly Val Arg Arg Glu Glu Glu Thr Gln Arg Gly Arg Arg Asp Arg Glu
            20                  25                  30

Ala Arg Arg Glu Leu Glu Phe Glu Thr Gly Arg Cys Ala Arg Pro Ser
        35                  40                  45

Pro Glu Pro Ala Val Arg Leu Thr Leu Pro Gly Leu Val Pro Ser
50                  55                  60

Leu Gly Leu Pro Trp Pro Leu Ser Ser Glu Thr Asn Arg Glu Val Ser
65                  70                  75                  80

Thr Arg Gly Phe Asp Asp Val Asn Arg Ala Leu Ser Val Ala Gly Ala
                85                  90                  95

Gly Ala Glu Glu Asp Glu Ala Ala Val Ala Ala Ala Thr Ala Ala Ala
            100                 105                 110

Ser Ser Ser Pro Asn Asn Ser Ser Gly Ser Phe Ala Met Asp Ile Ser
        115                 120                 125

Ala Gln Gly Gln Gly Gln Gly Gln Asp Gln Ala Ala Pro Ala Ala Asp
    130                 135                 140

Arg Ala Cys Ser Arg Ala Ser Asp Glu Asp Asp Gly Gly Ser Ala Arg
145                 150                 155                 160

Lys Lys Leu Arg Leu Ser Lys Glu Gln Ser Ala Phe Leu Glu Glu Ser
                165                 170                 175

Phe Lys Val Arg Ala Thr Pro Asn Pro Lys Gln Lys Leu Ala Leu Ala
            180                 185                 190

Arg Gln Leu Asn Leu Arg Ala Arg Gln Val Glu Val Trp Phe Gln Asn
        195                 200                 205

Arg Arg Ala Arg Thr Lys Leu Lys Gln Thr Glu Val Asp Cys Glu His
    210                 215                 220

Leu Lys Arg Cys Cys Glu Thr Leu Thr Gly Glu Asn Arg Arg Leu His
225                 230                 235                 240

Lys Glu Leu Ala Glu Leu Arg Ala Leu Lys Ala Val Arg Pro Leu Leu
                245                 250                 255

His Met His Leu Pro Ala Thr Thr Leu Ser Met Cys Pro Ser Cys Glu
            260                 265                 270
```

```
Arg Val Ala Ser Thr Ser Ser Ala Pro Ala Ala Pro Ala Pro Ala
        275                 280                 285

Ser Pro Ser Pro Ala Ala Gly Ala Gly Ile Ala Ala Ser Ala Pro Asp
        290                 295                 300

Pro Asp Gln Arg Pro Ser Ser Ser Phe Ala Ala
305                 310                 315

<210> SEQ ID NO 206
<211> LENGTH: 262
<212> TYPE: PRT
<213> ORGANISM: Zea mays

<400> SEQUENCE: 206

Met Glu Gln Glu Glu Val Gly Ala Ala Gly Ala Ser Leu Gly Ser
1               5                   10                  15

Gly His His His Gln Glu Leu Lys Pro Gln His Pro Ser His Pro Cys
                20                  25                  30

Ala Ala Leu Leu Glu Pro Ser Leu Ser Leu Ser Gly Pro Ala Thr Lys
            35                  40                  45

Asp Asp Gly Pro Thr Ala Pro Val Arg Arg Phe Ala Ala Val Lys Arg
50                  55                  60

Glu Leu Gln Thr Met Glu Gly Asn Asp Asp Glu Ala Thr Gly Arg Val
65                  70                  75                  80

Leu Val Tyr Ser Val Ala Ser Ser Ala Val Val Thr Ala Asp Asp Asp
                85                  90                  95

Glu Gly Cys Asn Ser Ser Arg Lys Lys Leu Arg Leu Ser Lys Glu Gln
            100                 105                 110

Ser Ala Leu Leu Glu Asp His Phe Lys Glu His Ser Thr Leu Asn Pro
        115                 120                 125

Lys Gln Lys Ala Ala Leu Ala Arg Gln Leu Asn Leu Ser Pro Arg Gln
130                 135                 140

Val Glu Val Trp Phe Gln Asn Arg Arg Ala Arg Thr Lys Leu Lys Gln
145                 150                 155                 160

Thr Glu Val Asp Cys Glu Ile Leu Lys Arg Cys Cys Glu Thr Leu Thr
                165                 170                 175

Glu Glu Asn Arg Arg Leu His Arg Glu Leu Gln Gln Leu Arg Ala Leu
            180                 185                 190

Ser His Pro His Pro His Pro Ala Ala Phe Phe Met Pro Thr Ala Ala
        195                 200                 205

Ala Ala Ala Leu Ser Ile Cys Pro Ser Cys Gln Arg Leu Val Ala Thr
210                 215                 220

Gly Ala Ser Ala Ala Ala Thr Thr Ala Gly Ala Asp Asn Lys Pro
225                 230                 235                 240

Lys Ala Gly Gly Pro Gly Gly Arg Ala Pro His Val Phe Ser Pro Phe
                245                 250                 255

Thr Asn Ser Ala Ala Cys
            260

<210> SEQ ID NO 207
<211> LENGTH: 227
<212> TYPE: PRT
<213> ORGANISM: Zea mays

<400> SEQUENCE: 207

Met Met Glu Arg Val Glu Asp Ala Gly Ala Ser Ala Ser Ala Ser Ser
1               5                   10                  15
```

Ser Leu Ala Ser Pro Arg Thr His His Val Ala Thr Met Leu Leu Arg
            20                  25                  30

Ala Pro Glu Lys Arg Phe Leu Glu Met Pro Leu Leu Leu Pro Ala Lys
            35                  40                  45

Arg Thr Thr Glu Val Thr Gly Glu Asp Gly Leu Arg Gly Gly Ser Asp
 50                  55                  60

Glu Glu Asp Gly Gly Cys Gly Ile Asp Gly Ser Arg Lys Lys Leu Arg
 65                  70                  75                  80

Leu Ser Lys Asp Gln Ser Ala Val Leu Glu Asp Ser Phe Arg Glu His
            85                  90                  95

Pro Thr Leu Asn Pro Arg Gln Lys Ala Ala Leu Ala Gln Gln Leu Gly
            100                 105                 110

Leu Arg Pro Arg Gln Val Glu Val Trp Phe Gln Asn Arg Arg Ala Arg
            115                 120                 125

Thr Lys Leu Lys Gln Thr Glu Val Asp Cys Glu Tyr Leu Lys Arg Cys
 130                 135                 140

Cys Glu Thr Leu Thr Glu Glu Asn Arg Arg Leu Gln Lys Glu Val Gln
145                 150                 155                 160

Glu Leu Arg Ala Leu Lys Leu Val Ser Pro His Leu Tyr Met His Met
            165                 170                 175

Ser Pro Pro Thr Thr Leu Thr Met Cys Pro Ser Cys Glu Arg Val Ser
            180                 185                 190

Ser Ser Asn Gly Asn Ser Ala Ala Ala Thr Ala Ala Ala Arg Ala Arg
            195                 200                 205

Ala Gly Ala Gly Ala Gly Ala Ile Val Cys His Pro Ile Asp Arg Ala
 210                 215                 220

Thr Ser Thr
225

<210> SEQ ID NO 208
<211> LENGTH: 227
<212> TYPE: PRT
<213> ORGANISM: Zea mays

<400> SEQUENCE: 208

Met Met Glu Arg Val Glu Asp Ala Gly Ala Ser Ala Ser Ala Ser Ser
1                   5                   10                  15

Ser Leu Ala Ser Pro Arg Thr His His Val Ala Thr Met Leu Leu Arg
            20                  25                  30

Ala Pro Glu Lys Arg Phe Leu Glu Met Pro Leu Leu Leu Pro Ala Lys
            35                  40                  45

Arg Thr Thr Glu Val Thr Gly Glu Asp Gly Leu Arg Gly Gly Ser Asp
 50                  55                  60

Glu Glu Asp Gly Gly Cys Gly Ile Asp Gly Ser Arg Lys Lys Leu Arg
 65                  70                  75                  80

Leu Ser Lys Asp Gln Ser Ala Val Leu Glu Asp Ser Phe Arg Glu His
            85                  90                  95

Pro Thr Leu Asn Pro Arg Gln Lys Ala Ala Leu Ala Gln Gln Leu Gly
            100                 105                 110

Leu Arg Pro Arg Gln Val Glu Val Trp Phe Gln Asn Arg Arg Ala Arg
            115                 120                 125

Thr Lys Leu Lys Gln Thr Glu Val Asp Cys Glu Tyr Leu Lys Arg Cys
 130                 135                 140

Cys Glu Thr Leu Thr Glu Glu Asn Arg Arg Leu Gln Lys Glu Val Gln

| | 145 | | | 150 | | | 155 | | | 160 |
|---|---|---|---|---|---|---|---|---|---|---|

Glu Leu Arg Ala Ala Lys Ala Val Ser Pro His Leu Tyr Met His Met
                165                  170                  175

Ser Pro Pro Thr Thr Leu Thr Met Cys Pro Ser Cys Glu Arg Val Ser
            180                  185                  190

Ser Ser Asn Gly Asn Ser Ala Ala Ala Thr Ala Ala Arg Ala Arg
        195                  200                  205

Ala Gly Ala Gly Ala Gly Ala Ile Val Cys His Pro Ile Asp Arg Ala
        210                  215                  220

Thr Ser Thr
225

<210> SEQ ID NO 209
<211> LENGTH: 227
<212> TYPE: PRT
<213> ORGANISM: Zea mays

<400> SEQUENCE: 209

Met Met Glu Arg Val Glu Asp Ala Gly Ala Ser Ala Ser Ala Ser Ser
1                  5                  10                15

Ser Leu Ala Ser Pro Arg Thr His His Val Ala Thr Met Leu Leu Arg
          20                  25                  30

Ala Pro Glu Lys Arg Phe Leu Glu Met Pro Ala Leu Ala Pro Ala Lys
        35                  40                  45

Arg Thr Thr Glu Val Thr Gly Glu Asp Gly Leu Arg Gly Gly Ser Asp
    50                  55                  60

Glu Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Leu Asn Pro Arg Gln Lys Ala Ala Leu Ala Gln Gln Leu Gly
                  100                  105                  110

Leu Arg Pro Arg Gln Val Glu Val Trp Phe Gln Asn Arg Arg Ala Arg
          115                  120                  125

Thr Lys Leu Lys Gln Thr Glu Val Asp Cys Glu Tyr Leu Lys Arg Cys
    130                  135                  140

Cys Glu Thr Leu Thr Glu Glu Asn Arg Arg Leu Gln Lys Glu Val Gln
145                  150                  155                  160

Glu Leu Arg Ala Leu Lys Leu Val Ser Pro His Leu Tyr Met His Met
                165                  170                  175

Ser Pro Pro Thr Thr Leu Thr Met Cys Pro Ser Cys Glu Arg Val Ser
            180                  185                  190

Ser Ser Asn Gly Asn Ser Ala Ala Ala Thr Ala Ala Arg Ala Arg
        195                  200                  205

Ala Gly Ala Gly Ala Gly Ala Ile Val Cys His Pro Ile Asp Arg Ala
        210                  215                  220

Thr Ser Thr
225

<210> SEQ ID NO 210
<211> LENGTH: 227
<212> TYPE: PRT
<213> ORGANISM: Zea mays

<400> SEQUENCE: 210

Met Met Glu Arg Val Glu Asp Ala Gly Ala Ser Ala Ser Ala Ser Ser

```
              1               5                  10                 15
            Ser Leu Ala Ser Pro Arg Thr His His Val Ala Thr Met Leu Leu Arg
                         20                  25                  30

Ala Pro Glu Lys Arg Phe Leu Glu Met Pro Ala Leu Ala Pro Ala Lys
                         35                  40                  45

Arg Thr Thr Glu Val Thr Gly Glu Asp Gly Leu Arg Gly Gly Ser Asp
                 50                  55                  60

Glu Glu Asp Gly Gly Cys Gly Ile Asp Gly Ser Arg Lys Lys Leu Arg
            65                  70                  75                  80

Leu Ser Lys Asp Gln Ser Ala Val Leu Glu Asp Ser Phe Arg Glu His
                             85                  90                  95

Pro Thr Leu Asn Pro Arg Gln Lys Ala Ala Leu Ala Gln Gln Leu Gly
                        100                 105                 110

Leu Arg Pro Arg Gln Val Glu Val Trp Phe Gln Asn Arg Arg Ala Arg
                        115                 120                 125

Thr Lys Leu Lys Gln Thr Glu Val Asp Cys Glu Tyr Leu Lys Arg Cys
                    130                 135                 140

Cys Glu Thr Leu Thr Glu Glu Asn Arg Arg Leu Gln Lys Glu Val Gln
            145                 150                 155                 160

Glu Leu Arg Ala Ala Lys Ala Val Ser Pro His Leu Tyr Met His Met
                                165                 170                 175

Ser Pro Pro Thr Thr Leu Thr Met Cys Pro Ser Cys Glu Arg Val Ser
                        180                 185                 190

Ser Ser Asn Gly Asn Ser Ala Ala Thr Ala Ala Ala Arg Ala Arg
                    195                 200                 205

Ala Gly Ala Gly Ala Gly Ala Ile Val Cys His Pro Ile Asp Arg Ala
                    210                 215                 220

Thr Ser Thr
            225

<210> SEQ ID NO 211
            <211> LENGTH: 262
            <212> TYPE: PRT
            <213> ORGANISM: Zea mays

<400> SEQUENCE: 211

Met Glu Gln Glu Glu Val Gly Ala Ala Gly Ala Ser Leu Gly Ser
            1               5                  10                 15

Gly His His His Gln Glu Leu Lys Pro Gln His Pro Ser His Pro Cys
                         20                  25                  30

Ala Ala Leu Leu Glu Pro Ser Ala Ser Ala Ser Gly Pro Ala Thr Lys
                         35                  40                  45

Asp Asp Gly Pro Thr Ala Pro Val Arg Arg Phe Ala Ala Val Lys Arg
                 50                  55                  60

Glu Leu Gln Thr Met Glu Gly Asn Asp Asp Glu Ala Thr Gly Arg Val
            65                  70                  75                  80

Leu Val Tyr Ser Val Ala Ser Ser Ala Val Val Thr Ala Asp Asp Asp
                             85                  90                  95

Glu Gly Cys Asn Ser Ser Arg Lys Lys Leu Arg Leu Ser Lys Glu Gln
                        100                 105                 110

Ser Ala Leu Leu Glu Asp His Phe Lys Glu His Ser Thr Leu Asn Pro
                        115                 120                 125

Lys Gln Lys Ala Ala Leu Ala Arg Gln Leu Asn Leu Ser Pro Arg Gln
                    130                 135                 140
```

```
Val Glu Val Trp Phe Gln Asn Arg Arg Ala Arg Thr Lys Leu Lys Gln
145                 150                 155                 160

Thr Glu Val Asp Cys Glu Ile Leu Lys Arg Cys Cys Glu Thr Leu Thr
            165                 170                 175

Glu Glu Asn Arg Arg Leu His Arg Glu Leu Gln Gln Leu Arg Ala Leu
        180                 185                 190

Ser His Pro His Pro His Pro Ala Ala Phe Phe Met Pro Thr Ala Ala
    195                 200                 205

Ala Ala Ala Leu Ser Ile Cys Pro Ser Cys Gln Arg Leu Val Ala Thr
        210                 215                 220

Gly Ala Ser Ala Ala Ala Thr Thr Ala Gly Ala Asp Asn Lys Pro
225                 230                 235                 240

Lys Ala Gly Gly Pro Gly Gly Arg Ala Pro His Val Phe Ser Pro Phe
                245                 250                 255

Thr Asn Ser Ala Ala Cys
            260

<210> SEQ ID NO 212
<211> LENGTH: 331
<212> TYPE: PRT
<213> ORGANISM: Zea mays

<400> SEQUENCE: 212

Met Glu Leu Glu Leu Ser Leu Gly Asp Ser Arg Ala Pro Ala Lys Ser
1               5                   10                  15

Ala Ser Thr Pro Ala Ala Leu Thr Pro Ile His Ala Gly Ala Gly Gly
            20                  25                  30

Glu Gly His Glu Leu Ala Leu Glu Leu Gly Val Gly Ala Ala Lys Arg
        35                  40                  45

Ala Glu Gln Asp Asn Gln Lys Thr Pro Val Gln Pro Glu His Val Gln
    50                  55                  60

Glu Glu Glu Glu Glu Glu Thr Cys Pro Tyr Ser Glu Ser Pro Ala
65                  70                  75                  80

Glu Ala Ser Ala Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
            100                 105                 110

Val Asp Ala Val Leu Val Asp Gly Gly Asp Ala Ala Gln Gly Arg Pro
        115                 120                 125

Ala Leu Ser Thr Ser Phe Leu Pro Ser Glu Phe Leu Val Arg Arg Gln
    130                 135                 140

Ala Asp Asp Gln Glu Ala Ala Ala Glu Asp Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
        195                 200                 205

Val Trp Phe Gln Asn Arg Arg Ala Arg Ser Lys Leu Lys Gln Thr Glu
    210                 215                 220

Val Asp Cys Glu Tyr Leu Lys Arg Trp Cys Glu Lys Leu Ala Gln Glu
225                 230                 235                 240

Asn Arg Arg Leu Gln Arg Glu Val Ala Glu Leu Arg Arg Leu Cys Ser
                245                 250                 255
```

-continued

```
Ala Ala Tyr Pro Phe Tyr Gly Ala Ala Gly Phe Gly Val Ala Thr
            260                 265                 270

Ala Arg Val Cys Pro Ser Ser Cys Asp Asn Asp Val Ser Glu Ala Ala
        275                 280                 285

Ile Ser Gly Ala Pro Ser Ala Ala Pro Pro Ser Thr Leu Phe
    290                 295                 300

Ala Ser Trp Pro Pro His Phe Gly Pro Phe Thr Val Val Pro Pro
305                 310                 315                 320

Leu Leu Arg Arg Gln Pro Ser Ala Thr Thr Ser
                325                 330

<210> SEQ ID NO 213
<211> LENGTH: 225
<212> TYPE: PRT
<213> ORGANISM: Zea mays

<400> SEQUENCE: 213

Met Gly Ser Thr Ser Pro Ser Gly Ala Glu Ala Thr Met Ala Val Pro
1               5                   10                  15

Gly Leu Ser Ser Ser Ser Gly Ser Glu Gly Phe Gly Cys Asn Asn Asn
                20                  25                  30

Asn Gly Ser Gly Asn Gly Asn Asn Met Arg Asp Leu Asp Met Asn Gln
            35                  40                  45

Pro Ala Ser Gly Gly Glu Glu Glu Phe Pro Met Gly Ser Val Glu
    50                  55                  60

Glu Glu Glu Asp Glu Arg Gly Gly Ala Gly Gly Pro His Arg Ala Lys
65                  70                  75                  80

Lys Leu Arg Leu Ser Lys Glu Gln Ser Arg Leu Leu Glu Glu Ser Phe
                85                  90                  95

Arg Leu Asn His Thr Leu Thr Pro Lys Gln Lys Glu Ala Leu Ala Val
            100                 105                 110

Lys Leu Lys Leu Arg Pro Arg Gln Val Glu Val Trp Phe Gln Asn Arg
        115                 120                 125

Arg Ala Arg Thr Lys Leu Lys Gln Thr Glu Leu Glu Cys Glu Tyr Leu
    130                 135                 140

Lys Arg Cys Phe Gly Ser Leu Thr Glu Glu Asn Arg Arg Leu Gln Arg
145                 150                 155                 160

Glu Val Glu Glu Leu Arg Ala Met Arg Val Ala Pro Pro Thr Val Leu
                165                 170                 175

Ser Pro His Thr Arg Gln Pro Leu Pro Ala Ser Ala Leu Thr Met Cys
            180                 185                 190

Pro Arg Cys Glu Arg Ile Thr Ala Ala Thr Ala Ala Arg Thr Pro Arg
        195                 200                 205

Pro Pro Pro Ala Ala Ser Pro Phe His Pro Arg Pro Ser Ala Ala
    210                 215                 220

Phe
225

<210> SEQ ID NO 214
<211> LENGTH: 295
<212> TYPE: PRT
<213> ORGANISM: Zea mays

<400> SEQUENCE: 214

Met Met Pro Gln Ala Ser Ala Ser Ala Asp Ala Gly Ala Ser Ala Gly
1               5                   10                  15
```

```
Ala Thr Ala Thr Ser Gln Gly Ser Leu Ser Ser Ser Thr Thr Thr Ala
            20                  25                  30

Gly Ser Ser Ser Pro Trp Ala Ala Ala Leu Ser Ser Val Val Ala Asp
                35                  40                  45

Val Ala Arg Ala Arg Gly Asp Ala Tyr Ala Gln His His Ala Gly Ala
 50                  55                  60

Ala Met Thr Met Arg Ala Ser Thr Ser Pro Asp Ser Gly Asp Thr Thr
 65                  70                  75                  80

Thr Ala Lys Arg Glu Arg Glu Gly Glu Leu Glu Arg Thr Gly Ser Ala
                85                  90                  95

Gly Gly Val Arg Ser Asp Glu Glu Asp Gly Ala Asp Gly Gly Ala Gly
                100                 105                 110

Gly Arg Lys Lys Leu Arg Leu Ser Lys Asp Gln Ala Ala Val Leu Glu
            115                 120                 125

Glu Cys Phe Lys Thr His Ser Thr Leu Asn Pro Lys Gln Lys Val Gln
    130                 135                 140

Leu Ala Asn Arg Leu Gly Leu Arg Pro Arg Gln Val Glu Val Trp Phe
145                 150                 155                 160

Gln Asn Arg Arg Ala Arg Thr Lys Leu Lys Gln Thr Glu Val Asp Cys
                165                 170                 175

Glu Tyr Leu Lys Arg Trp Cys Asp Arg Leu Ala Asp Glu Asn Lys Arg
                180                 185                 190

Leu Glu Lys Glu Leu Ala Asp Leu Arg Ala Leu Lys Ala Ala Pro Pro
            195                 200                 205

Ser Ser Ala Ala Ala Gln Pro Ala Ser Ala Ala Ala Thr Leu Thr Met
    210                 215                 220

Cys Pro Ser Cys Arg Arg Val Ala Ala Ala Ala Ser His His His Gln
225                 230                 235                 240

Pro Pro Pro Pro Gln Cys His Pro Lys Pro Thr Val Ala Ala Gly Gly
                245                 250                 255

Gly Ser Val Val Pro Arg Pro Ser His Cys Gln Phe Phe Pro Ala Ala
                260                 265                 270

Ala Val Asp Arg Thr Ser Gln Gly Thr Trp Asn Thr Ala Ala Pro Pro
            275                 280                 285

Leu Val Thr Arg Glu Leu Phe
        290                 295

<210> SEQ ID NO 215
<211> LENGTH: 223
<212> TYPE: PRT
<213> ORGANISM: Zea mays

<400> SEQUENCE: 215

Met Tyr Ser Cys Thr Arg Ala Met Glu Glu Glu Gly Val Gly Lys Ser
1               5                   10                  15

Trp Leu Gly Leu Gly Ile Gly Gly Gly Asp Leu Met Lys Arg Asn
            20                  25                  30

Asn Arg Pro Pro Val Gln Leu Asp Asp Leu Leu Ser Phe Pro Pro Gln
                35                  40                  45

Ser Val Ala Ala Ala Ser Lys Lys Gln Ala Glu Lys Gly Gly Gly Gly
    50                  55                  60

Arg Lys Arg His Lys Ile Val Val Thr Ala Asp Glu Asp Gly Arg Gln
65                  70                  75                  80

Ser Pro His Gly Gly Ala Arg Lys Lys Leu Arg Leu Thr Lys Ala Gln
```

```
            85                  90                  95
Ser Thr Leu Leu Glu Asp Thr Phe Arg Ala His Asn Ile Leu Ser His
        100                 105                 110

Ala Gln Lys Gln Glu Leu Ala Arg Gln Val Asn Leu Ser Ala Arg Gln
        115                 120                 125

Val Glu Val Trp Phe Gln Asn Arg Arg Ala Arg Thr Lys Leu Lys Gln
    130                 135                 140

Thr Glu Ala Asp Cys Glu Val Leu Lys Arg Tyr Cys Glu Arg Leu Thr
145                 150                 155                 160

Gly Glu Asn Gln Arg Ala Arg Ala Glu Ala Gln Leu Gln Arg Ser
                165                 170                 175

Pro Ala Ala Glu Glu Ala Gly Phe Tyr Val Gln Ser Ser Phe Pro Phe
                180                 185                 190

Pro Pro Leu Ala Thr Ala Met Ala Ser Val Cys Pro Ser Cys Asp Lys
            195                 200                 205

Val Val Ala Val Thr Ser Gly Lys Ser Ser Thr Ser Tyr Ser Ser
        210                 215                 220

<210> SEQ ID NO 216
<211> LENGTH: 227
<212> TYPE: PRT
<213> ORGANISM: Zea mays

<400> SEQUENCE: 216

Met Met Glu Arg Val Glu Asp Leu Gly Leu Ser Leu Ser Leu Ser Ser
1               5                   10                  15

Ser Leu Ala Ser Pro Arg Thr His His Val Ala Thr Met Leu Leu Arg
            20                  25                  30

Ala Pro Glu Lys Arg Phe Leu Glu Met Pro Leu Leu Leu Pro Ala Lys
        35                  40                  45

Arg Thr Thr Glu Val Thr Gly Glu Asp Gly Leu Arg Gly Gly Ser Asp
    50                  55                  60

Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Leu Asn Pro Arg Gln Lys Ala Ala Leu Ala Gln Gln Leu Gly
            100                 105                 110

Leu Arg Pro Arg Gln Val Glu Val Trp Phe Gln Asn Arg Arg Ala Arg
        115                 120                 125

Thr Lys Leu Lys Gln Ala Glu Val Asp Cys Glu Tyr Ala Lys Arg Cys
    130                 135                 140

Cys Glu Thr Ala Thr Glu Glu Asn Arg Arg Ala Gln Lys Glu Val Gln
145                 150                 155                 160

Glu Ala Arg Ala Leu Lys Leu Val Ser Pro His Leu Tyr Met His Met
                165                 170                 175

Ser Pro Pro Thr Thr Leu Thr Met Cys Pro Ser Cys Glu Arg Val Ser
            180                 185                 190

Ser Ser Asn Gly Asn Ser Ala Ala Ala Thr Ala Ala Arg Ala Arg
        195                 200                 205

Ala Gly Ala Gly Ala Gly Ala Ile Val Cys His Pro Ile Asp Arg Ala
    210                 215                 220

Thr Ser Thr
225
```

<210> SEQ ID NO 217
<211> LENGTH: 225
<212> TYPE: PRT
<213> ORGANISM: Zea mays

<400> SEQUENCE: 217

Met Gly Ser Thr Ser Pro Ser Gly Leu Glu Leu Thr Met Ala Val Pro
1               5                   10                  15

Gly Leu Ser Ser Ser Gly Ser Glu Gly Phe Gly Cys Asn Asn Asn
            20                  25                  30

Asn Gly Ser Gly Asn Gly Asn Asn Met Arg Asp Leu Asp Met Asn Gln
        35                  40                  45

Pro Ala Ser Gly Gly Glu Glu Glu Phe Pro Met Gly Ser Val Glu
    50                  55                  60

Glu Glu Glu Asp Glu Arg Gly Gly Ala Gly Gly Pro His Arg Ala Lys
65                  70                  75                  80

Lys Leu Arg Leu Ser Lys Glu Gln Ser Arg Leu Leu Glu Glu Ser Phe
                85                  90                  95

Arg Leu Asn His Thr Leu Thr Pro Lys Gln Lys Glu Ala Leu Ala Val
            100                 105                 110

Lys Leu Lys Leu Arg Pro Arg Gln Val Glu Val Trp Phe Gln Asn Arg
        115                 120                 125

Arg Ala Arg Thr Lys Leu Lys Gln Ala Glu Leu Glu Cys Glu Tyr Ala
130                 135                 140

Lys Arg Cys Phe Gly Ser Ala Thr Glu Glu Asn Arg Arg Ala Gln Arg
145                 150                 155                 160

Glu Val Glu Glu Ala Arg Ala Met Arg Val Ala Pro Pro Thr Val Leu
                165                 170                 175

Ser Pro His Thr Arg Gln Pro Leu Pro Ala Ser Ala Leu Thr Met Cys
            180                 185                 190

Pro Arg Cys Glu Arg Ile Thr Ala Ala Thr Ala Arg Thr Pro Arg
        195                 200                 205

Pro Pro Pro Ala Ala Ser Pro Phe His Pro Arg Arg Pro Ser Ala Ala
    210                 215                 220

Phe
225

<210> SEQ ID NO 218
<211> LENGTH: 261
<212> TYPE: PRT
<213> ORGANISM: Zea mays

<400> SEQUENCE: 218

Met Ala Pro Gln Ser Leu Asp Leu Gly Leu Ser Leu Gly Leu Val
1               5                   10                  15

Ala Ala Phe Gln Pro Ser Phe Cys His Pro Ala Gly Asn Asp Ala Ala
            20                  25                  30

Glu Arg Glu Ala Ser Pro Thr Ala Asp Glu Arg Glu Arg Cys Ser
        35                  40                  45

Pro Ala Gly Ser Pro Thr Ser Ser Gly Ser Gly Lys Arg Val Ala Ala
    50                  55                  60

Glu Arg Ser Ala Gly Ser Gly Ser Gly Asp Glu Asp Asp Gly Gly
65                  70                  75                  80

Ala Arg Lys Lys Leu Arg Leu Ser Lys Asp Gln Ala Ala Val Leu Glu
                85                  90                  95

```
Glu Cys Phe Lys Thr His His Thr Leu Thr Pro Lys Gln Lys Ala Ala
                100                 105                 110

Leu Ala Ser Arg Leu Gly Leu Arg Ala Arg Gln Val Glu Val Trp Phe
            115                 120                 125

Gln Asn Arg Arg Ala Arg Thr Lys Leu Lys Gln Ala Glu Val Asp Cys
        130                 135                 140

Glu Tyr Ala Arg Arg Trp Cys Glu Gln Ala Ala Glu Glu Asn Arg Arg
145                 150                 155                 160

Ala Gly Lys Glu Val Ala Glu Ala Arg Ala Leu Ser Ala Ala Pro Ala
                165                 170                 175

Pro Ala Ala Pro Leu Thr Ala Leu Thr Met Cys Leu Ser Cys Arg Arg
            180                 185                 190

Val Ser Ser Ser Cys Ser Ser Pro Pro Asn Thr His Ala His
            195                 200                 205

Ala Ala Ala Ala Gly Thr Gly Arg Ser Val Ala Ala Ala Ala Thr
        210                 215                 220

Thr Leu Pro Ala His Arg Gln Phe Leu Cys Gly Phe Arg Asp Gly Gly
225                 230                 235                 240

Ala Ala Ala Ala Ala Val Tyr Gly Thr Ser Ser Ala Leu Ala Lys Ala
                245                 250                 255

Leu Arg Ala Ala Arg
            260

<210> SEQ ID NO 219
<211> LENGTH: 221
<212> TYPE: PRT
<213> ORGANISM: Zea mays

<400> SEQUENCE: 219

Met Tyr Ser Thr Arg Glu Glu Gly Val Gly Lys Ser Trp Leu Gly
1               5                   10                  15

Leu Gly Ile Gly Gly Ser Gly Gly Cys Asp Leu Met Gln Arg Asn
            20                  25                  30

Asn Arg Pro Pro Val Gln Phe Asp Leu Leu Phe Pro Pro Gln Gly Val
        35                  40                  45

Val Glu Gly Val Ala Ala Ser Lys Lys Ala Glu Lys Gly Gly Gly Gly
    50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Val Trp Phe Gln Asn Arg Arg Ala Arg Thr Lys Leu Lys Gln Ala
    130                 135                 140

Glu Ala Asp Cys Glu Ile Ala Lys Arg Cys Cys Glu Ser Ala Thr Gly
145                 150                 155                 160

Glu Asn Gln Arg Ala Arg Leu Glu Leu Ala Gln Ala Gln Gly Ser Glu
                165                 170                 175

Ala Gly Leu Tyr Leu Gln Ser Ser Phe Pro Pro Leu Ala Ala Ala Met
            180                 185                 190

Ala Ser Val Cys Pro Ser Cys Asp Lys Val Ile Thr Val Ala Ser Gly
        195                 200                 205
```

Gly Glu Thr Ser Gly Arg Ser Ser Thr Ser Tyr Ser Ser
    210                 215                 220

<210> SEQ ID NO 220
<211> LENGTH: 223
<212> TYPE: PRT
<213> ORGANISM: Zea mays

<400> SEQUENCE: 220

Met Tyr Ser Cys Thr Arg Ala Met Glu Glu Gly Val Gly Lys Ser
1               5                   10                  15

Trp Leu Gly Leu Gly Ile Gly Gly Gly Asp Leu Met Lys Arg Asn
                20                  25                  30

Asn Arg Pro Pro Val Gln Leu Asp Asp Leu Leu Ser Phe Pro Pro Gln
            35                  40                  45

Ser Val Ala Ala Ser Lys Lys Gln Ala Glu Lys Gly Gly Gly Gly
        50                  55                  60

Arg Lys Arg His Lys Ile Val Val Thr Ala Asp Glu Asp Gly Arg Gln
65                  70                  75                  80

Ser Pro His Gly Gly Ala Arg Lys Lys Leu Arg Leu Thr Lys Ala Gln
                85                  90                  95

Ser Thr Leu Leu Glu Asp Thr Phe Arg Ala His Asn Ile Leu Ser His
                100                 105                 110

Ala Gln Lys Gln Glu Leu Ala Arg Gln Val Asn Leu Ser Ala Arg Gln
                115                 120                 125

Val Glu Val Trp Phe Gln Asn Arg Arg Ala Arg Thr Lys Leu Lys Gln
            130                 135                 140

Ala Glu Ala Asp Cys Glu Val Ala Lys Arg Tyr Cys Glu Arg Ala Thr
145                 150                 155                 160

Gly Glu Asn Gln Arg Ala Arg Leu Glu Leu Ala Gln Ala Gln Arg Ser
                165                 170                 175

Pro Ala Ala Glu Glu Ala Gly Phe Tyr Val Gln Ser Ser Phe Pro Phe
                180                 185                 190

Pro Pro Leu Ala Thr Ala Met Ala Ser Val Cys Pro Ser Cys Asp Lys
            195                 200                 205

Val Val Ala Val Thr Ser Gly Lys Ser Ser Thr Ser Tyr Ser Ser
    210                 215                 220

<210> SEQ ID NO 221
<211> LENGTH: 241
<212> TYPE: PRT
<213> ORGANISM: Zea mays

<400> SEQUENCE: 221

Met Glu Glu Glu Gly Val Gly Lys Ser Trp Leu Ala Leu Gly Ile Gly
1               5                   10                  15

Gly Gly Asp Leu Met Lys Arg Asn Asn Arg Pro Pro Val Gln Phe Asp
                20                  25                  30

Leu Leu Phe Pro Pro Gln Ser Val Lys Glu Glu Gly Ala Ala Ser Lys
            35                  40                  45

Lys Ala Glu Lys Gly Gly Gly Arg Lys Arg Leu Lys Val Val Thr Ala
        50                  55                  60

Asp Glu Asp Gly Arg Gln Ser Pro His Gly Gly Pro Gly Pro Ser Asp
65                  70                  75                  80

Gly Ser Gly Ala Gly Ala Arg Lys Lys Leu Arg Leu Thr Asn Glu Gln
                85                  90                  95

```
Ser Thr Leu Leu Glu Asp Thr Phe Arg Ala His Asn Ile Leu Ser Asn
            100                 105                 110

Ala Gln Lys Gln Glu Leu Ala Arg Gln Val Asp Leu Ser Ala Arg Gln
        115                 120                 125

Val Glu Val Trp Phe Gln Asn Arg Arg Ala Arg Thr Lys Leu Lys Gln
    130                 135                 140

Ala Glu Val Asp Cys Glu Ile Ala Lys Arg Cys Cys Glu Ser Ala Thr
145                 150                 155                 160

Gly Glu Asn Gln Arg Ala Arg Leu Glu Leu Ala Gln Ala Gln Arg Ser
                165                 170                 175

Ala Ala Ala Ala Ala Glu Ala Gly Leu Tyr Val Gln Ser Ser Phe Pro
            180                 185                 190

Pro Leu Ala Thr Ala Thr Ala Thr Ala Ser Val Cys Pro Ser Cys Asp
        195                 200                 205

Lys Val Ile Ala Val Ser Ser Gly Gly Glu Thr Ser Gly Lys Ser Ser
    210                 215                 220

Thr Ser Tyr Ser Ser Arg Arg Ala Gly Phe Pro Ser Ile Met Gly Ser
225                 230                 235                 240

Arg

<210> SEQ ID NO 222
<211> LENGTH: 272
<212> TYPE: PRT
<213> ORGANISM: Zea mays

<400> SEQUENCE: 222

Met Ala Pro Gln Ser Leu Asp Leu Gly Leu Ser Leu Gly Leu Gly Val
1               5                   10                  15

Ala Ala Phe Gln Pro Ser Ser Phe Cys His Pro Gly Asn Ala Val Val
            20                  25                  30

Val Pro Ala Ala Ala Glu Arg Glu Ala Ser Pro Ala Ala Ala Glu Glu
        35                  40                  45

Arg Glu Arg Arg Cys Ser Pro Ala Gly Ser Pro Val Ser Ser Gly Ser
    50                  55                  60

Gly Ser Gly Asn Lys Arg Ala Ala Glu Arg Ser Ala Gly Ala Gly
65                  70                  75                  80

Ala Gly Ser Gly Asp Glu Asp Asp Gly Ala Ala Arg Lys Lys Leu
                85                  90                  95

Arg Leu Ser Lys Asp Gln Ala Ala Val Leu Glu Glu Cys Phe Lys Thr
            100                 105                 110

His His Thr Leu Thr Pro Lys Gln Lys Val Ala Leu Ala Ser Ser Leu
        115                 120                 125

Gly Leu Arg Pro Arg Gln Val Glu Val Trp Phe Gln Asn Arg Arg Ala
    130                 135                 140

Arg Thr Lys Leu Lys Gln Ala Glu Val Asp Cys Glu Tyr Ala Lys Arg
145                 150                 155                 160

Trp Cys Glu Gln Ala Ala Glu Glu Asn Arg Arg Ala Gly Lys Glu Val
                165                 170                 175

Ala Glu Ala Arg Ala Leu Ser Ala Ala Pro Ala Ala Pro Leu Thr Thr
            180                 185                 190

Leu Thr Met Cys Leu Ser Cys Arg Arg Val Ala Ser Ser Ser Pro Ser
        195                 200                 205

Ser Ser Ser Ser Pro Arg Pro Ser Ile Pro Gly Ala Ala Ala Ala Ser
    210                 215                 220
```

Gly Gly Ser Met Ala Ser Pro Ala Ala Ala Thr Leu Pro Ala His
225                 230                 235                 240

Arg Gln Phe Phe Cys Gly Phe Arg Asp Ala Gly Ala Ala Ala Ala
            245                 250                 255

Tyr Gly Thr Ala Ser Ala Gly Leu Ala Lys Pro Val Arg Ala Ala Arg
        260                 265                 270

<210> SEQ ID NO 223
<211> LENGTH: 254
<212> TYPE: PRT
<213> ORGANISM: Zea mays

<400> SEQUENCE: 223

Met Tyr Thr Thr Thr Arg Ala Met Glu Lys Glu Glu Gly Phe Gly Lys
1               5                   10                  15

Ser Trp Leu Gly Leu Gly Ile Gly Gly Gly Arg Asp Leu Asn Leu
            20                  25                  30

Met Lys Arg Ser Arg Pro Leu Arg Pro Val Arg Leu Asp Leu Leu Phe
        35                  40                  45

Pro Pro Ser Val Glu Gly Gly Glu Ala Ala Arg Ser Arg Lys Ala
50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
                85                  90                  95

Asp Asp Gly Ala Gly Ala Arg Lys Lys Leu Arg Leu Thr Thr Glu Gln
            100                 105                 110

Ser Lys Leu Leu Glu Asp Thr Phe Arg Ala His Asn Ile Leu Ser His
        115                 120                 125

Ala Gln Lys His Glu Val Ala Arg Gln Val Asp Leu Ser Ala Arg Gln
    130                 135                 140

Val Glu Val Trp Phe Gln Asn Arg Arg Ala Arg Thr Lys Leu Lys Gln
145                 150                 155                 160

Ala Glu Val Asp Cys Glu Thr Ala Arg Arg Trp Arg Glu Ser Ala Ala
                165                 170                 175

Asp Glu Asn Leu Arg Ala Arg Leu Glu Leu Glu Gln Ala Gln Arg Trp
            180                 185                 190

Ala Thr Ala Ala Ala Gly Gln Ser Ser Ala Ser Pro Ser Pro Ala Thr
        195                 200                 205

Ala Thr Ala Ser Val Cys Pro Ser Cys Asp Lys Val Val Val Val Thr
    210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250

<210> SEQ ID NO 224
<211> LENGTH: 262
<212> TYPE: PRT
<213> ORGANISM: Zea mays

<400> SEQUENCE: 224

Met Glu Gln Glu Glu Val Gly Leu Ala Leu Gly Leu Ser Leu Gly Ser
1               5                   10                  15

Gly His His His Gln Glu Leu Lys Pro Gln His Pro Ser His Pro Cys
            20                  25                  30

Ala Ala Leu Leu Glu Pro Ser Leu Ser Leu Ser Gly Pro Ala Thr Lys
           35                  40                  45

Asp Asp Gly Pro Thr Ala Pro Val Arg Arg Phe Ala Ala Val Lys Arg
 50                  55                  60

Glu Leu Gln Thr Met Glu Gly Asn Asp Asp Glu Ala Thr Gly Arg Val
 65                  70                  75                  80

Leu Val Tyr Ser Val Ala Ser Ser Ala Val Val Thr Ala Asp Asp Asp
                 85                  90                  95

Glu Gly Cys Asn Ser Ser Arg Lys Lys Leu Arg Leu Ser Lys Glu Gln
                100                 105                 110

Ser Ala Leu Leu Glu Asp His Phe Lys Glu His Ser Thr Leu Asn Pro
            115                 120                 125

Lys Gln Lys Ala Ala Leu Ala Arg Gln Leu Asn Leu Ser Pro Arg Gln
        130                 135                 140

Val Glu Val Trp Phe Gln Asn Arg Arg Ala Arg Thr Lys Leu Lys Gln
145                 150                 155                 160

Ala Glu Val Asp Cys Glu Ile Ala Lys Arg Cys Cys Glu Thr Ala Thr
                165                 170                 175

Glu Glu Asn Arg Arg Ala His Arg Glu Leu Gln Gln Ala Arg Ala Leu
            180                 185                 190

Ser His Pro His Pro His Pro Ala Ala Phe Phe Met Pro Thr Ala Ala
        195                 200                 205

Ala Ala Ala Leu Ser Ile Cys Pro Ser Cys Gln Arg Leu Val Ala Thr
    210                 215                 220

Gly Ala Ser Ala Ala Ala Ala Thr Thr Ala Gly Ala Asp Asn Lys Pro
225                 230                 235                 240

Lys Ala Gly Gly Pro Gly Gly Arg Ala Pro His Val Phe Ser Pro Phe
                245                 250                 255

Thr Asn Ser Ala Ala Cys
            260

<210> SEQ ID NO 225
<211> LENGTH: 245
<212> TYPE: PRT
<213> ORGANISM: Zea mays

<400> SEQUENCE: 225

Met Ala Gln Glu Asp Val His Leu Asp Asp Ala Gly Leu Ala Leu Cys
1               5                   10                  15

Leu Ser Leu His Gly Thr Ser Ser Arg Leu Ser Thr Glu Ala Pro
            20                  25                  30

Arg Thr Leu Glu Pro Pro Ser Leu Thr Leu Ser Met Pro Asp Glu Ala
            35                  40                  45

Thr Ala Thr Ala Thr Gly Gly Ser Gly Gly Ser Gly Gly Ala Ala Arg
        50                  55                  60

Ser Val Ser Ser Arg Ser Val Glu Gly Val Lys Glu Arg Val Asp
65                  70                  75                  80

Asp Ala Glu Gly Glu Arg Ala Ser Ser Thr Ala Ala Ala Arg Val
                85                  90                  95

Cys Ala Gly Ala Glu Asp Asp Asp Gly Ser Thr Arg Lys Lys Leu
            100                 105                 110

Arg Leu Thr Lys Glu Gln Ser Lys Leu Leu Glu Asp Arg Phe Lys Asp
            115                 120                 125

His Ser Thr Leu Asn Pro Lys Gln Lys Ile Ala Leu Ala Lys Gln Leu

```
            130                 135                 140
Lys Leu Arg Pro Arg Gln Val Glu Val Trp Phe Gln Asn Arg Arg Ala
145                 150                 155                 160

Arg Thr Lys Leu Lys Gln Ala Glu Val Asp Cys Glu Leu Ala Lys Arg
                165                 170                 175

Cys Cys Glu Ser Ala Ser Glu Glu Asn Arg Arg Ala Gln Arg Glu Leu
            180                 185                 190

Gln Glu Ala Arg Ala Leu Lys Leu Ala Gly Pro His Pro Gln Ala Pro
            195                 200                 205

Ser Ser Ser Pro Ala Ala Ala Thr Gln Gly Val Pro Val Pro Val Pro
        210                 215                 220

Pro Pro Leu Tyr Val Gln Met Gln Met Gln Leu Ser Ser Cys Arg Cys
225                 230                 235                 240

Cys Arg Pro Pro Arg
                245

<210> SEQ ID NO 226
<211> LENGTH: 295
<212> TYPE: PRT
<213> ORGANISM: Zea mays

<400> SEQUENCE: 226

Met Met Pro Gln Ala Ser Ala Ser Leu Asp Leu Gly Leu Ser Leu Gly
1               5                   10                  15

Leu Thr Leu Thr Ser Gln Gly Ser Leu Ser Ser Ser Thr Thr Thr Ala
                20                  25                  30

Gly Ser Ser Ser Pro Trp Ala Ala Ala Leu Ser Ser Val Ala Asp
            35                  40                  45

Val Ala Arg Ala Arg Gly Asp Ala Tyr Ala Gln His His Ala Gly Ala
        50                  55                  60

Ala Met Thr Met Arg Ala Ser Thr Ser Pro Asp Ser Gly Asp Thr Thr
65              70                  75                  80

Thr Ala Lys Arg Glu Arg Glu Gly Glu Leu Glu Arg Thr Gly Ser Ala
                85                  90                  95

Gly Gly Val Arg Ser Asp Glu Glu Asp Gly Ala Asp Gly Gly Ala Gly
            100                 105                 110

Gly Arg Lys Lys Leu Arg Leu Ser Lys Asp Gln Ala Ala Val Leu Glu
        115                 120                 125

Glu Cys Phe Lys Thr His Ser Thr Leu Asn Pro Lys Gln Lys Val Gln
    130                 135                 140

Leu Ala Asn Arg Leu Gly Leu Arg Pro Arg Gln Val Glu Val Trp Phe
145                 150                 155                 160

Gln Asn Arg Arg Ala Arg Thr Lys Leu Lys Gln Ala Glu Val Asp Cys
                165                 170                 175

Glu Tyr Ala Lys Arg Trp Cys Asp Arg Ala Asp Glu Asn Lys Arg
            180                 185                 190

Ala Glu Lys Glu Leu Ala Asp Ala Arg Ala Leu Lys Ala Pro Pro
        195                 200                 205

Ser Ser Ala Ala Ala Gln Pro Ala Ser Ala Ala Thr Leu Thr Met
    210                 215                 220

Cys Pro Ser Cys Arg Arg Val Ala Ala Ala Ser His His His Gln
225                 230                 235                 240

Pro Pro Pro Pro Gln Cys His Pro Lys Pro Thr Val Ala Ala Gly Gly
                245                 250                 255
```

```
Gly Ser Val Val Pro Arg Pro Ser His Cys Gln Phe Phe Pro Ala Ala
            260                 265                 270

Ala Val Asp Arg Thr Ser Gln Gly Thr Trp Asn Thr Ala Ala Pro Pro
        275                 280                 285

Leu Val Thr Arg Glu Leu Phe
        290             295

<210> SEQ ID NO 227
<211> LENGTH: 292
<212> TYPE: PRT
<213> ORGANISM: Zea mays

<400> SEQUENCE: 227

Met Ala Gln Glu Asp Val His Leu Asp Asp Ala Gly Leu Ala Leu Gly
1               5                   10                  15

Leu Ser Leu Gly Ser Gly Ser Gly Gly Ala Ser Gly Ala Ala Arg His
            20                  25                  30

Gly Gly Ile Ser Arg Arg Leu Ser Arg Glu Val Arg Leu Pro Ser Pro
        35                  40                  45

His Pro Leu Glu Pro Ser Leu Thr Leu Ser Leu Pro Asp Glu Ala Thr
    50                  55                  60

Ala Thr Gly Ser Gly Gly Gly Ala Ala His Ser Val Ser Ser Leu
65              70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
            115                 120                 125

Glu Gln Ser Ala Leu Leu Glu Asp Arg Phe Lys Glu His Ser Thr Leu
        130                 135                 140

Asn Pro Lys Gln Lys Val Ala Leu Ala Lys Gln Leu Lys Leu Arg Pro
145                 150                 155                 160

Arg Gln Val Glu Val Trp Phe Gln Asn Arg Arg Ala Arg Thr Lys Leu
                165                 170                 175

Lys Gln Ala Glu Val Asp Cys Glu Leu Ala Lys Arg Cys Cys Glu Ser
            180                 185                 190

Ala Thr Glu Glu Asn Arg Arg Ala Gln Arg Glu Leu Gln Glu Ala Arg
        195                 200                 205

Ala Leu Lys Phe Ala Pro His Pro Gln Ala Pro Pro Ser Ser Ala Thr
    210                 215                 220

Gln Ala Gly Ala Ala Gly Val Val Pro Ala Pro Pro Pro Leu
225                 230                 235                 240

Tyr Met Gln Met Gln Met Pro Ala Ala Thr Leu Ser Leu Cys Pro
                245                 250                 255

Ser Cys Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
        275                 280                 285

Ser Ala Ala Cys
        290

<210> SEQ ID NO 228
<211> LENGTH: 267
<212> TYPE: PRT
<213> ORGANISM: Zea mays
```

<400> SEQUENCE: 228

```
Met Ser Ser Leu Thr Thr Ala Ala Ser Ser Ser Ser Met Glu Glu
1               5                   10                  15

His Cys Tyr Ser Val Ser Ala Glu Glu Val Val Gly Thr His Leu Ser
            20                  25                  30

Leu Gly Ile Gly Gly Gly Gly Gly Gly Gly Asp Lys Arg Thr Met
        35                  40                  45

Leu Thr Leu Pro Pro Ser Arg Thr Val Gln Leu Phe Gly Glu Val Leu
50                  55                  60

Ser Val Gln Asp Gly Asp Gly Thr Gln Ala Leu Arg His His His Thr
65                  70                  75                  80

Gly Arg Pro Pro Ala Ala Ser Ser Arg Lys Lys Lys Arg Lys Asp Ala
                85                  90                  95

Ala Ala Ala Gly Gly Ala Ser Ala Thr Asp Ala Ala Ala Asn Gly His
                100                 105                 110

His His Gln Ser Lys Lys Thr Lys Thr Thr Ala Ala Arg Arg Asp Asp
            115                 120                 125

Gly Gly Gly Gly Arg Lys Lys Leu Arg Leu Thr Ser Ala Gln Ala Thr
130                 135                 140

Leu Leu Glu Asp Ser Phe Arg Ala His Asn Ile Leu Ser His Gly Glu
145                 150                 155                 160

Lys Gln Glu Leu Ala Arg Gln Ala Gly Leu Ser Ala Arg Gln Val Glu
                165                 170                 175

Val Trp Phe Gln Asn Arg Arg Ala Arg Thr Lys Leu Lys Gln Ala Glu
            180                 185                 190

Val Asp Cys Asp Leu Ala Arg Arg Trp Cys Ala Arg Ala Ser Asp Asp
            195                 200                 205

Asn Asp Arg Ala Arg Arg Asp Leu Ala Asp Ala Arg Arg Ala Ala Ser
        210                 215                 220

Ser Ser Ala Gly Leu Gly Ala Val Val Cys Cys Ala Ser Cys Gly Ala
225                 230                 235                 240

Asp Arg Gln Leu Ala Leu Ala Ala Ala Asp Asn Val Leu Pro Ser
                245                 250                 255

Val Ala Ser Pro Ser His Ser Pro His Leu Thr
            260                 265
```

<210> SEQ ID NO 229
<211> LENGTH: 315
<212> TYPE: PRT
<213> ORGANISM: Zea mays

<400> SEQUENCE: 229

```
Met Ala Asp Ser Gly Ser Asp Leu Val Leu Gly Leu Gly Met Gly Val
1               5                   10                  15

Gly Val Arg Arg Glu Glu Glu Thr Gln Arg Gly Arg Arg Asp Arg Glu
            20                  25                  30

Ala Arg Arg Glu Leu Glu Phe Glu Thr Gly Arg Cys Ala Arg Pro Ser
        35                  40                  45

Pro Glu Pro Ala Val Arg Leu Thr Leu Leu Pro Gly Leu Val Pro Ser
    50                  55                  60

Leu Gly Leu Pro Trp Pro Leu Ser Ser Glu Thr Asn Arg Glu Val Ser
65                  70                  75                  80

Thr Arg Gly Phe Asp Asp Val Asn Arg Ala Leu Ser Val Ala Gly Ala
                85                  90                  95
```

```
Gly Ala Glu Glu Asp Glu Ala Ala Val Ala Ala Thr Ala Ala Ala
            100                 105                 110

Ser Ser Ser Pro Asn Asn Ser Ser Gly Ser Phe Ala Met Asp Ile Ser
            115                 120                 125

Ala Gln Gly Gln Gly Gln Gly Gln Asp Gln Ala Ala Pro Ala Ala Asp
130                 135                 140

Arg Ala Cys Ser Arg Ala Ser Asp Glu Asp Gly Gly Ser Ala Arg
145                 150                 155                 160

Lys Lys Leu Arg Leu Ser Lys Glu Gln Ser Ala Phe Leu Glu Glu Ser
                165                 170                 175

Phe Lys Val Arg Ala Thr Pro Asn Pro Lys Gln Lys Leu Ala Leu Ala
            180                 185                 190

Arg Gln Leu Asn Leu Arg Ala Arg Gln Val Glu Val Trp Phe Gln Asn
        195                 200                 205

Arg Arg Ala Arg Thr Lys Leu Lys Gln Ala Glu Val Asp Cys Glu His
        210                 215                 220

Ala Lys Arg Cys Cys Glu Thr Ala Thr Gly Glu Asn Arg Arg Ala His
225                 230                 235                 240

Lys Glu Leu Ala Glu Ala Arg Ala Leu Lys Ala Val Arg Pro Leu Leu
                245                 250                 255

His Met His Leu Pro Ala Thr Thr Leu Ser Met Cys Pro Ser Cys Glu
            260                 265                 270

Arg Val Ala Ser Thr Ser Ser Ala Ala Pro Ala Ala Pro Ala Pro Ala
        275                 280                 285

Ser Pro Ser Pro Ala Ala Gly Ala Gly Ile Ala Ala Ser Ala Pro Asp
        290                 295                 300

Pro Asp Gln Arg Pro Ser Ser Ser Phe Ala Ala
305                 310                 315

<210> SEQ ID NO 230
<211> LENGTH: 335
<212> TYPE: PRT
<213> ORGANISM: Zea mays

<400> SEQUENCE: 230

Met Glu Leu Ala Leu Ser Leu Gly Glu Thr Met Ala Asp Ala Gly Arg
1               5                   10                  15

Asp Leu Met Leu Gly Leu Gly Met Gly Val Gly Val Arg Arg Glu Glu
            20                  25                  30

Glu Ala Gln Arg Gly Arg Arg Asp Arg Glu Val Arg Arg Glu Leu Glu
        35                  40                  45

Phe Thr Ala Arg Ser Ala Arg Ser Ser Pro Glu Pro Ala Val Arg Leu
    50                  55                  60

Thr Leu Leu His Gly Leu Gly Leu Pro Trp Pro Pro Pro Ser Ser
65                  70                  75                  80

Glu Thr Asn Arg His Leu Glu Ala Ser Ala Arg Gly Phe Asp Val Asn
                85                  90                  95

Arg Ala Pro Ser Leu Ser Ala Ala Gly Ala Ala Ala Glu Glu Asp Glu
            100                 105                 110

Glu Gln Asp Glu Ala Gly Ala Ala Ala Ala Ala Ser Ser Ser Pro
        115                 120                 125

Asn Asn Ser Ala Ser Ser Phe Pro Thr Asp Phe Ser Ala His Gly Gln
    130                 135                 140

Val Ala Pro Gly Ala Asp Arg Ala Cys Ser Arg Ala Ser Asp Glu Asp
```

```
                145                 150                 155                 160
Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
        195                 200                 205

Glu Val Trp Phe Gln Asn Arg Arg Ala Arg Thr Lys Leu Lys Gln Ala
    210                 215                 220

Glu Val Asp Cys Glu Tyr Ala Lys Arg Cys Cys Glu Thr Ala Thr Glu
225                 230                 235                 240

Glu Asn Arg Arg Ala Gln Lys Glu Leu Ser Glu Ala Arg Ala Leu Lys
                245                 250                 255

Thr Val His Pro Phe Tyr Met His Leu Pro Ala Thr Thr Leu Ser Met
            260                 265                 270

Cys Pro Ser Cys Glu Arg Val Ala Ser Asn Ser Ala Pro Ala Pro Ala
        275                 280                 285

Ser Ser Pro Ser Pro Ala Thr Gly Ile Ala Ala Pro Ala Pro Glu Gln
    290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 231
<211> LENGTH: 354
<212> TYPE: PRT
<213> ORGANISM: Zea mays

<400> SEQUENCE: 231

Met Glu Leu Gly Leu Ser Leu Gly Asp Ala Ala Val Pro Asp Ala Gly
1               5                   10                  15

Arg Ala Ala Pro Glu Leu Gly Leu Gly Leu Val Gly Ile Gly Ser
            20                  25                  30

Asn Ala Ala Gly Thr Gly Arg Gly Ser Lys Ala Ala Gly Thr Thr Gly
        35                  40                  45

Thr Thr Gly Trp Trp Ala Ala Pro Ala Thr Pro Glu Ser Ala Val Arg
    50                  55                  60

Leu Ser Leu Val Ser Ser Leu Gly Leu Gln Trp Pro Pro Asp Gly
65                  70                  75                  80

Gly Ile Cys His Val Gly Arg Asp Glu Ala Pro Ala Arg Gly Phe Asp
                85                  90                  95

Val Asn Arg Ala Pro Ser Val Ala Gly Ser Ala Leu Ala Leu Glu Asp
            100                 105                 110

Asp Glu Glu Glu Pro Gly Ala Ala Ala Leu Ser Ser Ser Pro Asn Asp
        115                 120                 125

Ser Ala Gly Ser Phe Pro Leu Asp Leu Gly Gly Pro Arg Ala His Ala
    130                 135                 140

Glu Gly Ala Ala Ala Arg Ala Gly Gly Glu Arg Ser Ser Ser Arg Ala
145                 150                 155                 160

Ser Asp Glu Asp Glu Gly Ala Ser Ala Arg Lys Lys Leu Arg Leu Ser
                165                 170                 175

Lys Glu Gln Ser Ala Phe Leu Glu Glu Ser Phe Lys Glu His Ser Thr
            180                 185                 190
```

```
Leu Asn Pro Lys Gln Lys Ala Ala Leu Ala Lys Gln Leu Asn Leu Arg
            195                 200                 205

Pro Arg Gln Val Glu Val Trp Phe Gln Asn Arg Ala Arg Thr Lys
    210                 215                 220

Leu Lys Gln Ala Glu Val Asp Cys Glu Tyr Ala Lys Arg Cys Cys Glu
225                 230                 235                 240

Thr Ala Thr Glu Glu Asn Arg Arg Ala His Lys Glu Leu Ala Glu Ala
                245                 250                 255

Arg Ala Leu Lys Thr Ala Pro Pro Phe Met Arg Leu Pro Ala Thr
            260                 265                 270

Thr Leu Ser Met Cys Pro Ser Cys Glu Arg Val Ala Ser Gly Pro Ser
275                 280                 285

Pro Ala Ser Thr Ser Ala Pro Ala Ser Ser Thr Pro Pro Ala Thr Ala
    290                 295                 300

Ala Thr Thr Ala Ile Ser Tyr Ala Ala Ala Ala Ala Pro Val Arg
305                 310                 315                 320

Ala Asp His Arg Pro Ser Ser Phe Ala Ala Leu Phe Ala Ala Thr Arg
                325                 330                 335

Ser Phe Pro Leu Ala Ser Gln Pro Arg Pro Pro Ala Pro Ala Ser Asn
            340                 345                 350

Cys Leu

<210> SEQ ID NO 232
<211> LENGTH: 319
<212> TYPE: PRT
<213> ORGANISM: Zea mays

<400> SEQUENCE: 232

Met Asp Ile Met Ala Leu Asn Ala Arg Asp Glu Glu Gln Tyr Gly Asn
1               5                   10                  15

Asn His Leu Gly Leu Gly Leu Ser Leu Ser Leu Gly Leu Gly Val Ala
                20                  25                  30

Thr Ala Ala Pro Val Glu Val Glu Pro Pro Pro Pro Arg Gln Gln
            35                  40                  45

Gln Gln Arg Ala Ile Ser Val Ala Pro Ile Thr Ser Leu Pro Ala Pro
    50                  55                  60

Gln Trp Trp Lys Trp Asn Gly Pro Gly Leu Phe Phe Gly Thr Thr Met
65                  70                  75                  80

Asp Gln Gln Gln Pro Ala Ala Arg His Gly His Glu Met Pro
                85                  90                  95

Phe Leu Arg Gly Val Asp Val Asn Arg Ala Pro Ala Gly Asp Thr Arg
            100                 105                 110

Arg Gly Ser Cys Ser Glu Asp Glu Glu Pro Gly Gly Ala Ser Ser
        115                 120                 125

Ser Pro Asn Ser Thr Leu Ser Ser Ser Leu Ser Gly Lys Arg Ala Ala
    130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
                165                 170                 175

Arg Leu Ser Lys Asp Gln Ala Ala Val Leu Glu Glu Ser Phe Lys Glu
            180                 185                 190

His Asn Thr Leu Asn Pro Lys Gln Lys Ala Ala Leu Ala Lys Gln Leu
        195                 200                 205
```

```
Asn Leu Lys Pro Arg Gln Val Glu Val Trp Phe Gln Asn Arg Arg Ala
    210                 215                 220
Arg Thr Lys Leu Lys Gln Ala Glu Val Asp Cys Glu Phe Ala Lys Arg
225                 230                 235                 240
Cys Cys Glu Thr Ala Thr Glu Glu Asn Arg Arg Ala Gln Arg Glu Val
                245                 250                 255
Ala Glu Ala Arg Val Leu Lys Leu Val Ala Pro His His Tyr Ala Arg
            260                 265                 270
Met Pro Pro Thr Thr Leu Thr Met Cys Pro Ser Cys Glu Arg Leu
        275                 280                 285
Ala Ser Ala Ser Ala Ser Ala Asp Gln Ala Gly Arg Ala Gly Pro Cys
    290                 295                 300
Trp Gly Pro Leu Pro Val Phe Val Asp Gly Pro Ala Arg Arg Pro
305                 310                 315

<210> SEQ ID NO 233
<211> LENGTH: 331
<212> TYPE: PRT
<213> ORGANISM: Zea mays

<400> SEQUENCE: 233

Met Glu Leu Glu Leu Ser Leu Gly Asp Ser Arg Ala Pro Ala Lys Ser
1               5                   10                  15
Ala Ser Thr Pro Ala Ala Leu Thr Pro Ile His Ala Gly Ala Gly Gly
            20                  25                  30
Glu Gly His Glu Leu Ala Leu Glu Leu Gly Val Gly Ala Ala Lys Arg
        35                  40                  45
Ala Glu Gln Asp Asn Gln Lys Thr Pro Val Gln Pro Glu His Val Gln
    50                  55                  60
Glu Glu Glu Glu Glu Glu Thr Cys Pro Tyr Ser Glu Ser Pro Ala
65                  70                  75                  80
Glu Leu Ser Leu Ile Gly Cys Pro Leu Pro Ala Ala Ser Ala Glu
            85                  90                  95
Ile Gly Ser Val Asn Ser Ser Glu Val Cys Val Arg Arg Gly Phe Gly
            100                 105                 110
Val Asp Ala Val Leu Val Asp Gly Asp Ala Ala Gln Gly Arg Pro
        115                 120                 125
Ala Leu Ser Thr Ser Phe Leu Pro Ser Glu Phe Leu Val Arg Arg Gln
    130                 135                 140
Ala Asp Asp Gln Glu Ala Ala Glu Asp Glu Glu Met Ser Gly Val
145                 150                 155                 160
Gly Gly Gly Ala Arg Lys Lys Leu Arg Leu Ser Lys Glu Gln Ser Ala
                165                 170                 175
Phe Leu Glu Asp Ser Phe Lys Ala His Ser Thr Leu Thr Pro Lys Gln
            180                 185                 190
Lys Ser Asp Leu Ala Lys Arg Leu Lys Leu Arg Pro Arg Gln Val Glu
        195                 200                 205
Val Trp Phe Gln Asn Arg Arg Ala Arg Ser Lys Leu Lys Gln Ala Glu
    210                 215                 220
Val Asp Cys Glu Tyr Ala Lys Arg Trp Cys Glu Lys Ala Ala Gln Glu
225                 230                 235                 240
Asn Arg Arg Ala Gln Arg Glu Val Ala Glu Ala Arg Arg Leu Cys Ser
                245                 250                 255
Ala Ala Tyr Pro Phe Tyr Gly Ala Ala Ala Gly Phe Gly Val Ala Thr
            260                 265                 270
```

```
Ala Arg Val Cys Pro Ser Ser Cys Asp Asn Asp Val Ser Glu Ala Ala
            275                 280                 285

Ile Ser Gly Ala Pro Ser Ala Ala Pro Pro Ser Thr Leu Phe
    290                 295                 300

Ala Ser Trp Pro Pro His Phe Gly Pro Phe Thr Val Val Pro Pro
305                 310                 315                 320

Leu Leu Arg Arg Gln Pro Ser Ala Thr Thr Ser
            325                 330

<210> SEQ ID NO 234
<211> LENGTH: 227
<212> TYPE: PRT
<213> ORGANISM: Zea mays

<400> SEQUENCE: 234

Met Met Glu Arg Val Glu Asp Leu Gly Leu Ser Leu Ser Leu Ser Ser
1               5                   10                  15

Ser Leu Ala Ser Pro Arg Thr His His Val Ala Thr Met Leu Leu Arg
            20                  25                  30

Ala Pro Glu Lys Arg Phe Leu Glu Met Pro Leu Leu Leu Pro Ala Lys
        35                  40                  45

Arg Thr Thr Glu Val Thr Gly Glu Asp Gly Leu Arg Gly Gly Ser Asp
    50                  55                  60

Glu Glu Asp Gly Gly Cys Gly Ile Asp Gly Ser Arg Lys Lys Leu Arg
65                  70                  75                  80

Leu Ser Lys Asp Gln Ser Ala Val Leu Glu Asp Ser Phe Arg Glu His
                85                  90                  95

Pro Thr Leu Asn Pro Arg Gln Lys Ala Ala Leu Ala Gln Gln Leu Gly
            100                 105                 110

Leu Arg Pro Arg Gln Val Glu Ala Trp Phe Ala Ala Arg Arg Ala Arg
        115                 120                 125

Thr Lys Leu Lys Gln Thr Glu Val Asp Cys Glu Tyr Leu Lys Arg Cys
    130                 135                 140

Cys Glu Thr Leu Thr Glu Glu Asn Arg Arg Leu Gln Lys Glu Val Gln
145                 150                 155                 160

Glu Leu Arg Ala Leu Lys Leu Val Ser Pro His Leu Tyr Met His Met
                165                 170                 175

Ser Pro Pro Thr Thr Leu Thr Met Cys Pro Ser Cys Glu Arg Val Ser
            180                 185                 190

Ser Ser Asn Gly Asn Ser Ala Ala Ala Thr Ala Ala Arg Ala Arg
        195                 200                 205

Ala Gly Ala Gly Ala Gly Ala Ile Val Cys His Pro Ile Asp Arg Ala
    210                 215                 220

Thr Ser Thr
225

<210> SEQ ID NO 235
<211> LENGTH: 225
<212> TYPE: PRT
<213> ORGANISM: Zea mays

<400> SEQUENCE: 235

Met Gly Ser Thr Ser Pro Ser Gly Leu Glu Leu Thr Met Ala Val Pro
1               5                   10                  15

Gly Leu Ser Ser Ser Gly Ser Glu Gly Phe Gly Cys Asn Asn Asn
            20                  25                  30
```

```
Asn Gly Ser Gly Asn Gly Asn Met Arg Asp Leu Asp Met Asn Gln
        35                  40                  45

Pro Ala Ser Gly Gly Glu Glu Glu Phe Pro Met Gly Ser Val Glu
    50                  55                  60

Glu Glu Glu Asp Glu Arg Gly Gly Ala Gly Gly Pro His Arg Ala Lys
65                  70                  75                  80

Lys Leu Arg Leu Ser Lys Glu Gln Ser Arg Leu Leu Glu Ser Phe
                85                  90                  95

Arg Leu Asn His Thr Leu Thr Pro Lys Gln Lys Glu Ala Leu Ala Val
            100                 105                 110

Lys Leu Lys Leu Arg Pro Arg Gln Val Glu Ala Trp Phe Ala Ala Arg
            115                 120                 125

Arg Ala Arg Thr Lys Leu Lys Gln Thr Glu Leu Glu Cys Glu Tyr Leu
    130                 135                 140

Lys Arg Cys Phe Gly Ser Leu Thr Glu Glu Asn Arg Arg Leu Gln Arg
145                 150                 155                 160

Glu Val Glu Glu Leu Arg Ala Met Arg Val Ala Pro Pro Thr Val Leu
                165                 170                 175

Ser Pro His Thr Arg Gln Pro Leu Pro Ala Ser Ala Leu Thr Met Cys
            180                 185                 190

Pro Arg Cys Glu Arg Ile Thr Ala Ala Thr Ala Ala Arg Thr Pro Arg
            195                 200                 205

Pro Pro Pro Ala Ala Ser Pro Phe His Pro Arg Pro Ser Ala Ala
    210                 215                 220

Phe
225

<210> SEQ ID NO 236
<211> LENGTH: 261
<212> TYPE: PRT
<213> ORGANISM: Zea mays

<400> SEQUENCE: 236

Met Ala Pro Gln Ser Leu Asp Leu Gly Leu Ser Leu Gly Leu Gly Val
1               5                   10                  15

Ala Ala Phe Gln Pro Ser Phe Cys His Pro Ala Gly Asn Asp Ala Ala
                20                  25                  30

Glu Arg Glu Ala Ser Pro Thr Ala Asp Glu Arg Glu Arg Arg Cys Ser
            35                  40                  45

Pro Ala Gly Ser Pro Thr Ser Ser Gly Ser Gly Lys Arg Val Ala Ala
    50                  55                  60

Glu Arg Ser Ala Gly Ser Gly Ser Gly Asp Glu Asp Asp Gly Gly
65                  70                  75                  80

Ala Arg Lys Lys Leu Arg Leu Ser Lys Asp Gln Ala Ala Val Leu Glu
                85                  90                  95

Glu Cys Phe Lys Thr His His Thr Leu Thr Pro Lys Gln Lys Ala Ala
            100                 105                 110

Leu Ala Ser Arg Leu Gly Leu Arg Ala Arg Gln Val Glu Ala Trp Phe
            115                 120                 125

Ala Ala Arg Arg Ala Arg Thr Lys Leu Lys Gln Thr Glu Val Asp Cys
    130                 135                 140

Glu Tyr Leu Arg Arg Trp Cys Glu Gln Leu Ala Glu Glu Asn Arg Arg
145                 150                 155                 160

Leu Gly Lys Glu Val Ala Glu Leu Arg Ala Leu Ser Ala Ala Pro Ala
```

```
                165                 170                 175
Pro Ala Ala Pro Leu Thr Ala Leu Thr Met Cys Leu Ser Cys Arg Arg
            180                 185                 190

Val Ser Ser Ser Cys Ser Ser Ser Pro Pro Asn Thr His Ala His
            195                 200                 205

Ala Ala Ala Ala Gly Thr Gly Arg Ser Val Ala Ala Ala Ala Thr
            210                 215                 220

Thr Leu Pro Ala His Arg Gln Phe Leu Cys Gly Phe Arg Asp Gly Gly
225                 230                 235                 240

Ala Ala Ala Ala Ala Val Tyr Gly Thr Ser Ser Ala Leu Ala Lys Ala
            245                 250                 255

Leu Arg Ala Ala Arg
            260

<210> SEQ ID NO 237
<211> LENGTH: 221
<212> TYPE: PRT
<213> ORGANISM: Zea mays

<400> SEQUENCE: 237

Met Tyr Ser Thr Arg Glu Glu Glu Gly Val Gly Lys Ser Trp Leu Gly
1               5                   10                  15

Leu Gly Ile Gly Gly Gly Ser Gly Gly Cys Asp Leu Met Gln Arg Asn
            20                  25                  30

Asn Arg Pro Pro Val Gln Phe Asp Leu Leu Phe Pro Pro Gln Gly Val
        35                  40                  45

Val Glu Gly Val Ala Ala Ser Lys Lys Ala Glu Lys Gly Gly Gly Gly
    50                  55                  60

Arg Lys Arg Leu Lys Val Val Thr Gly Thr Ala Asp Glu Asp Gly Gln
65                  70                  75                  80

Gln Pro Pro Gly Ala Arg Lys Lys Leu Arg Leu Thr Lys Ala Gln Ser
                85                  90                  95

Thr Leu Leu Glu Asp Thr Phe Arg Ala His Ser Ile Leu Ser Asn Ala
            100                 105                 110

Gln Lys Gln Glu Leu Ala Arg Gln Val Asp Leu Ser Ala Arg Gln Val
        115                 120                 125

Glu Ala Trp Phe Ala Ala Arg Arg Ala Arg Thr Lys Leu Lys Gln Thr
    130                 135                 140

Glu Ala Asp Cys Glu Ile Leu Lys Arg Cys Cys Glu Ser Leu Thr Gly
145                 150                 155                 160

Glu Asn Gln Arg Leu Arg Leu Glu Leu Ala Gln Leu Gln Gly Ser Glu
                165                 170                 175

Ala Gly Leu Tyr Leu Gln Ser Ser Phe Pro Pro Leu Ala Ala Ala Met
            180                 185                 190

Ala Ser Val Cys Pro Ser Cys Asp Lys Val Ile Thr Val Ala Ser Gly
        195                 200                 205

Gly Glu Thr Ser Gly Arg Ser Ser Thr Ser Tyr Ser Ser
    210                 215                 220

<210> SEQ ID NO 238
<211> LENGTH: 223
<212> TYPE: PRT
<213> ORGANISM: Zea mays

<400> SEQUENCE: 238

Met Tyr Ser Cys Thr Arg Ala Met Glu Glu Glu Gly Val Gly Lys Ser
```

```
     1               5                  10                 15
   Trp Leu Gly Leu Gly Ile Gly Gly Gly Asp Leu Met Lys Arg Asn
                    20                 25                 30
   Asn Arg Pro Pro Val Gln Leu Asp Asp Leu Leu Ser Phe Pro Pro Gln
                    35                 40                 45
   Ser Val Ala Ala Ala Ser Lys Lys Gln Ala Glu Lys Gly Gly Gly Gly
                    50                 55                 60
   Arg Lys Arg His Lys Ile Val Val Thr Ala Asp Glu Asp Gly Arg Gln
    65                    70                 75                 80
   Ser Pro His Gly Gly Ala Arg Lys Lys Leu Arg Leu Thr Lys Ala Gln
                         85                 90                 95
   Ser Thr Leu Leu Glu Asp Thr Phe Arg Ala His Asn Ile Leu Ser His
                        100                105                110
   Ala Gln Lys Gln Glu Leu Ala Arg Gln Val Asn Leu Ser Ala Arg Gln
                        115                120                125
   Val Glu Ala Trp Phe Ala Ala Arg Arg Ala Arg Thr Lys Leu Lys Gln
                        130                135                140
   Thr Glu Ala Asp Cys Glu Val Leu Lys Arg Tyr Cys Glu Arg Leu Thr
   145                    150                155                160
   Gly Glu Asn Gln Arg Leu Arg Leu Glu Leu Ala Gln Leu Gln Arg Ser
                        165                170                175
   Pro Ala Glu Glu Ala Gly Phe Tyr Val Gln Ser Ser Phe Pro Phe
                        180                185                190
   Pro Pro Leu Ala Thr Ala Met Ala Ser Val Cys Pro Ser Cys Asp Lys
                        195                200                205
   Val Val Ala Val Thr Ser Gly Lys Ser Ser Thr Ser Tyr Ser Ser
                        210                215                220

<210> SEQ ID NO 239
<211> LENGTH: 241
<212> TYPE: PRT
<213> ORGANISM: Zea mays

<400> SEQUENCE: 239

Met Glu Glu Glu Gly Val Gly Lys Ser Trp Leu Ala Leu Gly Ile Gly
    1               5                  10                 15
   Gly Gly Asp Leu Met Lys Arg Asn Asn Arg Pro Val Gln Phe Asp
                    20                 25                 30
   Leu Leu Phe Pro Pro Gln Ser Val Lys Glu Glu Gly Ala Ala Ser Lys
                    35                 40                 45
   Lys Ala Glu Lys Gly Gly Arg Lys Arg Leu Lys Val Val Thr Ala
    50                    55                 60
   Asp Glu Asp Gly Arg Gln Ser Pro His Gly Gly Pro Gly Pro Ser Asp
    65                    70                 75                 80
   Gly Ser Gly Ala Gly Ala Arg Lys Lys Leu Arg Leu Thr Asn Glu Gln
                         85                 90                 95
   Ser Thr Leu Leu Glu Asp Thr Phe Arg Ala His Asn Ile Leu Ser Asn
                        100                105                110
   Ala Gln Lys Gln Glu Leu Ala Arg Gln Val Asp Leu Ser Ala Arg Gln
                        115                120                125
   Val Glu Ala Trp Phe Ala Ala Arg Arg Ala Arg Thr Lys Leu Lys Gln
                        130                135                140
   Thr Glu Val Asp Cys Glu Ile Leu Lys Arg Cys Cys Glu Ser Leu Thr
   145                    150                155                160
```

```
Gly Glu Asn Gln Arg Leu Arg Leu Glu Leu Ala Gln Leu Gln Arg Ser
                165                 170                 175

Ala Ala Ala Ala Ala Glu Ala Gly Leu Tyr Val Gln Ser Ser Phe Pro
            180                 185                 190

Pro Leu Ala Thr Ala Thr Ala Thr Ala Ser Val Cys Pro Ser Cys Asp
                195                 200                 205

Lys Val Ile Ala Val Ser Ser Gly Gly Glu Thr Ser Gly Lys Ser Ser
            210                 215                 220

Thr Ser Tyr Ser Ser Arg Arg Ala Gly Phe Pro Ser Ile Met Gly Ser
225                 230                 235                 240

Arg

<210> SEQ ID NO 240
<211> LENGTH: 272
<212> TYPE: PRT
<213> ORGANISM: Zea mays

<400> SEQUENCE: 240

Met Ala Pro Gln Ser Leu Asp Leu Gly Leu Ser Leu Gly Leu Gly Val
1               5                   10                  15

Ala Ala Phe Gln Pro Ser Ser Phe Cys His Pro Gly Asn Ala Val Val
                20                  25                  30

Val Pro Ala Ala Ala Glu Arg Glu Ala Ser Pro Ala Ala Ala Glu Glu
            35                  40                  45

Arg Glu Arg Arg Cys Ser Pro Ala Gly Ser Pro Val Ser Ser Gly Ser
        50                  55                  60

Gly Ser Gly Asn Lys Arg Ala Ala Ala Glu Arg Ser Ala Gly Ala Gly
65              70                  75                  80

Ala Gly Ser Gly Asp Glu Asp Asp Gly Ala Ala Arg Lys Lys Leu
                85                  90                  95

Arg Leu Ser Lys Asp Gln Ala Ala Val Leu Glu Glu Cys Phe Lys Thr
            100                 105                 110

His His Thr Leu Thr Pro Lys Gln Lys Val Ala Leu Ala Ser Ser Leu
        115                 120                 125

Gly Leu Arg Pro Arg Gln Val Glu Ala Trp Phe Ala Ala Arg Arg Ala
    130                 135                 140

Arg Thr Lys Leu Lys Gln Thr Glu Val Asp Cys Glu Tyr Leu Lys Arg
145                 150                 155                 160

Trp Cys Glu Gln Leu Ala Glu Glu Asn Arg Arg Leu Gly Lys Glu Val
                165                 170                 175

Ala Glu Leu Arg Ala Leu Ser Ala Ala Pro Ala Ala Pro Leu Thr Thr
            180                 185                 190

Leu Thr Met Cys Leu Ser Cys Arg Arg Val Ala Ser Ser Ser Pro Ser
        195                 200                 205

Ser Ser Ser Ser Pro Arg Pro Ser Ile Pro Gly Ala Ala Ala Ala Ser
    210                 215                 220

Gly Gly Ser Met Ala Ser Pro Ala Ala Ala Thr Leu Pro Ala His
225                 230                 235                 240

Arg Gln Phe Phe Cys Gly Phe Arg Asp Ala Gly Ala Ala Ala Ala
                245                 250                 255

Tyr Gly Thr Ala Ser Ala Gly Leu Ala Lys Pro Val Arg Ala Ala Arg
            260                 265                 270

<210> SEQ ID NO 241
<211> LENGTH: 254
```

<212> TYPE: PRT
<213> ORGANISM: Zea mays

<400> SEQUENCE: 241

```
Met Tyr Thr Thr Thr Arg Ala Met Glu Lys Glu Gly Phe Gly Lys
1               5                   10                  15

Ser Trp Leu Gly Leu Gly Ile Gly Gly Gly Arg Asp Leu Asn Leu
            20                  25                  30

Met Lys Arg Ser Arg Pro Leu Arg Pro Val Arg Leu Asp Leu Phe
        35                  40                  45

Pro Pro Ser Val Glu Gly Gly Glu Ala Ala Arg Ser Arg Lys Ala
50                  55                  60

Gly Ala Gly Ala Leu Arg Asn Met Ser Leu Lys Gln Val Ala Gly Asp
65                  70                  75                  80

Asp Asp Gly Gly Gln Ser Ser His Gly Gly Pro Ser Pro Ser Asp Asp
                85                  90                  95

Asp Asp Gly Ala Gly Ala Arg Lys Lys Leu Arg Leu Thr Thr Glu Gln
                100                 105                 110

Ser Lys Leu Leu Glu Asp Thr Phe Arg Ala His Asn Ile Leu Ser His
            115                 120                 125

Ala Gln Lys His Glu Val Ala Arg Gln Val Asp Leu Ser Ala Arg Gln
        130                 135                 140

Val Glu Ala Trp Phe Ala Ala Arg Arg Ala Arg Thr Lys Leu Lys Gln
145                 150                 155                 160

Thr Glu Val Asp Cys Glu Thr Leu Arg Arg Trp Arg Glu Ser Leu Ala
                165                 170                 175

Asp Glu Asn Leu Arg Leu Arg Leu Glu Leu Glu Gln Leu Gln Arg Trp
            180                 185                 190

Ala Thr Ala Ala Ala Gly Gln Ser Ser Ala Ser Pro Ser Pro Ala Thr
        195                 200                 205

Ala Thr Ala Ser Val Cys Pro Ser Cys Asp Lys Val Val Val Val Thr
210                 215                 220

Val Thr Ser Cys Gly Glu Thr Ser Gly Lys Ser Ser Thr Ser Ser Tyr
225                 230                 235                 240

Ser Ser Ser Pro Pro Leu Asp Met Leu Asp Arg Ser Val Gln
                245                 250
```

<210> SEQ ID NO 242
<211> LENGTH: 262
<212> TYPE: PRT
<213> ORGANISM: Zea mays

<400> SEQUENCE: 242

```
Met Glu Gln Glu Glu Val Gly Leu Ala Leu Gly Leu Ser Leu Gly Ser
1               5                   10                  15

Gly His His His Gln Glu Leu Lys Pro Gln His Pro Ser His Pro Cys
            20                  25                  30

Ala Ala Leu Leu Glu Pro Ser Leu Ser Leu Ser Gly Pro Ala Thr Lys
        35                  40                  45

Asp Asp Gly Pro Thr Ala Pro Val Arg Arg Phe Ala Ala Val Lys Arg
50                  55                  60

Glu Leu Gln Thr Met Glu Gly Asn Asp Asp Glu Ala Thr Gly Arg Val
65                  70                  75                  80

Leu Val Tyr Ser Val Ala Ser Ser Ala Val Val Thr Ala Asp Asp Asp
                85                  90                  95
```

```
Glu Gly Cys Asn Ser Ser Arg Lys Lys Leu Arg Leu Ser Lys Glu Gln
            100                 105                 110

Ser Ala Leu Leu Glu Asp His Phe Lys Glu His Ser Thr Leu Asn Pro
        115                 120                 125

Lys Gln Lys Ala Ala Leu Ala Arg Gln Leu Asn Leu Ser Pro Arg Gln
    130                 135                 140

Val Glu Ala Trp Phe Ala Ala Arg Arg Ala Arg Thr Lys Leu Lys Gln
145                 150                 155                 160

Thr Glu Val Asp Cys Glu Ile Leu Lys Arg Cys Cys Glu Thr Leu Thr
                165                 170                 175

Glu Glu Asn Arg Arg Leu His Arg Glu Leu Gln Gln Leu Arg Ala Leu
            180                 185                 190

Ser His Pro His Pro His Pro Ala Ala Phe Phe Met Pro Thr Ala Ala
        195                 200                 205

Ala Ala Ala Leu Ser Ile Cys Pro Ser Cys Gln Arg Leu Val Ala Thr
    210                 215                 220

Gly Ala Ser Ala Ala Ala Thr Thr Ala Gly Ala Asp Asn Lys Pro
225                 230                 235                 240

Lys Ala Gly Gly Pro Gly Gly Arg Ala Pro His Val Phe Ser Pro Phe
                245                 250                 255

Thr Asn Ser Ala Ala Cys
            260

<210> SEQ ID NO 243
<211> LENGTH: 245
<212> TYPE: PRT
<213> ORGANISM: Zea mays

<400> SEQUENCE: 243

Met Ala Gln Glu Asp Val His Leu Asp Asp Ala Gly Leu Ala Leu Cys
1               5                   10                  15

Leu Ser Leu His Gly Thr Ser Ser Arg Leu Ser Thr Glu Ala Pro
            20                  25                  30

Arg Thr Leu Glu Pro Pro Ser Leu Thr Leu Ser Met Pro Asp Glu Ala
        35                  40                  45

Thr Ala Thr Ala Thr Gly Gly Ser Gly Gly Ser Gly Gly Ala Ala Arg
    50                  55                  60

Ser Val Ser Ser Arg Ser Val Glu Gly Val Lys Arg Glu Arg Val Asp
65                  70                  75                  80

Asp Ala Glu Gly Glu Arg Ala Ser Ser Thr Ala Ala Ala Ala Arg Val
                85                  90                  95

Cys Ala Gly Ala Glu Asp Asp Asp Gly Ser Thr Arg Lys Lys Leu
            100                 105                 110

Arg Leu Thr Lys Glu Gln Ser Lys Leu Leu Glu Asp Arg Phe Lys Asp
        115                 120                 125

His Ser Thr Leu Asn Pro Lys Gln Lys Ile Ala Leu Ala Lys Gln Leu
    130                 135                 140

Lys Leu Arg Pro Arg Gln Val Glu Ala Trp Phe Ala Ala Arg Arg Ala
145                 150                 155                 160

Arg Thr Lys Leu Lys Gln Thr Glu Val Asp Cys Glu Leu Leu Lys Arg
                165                 170                 175

Cys Cys Glu Ser Leu Ser Glu Glu Asn Arg Arg Leu Gln Arg Glu Leu
            180                 185                 190

Gln Glu Leu Arg Ala Leu Lys Leu Ala Gly Pro His Pro Gln Ala Pro
        195                 200                 205
```

Ser Ser Ser Pro Ala Ala Thr Gln Gly Val Pro Val Pro
    210             215                 220

Pro Pro Leu Tyr Val Gln Met Gln Met Gln Leu Ser Ser Cys Arg Cys
225             230                 235                 240

Cys Arg Pro Pro Arg
            245

<210> SEQ ID NO 244
<211> LENGTH: 295
<212> TYPE: PRT
<213> ORGANISM: Zea mays

<400> SEQUENCE: 244

Met Met Pro Gln Ala Ser Ala Ser Leu Asp Leu Gly Leu Ser Leu Gly
1               5                   10                  15

Leu Thr Leu Thr Ser Gln Gly Ser Leu Ser Ser Ser Thr Thr Thr Ala
                20                  25                  30

Gly Ser Ser Ser Pro Trp Ala Ala Ala Leu Ser Ser Val Val Ala Asp
            35                  40                  45

Val Ala Arg Ala Arg Gly Asp Ala Tyr Ala Gln His His Ala Gly Ala
    50                  55                  60

Ala Met Thr Met Arg Ala Ser Thr Ser Pro Asp Ser Gly Asp Thr Thr
65                  70                  75                  80

Thr Ala Lys Arg Glu Arg Glu Gly Glu Leu Glu Arg Thr Gly Ser Ala
                85                  90                  95

Gly Gly Val Arg Ser Asp Glu Glu Asp Gly Ala Asp Gly Gly Ala Gly
            100                 105                 110

Gly Arg Lys Lys Leu Arg Leu Ser Lys Asp Gln Ala Ala Val Leu Glu
        115                 120                 125

Glu Cys Phe Lys Thr His Ser Thr Leu Asn Pro Lys Gln Lys Val Gln
130                 135                 140

Leu Ala Asn Arg Leu Gly Leu Arg Pro Arg Gln Val Glu Ala Trp Phe
145                 150                 155                 160

Ala Ala Arg Arg Ala Arg Thr Lys Leu Lys Gln Thr Glu Val Asp Cys
                165                 170                 175

Glu Tyr Leu Lys Arg Trp Cys Asp Arg Leu Ala Asp Glu Asn Lys Arg
            180                 185                 190

Leu Glu Lys Glu Leu Ala Asp Leu Arg Ala Leu Lys Ala Ala Pro Pro
        195                 200                 205

Ser Ser Ala Ala Ala Gln Pro Ala Ser Ala Ala Thr Leu Thr Met
    210                 215                 220

Cys Pro Ser Cys Arg Arg Val Ala Ala Ala Ser His His His Gln
225                 230                 235                 240

Pro Pro Pro Pro Gln Cys His Pro Lys Pro Thr Val Ala Ala Gly Gly
                245                 250                 255

Gly Ser Val Val Pro Arg Pro Ser His Cys Gln Phe Phe Pro Ala Ala
            260                 265                 270

Ala Val Asp Arg Thr Ser Gln Gly Thr Trp Asn Thr Ala Ala Pro Pro
        275                 280                 285

Leu Val Thr Arg Glu Leu Phe
    290                 295

<210> SEQ ID NO 245
<211> LENGTH: 292
<212> TYPE: PRT

<213> ORGANISM: Zea mays

<400> SEQUENCE: 245

Met Ala Gln Glu Asp Val His Leu Asp Asp Ala Gly Leu Ala Leu Gly
1               5                   10                  15

Leu Ser Leu Gly Ser Gly Ser Gly Gly Ala Ser Gly Ala Ala Arg His
            20                  25                  30

Gly Gly Ile Ser Arg Arg Leu Ser Arg Glu Val Arg Leu Pro Ser Pro
        35                  40                  45

His Pro Leu Glu Pro Ser Leu Thr Leu Ser Leu Pro Asp Glu Ala Thr
    50                  55                  60

Ala Thr Gly Ser Gly Gly Gly Ala Ala His Ser Val Ser Ser Leu
65                  70                  75                  80

Ser Val Ala Gly Val Lys Arg Glu Arg Val Asp Asp Ala Glu Gly Glu
                85                  90                  95

Arg Ala Ser Ser Thr Ala Ala Leu Pro Arg Ala Cys Ala Gly Ala Glu
            100                 105                 110

Asp Asp Asp Asp Gly Ser Thr Arg Lys Lys Leu Arg Leu Thr Lys
        115                 120                 125

Glu Gln Ser Ala Leu Leu Glu Asp Arg Phe Lys Glu His Ser Thr Leu
130                 135                 140

Asn Pro Lys Gln Lys Val Ala Leu Ala Lys Gln Leu Lys Leu Arg Pro
145                 150                 155                 160

Arg Gln Val Glu Ala Trp Phe Ala Ala Arg Arg Ala Arg Thr Lys Leu
                165                 170                 175

Lys Gln Thr Glu Val Asp Cys Glu Leu Leu Lys Arg Cys Cys Glu Ser
            180                 185                 190

Leu Thr Glu Glu Asn Arg Arg Leu Gln Arg Glu Leu Gln Glu Leu Arg
        195                 200                 205

Ala Leu Lys Phe Ala Pro His Pro Gln Ala Pro Pro Ser Ser Ala Thr
    210                 215                 220

Gln Ala Gly Ala Ala Ala Gly Val Val Pro Ala Pro Pro Pro Leu
225                 230                 235                 240

Tyr Met Gln Met Gln Met Pro Ala Ala Ala Thr Leu Ser Leu Cys Pro
                245                 250                 255

Ser Cys Asp Arg Leu Ala Gly Pro Gly Ala Ala Lys Ala Glu Pro
            260                 265                 270

Arg Pro Lys Ala Ala Ala Thr His His Phe Phe Asn Pro Phe Thr His
        275                 280                 285

Ser Ala Ala Cys
    290

<210> SEQ ID NO 246
<211> LENGTH: 267
<212> TYPE: PRT
<213> ORGANISM: Zea mays

<400> SEQUENCE: 246

Met Ser Ser Leu Thr Thr Ala Ala Ser Ser Ser Ser Met Glu Glu
1               5                   10                  15

His Cys Tyr Ser Val Ser Ala Glu Glu Val Val Gly Thr His Leu Ser
            20                  25                  30

Leu Gly Ile Gly Gly Gly Gly Gly Gly Gly Asp Lys Arg Thr Met
        35                  40                  45

Leu Thr Leu Pro Pro Ser Arg Thr Val Gln Leu Phe Gly Glu Val Leu

-continued

```
                50                  55                  60
Ser Val Gln Asp Gly Asp Gly Thr Gln Ala Leu Arg His His Thr
 65                  70                  75                  80

Gly Arg Pro Pro Ala Ala Ser Ser Arg Lys Lys Arg Lys Asp Ala
                 85                  90                  95

Ala Ala Ala Gly Gly Ala Ser Ala Thr Asp Ala Ala Ala Asn Gly His
                100                 105                 110

His His Gln Ser Lys Lys Thr Lys Thr Thr Ala Ala Arg Arg Asp Asp
                115                 120                 125

Gly Gly Gly Gly Arg Lys Lys Leu Arg Leu Thr Ser Ala Gln Ala Thr
130                 135                 140

Leu Leu Glu Asp Ser Phe Arg Ala His Asn Ile Leu Ser His Gly Glu
145                 150                 155                 160

Lys Gln Glu Leu Ala Arg Gln Ala Gly Leu Ser Ala Arg Gln Val Glu
                165                 170                 175

Ala Trp Phe Ala Ala Arg Arg Ala Arg Thr Lys Leu Lys Gln Thr Glu
                180                 185                 190

Val Asp Cys Asp Leu Leu Arg Arg Trp Cys Ala Arg Leu Ser Asp Asp
                195                 200                 205

Asn Asp Arg Leu Arg Arg Asp Leu Ala Asp Leu Arg Arg Ala Ala Ser
210                 215                 220

Ser Ser Ala Gly Leu Gly Ala Val Val Cys Cys Ala Ser Cys Gly Ala
225                 230                 235                 240

Asp Arg Gln Leu Ala Leu Ala Ala Ala Asp Asn Val Leu Pro Ser
                245                 250                 255

Val Ala Ser Pro Ser His Ser Pro His Leu Thr
                260                 265
```

<210> SEQ ID NO 247
<211> LENGTH: 315
<212> TYPE: PRT
<213> ORGANISM: Zea mays

<400> SEQUENCE: 247

```
Met Ala Asp Ser Gly Ser Asp Leu Val Leu Gly Leu Gly Met Gly Val
 1               5                  10                  15

Gly Val Arg Arg Glu Glu Glu Thr Gln Arg Gly Arg Arg Asp Arg Glu
                20                  25                  30

Ala Arg Arg Glu Leu Glu Phe Glu Thr Gly Arg Cys Ala Arg Pro Ser
            35                  40                  45

Pro Glu Pro Ala Val Arg Leu Thr Leu Leu Pro Gly Leu Val Pro Ser
 50                  55                  60

Leu Gly Leu Pro Trp Pro Leu Ser Ser Glu Thr Asn Arg Glu Val Ser
 65                  70                  75                  80

Thr Arg Gly Phe Asp Asp Val Asn Arg Ala Leu Ser Val Ala Gly Ala
                 85                  90                  95

Gly Ala Glu Glu Asp Glu Ala Val Ala Ala Ala Thr Ala Ala Ala
                100                 105                 110

Ser Ser Ser Pro Asn Asn Ser Ser Gly Ser Phe Ala Met Asp Ile Ser
                115                 120                 125

Ala Gln Gly Gln Gly Gln Gly Gln Asp Gln Ala Ala Pro Ala Ala Asp
                130                 135                 140

Arg Ala Cys Ser Arg Ala Ser Asp Glu Asp Gly Gly Ser Ala Arg
145                 150                 155                 160
```

```
Lys Lys Leu Arg Leu Ser Lys Glu Gln Ser Ala Phe Leu Glu Glu Ser
            165                 170                 175

Phe Lys Val Arg Ala Thr Pro Asn Pro Lys Gln Lys Leu Ala Leu Ala
        180                 185                 190

Arg Gln Leu Asn Leu Arg Ala Arg Gln Val Glu Ala Trp Phe Ala Ala
        195                 200                 205

Arg Arg Ala Arg Thr Lys Leu Lys Gln Thr Glu Val Asp Cys Glu His
    210                 215                 220

Leu Lys Arg Cys Cys Glu Thr Leu Thr Gly Glu Asn Arg Arg Leu His
225                 230                 235                 240

Lys Glu Leu Ala Glu Leu Arg Ala Leu Lys Ala Val Arg Pro Leu Leu
                245                 250                 255

His Met His Leu Pro Ala Thr Thr Leu Ser Met Cys Pro Ser Cys Glu
            260                 265                 270

Arg Val Ala Ser Thr Ser Ser Ala Ala Pro Ala Ala Pro Ala Pro Ala
        275                 280                 285

Ser Pro Ser Pro Ala Ala Gly Ala Gly Ile Ala Ala Ser Ala Pro Asp
        290                 295                 300

Pro Asp Gln Arg Pro Ser Ser Ser Phe Ala Ala
305                 310                 315

<210> SEQ ID NO 248
<211> LENGTH: 335
<212> TYPE: PRT
<213> ORGANISM: Zea mays

<400> SEQUENCE: 248

Met Glu Leu Ala Leu Ser Leu Gly Glu Thr Met Ala Asp Ala Gly Arg
1               5                   10                  15

Asp Leu Met Leu Gly Leu Gly Met Gly Val Gly Val Arg Arg Glu Glu
            20                  25                  30

Glu Ala Gln Arg Gly Arg Arg Asp Arg Glu Val Arg Arg Glu Leu Glu
        35                  40                  45

Phe Thr Ala Arg Ser Ala Arg Ser Ser Pro Glu Pro Ala Val Arg Leu
    50                  55                  60

Thr Leu Leu His Gly Leu Gly Leu Pro Trp Pro Pro Pro Ser Ser
65                  70                  75                  80

Glu Thr Asn Arg His Leu Glu Ala Ser Ala Arg Gly Phe Asp Val Asn
                85                  90                  95

Arg Ala Pro Ser Leu Ser Ala Ala Gly Ala Ala Glu Glu Asp Glu
            100                 105                 110

Glu Gln Asp Glu Ala Gly Ala Ala Ala Ala Ala Ser Ser Ser Pro
        115                 120                 125

Asn Asn Ser Ala Ser Ser Phe Pro Thr Asp Phe Ser Ala His Gly Gln
    130                 135                 140

Val Ala Pro Gly Ala Asp Arg Ala Cys Ser Arg Ala Ser Asp Glu Asp
145                 150                 155                 160

Asp Gly Gly Ser Ala Arg Lys Lys Leu Arg Leu Ser Lys Glu Gln Ser
                165                 170                 175

Ala Phe Leu Glu Asp Ser Phe Lys Glu His Ala Thr Leu Asn Pro Lys
            180                 185                 190

Gln Lys Leu Ala Leu Ala Lys Gln Leu Asn Leu Arg Pro Arg Gln Val
        195                 200                 205

Glu Ala Trp Phe Ala Ala Arg Arg Ala Arg Thr Lys Leu Lys Gln Thr
    210                 215                 220
```

```
Glu Val Asp Cys Glu Tyr Leu Lys Arg Cys Cys Glu Thr Leu Thr Glu
225                 230                 235                 240

Glu Asn Arg Arg Leu Gln Lys Glu Leu Ser Glu Leu Arg Ala Leu Lys
            245                 250                 255

Thr Val His Pro Phe Tyr Met His Leu Pro Ala Thr Thr Leu Ser Met
        260                 265                 270

Cys Pro Ser Cys Glu Arg Val Ala Ser Asn Ser Ala Pro Ala Pro Ala
        275                 280                 285

Ser Ser Pro Ser Pro Ala Thr Gly Ile Ala Ala Pro Ala Pro Glu Gln
        290                 295                 300

Arg Pro Ser Ser Phe Ala Ala Leu Phe Ser Ser Pro Leu Asn Arg Pro
305                 310                 315                 320

Leu Ala Ala Gln Ala Gln Pro Gln Pro Gln Ala Pro Ala Asn Ser
                325                 330                 335

<210> SEQ ID NO 249
<211> LENGTH: 354
<212> TYPE: PRT
<213> ORGANISM: Zea mays

<400> SEQUENCE: 249

Met Glu Leu Gly Leu Ser Leu Gly Asp Ala Ala Val Pro Asp Ala Gly
1               5                   10                  15

Arg Ala Ala Pro Glu Leu Gly Leu Gly Leu Gly Val Gly Ile Gly Ser
            20                  25                  30

Asn Ala Ala Gly Thr Gly Arg Gly Ser Lys Ala Ala Gly Thr Thr Gly
        35                  40                  45

Thr Thr Gly Trp Trp Ala Ala Pro Ala Thr Pro Glu Ser Ala Val Arg
    50                  55                  60

Leu Ser Leu Val Ser Ser Leu Gly Leu Gln Trp Pro Pro Asp Gly
65                  70                  75                  80

Gly Ile Cys His Val Gly Arg Asp Glu Ala Pro Ala Arg Gly Phe Asp
                85                  90                  95

Val Asn Arg Ala Pro Ser Val Ala Gly Ser Ala Leu Ala Leu Glu Asp
            100                 105                 110

Asp Glu Glu Glu Pro Gly Ala Ala Ala Leu Ser Ser Ser Pro Asn Asp
        115                 120                 125

Ser Ala Gly Ser Phe Pro Leu Asp Leu Gly Gly Pro Arg Ala His Ala
    130                 135                 140

Glu Gly Ala Ala Ala Arg Ala Gly Gly Glu Arg Ser Ser Ser Arg Ala
145                 150                 155                 160

Ser Asp Glu Asp Glu Gly Ala Ser Ala Arg Lys Lys Leu Arg Leu Ser
                165                 170                 175

Lys Glu Gln Ser Ala Phe Leu Glu Glu Ser Phe Lys Glu His Ser Thr
            180                 185                 190

Leu Asn Pro Lys Gln Lys Ala Ala Leu Ala Lys Gln Leu Asn Leu Arg
        195                 200                 205

Pro Arg Gln Val Glu Ala Trp Phe Ala Ala Arg Arg Ala Arg Thr Lys
    210                 215                 220

Leu Lys Gln Thr Glu Val Asp Cys Glu Tyr Leu Lys Arg Cys Cys Glu
225                 230                 235                 240

Thr Leu Thr Glu Glu Asn Arg Arg Leu His Lys Glu Leu Ala Glu Leu
                245                 250                 255

Arg Ala Leu Lys Thr Ala Pro Pro Phe Phe Met Arg Leu Pro Ala Thr
```

```
              260                 265                 270
Thr Leu Ser Met Cys Pro Ser Cys Glu Arg Val Ala Ser Gly Pro Ser
            275                 280                 285

Pro Ala Ser Thr Ser Ala Pro Ala Ser Ser Thr Pro Pro Ala Thr Ala
            290                 295                 300

Ala Thr Thr Ala Ile Ser Tyr Ala Ala Ala Ala Ala Ala Pro Val Arg
305                 310                 315                 320

Ala Asp His Arg Pro Ser Ser Phe Ala Ala Leu Phe Ala Ala Thr Arg
            325                 330                 335

Ser Phe Pro Leu Ala Ser Gln Pro Arg Pro Ala Pro Ala Ser Asn
            340                 345                 350

Cys Leu

<210> SEQ ID NO 250
<211> LENGTH: 319
<212> TYPE: PRT
<213> ORGANISM: Zea mays

<400> SEQUENCE: 250

Met Asp Ile Met Ala Leu Asn Ala Arg Asp Glu Glu Gln Tyr Gly Asn
1               5                   10                  15

Asn His Leu Gly Leu Gly Leu Ser Leu Ser Leu Gly Leu Gly Val Ala
            20                  25                  30

Thr Ala Ala Pro Val Glu Val Glu Pro Pro Pro Pro Arg Gln Gln
            35                  40                  45

Gln Gln Arg Ala Ile Ser Val Ala Pro Ile Thr Ser Leu Pro Ala Pro
        50                  55                  60

Gln Trp Trp Lys Trp Asn Gly Pro Gly Leu Phe Phe Gly Thr Thr Met
65              70                  75                  80

Asp Gln Gln Gln Pro Ala Ala Arg His Gly His Glu Met Pro
            85                  90                  95

Phe Leu Arg Gly Val Asp Val Asn Arg Ala Pro Ala Gly Asp Thr Arg
            100                 105                 110

Arg Gly Ser Cys Ser Glu Asp Asp Glu Glu Pro Gly Gly Ala Ser Ser
            115                 120                 125

Ser Pro Asn Ser Thr Leu Ser Ser Ser Leu Ser Gly Lys Arg Ala Ala
            130                 135                 140

Pro Ala Arg Ser Gly Gly Glu Val Ala Asp His Thr Pro Arg Ala Gly
145                 150                 155                 160

Gly Gly Ser Asp Asp Glu Asp Ser Gly Gly Gly Ser Arg Lys Lys Leu
            165                 170                 175

Arg Leu Ser Lys Asp Gln Ala Ala Val Leu Glu Glu Ser Phe Lys Glu
            180                 185                 190

His Asn Thr Leu Asn Pro Lys Gln Lys Ala Ala Leu Ala Lys Gln Leu
            195                 200                 205

Asn Leu Lys Pro Arg Gln Val Glu Ala Trp Phe Ala Ala Arg Arg Ala
        210                 215                 220

Arg Thr Lys Leu Lys Gln Thr Glu Val Asp Cys Glu Phe Leu Lys Arg
225                 230                 235                 240

Cys Cys Glu Thr Leu Thr Glu Glu Asn Arg Arg Leu Gln Arg Glu Val
                245                 250                 255

Ala Glu Leu Arg Val Leu Lys Leu Val Ala Pro His His Tyr Ala Arg
            260                 265                 270

Met Pro Pro Pro Thr Thr Leu Thr Met Cys Pro Ser Cys Glu Arg Leu
```

```
              275                 280                 285
Ala Ser Ala Ser Ala Ser Ala Asp Gln Ala Gly Arg Ala Gly Pro Cys
            290                 295                 300

Trp Gly Pro Leu Pro Val Phe Val Asp Gly Pro Ala Arg Arg Pro
305                 310                 315

<210> SEQ ID NO 251
<211> LENGTH: 331
<212> TYPE: PRT
<213> ORGANISM: Zea mays

<400> SEQUENCE: 251

Met Glu Leu Glu Leu Ser Leu Gly Asp Ser Arg Ala Pro Ala Lys Ser
1               5                   10                  15

Ala Ser Thr Pro Ala Ala Leu Thr Pro Ile His Ala Gly Ala Gly Gly
                20                  25                  30

Glu Gly His Glu Leu Ala Leu Glu Leu Gly Val Gly Ala Ala Lys Arg
            35                  40                  45

Ala Glu Gln Asp Asn Gln Lys Thr Pro Val Gln Pro Glu His Val Gln
    50                  55                  60

Glu Glu Glu Glu Glu Glu Thr Cys Pro Tyr Ser Glu Ser Pro Ala
65                  70                  75                  80

Glu Leu Ser Leu Ile Gly Cys Pro Leu Leu Pro Ala Ala Ser Ala Glu
                85                  90                  95

Ile Gly Ser Val Asn Ser Ser Glu Val Cys Val Arg Arg Gly Phe Gly
            100                 105                 110

Val Asp Ala Val Leu Val Asp Gly Gly Asp Ala Ala Gln Gly Arg Pro
        115                 120                 125

Ala Leu Ser Thr Ser Phe Leu Pro Ser Glu Phe Leu Val Arg Arg Gln
    130                 135                 140

Ala Asp Asp Gln Glu Ala Ala Glu Asp Glu Glu Met Ser Gly Val
145                 150                 155                 160

Gly Gly Gly Ala Arg Lys Lys Leu Arg Leu Ser Lys Glu Gln Ser Ala
                165                 170                 175

Phe Leu Glu Asp Ser Phe Lys Ala His Ser Thr Leu Thr Pro Lys Gln
            180                 185                 190

Lys Ser Asp Leu Ala Lys Arg Leu Lys Leu Arg Pro Arg Gln Val Glu
        195                 200                 205

Ala Trp Phe Ala Ala Arg Arg Ala Arg Ser Lys Leu Lys Gln Thr Glu
    210                 215                 220

Val Asp Cys Glu Tyr Leu Lys Arg Trp Cys Glu Lys Leu Ala Gln Glu
225                 230                 235                 240

Asn Arg Arg Leu Gln Arg Glu Val Ala Glu Leu Arg Arg Leu Cys Ser
                245                 250                 255

Ala Ala Tyr Pro Phe Tyr Gly Ala Ala Ala Gly Phe Gly Val Ala Thr
            260                 265                 270

Ala Arg Val Cys Pro Ser Ser Cys Asp Asn Asp Val Ser Glu Ala Ala
        275                 280                 285

Ile Ser Gly Ala Pro Ser Ala Ala Ala Pro Pro Ser Thr Leu Phe
    290                 295                 300

Ala Ser Trp Pro Pro His Phe Gly Pro Phe Thr Val Val Pro Pro
305                 310                 315                 320

Leu Leu Arg Arg Gln Pro Ser Ala Thr Thr Ser
                325                 330
```

<210> SEQ ID NO 252
<211> LENGTH: 202
<212> TYPE: PRT
<213> ORGANISM: Arabidopsis thaliana

<400> SEQUENCE: 252

Met Ala Ile Leu Pro Glu Asn Ser Ser Asn Ala Asp Ala Thr Ile Ser
1               5                   10                  15

Val Pro Gly Phe Ser Ser Pro Leu Ser Asp Glu Gly Ser Gly Gly
            20                  25                  30

Gly Arg Asp Gln Leu Arg Leu Asp Met Asn Arg Leu Pro Ser Ser Glu
            35                  40                  45

Asp Gly Asp Asp Glu Glu Phe Ser His Asp Asp Gly Ser Ala Pro Pro
        50                  55                  60

Arg Lys Lys Leu Arg Leu Thr Arg Glu Gln Ser Arg Leu Leu Glu Asp
65                  70                  75                  80

Ser Phe Arg Gln Asn His Thr Leu Asn Pro Lys Gln Lys Glu Val Leu
                85                  90                  95

Ala Lys His Leu Met Leu Arg Pro Arg Gln Ile Glu Val Trp Phe Gln
            100                 105                 110

Asn Arg Arg Ala Arg Ser Lys Leu Lys Gln Thr Glu Met Glu Cys Glu
            115                 120                 125

Tyr Leu Lys Arg Trp Phe Gly Ser Leu Thr Glu Glu Asn His Arg Leu
        130                 135                 140

His Arg Glu Val Glu Glu Leu Arg Ala Ile Lys Val Gly Pro Thr Thr
145                 150                 155                 160

Val Asn Ser Ala Ser Ser Leu Thr Met Cys Pro Arg Cys Glu Arg Val
                165                 170                 175

Thr Pro Ala Ala Ser Pro Ser Arg Ala Val Val Pro Val Pro Ala Lys
            180                 185                 190

Lys Thr Phe Pro Pro Gln Glu Arg Asp Arg
        195                 200

<210> SEQ ID NO 253
<211> LENGTH: 275
<212> TYPE: PRT
<213> ORGANISM: Arabidopsis thaliana

<400> SEQUENCE: 253

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
            35                  40                  45

Val Phe Leu Ser Asn Phe Thr Phe Ser Ser Ile Leu Ala Leu Lys
        50                  55                  60

Asn Pro Asn Asn Ser Leu Ile Lys Ile Met Ala Ile Leu Pro Glu Asn
65                  70                  75                  80

Ser Ser Asn Ala Asp Ala Thr Ile Ser Val Pro Gly Phe Ser Ser
                85                  90                  95

Pro Leu Ser Asp Glu Gly Ser Gly Gly Gly Arg Asp Gln Leu Arg Leu
            100                 105                 110

Asp Met Asn Arg Leu Pro Ser Ser Glu Asp Gly Asp Asp Glu Glu Phe
        115                 120                 125

```
Ser His Asp Asp Gly Ser Ala Pro Pro Arg Lys Lys Leu Arg Leu Thr
    130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275

<210> SEQ ID NO 254
<211> LENGTH: 254
<212> TYPE: PRT
<213> ORGANISM: Arabidopsis thaliana

<400> SEQUENCE: 254

Met Asp Tyr Ala Cys Val Cys Met Tyr Lys Tyr Lys Gly Ile Val Thr
1               5                   10                  15

Leu Gln Val Cys Leu Phe Tyr Ile Lys Leu Arg Val Phe Leu Ser Asn
                20                  25                  30

Phe Thr Phe Ser Ser Ser Ile Leu Ala Leu Lys Asn Pro Asn Asn Ser
            35                  40                  45

Leu Ile Lys Ile Met Ala Ile Leu Pro Glu Asn Ser Ser Asn Leu Asp
50                  55                  60

Leu Thr Ile Ser Val Pro Gly Phe Ser Ser Ser Pro Leu Ser Asp Glu
65                  70                  75                  80

Gly Ser Gly Gly Gly Arg Asp Gln Leu Arg Leu Asp Met Asn Arg Leu
                85                  90                  95

Pro Ser Ser Glu Asp Gly Asp Glu Glu Phe Ser His Asp Asp Gly
            100                 105                 110

Ser Ala Pro Pro Arg Lys Lys Leu Arg Leu Thr Arg Glu Gln Ser Arg
        115                 120                 125

Leu Leu Glu Asp Ser Phe Arg Gln Asn His Thr Leu Asn Pro Lys Gln
    130                 135                 140

Lys Glu Val Leu Ala Lys His Leu Met Leu Arg Pro Arg Gln Ile Glu
145                 150                 155                 160

Val Trp Phe Gln Asn Arg Arg Ala Arg Ser Lys Leu Lys Gln Thr Glu
                165                 170                 175

Met Glu Cys Glu Tyr Leu Lys Arg Trp Phe Gly Ser Leu Thr Glu Glu
            180                 185                 190

Asn His Arg Leu His Arg Glu Val Glu Glu Leu Arg Ala Ile Lys Val
        195                 200                 205

Gly Pro Thr Thr Val Asn Ser Ala Ser Ser Leu Thr Met Cys Pro Arg
    210                 215                 220
```

```
Cys Glu Arg Val Thr Pro Ala Ala Ser Pro Ser Arg Ala Val Pro
225                 230                 235                 240

Val Pro Ala Lys Lys Thr Phe Pro Pro Gln Glu Arg Asp Arg
                245                 250
```

```
<210> SEQ ID NO 255
<211> LENGTH: 275
<212> TYPE: PRT
<213> ORGANISM: Arabidopsis thaliana

<400> SEQUENCE: 255
```

```
Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
        115                 120                 125

Ser His Asp Asp Gly Ser Ala Pro Ala Lys Lys Leu Ala Leu Thr
    130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275
```

```
<210> SEQ ID NO 256
<211> LENGTH: 185
<212> TYPE: PRT
<213> ORGANISM: Arabidopsis thaliana

<400> SEQUENCE: 256
```

```
Met Gly Phe Ser Ser Ser Pro Leu Ser Asp Glu Gly Ser Gly Gly Gly
1               5                   10                  15
```

```
Arg Asp Gln Leu Arg Leu Asp Met Asn Arg Leu Pro Ser Ser Glu Asp
             20                  25                  30

Gly Asp Glu Glu Phe Ser His Asp Asp Gly Ser Ala Pro Pro Arg
         35                  40                  45

Lys Lys Leu Arg Leu Thr Arg Glu Gln Ser Arg Leu Leu Glu Asp Ser
 50                  55                  60

Phe Arg Gln Asn His Thr Leu Asn Pro Lys Gln Lys Glu Val Leu Ala
 65                  70                  75                  80

Lys His Leu Met Leu Arg Pro Arg Gln Ile Glu Val Trp Phe Gln Asn
                 85                  90                  95

Arg Arg Ala Arg Ser Lys Leu Lys Gln Thr Glu Met Glu Cys Glu Tyr
            100                 105                 110

Leu Lys Arg Trp Phe Gly Ser Leu Thr Glu Glu Asn His Arg Leu His
            115                 120                 125

Arg Glu Val Glu Glu Leu Arg Ala Ile Lys Val Gly Pro Thr Thr Val
130                 135                 140

Asn Ser Ala Ser Ser Leu Thr Met Cys Pro Arg Cys Glu Arg Val Thr
145                 150                 155                 160

Pro Ala Ala Ser Pro Ser Arg Ala Val Val Pro Val Pro Ala Lys Lys
                165                 170                 175

Thr Phe Pro Pro Gln Glu Arg Asp Arg
            180                 185

<210> SEQ ID NO 257
<211> LENGTH: 275
<212> TYPE: PRT
<213> ORGANISM: Arabidopsis thaliana

<400> SEQUENCE: 257

Met Ile Lys Leu Leu Phe Thr Tyr Ile Cys Thr Tyr Thr Tyr Lys Leu
 1               5                  10                  15

Tyr Ala Leu Tyr His Met Asp Tyr Ala Cys Val Cys Met Tyr Lys Tyr
             20                  25                  30

Lys Gly Ile Val Thr Leu Gln Val Cys Leu Phe Tyr Ile Lys Leu Arg
         35                  40                  45

Val Phe Leu Ser Asn Phe Thr Phe Ser Ser Ile Leu Ala Leu Lys
 50                  55                  60

Asn Pro Asn Asn Ser Leu Ile Lys Ile Met Ala Ile Leu Pro Glu Asn
 65                  70                  75                  80

Ser Ser Asn Leu Asp Leu Thr Ile Ser Val Pro Gly Phe Ser Ser Ser
                 85                  90                  95

Pro Leu Ser Asp Glu Gly Ser Gly Gly Arg Asp Gln Leu Arg Leu
            100                 105                 110

Asp Met Asn Arg Leu Pro Ser Ser Glu Asp Gly Asp Glu Glu Phe
            115                 120                 125

Ser His Asp Asp Gly Ser Ala Pro Pro Arg Lys Lys Leu Arg Leu Thr
130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Ala Glu Met Glu Cys Glu Tyr Ala Lys Arg Trp Phe Gly
```

```
                195                 200                 205
Ser Ala Thr Glu Glu Asn His Arg Ala His Arg Glu Val Glu Ala
210                 215                 220
Arg Ala Ile Lys Val Gly Pro Thr Thr Val Asn Ser Ala Ser Leu
225                 230                 235                 240
Thr Met Cys Pro Arg Cys Glu Arg Val Thr Pro Ala Ala Ser Pro Ser
            245                 250                 255
Arg Ala Val Val Pro Val Pro Ala Lys Lys Thr Phe Pro Pro Gln Glu
            260                 265                 270
Arg Asp Arg
        275

<210> SEQ ID NO 258
<211> LENGTH: 244
<212> TYPE: PRT
<213> ORGANISM: Arabidopsis thaliana

<400> SEQUENCE: 258

Met Ile Lys Leu Leu Phe Thr Tyr Ile Cys Thr Tyr Thr Tyr Lys Leu
1               5                   10                  15
Tyr Ala Leu Tyr His Met Asp Tyr Ala Cys Val Cys Met Tyr Lys Tyr
            20                  25                  30
Lys Gly Ile Val Thr Leu Gln Val Cys Leu Phe Tyr Ile Lys Leu Arg
        35                  40                  45
Val Phe Leu Ser Asn Phe Thr Phe Ser Ser Ile Leu Ala Leu Lys
50                  55                  60
Asn Pro Asn Asn Ser Leu Ile Lys Ile Met Ala Ile Leu Pro Glu Asn
65                  70                  75                  80
Ser Ser Asn Leu Asp Leu Thr Ile Ser Val Pro Gly Phe Ser Ser Ser
                85                  90                  95
Pro Leu Ser Asp Glu Gly Ser Gly Gly Arg Asp Gln Leu Arg Leu
            100                 105                 110
Asp Met Asn Arg Leu Pro Ser Ser Glu Asp Gly Asp Glu Glu Phe
        115                 120                 125
Ser His Asp Asp Gly Ser Ala Pro Pro Arg Lys Lys Leu Arg Leu Thr
130                 135                 140
Arg Glu Gln Ser Arg Leu Leu Glu Asp Ser Phe Arg Gln Asn His Thr
145                 150                 155                 160
Leu Asn Pro Lys Gln Lys Glu Val Leu Ala Lys His Leu Met Leu Arg
                165                 170                 175
Pro Arg Gln Ile Glu Val Trp Phe Gln Asn Arg Arg Ala Arg Ser Lys
            180                 185                 190
Leu Arg Ala Ile Lys Val Gly Pro Thr Thr Val Asn Ser Ala Ser Ser
        195                 200                 205
Leu Thr Met Cys Pro Arg Cys Glu Arg Val Thr Pro Ala Ala Ser Pro
    210                 215                 220
Ser Arg Ala Val Val Pro Val Pro Ala Lys Lys Thr Phe Pro Pro Gln
225                 230                 235                 240
Glu Arg Asp Arg

<210> SEQ ID NO 259
<211> LENGTH: 217
<212> TYPE: PRT
<213> ORGANISM: Arabidopsis thaliana

<400> SEQUENCE: 259
```

```
Met Ile Lys Leu Leu Phe Thr Tyr Ile Cys Thr Tyr Thr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Gly Arg Asp Gln Leu Arg Leu
            100                 105                 110

Asp Met Asn Arg Leu Pro Ser Ser Glu Asp Gly Asp Glu Glu Phe
            115                 120                 125

Ser His Asp Asp Gly Ser Ala Pro Pro Thr Glu Met Glu Cys Glu Tyr
        130                 135                 140

Leu Lys Arg Trp Phe Gly Ser Leu Thr Glu Glu Asn His Arg Leu His
145                 150                 155                 160

Arg Glu Val Glu Glu Leu Arg Ala Ile Lys Val Gly Pro Thr Thr Val
                165                 170                 175

Asn Ser Ala Ser Ser Leu Thr Met Cys Pro Arg Cys Glu Arg Val Thr
            180                 185                 190

Pro Ala Ala Ser Pro Ser Arg Ala Val Val Pro Val Pro Ala Lys Lys
            195                 200                 205

Thr Phe Pro Pro Gln Glu Arg Asp Arg
    210                 215
```

<210> SEQ ID NO 260
<211> LENGTH: 609
<212> TYPE: DNA
<213> ORGANISM: Arabidopsis thaliana

<400> SEQUENCE: 260

```
atggccatcc tccctgagaa ctccagcaac gcggacgcga ccatctccgt gcccggcttc      60
tccagctctc ccttgtccga cgagggcagc ggcggtgggc gcgaccagct tcgcctggac     120
atgaaccgcc tgcccagctc tgaggacggt gacgatgagg aattctctca cgatgatggg     180
tctgctcctc ctcgcaagaa actgaggctg actaggagc agtctcgcct gcttgaggat      240
agtttccgcc agaaccacac tctgaaccog aagcagaagg aggtcttggc taagcacctt     300
atgcttcgcc cgaggcagat tgaggtctgg tttcagaata ggcgtgctag gtcgaagttg     360
aagcagactg agatggagtg cgagtatctt aagcgttggt ttggatcgct tactgaggag     420
aatcatcgtt acatagaga gtcgaggaa ctacgggcta tcaaggtcgg acccacgaca       480
gtcaattcag cgtcatcact aacgatgtgt cccagatgtg agcgggttac gccagcggca     540
tcgccgagtc gggcggttgt accggttcca gcaagaaga cattcccacc acaagaaaga     600
gatcgctag                                                             609
```

<210> SEQ ID NO 261
<211> LENGTH: 828
<212> TYPE: DNA
<213> ORGANISM: Arabidopsis thaliana

<400> SEQUENCE: 261

```
atgattaagc tcctgttcac ctacatctgc acctacacct acaagctcta cgccctctac      60
cacatggact acgcctgcgt gtgcatgtac aagtacaagg gcatcgtgac cctccaagtg     120
tgcctcttct acattaagct gagggtgttc ctctccaact tcaccttctc cagctccatc     180
ctcgccctca agaaccctaa caatagcctc atcaagatca tggccatcct ccctgagaac     240
tccagcaacg cggacgcgac catctccgtg cccggcttct ccagctctcc cttgtccgac     300
gagggcagcg gcggtgggcg cgaccagctt cgcctggaca tgaaccgcct gcccagctct     360
gaggacggtg acgatgagga attctctcac gatgatgggt ctgctcctcc tcgcaagaaa     420
ctgaggctga ctagggagca gtctcgcctg cttgaggata gtttccgcca gaaccacact     480
ctgaacccga agcagaagga ggtcttggct aagcaccttg cttcgccc gaggcagatt       540
gaggtctggt ttcagaatag gcgtgctagg tcgaagttga agcagactga gatggagtgc     600
gagtatctta agcgttggtt tggatcgctt actgaggaga tcatcgtttt acatagagaa     660
gtcgaggaac tacgggctat caaggtcgga ccacgacag tcaattcagc gtcatcacta      720
acgatgtgtc ccagatgtga gcgggttacg ccagcggcat cgccgagtcg ggcggttgta     780
ccggttccag caagaagac attcccacca caagaaagag atcgctag                   828
```

<210> SEQ ID NO 262
<211> LENGTH: 765
<212> TYPE: DNA
<213> ORGANISM: Arabidopsis thaliana

<400> SEQUENCE: 262

```
atggattacg catgcgtgtg tatgtataaa tataaaggca tcgtcacgct tcaagtttgt      60
ctcttttata ttaaactgag agttttcctc tcaaacttta cctttttcttc ttcgatccta    120
gctcttaaga accctaataa ttcattgatc aaaataatgg cgattttgcc ggaaaactct     180
tcaaacttgg atcttactat ctccgttcca ggcttctctt catcccctct ctccgatgaa     240
ggaagtggcg gaggaagaga ccagctaagg ctagacatga tcggttaccg tcgtctgaa     300
gacggagacg atgaagaatt cagtcacgat gatggctctg ctcctccgcg aaagaaactc     360
cgtctaacca gagaacagtc acgtcttctt gaagatagtt tcagacagaa tcatcccctt    420
aatcccaaac aaaaggaagt acttgccaag catttgatgc tacggccaag acaaattgaa    480
gtttggtttc aaaaccgtag agcaaggagc aaattgaagc aaaccgagat ggaatgcgag    540
tatctcaaaa ggtggtttgg ttcattaacg gaagaaaacc acaggctcca tagagaagta   600
gaagagctta gagccataaa ggttggccca acaacggtga actctgcctc gagccttact    660
atgtgtcctc gctgcgagcg agttacccct gccgcgagcc cttcgagggc ggtggtgccg    720
gttccggcta agaaaacgtt tccgccgcaa gagcgtgatc gttag                     765
```

<210> SEQ ID NO 263
<211> LENGTH: 825
<212> TYPE: DNA
<213> ORGANISM: Arabidopsis thaliana

<400> SEQUENCE: 263

```
atgataaaac tactatttac gtacatatgc acatacacat ataaactata tgctctatat      60
catatggatt acgcatgcgt gtgtatgtat aaatataaag gcatcgtcac gcttcaagtt    120
tgtctctttt atattaaact gagagttttc ctctcaaact ttacctttc ttcttcgatc     180
ctagctctta agaaccctaa taattcattg atcaaaataa tggcgatttt gccggaaaac    240
```

```
tcttcaaact tggatcttac tatctccgtt ccaggcttct cttcatcccc tctctccgat    300
gaaggaagtg gcggaggaag agaccagcta aggctagaca tgaatcggtt accgtcgtct    360
gaagacggag acgatgaaga attcagtcac gatgatggct ctgctcctcc ggccaagaaa    420
ctcgccctaa ccagagaaca gtcacgtctt cttgaagata gtttcagaca gaatcatacc    480
cttaatccca aacaaaagga agtacttgcc aagcatttga tgctacggcc aagacaaatt    540
gaagtttggt ttcaaaaccg tagagcaagg agcaaattga agcaaccgga gatgaatgc     600 gagtatctca aaggtggttt ggttcattta acggaagaaa accacaggct ccatagagaa    660
gtagaagagc ttagagccat aaaggttggc caacaacgg tgaactctgc ctcgagcctt     720
actatgtgtc ctcgctgcga gcgagttacc cctgccgcga gcccttcgag ggcggtggtg    780
ccggttccgg ctaagaaaac gtttccgccg caagagcgtg atcgt                    825
```

<210> SEQ ID NO 264
<211> LENGTH: 558
<212> TYPE: DNA
<213> ORGANISM: Arabidopsis thaliana

<400> SEQUENCE: 264

```
atgggcttct ccagctctcc cttgtccgac gagggcagcg gcggtgggcg cgaccagctt     60
cgcctggaca tgaaccgcct gcccagctct gaggacggtg acgatgagga attctctcac    120
gatgatgggt ctgctcctcc tcgcaagaaa ctgaggctga ctagggagca gtctcgcctg    180
cttgaggata gtttccgcca gaaccacact ctgaacccga agcagaagga ggtcttggct    240
aagcacctta tgcttcgccc gaggcagatt gaggtctggt ttcagaatag gcgtgctagg    300
tcgaagttga agcagactga gatggagtgc gagtatctta agcgttggtt tggatcgctt    360
actgaggaga atcatcgttt acatagagaa gtcgaggaac tacgggctat caaggtcgga    420
cccacgacag tcaattcagc gtcatcacta acgatgtgtc ccagatgtga gcgggttacg    480
ccagcggcat cgccgagtcg ggcggttgta ccggttccag caagaagac attcccacca     540 caagaaagag atcgctag                                                  558
```

<210> SEQ ID NO 265
<211> LENGTH: 828
<212> TYPE: DNA
<213> ORGANISM: Arabidopsis thaliana

<400> SEQUENCE: 265

```
atgataaaac tactatttac gtacatatgc acatacacat ataaactata tgctctatat     60
catatggatt acgcatgcgt gtgtatgtat aaatataaag gcatcgtcac gcttcaagtt    120
tgtctctttt atattaaact gagagttttc ctctcaaact ttacctttc ttcttcgatc     180 ctagctctta agaaccctaa taattcattg atcaaaataa tggcgatttt gccggaaaac    240
tcttcaaact tggatcttac tatctccgtt ccaggcttct cttcatcccc tctctccgat    300
gaaggaagtg gcggaggaag agaccagcta aggctagaca tgaatcggtt accgtcgtct    360
gaagacggag acgatgaaga attcagtcac gatgatggct ctgctcctcc gcgaagaaa     420 ctccgtctaa ccagagaaca gtcacgtctt cttgaagata gtttcagaca gaatcatacc    480
cttaatccca aacaaaagga agtacttgcc aagcatttga tgctacggcc aagacaaatt    540
gaagtttggt ttcaaaaccg tagagcaagg agcaaattga agcaagccga gatgaatgc     600 gagtatgcca aaggtggttt ggttcagca acggaagaaa accacaggggc ccatagagaa    660
```

```
gtagaagagg ctagagccat aaaggttggc ccaacaacgg tgaactctgc ctcgagcctt    720
actatgtgtc ctcgctgcga gcgagttacc cctgccgcga gcccttcgag ggcggtggtg    780
ccggttccgg ctaagaaaac gtttccgccg caagagcgtg atcgttag                 828
```

<210> SEQ ID NO 266
<211> LENGTH: 735
<212> TYPE: DNA
<213> ORGANISM: Arabidopsis thaliana

<400> SEQUENCE: 266

```
atgataaaac tactatttac gtacatatgc acatacacat ataaactata tgctctatat     60
catatggatt acgcatgcgt gtgtatgtat aaatataaag gcatcgtcac gcttcaagtt    120
tgtctctttt atattaaact gagagttttc ctctcaaact ttaccttttc ttcttcgatc    180
ctagctctta agaaccctaa taattcattg atcaaaataa tggcgatttt gccggaaaac    240
tcttcaaact tggatcttac tatctccgtt ccaggcttct cttcatcccc tctctccgat    300
gaaggaagtg gcggaggaag agaccagcta aggctagaca tgaatcggtt accgtcgtct    360
gaagacggag acgatgaaga attcagtcac gatgatggct ctgctcctcc gcgaaagaaa    420
ctccgtctaa ccagagaaca gtcacgtctt cttgaagata gtttcagaca gaatcatacc    480
cttaatccca aacaaaagga agtacttgcc aagcatttga tgctacggcc aagacaaatt    540
gaagtttggt ttcaaaaccg tagagcaagg agcaaattga gagccataaa ggttggccca    600
acaacggtga actctgcctc gagccttact atgtgtcctc gctgcgagcg agttacccct    660
gccgcgagcc cttcgagggc ggtggtgccg gttccggcta agaaaacgtt tccgccgcaa    720
gagcgtgatc gttag                                                    735
```

<210> SEQ ID NO 267
<211> LENGTH: 654
<212> TYPE: DNA
<213> ORGANISM: Arabidopsis thaliana

<400> SEQUENCE: 267

```
atgataaaac tactatttac gtacatatgc acatacacat ataaactata tgctctatat     60
catatggatt acgcatgcgt gtgtatgtat aaatataaag gcatcgtcac gcttcaagtt    120
tgtctctttt atattaaact gagagttttc ctctcaaact ttaccttttc ttcttcgatc    180
ctagctctta agaaccctaa taattcattg atcaaaataa tggcgatttt gccggaaaac    240
tcttcaaact tggatcttac tatctccgtt ccaggcttct cttcatcccc tctctccgat    300
gaaggaagtg gcggaggaag agaccagcta aggctagaca tgaatcggtt accgtcgtct    360
gaagacggag acgatgaaga attcagtcac gatgatggct ctgctcctcc gaccgagatg    420
gaatgcgagt atctcaaaag gtggtttggt tcattaacgg aagaaaacca caggctccat    480
agagaagtag aagagcttag agccataaag gttggcccaa caacggtgaa ctctgcctcg    540
agccttacta tgtgtcctcg ctgcgagcga gttacccctg ccgcgagccc ttcgagggcg    600
gtggtgccgg ttccggctaa gaaaacgttt ccgccgcaag agcgtgatcg ttag          654
```

<210> SEQ ID NO 268
<211> LENGTH: 17
<212> TYPE: DNA
<213> ORGANISM: Artificial sequence
<220> FEATURE:
<223> OTHER INFORMATION: Oligonucleotide

```
<400> SEQUENCE: 268
cagacaatca ttgcggc                                                    17

<210> SEQ ID NO 269
<211> LENGTH: 17
<212> TYPE: DNA
<213> ORGANISM: Artificial sequence
<220> FEATURE:
<223> OTHER INFORMATION: Oligonucleotide

<400> SEQUENCE: 269
cagacaatta ttgcggc                                                    17

<210> SEQ ID NO 270
<211> LENGTH: 17
<212> TYPE: DNA
<213> ORGANISM: Artificial sequence
<220> FEATURE:
<223> OTHER INFORMATION: Oligonucleotide

<400> SEQUENCE: 270
cagctcagtc tgacggc                                                    17
```

INTERFERING WITH HD-ZIP TRANSCRIPTION FACTOR REPRESSION OF GENE EXPRESSION TO PRODUCE PLANTS WITH ENHANCED TRAITS

CROSS REFERENCE TO RELATED APPLICATIONS

This application is a divisional of U.S. patent application Ser. No. 15/028,381, filed Apr. 8, 2016, which is a 371 National Stage application of International Application No. PCT/US2014/058594, filed Oct. 1, 2014, which claims the benefit of U.S. Provisional Application No. 61/888,980 filed Oct. 9, 2013, each of which are herein incorporated by reference in its entirety.

INCORPORATION OF SEQUENCE LISTING

The sequence listing that is contained in the file named "MONS348US-revised ST25.txt", which is 548 kilobytes (as measured in Microsoft Windows®) and was created on Aug. 3, 2016 is filed herewith by electronic submission and is incorporated by reference herein in its entirety.

FIELD

The present disclosure relates to the production of plants with enhanced traits, more particularly, to DNA constructs and methods for producing plants with an enhanced trait by interfering with the ability of endogenous homeodomain-leucine zipper (HD-Zip) class II transcription factors to repress gene expression, along with the plants produced thereby.

BACKGROUND

Improving plant growth and development through genetic modification typically involves understanding the natural mechanisms regulating the processes. Studies have shown that the large family of HD-Zip transcription factors plays an important role in the regulation of plant growth and development and that HD-Zip transcription factors mediate a plant's response to environmental conditions. The large family of HD-Zip transcription factors comprises four distinct subfamilies or classes designated as I, II, III, and IV. Despite studies identifying roles for class I, class III, and class IV HD-Zip proteins in plant growth and development, attempts to elucidate the functional role of class II HD-Zip proteins have been less successful, as null mutations in members of this class of HD-Zip proteins have produced no detectable phenotypes (Hymus et al., *J Exp Botany* 64(4): 4479-4490, 2013). It is known that HD-Zip class II transcription factors repress gene expression. Understanding the role of this class of HD-Zip proteins in plant growth and development may allow researchers to enhance plant growth and development through transgenic means.

The present disclosure describes the mode of action of an HD-Zip class II protein, ATHB17, in the regulation of plant growth and development. Based on this information, the disclosure provides constructs and methods for producing plants with enhanced traits, along with the plants produced thereby.

SUMMARY

The inventors have found that agronomic traits can be enhanced in crop plants if repression of genes regulated by HD-Zip class II transcription factors is reduced through transgenic manipulation of such HD-Zip class II transcription factors. The inventors have also discovered that some endogenous HD-Zip II transcription factors may be regulated by transgenes encoding heterologous HD-Zip II transcription factors. Transgenic manipulation of HD-Zip class II transcription factors in accordance with the invention can occur, for example, by transforming a plant with a recombinant construct comprising a protein- or RNA-coding DNA molecule that interferes with the ability of an endogenous HD-Zip class II transcription factor to repress its target genes.

A recombinant DNA construct is disclosed herein. The recombinant DNA construct comprises a protein-coding DNA molecule that is operably linked to a heterologous promoter. When the recombinant DNA construct is expressed in a plant or a plant cell, it produces a protein that interferes with the ability of endogenous HD-Zip class II proteins to repress DNA transcription of genes regulated by the endogenous HD-Zip class II proteins. In some aspects, the protein produced from the expression of the recombinant DNA construct in a plant or plant cell is an HD-Zip class II transcription factor, a little zipper protein, or small-interfering peptides (siPEPs). In some aspects, the produced protein is an HD-Zip class II transcription factor with a loss-of-function mutation in a domain selected from the group consisting of a transcriptional repression domain, a homeodomain, a leucine zipper domain, and a CXXCX-like motif in the C-terminus. In yet other aspects, the protein-coding DNA molecule in the recombinant DNA construct codes for a protein that has an amino acid sequence with at least 60% identity to a protein with an amino acid sequence selected from the group consisting of SEQ ID NO:92 to SEQ ID NO:130. In other aspects, when the recombinant DNA construct is expressed in a plant or a plant cell, it produces a protein that interferes with the ability of endogenous HD-Zip class II proteins to repress DNA transcription of a gene encoding an HD-Zip class II protein, for example a corn HD-Zip class II protein. In other aspects, such a corn HD-Zip class II protein is selected from the group consisting of SEQ ID NO:19 to SEQ ID NO:36.

Also provided is a recombinant DNA construct comprising an RNA-coding DNA molecule that is operably linked to a heterologous promoter. When the recombinant DNA construct is expressed in a plant or a plant cell, it produces an RNA molecule that suppresses the expression of a target HD-Zip class II protein. In some aspects, the RNA molecule is an RNA molecule selected from the group consisting of an antisense RNA, an siRNA, a miRNA, and a long non-coding RNA. In other aspects, when the recombinant DNA construct is expressed in a corn plant or a plant cell, it produces an RNA molecule that suppresses the expression of a corn HD-Zip class II protein. In other aspects, that corn HD-Zip class II protein is selected from the group consisting of SEQ ID NO:19 to SEQ ID NO:36.

Also provided is a recombinant DNA construct comprising a DNA molecule that is operably linked to a heterologous promoter. When the recombinant DNA construct is expressed in a plant or a plant cell, it produces a loss-of-function mutation in an endogenous HD-Zip class II gene. In some aspects, the loss-of-function mutation is in the coding region of the gene in a domain selected from the group consisting of a transcriptional repression domain, a homeodomain, a leucine zipper domain and a CXXCX-like motif in the C-terminus. In other aspects, the loss-of-function mutation is in the regulatory region of the gene. In yet other aspects, the loss-of-function mutation in the endogenous HD-Zip class II gene is a knock-out mutation. In other aspects, when the recombinant DNA construct is expressed in a corn plant or a plant cell, it produces a loss-of-function mutation in an endogenous corn HD-Zip class II gene. In other aspects, that corn HD-Zip class II protein is selected from the group consisting of SEQ ID NO:19 to SEQ ID NO:36.

Also provided are plants and plant cells that comprise the disclosed recombinant DNA constructs. In some aspects, the plants and plant cells comprise a recombinant DNA construct, that, when expressed in a plant or a plant cell, produces (i) a protein that interferes with the ability of endogenous HD-Zip class II proteins to repress DNA transcription of genes regulated by the endogenous HD-Zip class II proteins, (ii) an RNA molecule that suppresses the expression of a target HD-Zip class II protein, or (iii) a loss-of-function mutation in an endogenous HD-Zip class II gene. In some aspects, the plants or the plants grown from the plant cells that comprise the recombinant DNA construct have an enhanced trait relative to control plants that lack the recombinant DNA construct. In further aspects, the enhanced trait is selected from the group consisting of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield. In some aspects, the plants are corn plants.

In another aspect, a method for producing plants with an enhanced trait relative to a control plant that does not comprise the recombinant DNA construct is disclosed. The method comprises the steps of (a) incorporating into the plants a recombinant DNA construct, that, when expressed in the plant, produces a protein that interferes with the ability of endogenous HD-Zip class II proteins to repress DNA transcription of genes regulated by the endogenous HD-Zip class II proteins, and (b) selecting a plant from the sub-population of plants comprising the recombinant DNA construct, where the selected plant has an enhanced trait selected from the group consisting of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield, relative to a control plant lacking the recombinant DNA construct. In some aspects, the protein produced from the expression of the recombinant DNA construct in the transformed plants is an HD-Zip class II transcription factor. In some aspects, the produced protein is an HD-Zip class II transcription factor with a loss-of-function mutation in a domain selected from the group consisting of a transcriptional repression domain, a homeodomain, a leucine zipper domain, and a CXXCX-like motif in the C-terminus. In even further aspects, the recombinant DNA construct with which the plants are transformed comprises a protein-coding DNA molecule that codes for a protein that has an amino acid sequence that has at least 60% identity to a protein with an amino acid sequence selected from the group consisting of SEQ ID NO:92 to SEQ ID NO:130. In another aspect, the plants that are produced by the method are corn plants.

In one aspect, another method for producing plants with an enhanced trait relative to a control plant that does not comprise the recombinant DNA construct is disclosed. The method comprises the steps of (a) incorporating into the plants a recombinant DNA construct, that, when expressed in the plant, produces an RNA molecule that suppresses the expression of a target HD-Zip class II protein, and (b) selecting a plant from the sub-population of plants comprising the recombinant DNA construct, where the selected plant has an enhanced trait selected from the group consisting of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield, relative to a control plant lacking the recombinant DNA construct. In another aspect, the RNA molecule produced from the expression of the recombinant DNA construct in the transformed plants is an RNA molecule selected from the group consisting of an antisense RNA, an siRNA, a miRNA, and a long non-coding RNA. In another aspect, the plants produced by the method are corn plants and the target HD-Zip class II protein is a corn HD-Zip class II protein. In yet another aspect, the corn HD-Zip class II protein is selected from the group consisting of SEQ ID NO:19 to SEQ ID NO:36.

In yet another aspect, another method for producing plants with an enhanced trait relative to a control plant that does not comprise the recombinant DNA construct is disclosed. The method comprises the steps of (a) incorporating into the plants a recombinant DNA construct, that, when expressed in the plant, produces a loss-of-function mutation in an endogenous HD-Zip class II gene, and (b) selecting a plant from the sub-population of plants comprising the recombinant DNA construct, where the selected plant has an enhanced trait selected from the group consisting of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield, relative to a control plant lacking the recombinant DNA construct. In another aspect, the loss-of-function mutation produced from the expression of the recombinant DNA construct in the transformed plants is in the coding region of the gene in a domain selected from the group consisting of a transcriptional repression domain, a homeodomain, a leucine zipper domain, and a CXXCX-like motif in the C-terminus. In another aspect, the loss-of-function mutation is in the regulatory region of the gene. In other aspects, the loss-of-function mutation in the endogenous HD-Zip class II gene is a knock-out mutation. In yet another aspect, the plants produced by the method are corn plants and the endogenous HD-Zip class II protein is a corn HD-Zip class IT protein. In yet another aspect, the corn HD-Zip class II protein is selected from the group consisting of SEQ ID NO:19 to SEQ ID NO:36.

In another aspect, another method for reproducing plants with an enhanced trait relative to a control plant that does not comprise the recombinant DNA construct is disclosed. The method includes the steps of (a) obtaining seed produced by a plant having the enhanced trait and comprising a recombinant DNA construct, that, when expressed in a plant or plant cell, produces (i) a protein that interferes with the ability of endogenous HD-Zip class II proteins to repress DNA transcription of genes regulated by the endogenous HD-Zip class II proteins, (ii) an RNA molecule that suppresses the expression of a target HD-Zip class II protein, or (iii) a loss-of-function mutation in an endogenous HD-Zip class II gene, and (b) planting the obtained seed, where a plant grown from the planted seed is a progeny plant with an enhanced trait selected from the group consisting of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield. In some aspects, the seed comprises a recombinant DNA construct, that, when expressed in a plant or plant cell, produces (i) a protein that interferes with the ability of endogenous HD-Zip class II proteins to repress DNA transcription of genes regulated by the endogenous HD-Zip class II proteins, (ii) an RNA molecule that suppresses the expression of a target HD-Zip class II protein, or (iii) a loss-of-function mutation in an endogenous HD-Zip class II gene. In yet other aspects, the plant is a corn plant.

Further areas of applicability of the present disclosure will become apparent from the detailed description, drawings and claims provided hereinafter. It should be understood that the detailed description, including disclosed embodiments and drawings, are merely exemplary in nature, are only intended for purposes of illustration, and are not intended to limit the scope of the invention, its application, or use. Thus, variations that do not depart from the gist of the invention are intended to be within the scope of the invention.

BRIEF DESCRIPTION OF THE SEQUENCES

SED ID NOs:1-18: Nucleotide sequences encoding *Zea mays* HD-Zip class II proteins.

SED ID NOs:19-36: Amino acid sequences of *Zea mays* HD-Zip class II proteins.

SED ID NOs:37-54: Nucleotide sequences of the upstream promoter regions of *Zea mays* HD-Zip class II genes.

SED ID NOs:55-56: Nucleotide sequences of class II and class I DNA binding sites.

SEQ ID NO:57: Nucleotide sequence of *Arabidopsis thaliana* gene HB17 (ATHB17).

SEQ ID NO:58: Amino acid sequence of *Arabidopsis thaliana* HB17 protein.

SEQ ID NO:59: Amino acid sequence of *Arabidopsis thaliana* HB17 gene with N-terminal 113 amino acid deletion (ATHB17Δ113).

SEQ ID NO:60-69: Amino acid sequences of protein variants of *Arabidopsis thaliana* HB17Δ113.

SEQ ID NO:70-73: Amino acid sequences of protein variants of *Arabidopsis thaliana* HB17.

SEQ ID NO:74: Amino acid sequence of protein variant of *Arabidopsis thaliana* HB17gene with N-terminal 73 amino acid deletion (ATHB17Δ73).

SEQ ID NO:75-76: Nucleotide sequences of *Zea mays* miR159a precursor and mature miRNA.

SEQ ID NO:77-78: Nucleotide sequences of engineered miRNA "miRZmhdz26" precursor and mature "miRZmhdz26" miRNA.

SEQ ID NO:79: Nucleotide sequence of miRNA recognition site of *Zea mays* Zmhdz26 (SEQ ID NO:9).

SEQ ID NO:80-82: Nucleotide sequences of TALE binding site 1, TALEN spacer and TALE binding site 2 for target site 1 of SEQ ID NO:17.

SEQ ID NO:83-85: Nucleotide sequences of TALE binding site 1, TALEN spacer and TALE binding site 2 for target site 2 of SEQ ID NO:17.

SEQ ID NO:86-88: Nucleotide sequences of TALE binding site 1, TALEN spacer and TALE binding site 2 for target site 3 of SEQ ID NO:17.

SEQ ID NO:89-91: Nucleotide sequences of TALE binding site 1, TALEN spacer and TALE binding site 2 for target site 4 of SEQ ID NO:17.

SEQ ID NO:92-130: Amino acid sequences of *Zea mays* HD-Zip class II protein N-terminal truncation variants.

SEQ ID NO:131-147: Amino acid sequences of *Zea mays* HD-Zip class II protein C-terminal mutation variants.

SEQ ID NO:148-215: Amino acid sequences of *Zea mays* HD-Zip class II protein EAR-like mutation variants.

SEQ ID NO:216-233: Amino acid sequences of *Zea mays* HD-Zip class II protein leucine zipper mutation variants.

SEQ ID NO:234-251: Amino acid sequences of *Zea mays* HD-Zip class II protein homeodomain mutation variants.

SEQ ID NO:252-259: Amino acid sequences of *Arabidopsis thaliana* HB17 protein variants.

SEQ ID NO:260-267: Nucleotide sequences of *Arabidopsis thaliana* HB17 protein variants corresponding to SEQ ID NOs:252-259, respectively.

All of the sequences with the corresponding SEQ ID NOs are listed in Table 1.

TABLE 1

Figure 1:
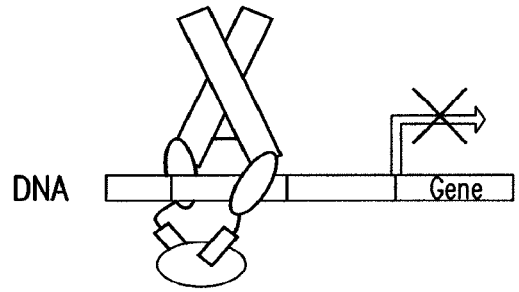
FIG. 1—Shows a schematic depicting ATHB17Δ113 functioning via a dominant negative mechanism, either by interacting with endogenous HD-Zip class II proteins and sequestering endogenous proteins from binding to their targets, resulting in relief of repression, or by forming heterodimers with endogenous HD-Zip class II proteins or ATHB17Δ113 homodimers to compete for DNA binding, resulting in altered target expression due to inability to cause active repression.
Figure 1:
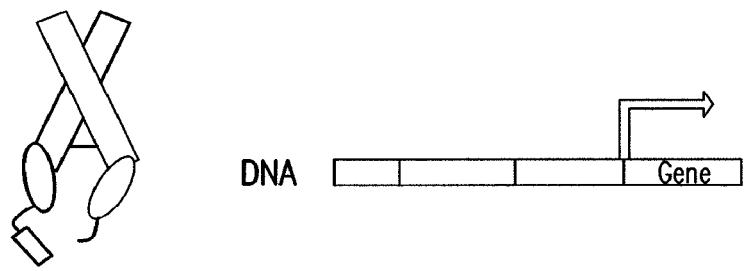
Figure 1:
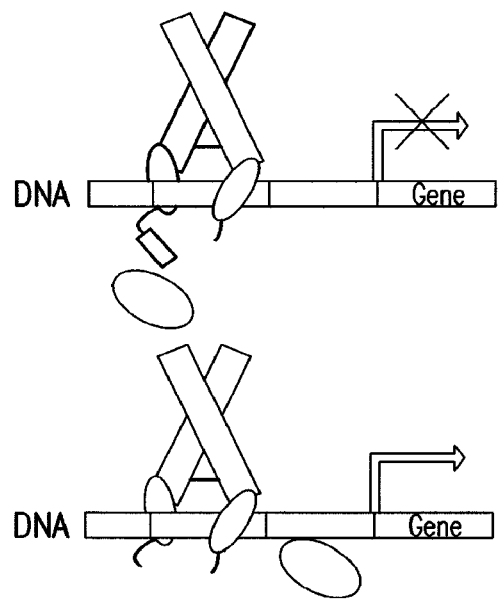

Polynucleotides and polypeptides.

| SEQ ID NO: | Name | Sequence Type |
|---|---|---|
| 1 | Zmhdz18 | Nucleotide sequence of coding region |
| 2 | Zmhdz19 | Nucleotide sequence of coding region |
| 3 | Zmhdz20 | Nucleotide sequence of coding region |
| 4 | Zmhdz21 | Nucleotide sequence of coding region |
| 5 | Zmhdz22 | Nucleotide sequence of coding region |
| 6 | Zmhdz23 | Nucleotide sequence of coding region |
| 7 | Zmhdz24 | Nucleotide sequence of coding region |
| 8 | Zmhdz25 | Nucleotide sequence of coding region |
| 9 | Zmhdz26 | Nucleotide sequence of coding region |
| 10 | Zmhdz27 | Nucleotide sequence of coding region |
| 11 | Zmhdz28 | Nucleotide sequence of coding region |
| 12 | Zmhdz29 | Nucleotide sequence of coding region |
| 13 | Zmhdz30 | Nucleotide sequence of coding region |
| 14 | Zmhdz31 | Nucleotide sequence of coding region |
| 15 | Zmhdz32 | Nucleotide sequence of coding region |
| 16 | Zmhdz33 | Nucleotide sequence of coding region |
| 17 | Zmhdz34 | Nucleotide sequence of coding region |
| 18 | Zmhdz35 | Nucleotide sequence of coding region |
| 19 | Zmhdz18 | Amino acid sequence of the protein |
| 20 | Zmhdz19 | Amino acid sequence of the protein |
| 21 | Zmhdz20 | Amino acid sequence of the protein |
| 22 | Zmhdz21 | Amino acid sequence of the protein |
| 23 | Zmhdz22 | Amino acid sequence of the protein |
| 24 | Zmhdz23 | Amino acid sequence of the protein |
| 25 | Zmhdz24 | Amino acid sequence of the protein |
| 26 | Zmhdz25 | Amino acid sequence of the protein |
| 27 | Zmhdz26 | Amino acid sequence of the protein |
| 28 | Zmhdz27 | Amino acid sequence of the protein |
| 29 | Zmhdz28 | Amino acid sequence of the protein |
| 30 | Zmhdz29 | Amino acid sequence of the protein |
| 31 | Zmhdz30 | Amino acid sequence of the protein |
| 32 | Zmhdz31 | Amino acid sequence of the protein |
| 33 | Zmhdz32 | Amino acid sequence of the protein |
| 34 | Zmhdz33 | Amino acid sequence of the protein |
| 35 | Zmhdz34 | Amino acid sequence of the protein |
| 36 | Zmhdz35 | Amino acid sequence of the protein |
| 37 | Zmhdz18 | Nucleotide sequence of promoter region |
| 38 | Zmhdz19 | Nucleotide sequence of promoter region |
| 39 | Zmhdz20 | Nucleotide sequence of promoter region |
| 40 | Zmhdz21 | Nucleotide sequence of promoter region |
| 41 | Zmhdz22 | Nucleotide sequence of promoter region |
| 42 | Zmhdz23 | Nucleotide sequence of promoter region |
| 43 | Zmhdz24 | Nucleotide sequence of promoter region |
| 44 | Zmhdz25 | Nucleotide sequence of promoter region |
| 45 | Zmhdz26 | Nucleotide sequence of promoter region |
| 46 | Zmhdz27 | Nucleotide sequence of promoter region |
| 47 | Zmhdz28 | Nucleotide sequence of promoter region |
| 48 | Zmhdz29 | Nucleotide sequence of promoter region |
| 49 | Zmhdz30 | Nucleotide sequence of promoter region |
| 50 | Zmhdz31 | Nucleotide sequence of promoter region |
| 51 | Zmhdz32 | Nucleotide sequence of promoter region |
| 52 | Zmhdz33 | Nucleotide sequence of promoter region |
| 53 | Zmhdz34 | Nucleotide sequence of promoter region |
| 54 | Zmhdz35 | Nucleotide sequence of promoter region |
| 55 | Class II DNA binding site | Nucleotide sequence |
| 56 | Class I DNA binding site | Nucleotide sequence |
| 57 | ATHB17 | Nucleotide sequence of coding region |
| 58 | ATHB17 | Amino acid sequence of the protein |
| 59 | ATHB17Δ113* | Amino acid sequence of the truncation variant |
| 60 | ATHB17Δ113-V182A-Q185A-N186A | Amino acid sequence of the ATHB17Δ113 variant |
| 61 | ATHB17Δ113-Δ138-195 | Amino acid sequence of the ATHB17Δ113 variant |
| 62 | ATHB17Δ113-W183F | Amino acid sequence of the ATHB17Δ113 variant |
| 63 | ATHB17Δ113-F155L | Amino acid sequence of the ATHB17Δ113 variant |
| 64 | ATHB17Δ113-Δ194-224 | Amino acid sequence of the ATHB17Δ113 variant |
| 65 | ATHB17Δ113-T196A-L203A-L210A-L217A-L224A | Amino acid sequence of the ATHB17Δ113 variant |
| 66 | ATHB17Δ113-C200A-C243S-C246S | Amino acid sequence of the ATHB17Δ113 variant |
| 67 | ATHB17Δ113-C243S-C246S | Amino acid sequence of the ATHB17Δ113 variant |
| 68 | ATHB17Δ113-C246S | Amino acid sequence of the ATHB17Δ113 variant |
| 69 | ATHB17Δ113-C243S | Amino acid sequence of the ATHB17Δ113 variant |
| 70 | ATHB17-C243S-C246S | Amino acid sequence of the ATHB17 variant |
| 71 | ATHB17-R190K | Amino acid sequence of the ATHB17 variant |
| 72 | ATHB17-Δ138-195 | Amino acid sequence of the ATHB17 variant |
| 73 | ATHB17-F155L | Amino acid sequence of the ATHB17 variant |
| 74 | ATHB17Δ73-C243S-C246S | Amino acid sequence of the ATHB17Δ73 variant |
| 75 | Corn miR159a precursor | Nucleotide sequence |
| 76 | Corn mature miR159a miRNA | Nucleotide sequence |
| 77 | Synthetic miRNA (miRZmhdz26) precursor designed to suppress target | Nucleotide sequence |
| 78 | Mature engineered miRNA (miRZmhdz26) | Nucleotide sequence |
| 79 | Corn miRNA recognition site | Nucleotide sequence |
| 80 | TALE binding site 1 of target site 1 | Nucleotide sequence |
| 81 | TALEN spacer sequence of target site 1 | Nucleotide sequence |

TABLE 1-continued

Polynucleotides and polypeptides.

| SEQ ID NO: | Name | Sequence Type |
|---|---|---|
| 82 | TALE binding site 2 of target site 1 | Nucleotide sequence |
| 83 | TALE binding site 1 of target site 2 | Nucleotide sequence |
| 84 | TALEN spacer sequence of target site 2 | Nucleotide sequence |
| 85 | TALE binding site 2 of target site 2 | Nucleotide sequence |
| 86 | TALE binding site 1 of target site 3 | Nucleotide sequence |
| 87 | TALEN spacer sequence of target site 3 | Nucleotide sequence |
| 88 | TALE binding site 2 of target site 3 | Nucleotide sequence |
| 89 | TALE binding site 1 of target site 4 | Nucleotide sequence |
| 90 | TALEN spacer sequence of target site 4 | Nucleotide sequence |
| 91 | TALE binding site 2 of target site 4 | Nucleotide sequence |
| 92 | Zmhdz26_Δ1-102* | Amino acid sequence of N-terminal truncation variant |
| 93 | Zmhdz18_Δ1-12 | Amino acid sequence of N-terminal truncation variant |
| 94 | Zmhdz20_Δ1-124 | Amino acid sequence of N-terminal truncation variant |
| 95 | Zmhdz21_Δ1-15 | Amino acid sequence of N-terminal truncation variant |
| 96 | Zmhdz27_Δ1-156 | Amino acid sequence of N-terminal truncation variant |
| 97 | Zmhdz23_Δ1-20 | Amino acid sequence of N-terminal truncation variant |
| 98 | Zmhdz33_Δ1-23 | Amino acid sequence of N-terminal truncation variant |
| 99 | Zmhdz22_Δ1-28 | Amino acid sequence of N-terminal truncation variant |
| 100 | Zmhdz28_Δ1-28 | Amino acid sequence of N-terminal truncation variant |
| 101 | Zmhdz34_Δ1-28 | Amino acid sequence of N-terminal truncation variant |
| 102 | Zmhdz29_Δ1-30 | Amino acid sequence of N-terminal truncation variant |
| 103 | Zmhdz31_Δ1-32 | Amino acid sequence of N-terminal truncation variant |
| 104 | Zmhdz18_Δ1-40 | Amino acid sequence of N-terminal truncation variant |
| 105 | Zmhdz34_Δ1-40 | Amino acid sequence of N-terminal truncation variant |
| 106 | Zmhdz30_Δ1-43 | Amino acid sequence of N-terminal truncation variant |
| 107 | Zmhdz18_Δ1-45 | Amino acid sequence of N-terminal truncation variant |
| 108 | Zmhdz24_Δ1-47 | Amino acid sequence of N-terminal truncation variant |
| 109 | Zmhdz21_Δ1-54 | Amino acid sequence of N-terminal truncation variant |
| 110 | Zmhdz18_Δ1-59 | Amino acid sequence of N-terminal truncation variant |
| 111 | Zmhdz19_Δ1-59 | Amino acid sequence of N-terminal truncation variant |
| 112 | Zmhdz23_Δ1-59 | Amino acid sequence of N-terminal truncation variant |
| 113 | Zmhdz25_Δ1-59 | Amino acid sequence of N-terminal truncation variant |
| 114 | Zmhdz29_Δ1-59 | Amino acid sequence of N-terminal truncation variant |
| 115 | Zmhdz31_Δ1-64 | Amino acid sequence of N-terminal truncation variant |
| 116 | Zmhdz19_Δ1-65 | Amino acid sequence of N-terminal truncation variant |
| 117 | Zmhdz30_Δ1-65 | Amino acid sequence of N-terminal truncation variant |
| 118 | Zmhdz19_Δ1-67 | Amino acid sequence of N-terminal truncation variant |
| 119 | Zmhdz22_Δ1-68 | Amino acid sequence of N-terminal truncation variant |
| 120 | Zmhdz28_Δ1-68 | Amino acid sequence of N-terminal truncation variant |
| 121 | Zmhdz32_Δ1-68 | Amino acid sequence of N-terminal truncation variant |
| 122 | Zmhdz31_Δ1-71 | Amino acid sequence of N-terminal truncation variant |
| 123 | Zmhdz35_Δ1-76 | Amino acid sequence of N-terminal truncation variant |
| 124 | Zmhdz25_Δ1-79 | Amino acid sequence of N-terminal truncation variant |
| 125 | Zmhdz24_Δ1-86 | Amino acid sequence of N-terminal truncation variant |
| 126 | Zmhdz25_Δ1-86 | Amino acid sequence of N-terminal truncation variant |
| 127 | Zmhdz20_Δ1-87 | Amino acid sequence of N-terminal truncation variant |
| 128 | Zmhdz25_Δ1-94 | Amino acid sequence of N-terminal truncation variant |
| 129 | Zmhdz33_Δ1-94 | Amino acid sequence of N-terminal truncation variant |
| 130 | Zmhdz26_Δ1-96 | Amino acid sequence of N-terminal truncation variant |
| 131 | Zmhdz34_C185S, C188S | Amino acid sequence of C-terminal mutation variant |
| 132 | Zmhdz21_C187S, C190S | Amino acid sequence of C-terminal mutation variant |
| 133 | Zmhdz18_C192S, C195S | Amino acid sequence of C-terminal mutation variant |
| 134 | Zmhdz28_C196S, C199S | Amino acid sequence of C-terminal mutation variant |
| 135 | Zmhdz29_C196S, C199S | Amino acid sequence of C-terminal mutation variant |
| 136 | Zmhdz22_C203S, C206S | Amino acid sequence of C-terminal mutation variant |
| 137 | Zmhdz23_C204S, C207S | Amino acid sequence of C-terminal mutation variant |
| 138 | Zmhdz32_C215S, C218S | Amino acid sequence of C-terminal mutation variant |
| 139 | Zmhdz19_C225S, C228S | Amino acid sequence of C-terminal mutation variant |
| 140 | Zmhdz24_C235S, C238S | Amino acid sequence of C-terminal mutation variant |
| 141 | Zmhdz30_C238S, C241S | Amino acid sequence of C-terminal mutation variant |
| 142 | Zmhdz35_C255S, C258S | Amino acid sequence of C-terminal mutation variant |
| 143 | Zmhdz20_C268S, C271S | Amino acid sequence of C-terminal mutation variant |
| 144 | Zmhdz33_C273S, C276S | Amino acid sequence of C-terminal mutation variant |
| 145 | Zmhdz26_C277S, C280S | Amino acid sequence of C-terminal mutation variant |
| 146 | Zmhdz25_C282S, C285S | Amino acid sequence of C-terminal mutation variant |
| 147 | Zmhdz27_C276S, C280S | Amino acid sequence of C-terminal mutation variant |
| 148 | Zmhdz23_L11A, L13A | Amino acid sequence of EAR-like mutation variant |
| 149 | Zmhdz23_L11A, L13A, L166A, L168A, L170A | Amino acid sequence of EAR-like mutation variant |
| 150 | Zmhdz30_L13A, L15A, L17A, L19A | Amino acid sequence of EAR-like mutation variant |
| 151 | Zmhdz35_L13A, L15A, L17A, L19A | Amino acid sequence of EAR-like mutation variant |
| 152 | Zmhdz35_L13A, L15A, L17A, L19A, L156A, L158A | Amino acid sequence of EAR-like mutation variant |
| 153 | Zmhdz30_L13A, L15A, L17A, L19A, L40A, L42A | Amino acid sequence of EAR-like mutation variant |
| 154 | Zmhdz35_L13A, L15A, L17A, L19A, L55A, L57A, L59A | Amino acid sequence of EAR-like mutation variant |

TABLE 1-continued

Polynucleotides and polypeptides.

| SEQ ID NO: | Name | Sequence Type |
|---|---|---|
| 155 | Zmhdz35_L13A, L15A, L17A, L19A, L55A, L57A, L59A, L156A, L158A | Amino acid sequence of EAR-like mutation variant |
| 156 | Zmhdz35_L156A, L158A | Amino acid sequence of EAR-like mutation variant |
| 157 | Zmhdz28_L15A, L17A | Amino acid sequence of EAR-like mutation variant |
| 158 | Zmhdz28_L15A, L17A, L165A, L167A, L169A | Amino acid sequence of EAR-like mutation variant |
| 159 | Zmhdz28_L15A, L17A, L165A, L167A, L169A, L179A, L181A | Amino acid sequence of EAR-like mutation variant |
| 160 | Zmhdz28_L15A, L17A, L179A, L181A | Amino acid sequence of EAR-like mutation variant |
| 161 | Zmhdz34_L165A, L167A | Amino acid sequence of EAR-like mutation variant |
| 162 | Zmhdz28_L165A, L167A, L169A | Amino acid sequence of EAR-like mutation variant |
| 163 | Zmhdz28_L165A, L167A, L169A, L179A, L181A | Amino acid sequence of EAR-like mutation variant |
| 164 | Zmhdz23_L166A, L168A, L170A | Amino acid sequence of EAR-like mutation variant |
| 165 | Zmhdz28_L179A, L181A | Amino acid sequence of EAR-like mutation variant |
| 166 | Zmhdz31_L182A, L184A, L186A | Amino acid sequence of EAR-like mutation variant |
| 167 | Zmhdz22_L18A, L20A | Amino acid sequence of EAR-like mutation variant |
| 168 | Zmhdz22_L18A, L20A, L166A, L168A, L170A | Amino acid sequence of EAR-like mutation variant |
| 169 | Zmhdz33_L18A, L20A, L22A | Amino acid sequence of EAR-like mutation variant |
| 170 | Zmhdz33_L18A, L20A, L22A, L70A, L72A | Amino acid sequence of EAR-like mutation variant |
| 171 | Zmhdz31_L19A, L21A | Amino acid sequence of EAR-like mutation variant |
| 172 | Zmhdz31_L19A, L21A, L182A, L184A, L186A | Amino acid sequence of EAR-like mutation variant |
| 173 | Zmhdz25_L19A, L21A, L23A, L25A, L27A, L29A | Amino acid sequence of EAR-like mutation variant |
| 174 | Zmhdz25_L19A, L21A, L23A, L25A, L27A, L29A, L262A, L264A | Amino acid sequence of EAR-like mutation variant |
| 175 | Zmhdz31_L19A, L21A, L30A, L32A | Amino acid sequence of EAR-like mutation variant |
| 176 | Zmhdz31_L19A, L21A, L30A, L32A, L182A, L184A, L186A | Amino acid sequence of EAR-like mutation variant |
| 177 | Zmhdz27_L5A, L7A | Amino acid sequence of EAR-like mutation variant |
| 178 | Zmhdz27_L5A, L7A, L37A, L39A, L41A | Amino acid sequence of EAR-like mutation variant |
| 179 | Zmhdz27_L5A, L7A, L37A, L39A, L41A, L82A, L84A | Amino acid sequence of EAR-like mutation variant |
| 180 | Zmhdz27_L5A, L7A, L82A, L84A | Amino acid sequence of EAR-like mutation variant |
| 181 | Zmhdz26_L22A, L24A, L26A | Amino acid sequence of EAR-like mutation variant |
| 182 | Zmhdz24_L244A, L246A | Amino acid sequence of EAR-like mutation variant |
| 183 | Zmhdz25_L262A, L264A | Amino acid sequence of EAR-like mutation variant |
| 184 | Zmhdz31_L30A, L32A | Amino acid sequence of EAR-like mutation variant |
| 185 | Zmhdz31_L30A, L32A, L182A, L184A, L186A | Amino acid sequence of EAR-like mutation variant |
| 186 | Zmhdz24_L31A, L33A | Amino acid sequence of EAR-like mutation variant |
| 187 | Zmhdz24_L31A, L33A, L244A, L246A | Amino acid sequence of EAR-like mutation variant |
| 188 | Zmhdz26_L3A, L5A, L7A | Amino acid sequence of EAR-like mutation variant |
| 189 | Zmhdz33_L3A, L5A, L7A | Amino acid sequence of EAR-like mutation variant |
| 190 | Zmhdz33_L3A, L5A, L7A, L18A, L20A, L22A | Amino acid sequence of EAR-like mutation variant |
| 191 | Zmhdz33_L3A, L5A, L7A, L18A, L20A, L22A, L70A, L72A | Amino acid sequence of EAR-like mutation variant |
| 192 | Zmhdz33_L3A, L5A, L7A, L70A, L72A | Amino acid sequence of EAR-like mutation variant |
| 193 | Zmhdz26_L3A, L5A, L7AL22A, L24A, L26A | Amino acid sequence of EAR-like mutation variant |
| 194 | Zmhdz32_L40A, L42A | Amino acid sequence of EAR-like mutation variant |
| 195 | Zmhdz30_L40A, L42A | Amino acid sequence of EAR-like mutation variant |
| 196 | Zmhdz34_L43A, L45A | Amino acid sequence of EAR-like mutation variant |
| 197 | Zmhdz34_L43A, L45A, L165A, L167A | Amino acid sequence of EAR-like mutation variant |
| 198 | Zmhdz27_L37A, L39A, L41A | Amino acid sequence of EAR-like mutation variant |
| 199 | Zmhdz27_L37A, L39A, L41A, L82A, L84A | Amino acid sequence of EAR-like mutation variant |
| 200 | Zmhdz35_L55A, L57A, L59A | Amino acid sequence of EAR-like mutation variant |
| 201 | Zmhdz35_L55A, L57A, L59A, L156A, L158A | Amino acid sequence of EAR-like mutation variant |
| 202 | Zmhdz21_L6A, L8A, L10A, L12A, L14A | Amino acid sequence of EAR-like mutation variant |
| 203 | Zmhdz29_L6A, L8A, L10A, L12A, L14A | Amino acid sequence of EAR-like mutation variant |
| 204 | Zmhdz33_L70A, L72A | Amino acid sequence of EAR-like mutation variant |
| 205 | Zmhdz20_L8A, L10A, L12A | Amino acid sequence of EAR-like mutation variant |
| 206 | Zmhdz32_L8A, L10A, L12A | Amino acid sequence of EAR-like mutation variant |
| 207 | Zmhdz34_L8A, L10A, L12A, L14A | Amino acid sequence of EAR-like mutation variant |
| 208 | Zmhdz34_L8A, L10A, L12A, L14A, L165A, L167A | Amino acid sequence of EAR-like mutation variant |
| 209 | Zmhdz34_L8A, L10A, L12A, L14A, L43A, L45A | Amino acid sequence of EAR-like mutation variant |
| 210 | Zmhdz34_L8A, L10A, L12A, L14A, L43A, L45A, L165A, L167A | Amino acid sequence of EAR-like mutation variant |
| 211 | Zmhdz32_L8A, L10A, L12A, L40A, L42A | Amino acid sequence of EAR-like mutation variant |
| 212 | Zmhdz27_L82A, L84A | Amino acid sequence of EAR-like mutation variant |
| 213 | Zmhdz18_L9A, L11A | Amino acid sequence of EAR-like mutation variant |
| 214 | Zmhdz19_L9A, L11A, L13A, L15A, L17A, L19A | Amino acid sequence of EAR-like mutation variant |
| 215 | Zmhdz22_L166A, L168A, L170A | Amino acid sequence of EAR-like mutation variant |
| 216 | Zmhdz34_T134A, L141A, L148A, L155A, L162A | Amino acid sequence of Leucine Zipper mutation variant |
| 217 | Zmhdz18_T137A, L144A, L151A, L158A, L165A | Amino acid sequence of Leucine Zipper mutation variant |
| 218 | Zmhdz21_T140A, L147A, L154A, L161A, L168A | Amino acid sequence of Leucine Zipper mutation variant |
| 219 | Zmhdz28_T144A, L151A, L158A, L165A, L172A | Amino acid sequence of Leucine Zipper mutation variant |
| 220 | Zmhdz22_T145A, L152A, L159A, L166A, L173A | Amino acid sequence of Leucine Zipper mutation variant |
| 221 | Zmhdz23_T145A, L152A, L159A, L166A, L173A | Amino acid sequence of Leucine Zipper mutation variant |
| 222 | Zmhdz29_T151A, L158A, L165A, L172A, L179A | Amino acid sequence of Leucine Zipper mutation variant |
| 223 | Zmhdz31_T161A, L168A, L175A, L182A, L189A | Amino acid sequence of Leucine Zipper mutation variant |
| 224 | Zmhdz32_T161A, L168A, L175A, L182A, L189A | Amino acid sequence of Leucine Zipper mutation variant |

TABLE 1-continued

Polynucleotides and polypeptides.

| SEQ ID NO: | Name | Sequence Type |
|---|---|---|
| 225 | Zmhdz30_T167A, L174A, L181A, L188A, L195A | Amino acid sequence of Leucine Zipper mutation variant |
| 226 | Zmhdz19_T172A, L179A, L186A, L193A, L200A | Amino acid sequence of Leucine Zipper mutation variant |
| 227 | Zmhdz35_T179A, L186A, L193A, L200A, L207A | Amino acid sequence of Leucine Zipper mutation variant |
| 228 | Zmhdz24_T191A, L198A, L205A, L212A, L219A | Amino acid sequence of Leucine Zipper mutation variant |
| 229 | Zmhdz20_T218A, L225A, L232A, L239A, L246A | Amino acid sequence of Leucine Zipper mutation variant |
| 230 | Zmhdz33_T224A, L231A, L238A, L245A, L252A | Amino acid sequence of Leucine Zipper mutation variant |
| 231 | Zmhdz26_T228A, L235A, L242A, L249A, L256A | Amino acid sequence of Leucine Zipper mutation variant |
| 232 | Zmhdz25_T231A, L238A, L245A, L252A, L259A | Amino acid sequence of Leucine Zipper mutation variant |
| 233 | Zmhdz27_T223A, L230A, L237A, L244A, L251A | Amino acid sequence of Leucine Zipper mutation variant |
| 234 | Zmhdz34_V120A, Q123A, N124A | Amino acid sequence of Homeodomain mutation variant |
| 235 | Zmhdz18_V123A, Q126A, N127A | Amino acid sequence of Homeodomain mutation variant |
| 236 | Zmhdz21_V126A, Q129A, N130A | Amino acid sequence of Homeodomain mutation variant |
| 237 | Zmhdz28_V130A, Q133A, N134A | Amino acid sequence of Homeodomain mutation variant |
| 238 | Zmhdz22_V131A, Q134A, N135A | Amino acid sequence of Homeodomain mutation variant |
| 239 | Zmhdz23_V131A, Q134A, N135A | Amino acid sequence of Homeodomain mutation variant |
| 240 | Zmhdz29_V137A, Q140A, N141A | Amino acid sequence of Homeodomain mutation variant |
| 241 | Zmhdz31_V147A, Q150A, N151A | Amino acid sequence of Homeodomain mutation variant |
| 242 | Zmhdz32_V147A, Q150A, N151A | Amino acid sequence of Homeodomain mutation variant |
| 243 | Zmhdz30_V153A, Q156A, N157A | Amino acid sequence of Homeodomain mutation variant |
| 244 | Zmhdz19_V158A, Q161A, N162A | Amino acid sequence of Homeodomain mutation variant |
| 245 | Zmhdz35_V165A, Q168A, N169A | Amino acid sequence of Homeodomain mutation variant |
| 246 | Zmhdz24_V177A, Q180A, N181A | Amino acid sequence of Homeodomain mutation variant |
| 247 | Zmhdz20_V204A, Q207A, N208A | Amino acid sequence of Homeodomain mutation variant |
| 248 | Zmhdz33_V210A, Q213A, N214A | Amino acid sequence of Homeodomain mutation variant |
| 249 | Zmhdz26_V214A, Q217A, N218A | Amino acid sequence of Homeodomain mutation variant |
| 250 | Zmhdz25_V217Δ, Q220A, N221A | Amino acid sequence of Homeodomain mutation variant |
| 251 | Zmhdz27_V209A, Q212A, N213A | Amino acid sequence of Homeodomain mutation variant |
| 252 | ATHB17_Δ73_L11A_L13A | Amino acid sequence of ATHB17 variant |
| 253 | ATHHB17_L84A_L86A | Amino acid sequence of ATHB17 variant |
| 254 | ATHB17_Δ1-21 | Amino acid sequence of ATHB17 variant |
| 255 | ATHB17_R138A_R142A | Amino acid sequence of ATHB17 variant |
| 256 | ATHB17_Δ1-91 | Amino acid sequence of ATHB17 variant |
| 257 | ATHB17_T196A_L203A_L210A_L217A_L224A | Amino acid sequence of ATHB17 variant |
| 258 | ATHB17_Δ194_224 | Amino acid sequence of ATHB17 variant |
| 259 | ATHB17_Δ138-195 | Amino acid sequence of ATHB17 variant |
| 260 | ATHB17_Δ73_L11A_L13A | Nucleotide sequence of ATHB17 variant |
| 261 | ATHHB17_L84A_L86A | Nucleotide sequence of ATHB17 variant |
| 262 | ATHB17_Δ1-21 | Nucleotide sequence of ATHB17 variant |
| 263 | ATHB17_R138A_R142A | Nucleotide sequence of ATHB17 variant |
| 264 | ATHB17_Δ1-91 | Nucleotide sequence of ATHB17 variant |
| 265 | ATHB17_T196A_L203A_L210A_L217A_L224A | Nucleotide sequence of ATHB17 variant |
| 266 | ATHB17_Δ194_224 | Nucleotide sequence of ATHB17 variant |
| 267 | ATHB17_Δ138-195 | Nucleotide sequence of ATHB17 variant |

*For truncation variants, the number after the truncation symbol "Δ" denotes the number of amino acid residues truncated. For example, ATHB17Δ113 means the N-terminal 113 amino acids are truncated, or Zmhdz26_Δ1-102 means amino acids 1-102 of the Zmhdz26 protein are truncated.

DETAILED DESCRIPTION

The disclosure provides constructs and methods for producing plants with an enhanced trait by interfering with the ability of endogenous homeodomain-leucine zipper (HD-Zip) class II transcription factors to repress gene expression, along with the plants produced thereby. Any recombinant DNA construct that causes an endogenous HD-Zip class II transcription factor to lose its ability to repress its target genes may be employed in accordance with the invention. In some embodiments, the recombinant DNA construct comprises a protein-coding DNA molecule that is expressed in a plant or a plant cell, where it produces a protein that interferes with the ability of endogenous HD-Zip class II proteins to repress DNA transcription of genes regulated by the endogenous HD-Zip class II proteins. In other embodiments, the recombinant DNA construct comprises an RNA-coding DNA molecule that is expressed in a plant or a plant cell, where it produces an RNA molecule that suppresses the expression of a target HD-Zip class II protein. In another embodiment, the recombinant DNA construct comprises protein-coding DNA molecules that are expressed in a plant or plant cell, where they transcribe one or more proteins that, alone or as a complex, cleave the DNA of an endogenous HD-Zip class II gene in its coding or regulatory region, leading to a mutation in the protein or disruption or down-regulation of expression of the gene.

The following definitions and methods are provided to better define the present invention and to guide those of ordinary skill in the art in the practice of the present invention. Unless otherwise noted, terms are to be understood according to conventional usage by those of ordinary skill in the relevant art.

Recombinant DNA Constructs

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. The DNA molecule of the present disclosure comprises a polynucleotide that may code for a protein of the present disclosure, or a RNA molecule that suppresses the expression of an endogenous HD-Zip class II protein, or one or more proteins that cleave the DNA of an endogenous HD-Zip class II gene in its coding or regulatory region, leading to a mutation in the protein or disruption or down-regulation of expression of the gene.

Therefore, the term "gene" in the context of disruption or down-regulation of endogenous HD-Zip class II gene expression includes not only the coding region, but also the regulatory region of the gene. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, the term "recombinant" refers to a technique of combining two or more macromolecules (polynucleotides or polypeptides) or the combined molecule resulting therefrom. Any number of methods well-known to those skilled in the art can be used to isolate and manipulate a DNA molecule, or fragment thereof, disclosed in the present disclosure. For example, PCR (polymerase chain reaction) technology can be used to amplify a particular starting DNA molecule and/or to produce variants of the original molecule. DNA molecules, or fragments thereof, can also be obtained by other techniques such as by directly synthesizing the fragment by chemical means, as is commonly practiced by using an automated oligonucleotide synthesizer. The disclosed recombinant DNA constructs may be made by standard techniques known in the art (see, e.g., *Molecular Cloning: A Laboratory Manual, 3$^{rd}$ edition Volumes 1, 2, and 3*, J. Sambrook, D. W. Russell, and N. Irwin, Cold Spring Harbor Laboratory Press, 2000).

As used herein, the term "operably linked" refers to a first molecule joined to a second molecule, wherein the molecules are so arranged that the first molecule affects the function of the second molecule. Typically, the first molecule is a gene regulatory molecule such as a promoter, operably linked to the 5' of the second molecule such as a protein- or a RNA-coding DNA molecule. The two molecules may or may not be part of a single contiguous molecule and may or may not be adjacent. For example, a promoter regulatory element is operably-linked to a transcribable polynucleotide molecule if the promoter regulates transcription of the transcribable polynucleotide molecule of interest in a cell. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species.

In a first embodiment, a recombinant DNA construct is disclosed. The recombinant DNA construct comprises a protein-coding DNA molecule. The protein-coding DNA molecule is operably linked to a heterologous promoter. When the recombinant DNA construct is expressed in a plant or a plant cell, it produces a protein that interferes with the ability of endogenous HD-Zip class II proteins to repress DNA transcription of genes regulated by the endogenous HD-Zip class II proteins.

Figure 2:
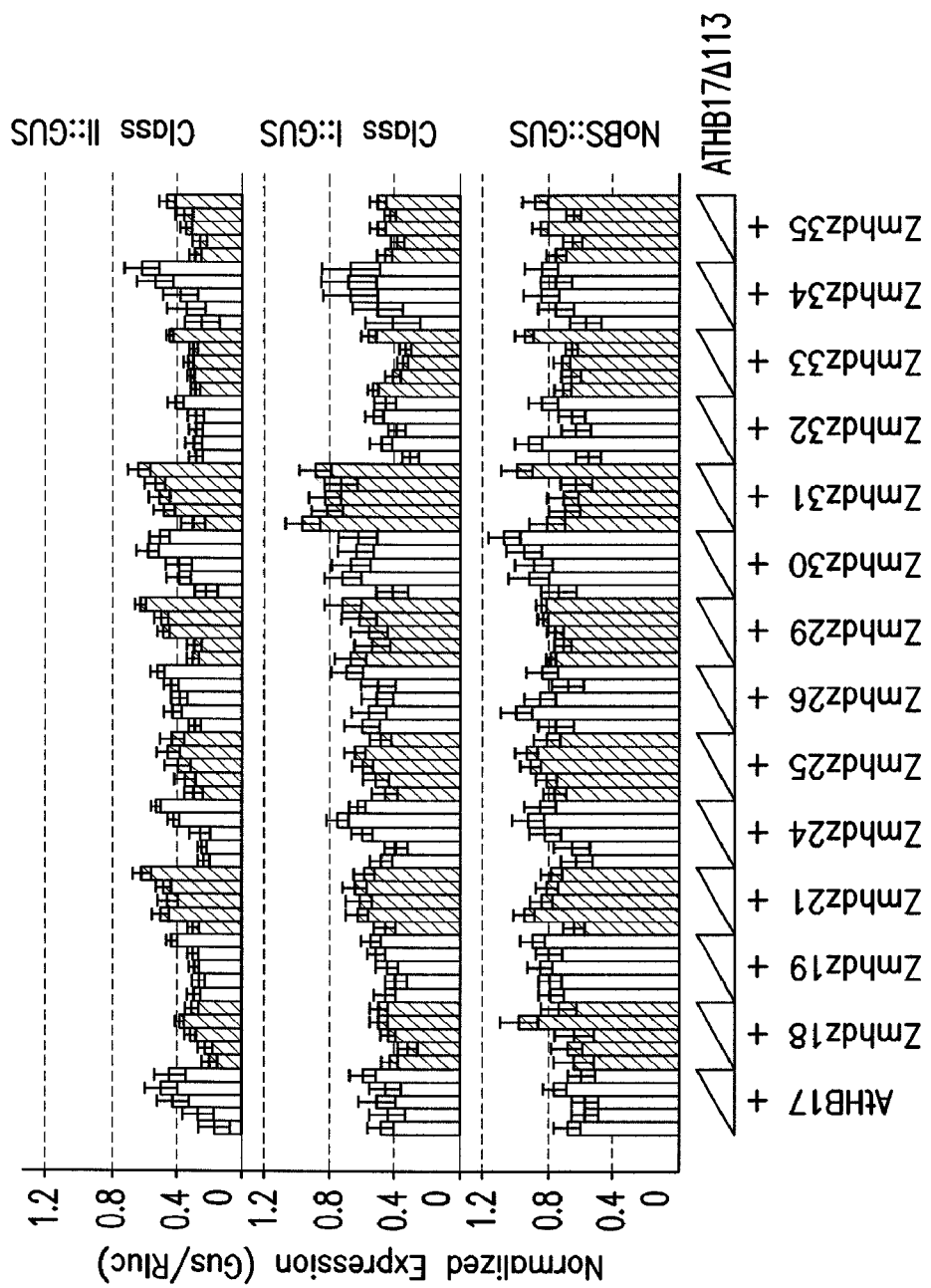
FIG. 2—Shows corn protoplast transcriptional activation/repression assays demonstrating ATHB17Δ113 relief of repression caused by corn HD-Zip class II proteins. Grey triangles represent an increasing amount of ATHB17Δ113 DNA. The reporter gene construct contains the class II DNA binding site (Class II::GUS), or the class I DNA binding site (Class I::GUS), or no Class I/Class II DNA binding site (No BS::GUS).

The protein-coding DNA molecule in the recombinant DNA construct is not limited to any particular protein-coding DNA molecule, but, rather, may be any protein-coding DNA molecule that codes for a protein that interferes with the ability of an HD-Zip class II protein that is endogenous to a plant or plant cell to repress DNA transcription in the plant or plant cell. A protein expressed from the recombinant DNA construct may interfere with the ability of an endogenous HD-Zip class II protein to repress DNA transcription in the plant or plant cell in any number of ways, e.g., through protein-protein interactions with the endogenous HD-Zip class II proteins or by competing with endogenous HD-Zip class II proteins for binding to target DNA (FIG. 1). Moreover, proteins that interfere through protein-protein interactions may act in either the cytosol or the nucleus. Proteins that interfere through interactions in the cytosol can interfere with the nuclear localization of endogenous HD-Zip class II proteins. Proteins that interfere through interactions in the nucleus can (1) form homodimers and compete with homodimers of endogenous HD-Zip class II proteins for the same DNA binding site, (2) form heterodimers with endogenous HD-Zip class II proteins to form complexes that can bind to DNA, but are not active, and/or (3) form heterodimers with endogenous HD-Zip class II proteins to form complexes that cannot bind to DNA. DNA molecules that code for proteins that interfere with the ability of an endogenous HD-Zip class II protein to repress DNA transcription in a plant or plant cell can be identified by comparing (1) the expression of a beta-glucuronidase or uidA gene (GUS) reporter construct that includes the known DNA binding site for HD-Zip class II proteins (CAATC/GATTG, SEQ ID NO:55) (Sessa et al., *EMBO J* 12:3507-3517, 1993) in the promoter in plant protoplasts transiently expressing an introduced HD-Zip class II protein with (2) the expression of the GUS reporter construct in protoplasts in which the same HD-Zip class II protein is co-expressed with a putative interfering protein as described in Example 5. Interfering proteins can be identified as those that provide increased expression from the reporter in co-transformed protoplasts relative to protoplasts expressing the HD-Zip class II protein alone. When this method was applied to corn protoplasts transiently expressing ATHB17Δ113, the data showed that ATHB17Δ113 interfered with the ability of the corn HD-Zip class II proteins to repress transcription. As shown in FIG. 2, increased expression from a GUS reporter construct was seen when the corn HD-Zip class II proteins were co-expressed in corn protoplasts with increasing amounts of ATHB17Δ113 when the GUS reporter construct contained the known DNA binding site for HD-Zip class II proteins (Class II::GUS). Proteins that interfere with HD-Zip class II protein repression activity can be identified, for example, by comparing GUS expression from reporter constructs containing the known HD-Zip class II DNA binding site to constructs lacking the HD-Zip class II DNA binding site or comprising a non-specific DNA binding site. Proteins that interfere with HD-Zip class II protein repression activity can be identified as those that show increases in GUS expression in protoplasts expressing the GUS reporter with the HD-Zip class II DNA binding site relative to those lacking the HD-Zip class II DNA binding site. Binding to the HD-Zip class II DNA binding site can be confirmed in vitro using a Surface Plasmon Resonance (SPR) assay as described in Example 2. Proteins that interfere with HD-Zip class II protein repression activity can also be identified, e.g., through yeast two-hybrid assays where a putative interfering protein is used as the bait and a plant total RNA library is used as the prey as described in Example 3. To account for potential false positives, specific putative interactions can be validated through a bead-based co-immunoprecipitation assay by co-expressing the putative interacting proteins in plant protoplasts and detecting the presence of a complex through the use of antibodies specific to tags on each of the putative interacting proteins, as described in Example 4.

In an embodiment, the protein produced from the expression of the recombinant DNA construct in a plant or plant cell is an HD-Zip class II transcription factor, a little zipper protein, or a small-interfering peptide (siPEP). Little zipper proteins (Wenkel et al., *Plant Cell* 19:3379-3390, 2007) and siPEPs (Seo et al., *Trends Plant Sci* 16:541-549, 2011) can be identified as described in the art. Little zipper proteins (Wenkel et al., *Plant Cell* 19:3379-3390, 2007) and siPEPs (Seo et al., *Trends Plant Sci* 16:541-549, 2011) do not bind DNA, and, therefore, do not directly regulate gene transcription, but are able to regulate transcription through protein-protein interactions with endogenous transcription factors.

Figure 3:
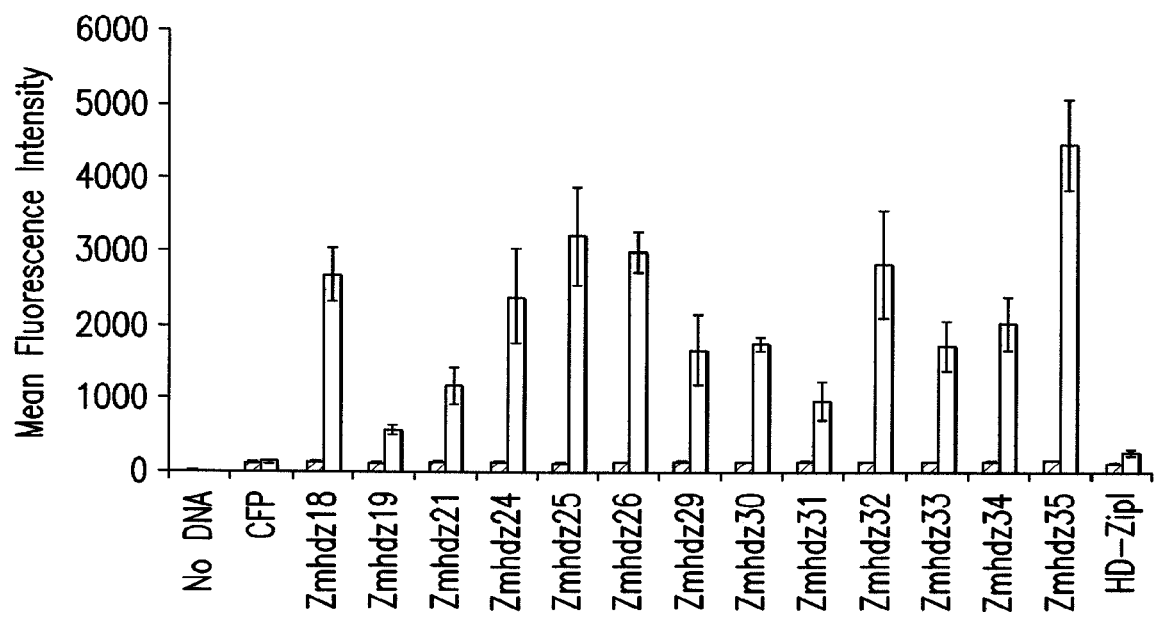
FIG. 3—Shows a bead-based co-immunoprecipitation assay in corn protoplasts demonstrating heterodimer formation between ATHB17Δ113 and endogenous corn HD-Zip class II proteins. Corn leaf protoplasts were transformed with constructs expressing CFP or a CFP-tagged HD-Zip class II protein alone (filled bars) or co-transformed with a construct expressing ATHB17Δ113::MYC-HA (empty bars). HD-Zip I is Zmhdz3.

HD-Zip class II transcription factors can be identified by using comparative sequence analysis methods as described (Zhao et al., *PLoS One* 6:e28488, 2011) to search for proteins containing a homeodomain (HD) immediately adjacent to a leucine-zipper domain and, among these proteins, to identify proteins comprising a redox sensing motif (CPXCE-like motif) (Ariel et al., *Trends in Plant Sci* 12:419-426, 2007). HD-Zip class II transcription factors can interfere with the ability of endogenous HD-Zip class II transcription factors to repress transcription through either protein-protein interactions or through competition for DNA binding. FIG. 3 demonstrates protein-protein interactions between ATHB17Δ113 and corn HD-Zip class II proteins in a corn protoplast assay. As shown in the figure, co-expression of tagged ATHB17Δ113 with labeled corn HD-Zip class II proteins in corn protoplasts produced clear signals (empty boxes) relative to protoplasts expressing the proteins alone (filled boxes) in a bead-based co-immunoprecipitation assay. No protein-protein interactions were seen when ATHB17Δ113 was co-expressed with an HD-Zip class I protein (HD-Zip I). FIG. 2 demonstrates the ability of ATHB17Δ113 to interfere with HD-Zip class II protein repression activity. As shown in the figure, co-expression of ATHB17Δ113 with corn HD-Zip class II proteins produced increased GUS expression from the GUS reporter construct containing the HD-Zip class II DNA binding site (Class II::GUS), but not from the reporter construct containing the HD-Zip class I DNA binding site (Class I::GUS), or in construct with neither binding site (No BS::GUS).

As used herein, a "mutation" is a change in the nucleotide sequence of a gene. Mutations in genes can either have no effect, or alter the product of a gene, or prevent the gene from functioning properly or completely, and may or may not produce discernible changes in the observable characteristics (phenotype) of an organism. A "loss-of-function mutation" is a mutation that results in reduced or abolished gene expression or protein function. A "dominant negative mutation" has an altered gene product that acts antagonistically to the wild-type allele. These mutations usually result in an altered molecular function (often inactive) and are characterized by a dominant or semi-dominant phenotype. A loss-of function mutation of the present disclosure results in the inability of an endogenous HD-Zip class II protein to interfere with transcriptional repression of genes regulated by the HD-Zip class II protein. As used herein, the term "variant" refers to a second polynucleotide or polypeptide molecule that is in composition similar, but not identical to, a first polynucleotide or polypeptide molecule. A variant may be a shorter or truncated version of the first polynucleotide or polypeptide molecule and/or an altered version of the sequence of the first polynucleotide or polypeptide molecule, such as one with terminal and/or internal deletions, substitutions, and/or insertions.

In some embodiments, the protein produced from the expression of the recombinant DNA construct in a plant or plant cell is an HD-Zip class II transcription factor with one or more loss-of-function mutations in a domain selected from the group consisting of a transcriptional repression domain (also called a transcriptional repression/activation domain), a homeodomain, a leucine zipper domain, and a CXXCX-like motif in the C-terminus. HD-Zip class II transcription factors can be identified based on their canonical domain structure (as described above). Briefly, these proteins may contain a repression/activation domain for transcriptional repression/activation, a homeodomain for DNA binding, a leucine zipper domain for protein dimerization, and a C-terminus involved in cellular redox status perception. The repression/activation domain affects transcriptional repression/activation. The homeodomain affects transcription repression and DNA binding, whereas the leucine zipper domain and the c-terminus affect transcription repression, DNA binding, and protein dimerization. Therefore, any loss-of-function mutation in any of these domains is expected to affect transcriptional repression activity of the protein. While the disclosure provides several specific HD-Zip class II transcription factors and examples of their loss-of-function variants, it should be understood that the scope is not limited thereto, but, rather, includes other proteins with the same domain structure, other loss-of-function variants and combination thereof.

Figure 4A:
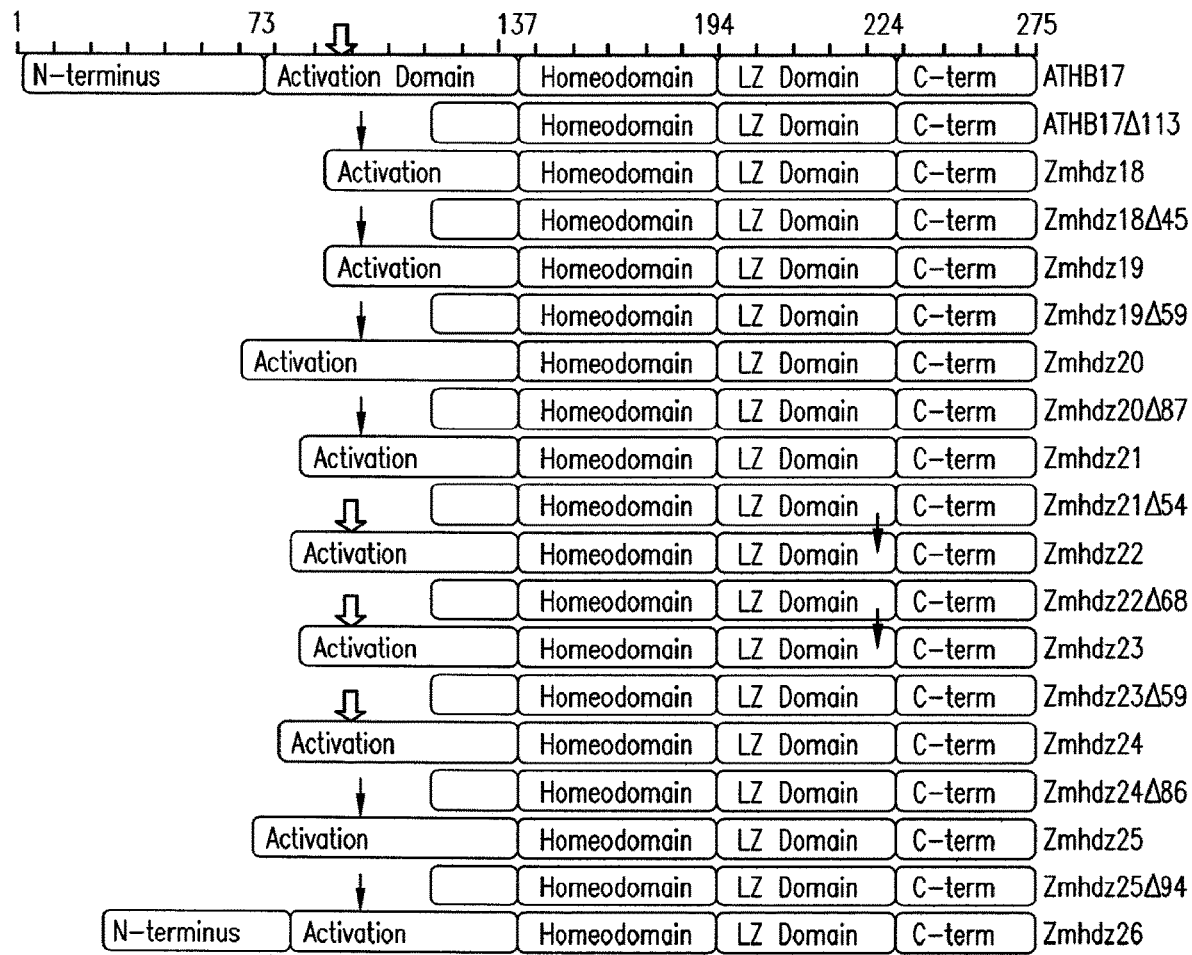
FIG. 4—Shows domain structure of various HD-Zip class II proteins and examples of their N-terminal truncation variants. For each protein, the truncation variant is provided below the full-length protein, with the amino acid position of the deletion identified (e.g., ATHB17Δ113 refers to the N-terminal truncation of the ATHB17 protein from amino acid 1 to amino acid 113). Canonical (filled arrows) and putative (empty arrows) ERF-associated Amphilic Repression (EAR) motifs within the sequences are identified.
Figure 4B:
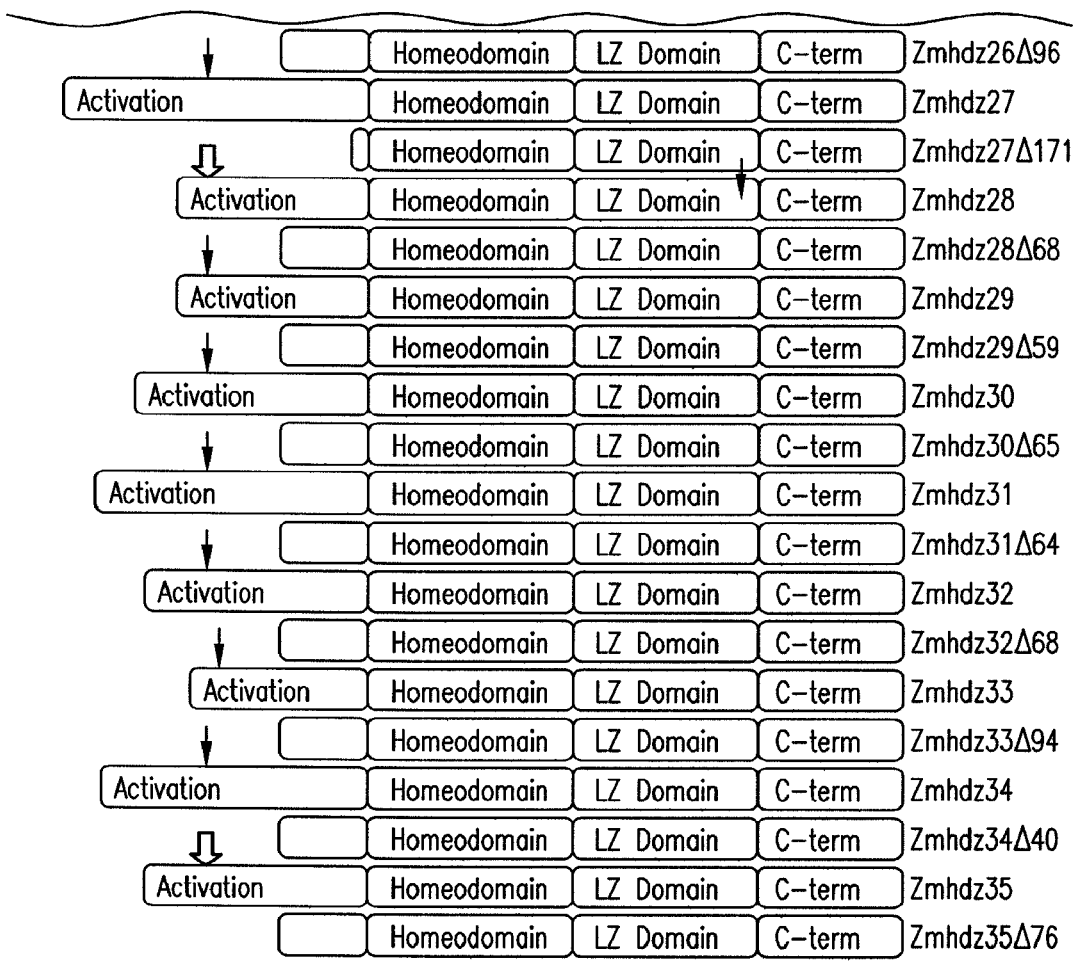

In certain embodiments, the HD-Zip class II transcription factor produced from the expression of the recombinant DNA construct in a plant or plant cell has a loss-of-function mutation in a transcriptional repression domain. Several HD-Zip class II proteins have been found to contain an EAR motif characterized by its canonical sequence (LxLxL) and associated with transcriptional repression (Ciarbelli et al., *Plant Mol. Biol.*, 68:465-478 (2008)). HD-Zip class II transcription factors with a loss-of-function mutation in a transcriptional repression domain, can, therefore, be produced by mutating residues in this or a similar repression domain. Several HD-Zip class II transcription factors with mutations that are expected to produce a loss-of-function in the transcriptional repression domain are disclosed in Table 1, FIG. 4 and in the attached sequence listing. In FIG. 4, examples of the deletion variants are provided below the full-length proteins with the amino acid positions of the deletions identified. Loss-of-function mutations include, e.g., substitution of residues in the repression domain with non-canonical residues that abrogate repression function, partial or complete deletion of the sequence coding for the domain residues, and insertion of residues within the domain, and, in proteins where multiple repression domains are present, insertion of residues between the multiple domains. Substitutions that produce loss of repression function in EAR motifs have been described in the art (International patent application No. PCT/US13/35640; U.S. Provisional patent application No. 60/621,980).

In other embodiments, the loss-of-function mutation in the HD-Zip class II transcription factor produced by the expression of the DNA construct is in the leucine zipper domain. Dimerization via the leucine zipper domain is critical for the homeodomain DNA binding, which, in turn, regulates the transcriptional function. Mutations in the leucine zipper domain can be designed to abolish or reduce protein-protein interaction. The reduced protein-protein interaction or lack thereof can be evaluated using a bead-based protoplast assay qualitatively and/or quantitatively as described in Example 4. The selected variants can further be validated for DNA binding using a biosensor as described in Example 2, and for transcriptional activity as described in Examples 5 and 6. Loss-of-function mutations include, e.g., substitution of residues in the leucine zipper domain that abolishes dimerization function, partial or complete deletion of the sequence coding for the domain residues, and insertion of residues within the domain. Mutations that result in loss-of-function in the leucine zipper domain have been described in the art (Sessa et al. *EMBO J*, 12: 3507-3517 (1993)).

In yet other embodiments, the loss-of-function mutation in the HD-Zip class II transcription factor produced by the expression of the DNA construct is in the homeodomain. The homeodomain functions in DNA binding. Mutations in the homeodomain can affect DNA binding and transcriptional activity. Mutations can, therefore, be designed and tested for DNA binding using a biosensor as described in Example 2, and for transcriptional activity as described in Examples 5 and 6. Loss-of-function mutations include, e.g., substitution of residues in the homeodomain that abolishes or reduces DNA binding, partial or complete deletion of the sequence coding for the domain residues, and insertion of residues within the domain. Mutations that result in loss-of-function in the homeodomain have been described in the art (Sessa et al., *J. Mol. Biol* 274:303-309, 1997).

In other embodiments, the loss-of-function mutation in the HD-Zip class II transcription factor produced by the expression of the DNA construct is in the CXXCX-like motif in the C-terminus. Mutations in the CXXCX-like motif in the C-terminus can affect DNA binding, protein-protein interaction and transcriptional activity. Mutations can, therefore, be designed and tested for DNA binding using a biosensor as described in Example 2, for protein-protein interaction or no interaction using a bead-based protoplast assay qualitatively and/or quantitatively as described in Example 4, and for transcriptional activity as described in Examples 5 and 6. Loss-of-function mutations include, e.g., substitution of residues in the C-terminus, especially in the CXXCX-like motif, partial or complete deletion of the sequence coding for the domain/CXXCX-like motif residues, and insertion of residues within the domain/CXXCX-like motif. Mutations that result in loss-of-function in the C-terminus/CXXCX-like motif have been described in the art (Comelli et al., *Arch Biochem Biophys* 467(1):41-7, 2007).

In some embodiments of the present disclosure, loss-of-function mutations that interfere with the ability of the endogenous HD-Zip class II proteins to repress gene transcription include mutations in the coding sequences resulting in amino acid substitutions, insertions, inversions or deletions of a part of the proteins. Mutations in a specific domain, for example, in a transcriptional repression domain, a homeodomain, a leucine zipper domain, or a CXXCX-like motif in the C-terminus, can be produced by genetically engineering changes in the coding sequences for naturally occurring HD-Zip class II proteins comprising the specific domains, or can be introduced by species-specific alternative splicing. Genetically engineered changes can be introduced into the coding sequences for HD-Zip class II proteins through in vitro DNA synthesis or PCR-based site-directed mutagenesis. Genetically engineered coding sequences are cloned into plant expression vectors by standard techniques (Sambrook et al., 1989). Alternatively, HD-Zip class II proteins lacking transcriptional repression activity can be produced through species-specific alternative splicing. For example, as described in Example 1, below, and shown in FIG. 5, species-specific alternative splicing in corn plants comprising the full-length *Arabidopsis thaliana* ATHB17 coding sequence produced a protein (ATHB17Δ113) with a deletion of the first 113 amino acid residues from the N-terminal region relative to the full-length protein (ATHB17), including part of the repression domain. HD-Zip class II transcription factors with a loss-of-function mutation in any of the domains resulting in reduced or loss of repression activity can also be identified by measuring expression from a GUS reporter construct in plant protoplasts as described in Example 5. HD-Zip class II proteins with mutations in any domain can be tested for a loss of repression activity by expressing the proteins in the plant protoplasts along with GUS reporter constructs with or without the class II DNA recognition site sequence. Proteins lacking repression activity can be identified as those proteins that fail to decrease GUS expression in protoplasts containing GUS constructs with the class II DNA recognition site sequence relative to protoplasts containing GUS control constructs lacking the DNA recognition site. FIG. 6 shows the loss of repression activity in ATHB17 resulting from the deletion of the first 113 amino acid residues from the N-terminal region. As shown in the figure, whereas expression of full-length ATHB17 resulted in a decrease in expression from GUS reporter constructs containing the HD-Zip class II DNA recognition site (Class II::GUS) relative to control constructs lacking the DNA recognition site (No BS::GUS), expression of ATHB17Δ113 caused no such decrease.

In some embodiments of the present disclosure, interference with the ability of the endogenous HD-Zip class II proteins to repress gene transcription can be accomplished via (1) mutations in the coding region of an endogenous HD-Zip class II gene, resulting in amino acid substitutions, insertions, inversions or deletions of part the protein, (2) gene knockouts, (3) modified gene expression by making changes in the promoter sequence of an endogenous HD-Zip class II gene, for example in the class II DNA binding site, and (4) suppression of the expression of an endogenous HD-Zip class II protein. Mutations in specific domains, for example, in a transcriptional repression domain, a homeodomain, a leucine zipper domain, or a CXXCX-like motif in the C-terminus, can be produced by genetically engineering changes in the coding sequences of an endogenous HD-Zip class II gene comprising such domains.

In one embodiment, one or more recombinant DNA constructs are disclosed. Each recombinant DNA construct comprises one or more protein-coding DNA molecules. Each of the one or more protein-coding DNA molecules is operably linked to a heterologous promoter. When the recombinant DNA constructs are expressed in a plant or plant cell, they produce one or more proteins that, alone or as a complex, cleave the DNA of an endogenous HD-Zip class II gene in its coding or regulatory region, leading to a mutation in the protein or disruption or down-regulation of expression of the gene. Loss-of-function mutations, such as disruption or down-regulation of expression of the gene, in the endogenous HD-Zip class II genes can be achieved using technologies well known in the art. Genome editing, in which DNA is inserted, replaced or removed from a genome uses artificially engineered proteins or protein complexes that comprise a DNA-modifying enzyme, such as endonucleases, helicases, ligases, kinases and recombinases that are known in the art. Endonucleases create specific double-stranded breaks at desired locations in the genome, and harness the cell's endogenous mechanisms to repair the induced break by natural processes of homologous recombination and non-homologous end-joining. Examples of the engineered nucleases include zinc finger nucleases (ZFNs), transcription activator-like effector nucleases (TALENs), CRISPR and engineered meganucleases. Recombinases are genetic recombination enzymes. DNA recombinases are widely used in multicellular organisms to manipulate the structure of genomes, and to control gene expression. These enzymes catalyze directionally sensitive DNA exchange reactions between short (30-40 nucleotides) target site sequences that are specific to each recombinase for excision/insertion, inversion, translocation and cassette exchange. Examples of recombinases include Cre recombinase, FLP recombinase, TALE-recombinase and zinc finger recombinase. Other technologies include, but are not limited to, programmed group II introns, zinc finger or TALE chimeric transposases, and homology arm-mediated gene targeting, optionally employing a plus/minus selection scheme. Other methodologies that are useful to generate loss-of-function mutations in the endogenous HD-Zip class II proteins may be employed by the present invention. Identification and confirmation of a DNA molecule that, when expressed in a plant or plant cell, interferes with the ability of an endogenous HD-Zip class II protein to repress DNA transcription can be done using methods described above. Identification and confirmation of mutations that interfere with the ability of an HD-Zip class II protein to repress DNA transcription through protein-protein interaction, or DNA binding can be done also using methods described in the previous sections.

HD-Zip proteins bind DNA as homo- or hetero-dimers and many are known to function as active repressors of gene expression and to down-regulate transcription of genes within the HD-Zip family. Therefore, suppression of one HD-Zip class II protein could affect dimerization or DNA binding of other HD-Zip class II proteins leading to interference with repression of DNA transcription in the HD-Zip class II auto-regulation network. In one embodiment, a recombinant DNA construct is disclosed. The recombinant DNA construct comprises a RNA-coding DNA molecule. The RNA-coding DNA molecule is operably linked to a heterologous promoter. When the recombinant DNA construct is expressed in a plant or a plant cell, it produces an RNA molecule that suppresses the expression of a target HD-Zip class II protein.

The term "suppression" as used herein refers to a lower expression level of a target polynucleotide or target protein in a plant or plant cell as compared to the expression in its native state or wild-type state for the gene. The term "target protein" as used in the context of suppression refers to a protein that is suppressed; similarly, "target DNA" or "target polynucleotide" refers to a polynucleotide that can be suppressed or, once expressed, degraded so as to result in suppression of the target protein it encodes. In one embodiment, the target gene regulates itself or other endogenous HD-Zip class II genes. In some embodiments, the target HD-Zip class II protein is selected from the group consisting of SEQ ID NO:19 to SEQ ID NO:36.

Many RNA-mediated suppression methods are known in the art. Non-limiting examples include, but are not limited to, antisense RNAs, miRNAs, siRNAs and long non-coding RNAs. Antisense RNA is a single-stranded RNA that is complementary to a messenger RNA (mRNA) strand transcribed in a cell. When antisense RNA is expressed in a cell, it binds to a specific messenger RNA molecule and inactivates it. An siRNA is a double-stranded RNA molecule, 20-25 base pairs in length. After separating into single strands and integrating into an active RISC complex, it base-pairs to its target mRNA and induces cleavage of the target mRNA, thereby preventing it from being used as a translation template. A miRNA is a small RNA, typically about 21 nucleotides, that has the ability to modulate the expression of a target gene by binding to mRNA for the target protein, leading to destabilization or translational inhibition of the target protein mRNA, ultimately resulting in reduction of the target protein. Methods for selecting and designing siRNAs and miRNAs for gene suppression are well known in the art. Long non-coding RNAs (long ncRNA or lncRNA) are non-protein coding transcripts longer than 200 nucleotides (Perkel, BioTechniques, 54 (6):301-304 (2013)). In contrast to many small RNAs which exhibit strong conservation across diverse species, long ncRNAs in general lack strong conservation. Long ncRNAs can be categorized, according to their proximity to protein coding genes in the genome, into five categories; sense, antisense, bidirectional, intronic, and intergenic, and regulate gene expression through a diverse group of mechanisms, such as through gene transcription (e.g., through gene-specific transcription regulation and regulation of basal transcription machinery), post-transcriptional regulation (e.g., through mRNA translation and siRNA-directed gene regulation) or through epigenetic regulation. The effect of an siRNA, a miRNA or a long non-coding RNA on target gene suppression can be assessed by comparing expression of a beta-glucuronidase or uidA gene (GUS) reporter construct that includes the known DNA binding site for HD-Zip class II proteins (CAATC/GATTG) in plant protoplasts transiently expressing an introduced HD-Zip class II protein alone, to the expression of the GUS reporter construct in protoplasts in which the same HD-Zip class II protein is co-expressed with a RNA-coding DNA molecule, similar to what is described in Example 5 for co-expression with a protein-coding DNA molecule. An antisense RNA, an siRNA, a miRNA or a long non-coding RNA molecule that suppresses a target HD-Zip class II protein can be identified as the one that provides increased expression from the reporter in co-transformed protoplasts relative to protoplasts expressing the HD-Zip class II protein alone.

Further embodiments of the present disclosure include heterologous promoters that direct expression of the operably linked DNA sequence in a manner that allows for the produced product to be expressed in cells or tissues that express endogenous HD-Zip class II proteins. Cells or tissues in which endogenous HD-Zip class II proteins are expressed can be identified, e.g., by targeted transcript analysis as described in Example 11. Plant tissues in which such proteins are expressed in corn at various developmental timepoints are shown in FIG. 7. Numerous promoters that are active in plant cells or tissues have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV 35S promoters from the cauliflower mosaic virus as disclosed in U.S. Pat. Nos. 5,164,316 and 5,322,938. Useful promoters derived from plant genes are found in U.S. Pat. No. 5,641,876, which discloses a rice actin promoter, U.S. Pat. No. 7,151,204, which discloses a corn chloroplast aldolase promoter and a corn aldolase (FDA) promoter, and US Patent Application Publication 2003/0131377, A1 which discloses a corn nicotianamine synthase promoter. These and numerous other promoters that function in plant cells are known to those skilled in the art and available for use as heterologous promoters for expressing the operably linked DNA molecules disclosed herein.

In some embodiments, the recombinant DNA construct includes other DNA elements. Other construct components may include additional regulatory elements, such as 5' leaders and introns for enhancing transcription, 3' untranslated regions (such as polyadenylation signals and sites), DNA for transit or signal peptides. Such elements are known in the art. Useful enhancers include the 5' introns of the rice actin 1 (see U.S. Pat. No. 5,641,876) and rice actin 2 genes, the corn alcohol dehydrogenase gene intron, the corn heat shock protein 70 gene intron (U.S. Pat. No. 5,593,874) and the corn shrunken 1 gene. See also U.S. Patent Application Publication 2002/0192813A1, which discloses 5', 3' and intron elements useful in the design of effective plant expression vectors. In some embodiments, the recombinant DNA construct includes a translational enhancer from the 5' leader of Tobacco mosaic virus (Shuzeski et al., 1990). Well-known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in U.S. Patent Application Publication 2002/0192813 A1; and the pea (*Pisum sativum*) ribulose biphosphate carboxylase gene (rbs 3'), and 3' elements from the genes within the host plant. The recombinant DNA constructs may include DNA for transit or signal peptides. In some embodiments, it is desired that the recombinant DNA constructs include nuclear localization signals to target produced proteins to the nucleus to facilitate the interference of the repression activity of nuclear HD-Zip class II proteins. In the practice of transformation, the recombinant DNA construct is typically introduced into only a small percentage of target plant cells in any one transformation experiment. Therefore, in some embodiments, it is desired that the disclosed recombinant DNA constructs also include selectable markers that allow for the identification of transformed cells. Certain marker genes provide selectable markers that confer resistance to a selective agent, such as an antibiotic or an herbicide. Any of the herbicides to which plants of this invention may be resistant are useful agents for selectable markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selectable marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers that provide an ability to visually screen transformants can also be employed, for example, a gene expressing a colored or fluorescent protein such as a luciferase or green fluorescent protein (GFP) or a gene expressing the GUS protein for which various chromogenic substrates are known.

In some embodiments, genes regulated by endogenous HD-Zip class II proteins are genes encoding HD-Zip class II proteins (auto regulation of HD-Zip class II proteins). In other embodiments, genes regulated by endogenous HD-Zip class II proteins are corn HD-Zip class II proteins. In further embodiments, genes regulated by endogenous HD-Zip class II proteins are corn HD-Zip class II proteins having an amino acid sequence selected from the group consisting of SEQ ID NO:19 to SEQ ID NO:36. Genes subject to transcriptional regulation by HD-Zip class II proteins may undergo changes in expression upon the expression of a protein that interferes with the ability of HD-Zip class II proteins to repress gene expression. Genes regulated by endogenous HD-Zip class II proteins can, therefore, be identified by transcript analysis that measures changes in gene expression between plants lacking a protein that interferes with HD-Zip class II repression activity and those plants that express such a protein. Plants that express such a protein can be analyzed for changes in expression of endogenous HD-Zip class II transcripts. Changes in endogenous HD-Zip class II expression can be identified by targeted transcript analysis or by global transcriptome analysis.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided, as examples, as the polynucleotide sequences of SEQ ID NO:92 to SEQ ID NO:130.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment, the protein-coding DNA molecule included in the recombinant DNA construct codes for a protein that has an amino acid sequence with at least 60% identity to a protein with an amino acid sequence represented by one of SEQ ID NO:92 to SEQ ID NO:130. In other embodiments, the protein-coding DNA molecule included in the recombinant DNA construct codes for a protein that has an amino acid sequence with at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity over the full length of a protein represented by one of SEQ ID NO:92 to SEQ ID NO:130. Proteins having at least a specified percent identity to a protein with an amino acid sequence represented by one of SEQ ID NO:92 to SEQ ID NO:130 are identified by comparison of the amino acid sequences, e.g. manually or by use of a computer-based tool using known homology-based search algorithms such as the suite of BLAST programs available from NCBI.

Plants and Plant Cells

In other embodiments, plants and plant cells that comprise the disclosed recombinant DNA constructs are provided. While the plants and plant cells can be any commercial plant (e.g., soybean, corn, wheat, rice, cotton, canola, sugarcane and sugar beet), in one embodiment, the plants and plant cells are from corn.

Plants comprising the disclosed recombinant DNA constructs can be produced through the process of transformation via targeted or random insertion. Numerous methods for transforming chromosomes in a plant cell with recombinant DNA are known in the art and are used in methods of preparing a transgenic plant cell, and plant. Two exemplary methods for such transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914, 451 (soybean); U.S. Pat. No. 6,160,208 (corn); U.S. Pat. No.

6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), U.S. Patent Application Publication No. 2004/0087030 A1 (cotton), U.S. Patent Application Publication No. 2013/0055472 (sugarcane), U.S. Patent Application Publication No. 2013/0152232 (sugarcane) and U.S. Patent Application Publication No. 2001/0042257 A1 (sugar beet), all of which are incorporated herein by reference for enabling the production of transgenic plants.

Proteins used for genome editing can also be prepared in vitro prior to introduction to a plant cell. The method of preparing such proteins depends on their type and properties and would be known by one of skill in the art. Once crude, partially purified, or more completely purified proteins are obtained, they can be introduced into, for example, a plant cell via electroporation, by bombardment with particles coated with such protein, by chemical transfection or by some other means of transport across a cell membrane.

In addition to direct transformation of a plant material with a recombinant DNA, a transgenic plant cell or plant can be prepared by crossing a first plant having cells with the recombinant DNA or altered endogenous gene in the nuclei with a second plant lacking the recombinant DNA or altered endogenous gene. For example, recombinant DNA can be introduced into a first plant line that is amenable to transformation and crossing that line with a second plant line to introgress the recombinant DNA into the second plant line. In another example, an endogenous gene can be altered by genome editing in a first plant line and the altered endogenous gene can be introgressed into a second plant line by crossing. A plant with recombinant DNA or an altered endogenous gene providing an enhanced trait disclosed herein can be crossed with a transgenic plant line having other recombinant DNA and/or altered endogenous gene that confers another trait, for example herbicide tolerance or pest resistance, to produce progeny plants having recombinant DNA and/or altered endogenous gene that confers both traits. The progeny of this cross will segregate such that some of the plants will carry the DNA for both parental traits and some will carry DNA for one parental trait; such plants can be identified by markers associated with parental recombinant DNA or altered endogenous gene, e.g. marker identification by analysis for the recombinant DNA or the altered endogenous gene or, in the case where a selectable marker is included in the recombinant DNA construct, by application of the selecting agent such as a herbicide for use with an herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but with the recombinant DNA or altered endogenous gene of the other transgenic parental line.

In other embodiments, the plants and plant cells comprise a recombinant DNA construct that produces a protein, where the produced protein is an HD-Zip class II transcription factor with a loss-of-function mutation in a domain selected from the group consisting of a transcriptional repression domain, a homeodomain, a leucine zipper domain, and a CXXCX-like motif in the C-terminus. Such plants and plant cells are produced by introducing a recombinant DNA construct that produces an HD-Zip class II transcription factor with a loss-of-function mutation in one of the domains when expressed in plant cells (as produced by the methods described in the section on recombinant DNA constructs) by transformation or crossing of plant lines, as described above.

In other embodiments, the plants and plant cells comprise a recombinant DNA construct that produces an RNA molecule, where the produced RNA molecule suppresses the expression of a target HD-Zip class II protein. Such plants and plant cells are produced by introducing a recombinant DNA construct that produces an RNA molecule that suppresses the expression of a target HD-Zip class II protein when expressed in plant cells (as produced by the suppression methods described in the section on recombinant DNA constructs) by transformation or crossing of plant lines, as described above.

In still other embodiments, the plants and plant cells comprise a recombinant DNA construct that, when expressed in a plant or a plant cell, produces a loss-of-function mutation in a gene encoding an endogenous HD-Zip class II protein or alters the expression of an endogenous HD-Zip class II protein. In some embodiments, the plant or plant cell comprises a recombinant DNA construct that, when expressed in a plant or a plant cell, produces a loss-of-function mutation that increases the expression of an endogenous HD-Zip class II protein. Such loss-of-function mutation may be in a domain selected from the group consisting of transcriptional repression domain, a homeodomain, a leucine zipper domain, or a CXXCX-like motif in the C-terminus. Such plants and plant cells are produced by introducing a recombinant DNA construct that produces a loss-of-function mutation in a gene encoding an endogenous HD-Zip class II protein or alters the expression of an endogenous HD-Zip class II protein when expressed in plant cells (as produced by the genome editing methods described in the section on recombinant DNA constructs) by transformation or crossing of plant lines, as described above.

In certain embodiments, corn plants comprising the recombinant DNA construct or altered endogenous gene have an enhanced trait relative to control corn plants that lack the recombinant DNA construct or altered endogenous gene. In some aspects, the enhanced trait is staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles and increased yield. Plants with increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield can be identified by measuring these characteristics from plants grown to the R1 stage as described in Example 9 and identifying those plants with the recombinant DNA construct or altered endogenous gene that show enhancements in these characteristics relative to those plants lacking the recombinant DNA construct. Plants exhibiting a staygreen phenotype can be identified by identifying, at the R5 stage of plant growth, plants having leaves showing at least 50% of its area green below the ear as described in Example 10 and identifying those plants with the recombinant DNA construct or altered endogenous gene that show enhancements in these characteristics relative to those plants lacking the recombinant DNA construct.

Table 2 provides a summary of certain phenotypic characteristics (Trait Name) of corn plants expressing ATHB17Δ113, which has a partial repression domain. A mean (Mean) value was calculated for each phenotype across a number (N) of different plants from two transgenic events (Event) and compared to the mean for non-transgenic controls (Control mean). The statistical significance (P-value) of changes between transgenic and non-transgenic plants was assessed based on the absolute (Delta) and percentage change (% Delta) in each phenotype between transgenic and non-transgenic plants. As used herein, the term "ear" may refer to the ear alone, or any combination of the ear, the associated husk, the associated silk tissues, and the associated shank tissues.

TABLE 2

Phenotypic characteristics of transgenic corn events expressing ATHB17Δ113.

| Trait Name | Event | Mean | Control mean | Delta | % Delta | P-value | N |
|---|---|---|---|---|---|---|---|
| Ear dry weight | Event 1 | 99.2 | 93.1 | 6.2 | 6.6 | 0.006 | 109 |
| (g/m$^2$) | Event 2 | 99.7 | 93.1 | 6.6 | 7.1 | 0.003 | 109 |
| Stover dry weight | Event 1 | 993.2 | 956.6 | 36.6 | 3.8 | 0.114 | 108 |
| (g/m$^2$) | Event 2 | 951.4 | 956.6 | −5.1 | −0.5 | 0.804 | 108 |
| Total dry weight | Event 1 | 1069 | 1052 | 16.8 | 1.6 | 0.482 | 110 |
| (g/m$^2$) | Event 2 | 1055 | 1052 | 3.1 | 0.3 | 0.892 | 110 |
| Ear partitioning | Event 1 | 0.089 | 0.086 | 0.003 | 3.9 | 0.085 | 110 |
| coefficient | Event 2 | 0.091 | 0.086 | 0.005 | 5.6 | 0.013 | 110 |

Methods for Producing and Breeding Plants with Enhanced Traits

In another embodiment, a method for producing plants with an enhanced trait is disclosed. The enhanced trait can include, but is not limited to, staygreen, increased ear biomass, increased ear size, increased ear diameter, increased ear length, increased seed size, increased seed number, increased seed weight, increased pod/silique size, increased pod/silique number per plant, increased pod/silique weight, increased size of cotton boll, increased number of bolls per plant, increased panicles, and increased yield. The method comprises the steps of (a) incorporating into a plant a recombinant DNA construct that, when expressed in the plant, produces a protein that interferes with the ability of endogenous HD-Zip class II proteins to repress DNA transcription of genes regulated by the endogenous HD-Zip class II proteins; and (b) selecting a plant from the plants expressing the recombinant DNA construct, where the selected plant has an enhanced trait selected from the group consisting of staygreen, increased ear biomass, increased ear size, increased ear diameter, increased ear length, increased seed size, increased seed number, increased seed weight, increased pod/silique size, increased pod/silique number per plant, increased pod/silique weight, increased size of cotton boll, increased number of bolls per plant, increased panicles, and increased yield, relative to a control plant lacking the recombinant DNA construct. In certain embodiments, the method further comprises determining whether the DNA construct is stably integrated into the genome of the plant or whether the protein produced by the recombinant DNA construct is expressed. In other embodiments, the plant is a corn plant.

In one embodiment, the protein produced from the expression of the recombinant DNA construct in the plants incorporating the recombinant DNA construct is an HD-Zip class II transcription factor with a loss-of-function mutation in a domain selected from the group consisting of a transcriptional repression domain, a homeodomain, a leucine zipper domain and a CXXCX-like motif in the C-terminus. In another embodiment, the protein produced interferes with the ability of endogenous HD-Zip class II proteins to repress DNA transcription through protein-protein interactions with the endogenous HD-Zip class II proteins. In other embodiments, the protein produced interferes with the ability of endogenous HD-Zip class II proteins to repress DNA transcription by competing with endogenous HD-Zip class II proteins for DNA binding. In another embodiment, the recombinant DNA construct with which plants are transformed comprises a protein-coding DNA molecule that codes for a protein that has an amino acid sequence with at least 60% identity to a protein with an amino acid sequence represented by one of SEQ ID NO:92 to SEQ III NO:130. Examples of proteins to be used in the methods are identified as described above and as listed in Table 11 in Example 15.

In another embodiment, a method for producing plants with an enhanced trait is disclosed. The method comprises the steps of a) incorporating into the plants a recombinant DNA construct that, when expressed in the plant, produces an RNA molecule that suppresses the expression of a target HD-Zip class II; and b) selecting a plant from a sub-population of plants expressing the recombinant DNA construct, wherein the selected plant has an enhanced trait selected from the group of enhanced traits consisting of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield, relative to a control plant that does not comprise the recombinant DNA construct. In certain embodiments, the method further comprises determining whether the DNA construct is stably integrated into the genome of the plant, or whether the RNA molecule produced by the recombinant DNA construct is expressed, or expression of the target endogenous HD-Zip class II protein is reduced or suppressed. In other embodiments, the plant is a corn plant.

In yet another embodiment, a method for producing plants with an enhanced trait is disclosed. The method comprises the steps of a) incorporating into the plants a recombinant DNA construct that, when expressed, produces a loss-of-function mutation in a gene encoding an endogenous HD-Zip class II protein or alters the expression of an endogenous HD-Zip class II protein; and h) selecting a plant from a sub-population of plants comprising the loss-of-function mutation, wherein the selected plant has an enhanced trait selected from the group of enhanced traits consisting of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield, relative to a control plant that does not comprise the loss-of-function mutation. In certain embodiments, the method further comprises determining whether expression of the endogenous HD-Zip class II protein is altered. In other embodiments, the plant is a corn plant.

In another embodiment, the endogenous protein with a loss-of-function mutation is an HD-Zip class II transcription factor with a loss-of-function mutation in a domain selected from the group consisting of a transcriptional repression domain, a hemeodomain, a leucine zipper domain and a CXXCX-like motif in the C-terminus. In another embodiment, the endogenous protein with a loss-of-function mutation interferes with the ability of endogenous HD-Zip class II proteins to repress DNA transcription through protein-protein interactions with the endogenous HD-Zip class II proteins. In other embodiments, the loss-of-function protein produced interferes with the ability of endogenous HD-Zip class II proteins to repress DNA transcription by competing with endogenous HD-Zip class II proteins for DNA binding. In yet other embodiments, the loss-of-function mutation in an endogenous HD-Zip class II gene is in the class II DNA recognition site in the promoter and interferes with the ability of endogenous HD-Zip class II proteins to repress DNA transcription by preventing endogenous HD-Zip class II proteins to bind to its promoter.

The recombinant DNA construct can be incorporated either through direct transformation of plants or plant cells, or by crossing plants with and without the recombinant DNA construct as described above. Expression of the recombinant DNA construct in plants incorporating the recombinant DNA construct can occur through the use of any number of different promoters, e.g., constitutive, inducible, tissue-specific, etc. Depending on the type of promoter used, expression may require induction by an inducing agent, or may occur directly as a result of the presence of the recombinant DNA construct in the plant or plant cells. Plants with an enhanced trait can be selected from the population expressing the recombinant DNA construct based, e.g., on visual inspection for one or more of the traits using the methods described.

In yet another embodiment, a method for breeding plants with an enhanced trait is disclosed. The method includes the steps of: (a) obtaining seed produced by a plant having staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles or increased yield, where the obtained seed comprises a recombinant DNA construct that, when expressed in a plant or plant cell, produces an HD-Zip class II protein with a loss-of-function mutation in a transcriptional repression domain, a homeodomain, a leucine zipper domain or a CXXCX-like motif in the C-terminus, and (b) planting the obtained seed, where a plant grown from the planted seed is a progeny plant of a plant comprising the recombinant DNA construct and having an enhanced trait of staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles or increased yield. Seed from plants comprising the recombinant DNA construct and having an enhanced trait may be obtained from any number of sources.

In one embodiment, the seed or plant comprises a recombinant DNA construct that includes a protein-coding DNA molecule that codes for a protein that has an amino acid sequence with at least 60% identity to a protein with an amino acid sequence represented by one of SEQ ID NO:92 to SEQ ID NO:130. In one embodiment, the seed or plant is a corn seed or plant.

In yet another embodiment, a method for breeding plants with an enhanced trait is disclosed. The method includes the steps of (a) obtaining seed produced by a plant having staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield, where the obtained seed comprises a recombinant DNA construct, that, when expressed in a plant or plant cell, produces an RNA molecule that suppresses the expression of a target endogenous HD-Zip class II protein; and (h) planting the obtained seed, where a plant grown from the planted seed is a progeny plant of a plant comprising the recombinant DNA construct and having an enhanced trait of staygreen, increased ear biomass, increased ear size, increased ear diameter, increased ear length, increased seed size, increased seed number, increased seed weight, increased pod/silique size, increased pod/silique number per plant, increased pod/silique weight, increased size of cotton boll, increased number of bolls per plant, increased panicles, and increased yield. Seed from plants comprising the recombinant DNA construct and having an enhanced trait may be obtained from any number of sources. In one embodiment, the seed or plant is a corn seed or plant.

In still another embodiment, a method for breeding plants with an enhanced trait is disclosed. The method includes the steps of (a) obtaining seed produced by a plant having staygreen, increased ear biomass, increased ear size, increased ear diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield, where the obtained seed comprises an altered endogenous HD-Zip class II gene; and (b) planting the obtained seed, where a plant grown from the planted seed is a progeny plant of a plant comprising the altered endogenous HD-Zip class II gene and having an enhanced trait of staygreen, increased ear biomass, increased ear size, increased car diameter, increased ear length, increased seed size, increased seed number per plant, increased seed weight, increased pod/silique size, increased pod/silique number per plant, increased pod/silique weight, increased size of cotton boll, increased cotton fiber length, increased number of bolls per plant, increased panicles, and increased yield.

In one embodiment, the plant or seed is a corn plant or seed. Seed from plants comprising the altered endogenous HD-Zip class II gene and having an enhanced trait may be obtained from any number of sources.

EXAMPLES

The disclosure, having been generally described, will be more readily understood by reference to the following examples, which are included merely for purposes of illustration of certain aspects and embodiments of the present, and are not intended to limit the specification or claims. It will be understood by one of skill in the art, that similar techniques can be applied to other genes and/or proteins that can be expressed in any commercial plant or plant cell to interfere with endogenous HD-Zip class II transcription factor repression activity.

Example 1: ATHB17-Transgenic Corn Plants Produced a Truncated Protein that Lack the Repression Domain A recombinant DNA construct was constructed that contained the full-length ATHB17 coding sequence under the control of a rice actin 1 promoter with a 35S enhancer, a wheat chlorophyll a/b binding protein leader and a rice actin intron, and an hsp17 3'polyadenylation sequence. *Agrobacterium*-mediated transformation was used to generate transgenic corn plants.

Figure 5:
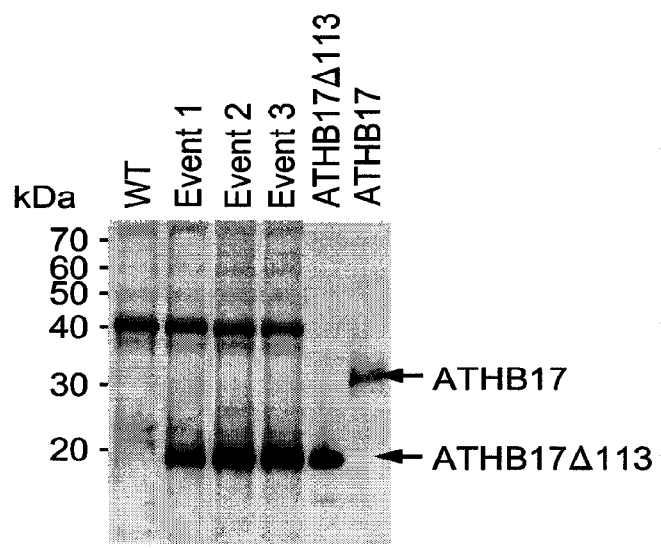
FIG. 5—Shows a western blot of ATHB17 expressed in transgenic corn plants.
Figure 6:
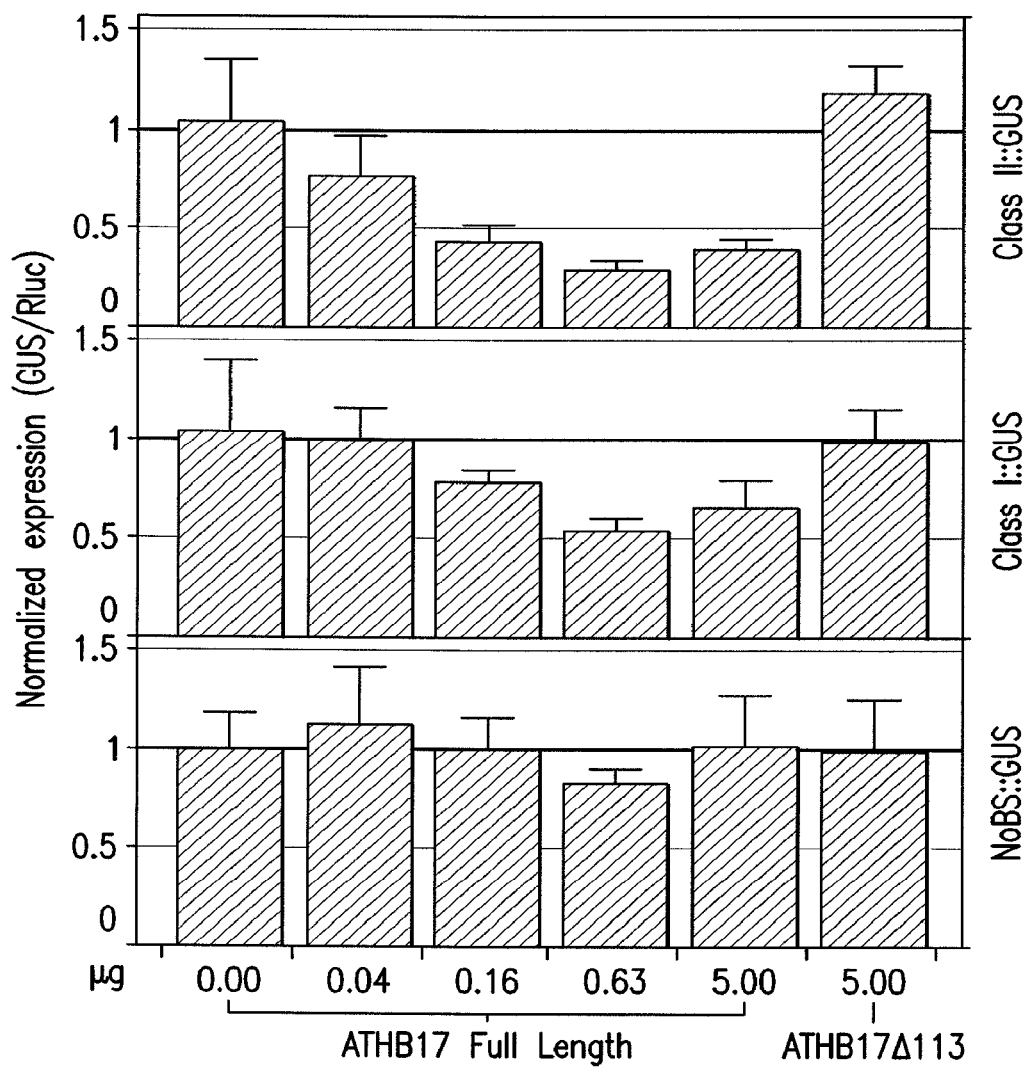
FIG. 6—Shows that the full-length ATHB17 protein functions as a transcriptional repressor in corn protoplast transcriptional activation/repression assays.

Western blot analysis revealed that the expressed protein was smaller (approximately 20 kDa) than the expected size for the full length protein (approximately 30 kDa) (FIG. 5). ATHB17 transcript sequence analysis confirmed that a truncated transcript was produced due to alternative splicing of the rice actin intron, resulting in an ATHB17 protein lacking the first 113 amino acids compared to the full length ATHB17. As a result of the loss of the first 113 amino acid residues, the protein expressed in corn lacked its unique N-terminus containing putative transmembrane domains and a large portion of the repression domain including the ERF-associated Amphilic Repression (EAR)-like motif, but retained its intact HD and LZ domains. Based on the known functions of the ATHB17 domains, it was likely that the truncated protein would lose its transcription repression activity, but retained its dimerization and DNA binding properties based on the know functions of the AtIIB17 domains.

Example 2: Testing DNA Binding Properties of HD-Zip Class II Proteins

HD-Zip I and II proteins bind to similar cis elements (CAAT(N)ATTG) under in vitro conditions (Sessa et al., *EMBO J* 12:3507-3517, 1993); Meijer et al., *Mol Gen Genet* 263:12-21, 2000); Frank et al., *Plant J Cell Molec Biol* 15:413-421, 1998); Deng et al., *Plant Mol Biol* 49:601-610, 2002). HD-Zip II members bind preferentially to the pseudo-palindromic sequence CAAT(C/G)ATTG (SEQ ID NO:55) (Sessa et al., *EMBO J* 12:3507-3517, 1993), whereas members of the HD-Zip I subfamily bind preferentially to a pseudo-palindromic sequence that differs from that of HD-Zip II at the central nucleotide (CAAT(A/T)ATTG) (SEQ ID NO:56) (Ariel et al., *Trends Plant Sci* 12:419-426, 2007). The DNA-binding properties of ATHB17Δ113 was tested in vitro using a surface plasmon resonance (SPR) assay for both class I and class II recognition sequences. The oligonucleotides used in this assay were CAGACAATCATTGCGGC (SEQ ID NO:268) (Class II), CAGACAATTATTGCGGC (SEQ ID NO:269) (Class I), and CAGCTCAGTCTGACGGC (SEQ ID NO:270) (non consensus), where the pseudo-palindromic sequences flanked by four nucleotides at the 5' end and 3'end of the oligo are underlined.

The results showed that ATHB17Δ113 protein binds both class I ($K_D$=37.7+14.0) and class II ($K_D$=20.4+3.3) DNA recognition sequences. Kinetic analysis of the binding demonstrated that the class I sequence had higher equilibrium dissociation constant indicating that ATHB17Δ113 has a higher affinity of binding to class II DNA recognition sequence in vitro.

Example 3: Identifying Putative Interactions Between ATHB17Δ113 and Endogenous Corn HD-Zip Class II Proteins Putative protein-protein interactions between ATHB17Δ113 and endogenous corn HD-Zip class II proteins were identified by yeast two-hybrid assay. ATHB17 full length and multiple fragments were used as the baits in a yeast-two-hybrid screen performed by Hybrigenics SA (Paris, France). cDNA encoding full-length ATHB17 was cloned into pB27 and pB29 (LexA-C and N terminal fusions), EAR motif region 1-91 into pB29 (LexA N-terminal fusion), homeodomain region 128-234 into pB27 (LexA C-terminal fusion), leucine zipper domain region 114-275 into pB27 (LexA C-terminal fusion). These bait constructs were used to screen a randomly-primed cDNA library prepared from corn RNAs from callus tissue, etiolated seedlings, V3 seedlings, ear inflorescence, developing kernels, and ear leaf. 111-139 million clones (11-14 fold coverage of the library) were screened. cDNA fragments corresponding to positive 330 "prey" clones were amplified by PCR and sequenced at their 5' and 3' junctions. The resulting sequences were searched against a proprietary database and assigned a quality score, indicative of the confidence of interaction.

Several corn HD-Zip Class II proteins, but none of the other classes of HD-Zip proteins, were identified as putative interactive proteins with ATHB17Δ113. Additional corn HD-Zip class II proteins were identified using bioinformatic approaches based on the known domain structures of HD-Zip class II proteins.

Example 4: Confirming ATHB17Δ113 Protein-Protein Interactions with Endogenous Corn HD-Zip Class II Proteins Thirteen of the 18 identified corn HD-Zip class II proteins were tested for protein-protein interaction with ATHB17Δ113 in corn protoplasts using the bead-based co-immunoprecipitation assay. The C-terminal MYC-HA fusion of ATHB17Δ113 was co-transformed with a C-terminal CFP fusion of each of the corn HD-Zip class II coding sequences into corn leaf protoplasts. Corn Leaf protoplasts were isolated from 12-day-old plants (Sheen et al., *Plant Physiology* 79:1072-1076, 1985) and transformed using a PEG-mediated transformation method. Protoplasts were incubated for 18 to 24 hours at 22° C. and pelleted at 150×g for 3 minutes. The protoplast pellets were resuspended and 300 µl were transferred to a 96-deep well plate and centrifuged at 150×g for 3 minutes. After resuspending in 20 µl of incubation buffer, the protoplasts were lysed. The protein lysate was centrifuged at 3000×g for 5 minutes and soluble fractions were retained for use in Luminex based co-immunoprecipitation (co-IP) assay.

Capture antibodies for CFP, Myc, and HA were covalently coupled to carboxylated fluorescent microspheres (Luminex). Biotinylated antibodies for CFP, Myc, and HA were used for detection of interacting prey proteins in the miniaturized sandwich immunoassay. NeutrAvidin R-phycoerythrin was used as the reporter. Protein expression for ATHB17MYC::HA dual tag and CFP constructs was detected using the miniaturized sandwich immunoassay and co-IP methods as described by Qi et al. (*J Biol Chem* 287:31482-31493, 2012). Samples of mock transformed protoplasts, bait alone, and prey alone were used to determine the background signal of the Luminex assay.

Antibody against CFP conjugated to biotin was used to determine if the complex included corn HD-Zip II proteins. As shown in FIG. 5, no signal above background level was identified when either ATHB17Δ113::MYC-HA or HD-Zip class II::CFP was transformed alone. However, a positive signal was observed when ATHB17Δ113::MYC-HA was co-transformed with constructs containing HD-Zip class II::CFP. Furthermore, no interaction was detected between a HD-Zip class I protein and ATHB17Δ113. These results indicate that when expressed in corn, ATHB17Δ113 form heterodimers with HD-Zip class II proteins and, therefore, has the potential to affect activities and pathways associated with corn HD-Zip class II proteins.

Example 5: Assaying ATHB17Δ113 for Transcriptional Repression

The ATHB17 protein has been shown to function as a transcriptional repressor similar to several other HD-Zip class II proteins including AtHB2 and HAT2 (Ohgishi et al., *Plant J* 25:389-398, 2001; Agalou et al., *Plant Mol Biol* 66:87-103, 2007; Zhao et al., *PLoS One* 6:e28488, 2011). Since ATHB17Δ113 lacks a large portion of the repression domain, it was tested in a corn leaf protoplast repression/ activation assay to determine whether it could act as a transcriptional activator or repressor using two reporter constructs consisting of the GUS gene and either a class I or a class II DNA binding sequence positioned between the 35S (−45) minimal promoter and the e35S double enhancer. A control reporter construct contained neither a class I nor a class II binding sequence. Protoplasts were transformed as described in the previous example. Each treatment was tested in four technical replicates per transformation. Biological replicates consisted of identical treatments tested in protoplasts isolated on different days.

Transcription was measured by co-transforming increasing amounts of ATHB17 expression plasmid with a constant amount of the reporter plasmid. Repression of the class II promoter was observed with as little as 40 ng of ATHB17 expression plasmid and was dose-responsive up to 630 ng of the ATHB17 expression plasmid (FIG. 6). Repression of the class I promoter was observed at 160 ng of ATHB17 expression plasmid and increased at 630 ng. No repression of the control promoter lacking a DNA binding site was observed. Therefore, ATHB17 can repress transcription from promoters containing class II and, to a lesser degree, class I DNA binding sites. In contrast to the repression of the GUS expression demonstrated by the full-length ATHB17 protein, no repression or activation of the Class I::GUS or Class II::GUS expression was observed when the ATHB17Δ113 plasmid was co-transformed with the reporter plasmid (FIG. 6). This result shows that the repression activity was lost as a result of truncation of the repression domain.

Example 6: ATHB17Δ113 Acts as a Dominant Negative Regulator of HD-Zip Class II Proteins Although ATHB17Δ113 does not function as a repressor, the protein retains its dimerization and DNA binding properties. Therefore, its likely function is to attenuate the activity of endogenous HD-Zip class II proteins through a dominant-negative mechanism. The dominant-negative mechanism can occur through formation of non-functional homo- or heterodimers with reduced DNA-binding activity or through competition for DNA-binding.

To evaluate the ability of ATHB17Δ113 to act as a dominant negative regulator, its ability to relieve the repressional activity of the full-length ATHB17 protein was examined. A corn protoplast system described in the previous examples was used to co-transform the reporter construct with 0.20 μg of the full-length ATHB17 plasmid, and increasing amounts of ATHB17Δ113 plasmid. The repression of the reporter gene expression caused by the full-length ATHB17 was gradually relieved as increasing amounts of ATHB17Δ113 were added. This dominant-negative effect was only observed when the reporter gene cassette contained the class II DNA binding sequence. No significant change in the level of expression was detected when the reporter gene cassette contained class I DNA binding sequence or no DNA binding sequence. Based on the observation of lower affinity of binding to the class I sequence in the in vitro assay as described in the previous example, and an overall smaller effect on expression when the reporter construct contained a class I sequence, ATHB17 is more active against genes with class II DNA binding sequence in the promoter regions.

To evaluate further whether ATHB17Δ113 could also act as a dominant negative regulator of endogenous corn HD-Zip class II transcription factors, 13 members of the corn HD-Zip class II family were cloned and tested first for their activity in corn leaf protoplasts as described in previous examples. All 13 HD-Zip class II proteins showed repression activity against GUS expression in a dosage-dependent manner when the GUS construct contained either a class I or a class II DNA binding sequence, suggesting that corn HD-Zip class II proteins act as transcriptional repressors in vivo. To determine whether ATHB17Δ113 has the ability to act as a dominant negative regulator of corn HD-Zip class II proteins, each corn HD-Zip class II construct (20 ng) was co-transformed with the reporter constructs and an increasing amount of the ATHB17Δ113 construct. Dosage-dependent relief of the corn HD-Zip class II repressional activity by increasing the amount of ATHB17Δ113 DNA was observed for all tested HD-Zip class II proteins when the reporter construct contained the class II DNA binding sequence in the promoter region (FIG. 2). In contrast, when the reporter construct contained the class I DNA binding sequence or no DNA binding sequence (control construct), no consistent dosage-dependent effect of ATHB17Δ113 on the reporter expression was observed. These results confirmed that ATHB17Δ113 protein can act as a dominant-negative regulator of endogenous corn HD-Zip class II proteins that repress transcription from promoters containing the class II DNA binding site. This result further indicates that a mechanism of dominant negative regulation exerted by ATHB17Δ113 should include a competition for the class II DNA-binding site.

Example 7: ATHB17 Loss-of Function Mutations and their Effect on DNA Binding ATHB17 amino acid substitutions and domain deletions were generated by comparing the ATHB17 protein sequence with those of mammalian HD and other plant HD-Zip transcription factors. These variants were evaluated for their DNA binding properties using SPR on Biacore 2000 as described in Example 2.

Mutations in Homeodomain on DNA Binding

Homeodomains (HD) are structurally composed of three conserved α-helices responsible for DNA binding. Amino acids V47, Q50, and N51 within α-helix-III of AtHB-1 (HD-Zip I) and AtIIB-2 (HD-Zip II) from *Arabidopsis* have been shown to play a critical role in DNA binding (Sessa et al., *J Mol Biol* 274:303-309, 1997). Similar structural and functional properties have been described for the engrailed HD (Gehring et al., *Cell* 78:211-223, 1994). Mutations were generated in corresponding residues V182, Q185, and N186 within the DNA recognition α-helix-III of ATHB17Δ113. The ATHB17Δ113-V182A-Q185A-N186A variant was generated to measure real-time interactions with target DNA sequences using Biacore 2000. The results indicate that ATHB17Δ113-V182A-Q185A-N186A loses its ability to interact with CAAT(G/C)ATTG (BS2) and CAAT(T/A)ATTG (BS1) (Table 3). Similar results were observed with the ATHB17Δ113 homeodomain deletion variant ATHB17Δ113-Δ138-195) (Table 3).

Sessa et al. (*J Mol Biol* 274:303-309, 1997) observed that AtHB-2 mutation R55K abolished preferential recognition of the central nucleotide (G/C) within the pseudopalindromic sequence, CAAT(G/C)ATTG, that confers specificity to HD-Zip class II. To evaluate the role of the AtHB-2-R55K equivalent in ATHB17Δ113, variant ATHB17Δ113-R190K was produced for DNA binding analyses. The binding dissociation constants, $K_D$=25.70±11.6 nM and $K_D$=68.24±4.2 nM were obtained for ATHB17Δ113-R190K binding to BS1 and BS2, respectively. Wild type ATHB17Δ113 has been shown to interact with BS1 and BS2 with an affinity of 37.7±14.0 nM and 20±3.3 nM, respectively. The results indicate that the amino acid substitution R190K substantially reduces the affinity of ATHB17Δ113 to BS2. However, no significant change in the affinity of ATHB17Δ113-R190K to BS1 was observed.

A conserved tryptophan-48 substitution to phenylalanine (W48F) in the Bicoid homeodomain of *Drosophila Melanogaster* suggested the critical role of W-48 in stabilizing the structural features of IID necessary for DNA recognition (Subramaniam et al., *J Biol Chem* 276(24):21506-21511, 2001). Phenylalanine-20 in HAB-4 (HD-Zip I), which maps in helix 1, is part the hydrophobic core that is required to maintain the conformation of most HD. F20L in HAB-4 loses the ability to bind DNA (Palena et al., *Biochem J* 341:81-87, 1999). DNA binding analyses with the corresponding W183F and F155L in ATHB17Δ113 were conducted. The affinities of W183F and F155L to BS2 DNA target were 11 µM and 3.6 µM, respectively (Table 3). BS2 DNA binding was significantly reduced for both variants but not completely suppressed. Although complete loss of binding was not observed, the magnitude of the reduction in binding affinity indicates that, like the conserved W48 in Bc-HD and F20 in HAB-4, W183 and F155 in ATHB17Δ113 appear to stabilize the structural integrity of the HD required for DNA recognition.

Mutations in Leucine Zipper Domain on DNA Binding

The requirement for specific homo-dimerization of AtHB-1 and HaHB-4 for DNA binding has been previously demonstrated (Sessa et al., *EMBO J* 12(9)9:3507-3517, 1993; Palena et al., *Biochem J* 341:81-87, 1999). HD-Zip homo-dimerization is mediated by a specific leucine zipper domain adjacent to the HD. The leucine zipper domain is typically an alpha helical structure composed of seven amino acids (heptad) repeats, abcdefg, implicated in protein-protein interaction such as homo- and hetero-dimerization that results in a wrap-around structure called a coiled coil. Protein-protein interaction is driven by hydrophobic residues at positions a and d (position d is always a leucine), forming the hydrophobic core. Aside from the hydrophobic core, protein-protein interaction also occurs via charged residues at positions e and g. Other amino acids at position b, c, and f are solvent exposed (O'Shea et al., *Science* 254:539-544, 1991). The leucine zipper of ATHB17Δ113 is composed of 4 heptad repeats. The contribution of the leucine zipper and the critical amino acid residues within the

TABLE 3

Binding isotherms of ATHB17Δ113 variants interacting with BS2 DNA.

| Polypeptide SEQ ID NO: | Gene Name | $k_{on}$ $M^{-1} s^{-1} \times 10^5$ | $k_{off}$ $s^{-1} \times 10^{-4}$ | $K_D$ (nM) |
|---|---|---|---|---|
| 59 | ATHB17Δ113 | 42.3 ± 16.0 | 880.6 ± 416 | 20.4 ± 3.3 |
| 60 | ATHB17Δ113-V182A-Q185A-N186A | — | — | NB |
| 61 | ATHB17Δ113-Δ138-195 | — | — | NB |
| 62 | ATHB17Δ113-W183F | 1.5 | 16320 | 11036.4 * |
| 63 | ATHB17Δ113-F155L | 2.0 ± 1.7 | 6540 ± 472 | 3630 ± 2932 |
| 64 | ATHB17Δ113-Δ194-224 | 2.67 ± 0.5 | 12000 ± 5724 | 4800 ± 3113 |
| 65 | ATHB17Δ113-T196A-L203A-L210A-L217A-L224A | — | — | NB |
| 66 | ATHB17Δ113-C200A-C243S-C246S | — | — | NB |
| 67 | ATHB17Δ113-C243S-C246S | 50.5 ± 7.6 | 2060 ± 223 | 41.1 ± 3.4 |
| 68 | ATHB17Δ113-C246S | 27.7 ± 6.6 | 1560 ± 237 | 63.6 ± 17.3 |
| 69 | ATHB17Δ113-C243S | 23.4 ± 1.2 | 1930 ± 43 | 82.2 ± 14 |

* No binding (NB) of variant within the concentration range used is indicated. Random DNA did not interact with any of the proteins tested.

leucine zipper of ATHB17Δ113 to DNA binding were investigated. Removal of critical leucine residues in the dimerization interface of the leucine zipper in the ATHB17Δ113-T196A-L203A-L210A-L217A-L224A variant completely abolished DNA binding to BS2 (Table 3), confirming the requirement of homo-dimerization for DNA binding. Deletion of the leucine zipper domain in an ATHB17Δ113 variant (ATHB17Δ113-A194-224) resulted in a significant loss of DNA binding activity (KD=4800±3113 nM) compared to ATHB17Δ113 (KD=20.4±3.3 nM) (Table 3).

Mutations in a CXXCX-Like Motif in the C-Terminus on DNA Binding

To evaluate the effect of cysteine residues in a CXXCX-like motif in the C-terminus on DNA binding, variants of ATHB17Δ113 were generated. Variant ATHB17Δ113-C243S-C246S exhibited a reduction in the binding affinity to BS2 (Table 3).

In addition, variant ATHB17Δ113-C200A-C243S-C246S, which also contained a mutation of the cysteine at position $a_1$ of the leucine zipper (C200A), completely lost the ability to bind DNA (Table 3). This observation suggests that cysteine-200 is critical in stabilizing the structural organization of the leucine zipper, thereby enabling dimer ATHB17Δ113 to efficiently bind to cognate DNA targets.

Example 8: Effect of Loss-of-Function Mutations in ATHB17 on Transgenic Rice and Corn Transgenic rice plants comprising ATHB17 loss-of-function variants were generated using methods known in the art, and tested in an automated greenhouse for total seed weight under standard conditions. In one experiment, the results in Table 4 show that three variants (ATHB17-C243S-C246S, ATHB17-R190K and ATHB17Δ73-C243S-C246S) had significant increase in total seed weight compared to the control plants.

TABLE 4

Total seed weight of transgenic rice with HD-Zip class II variants.

| Crop | Polypeptide SEQ ID NO: | Gene Name | Mean Construct Effect (% over control) |
|---|---|---|---|
| Rice | 70 | ATHB17-C243S-C246S | 39.6* |
| Rice | 71 | ATHB17-R190K | 32.8* |

TABLE 4-continued

Total seed weight of transgenic rice with HD-Zip class II variants.

| Crop | Polypeptide SEQ ID NO: | Gene Name | Mean Construct Effect (% over control) |
|---|---|---|---|
| Rice | 74 | ATHB17Δ73-C243S-C246S | 30.9* |
| Rice | 72 | ATHB17-Δ138-195 | 12.5 |
| Rice | 107 | Zmhdz18Δ45 | 3.9 |
| Rice | 73 | ATHB17-F155L | 3.9 |

*Significant at $p \leq 0.1$

In a second experiment, three of the top performing variants from Table 4 were tested under standard conditions. Eighteen transgene-positive and eighteen transgene-negative plants were sown for each construct, but only three events per construct were selected for evaluation. The results shown in Table 5 represent total weight of seeds per plant based on the overall effect of the three selected events. At construct level, transgenic plants comprising ATHB17-R190K or ATHB17-C243S-C246S had neutral total seed weight, whereas transgenic plants comprising ATHB17Δ73-C243S-C246S showed a significantly increase in total seed weight.

TABLE 5

Total seed weight of transgenic rice with HD-Zip II variants.

| Crop | Polypeptide SEQ ID NO: | Gene Name | Mean Construct Effect (% over control) | p-Value |
|---|---|---|---|---|
| Rice | 74 | ATHB17Δ73-C243S-C246S | 24.9 | 0.01 |
| Rice | 71 | ATHB17-R190K | -7.7 | 0.4 |
| Rice | 70 | ATHB17-C243S-C246S | -5.4 | 0.5 |

Transgenic corn plants comprising ATHB17 loss-of-function variants were also generated using methods known in the art, and tested in the field for broad acre yield each with about 4-5 locations. The results are summarized in Table 6. Most of the events for the variants showed neutral yield. However, several events from a few variants had statistically significant decreased yield.

TABLE 6

Broad acre yield of transgenic corn plants with ATHB17 variants.

| Crop | SEQ ID NO: | Gene_Name | Event Name | Delta | Perc | p_Value |
|---|---|---|---|---|---|---|
| Corn | 252 | ATHB17_Δ73_L11A_L13A | 281 | 2.1 | 1.07 | 0.8 |
| | | | 364 | 0.4 | 0.20 | 0.96 |
| | | | 401 | -3.3 | -1.63 | 0.71 |
| | | | 48 | -18.5 | -9.21 | 0.05 |
| Corn | 253 | ATHHB17_L84A_L86A | 386 | -7.3 | -3.65 | 0.4 |
| | | | 389 | -9.3 | -4.63 | 0.28 |
| | | | 583 | -10.2 | -5.08 | 0.24 |
| | | | 606 | -4.3 | -2.14 | 0.62 |
| Corn | 254 | ATHB17_Δ1-21 | 712 | -3 | -1.58 | 0.74 |
| | | | 796 | 3.5 | 1.84 | 0.72 |
| | | | 756 | -15.1 | -7.95 | 0.1 |
| | | | 719 | -0.8 | -0.43 | 0.93 |
| | | | 701 | -3.7 | -1.93 | 0.69 |
| | | | 755 | -5.3 | -2.80 | 0.56 |
| | | | 792 | -17.9 | -9.42 | 0.05 |

TABLE 6-continued

Broad acre yield of transgenic corn plants with ATHB17 variants.

| Crop | SEQ ID NO: | Gene_Name | Event Name | Delta | Perc | p_Value |
|---|---|---|---|---|---|---|
| | | | 758 | −7.7 | −4.06 | 0.42 |
| | | | 747 | −12.8 | −7.10 | 0.18 |
| Corn | 255 | ATHB17_R138A_R142A | 578 | −3.3 | −1.84 | 0.71 |
| | | | 586 | −5.9 | −3.26 | 0.51 |
| | | | 597 | −8.3 | −4.62 | 0.41 |
| | | | 596 | −7.8 | −4.33 | 0.39 |
| | | | 583 | −0.2 | −0.11 | 0.98 |
| | | | 875 | −4.1 | −2.24 | 0.67 |
| | | | 576 | −2.8 | −1.53 | 0.78 |
| Corn | 256 | ATHB17_Δ1-91 | 801 | −9.6 | −4.77 | 0.07 |
| | | | 48 | −26.4 | −13.06 | 0 |
| | | | 49 | −11.6 | −5.73 | 0.06 |
| | | | 640 | −23.3 | −11.56 | 0 |
| | | | 971 | −9.3 | −4.61 | 0.1 |
| | | | 682 | −8.8 | −4.35 | 0.48 |
| Corn | 257 | ATHB17_T196A_L203A_L210A_L217A_L224A | 684 | −9.1 | −3.84 | 0.04 |
| | | | 702 | −3.9 | −1.64 | 0.41 |
| | | | 697 | 7.3 | 3.06 | 0.13 |
| | | | 726 | −0.6 | −0.26 | 0.9 |
| | | | 316 | −1.9 | −0.81 | 0.68 |
| | | | 311 | −3.5 | −1.47 | 0.44 |
| | | | 324 | 0.7 | 0.29 | 0.87 |
| | | | 320 | 4.3 | 1.80 | 0.34 |
| Corn | 73 | ATHB17-F155L | 932 | −4.9 | −3.22 | 0.4 |
| | | | 934 | 3.9 | 2.55 | 0.5 |
| | | | 184 | −6.3 | −4.11 | 0.28 |
| | | | 943 | −1.8 | −1.18 | 0.76 |
| | | | 200 | 1.6 | 1.03 | 0.8 |
| | | | 963 | −5.1 | −3.32 | 0.39 |
| | | | 173 | −3.8 | −2.52 | 0.51 |
| | | | 936 | 1.7 | 1.13 | 0.76 |
| Corn | 71 | ATHB17-R190K | 864 | 2.5 | 1.04 | 0.58 |
| | | | 271 | 1.9 | 0.81 | 0.69 |
| | | | 850 | −4.2 | −1.77 | 0.35 |
| | | | 288 | 4.6 | 1.93 | 0.3 |
| | | | 854 | −19.8 | −8.32 | 0 |
| | | | 857 | −36.6 | −15.37 | 0 |
| | | | 855 | −1.3 | −0.53 | 0.78 |
| | | | 858 | 10.4 | 4.36 | 0.02 |
| Corn | 258 | ATHB17_Δ194_224 | 447 | −2.1 | −1.03 | 0.73 |
| | | | 454 | −6 | −2.93 | 0.33 |
| | | | 47 | 1.2 | 0.60 | 0.84 |
| | | | 449 | −11.7 | −5.67 | 0.07 |
| | | | 456 | −8.5 | −4.14 | 0.17 |
| | | | 457 | −3.6 | −1.74 | 0.56 |
| | | | 43 | −6.7 | −3.27 | 0.28 |
| Corn | 259 | ATHB17_Δ138-195 | 316 | −6.1 | −2.55 | 0.23 |
| | | | 312 | −11.2 | −4.72 | 0.01 |
| | | | 265 | −29.1 | −12.22 | 0 |
| | | | 640 | −11 | −4.62 | 0.01 |
| | | | 644 | −2.7 | −1.15 | 0.57 |
| | | | 266 | −10.2 | −4.28 | 0.03 |
| | | | 311 | −4.6 | −1.95 | 0.3 |
| | | | 320 | 4 | 1.70 | 0.4 |
| Corn | 70 | ATHB17-C243S-C246S | 167 | −2.9 | −1.41 | 0.64 |
| | | | 192 | 1.8 | 0.87 | 0.77 |
| | | | 187 | −8.7 | −4.21 | 0.18 |
| | | | 621 | 5.2 | 2.52 | 0.4 |
| | | | 170 | 1 | 0.50 | 0.87 |
| | | | 169 | −0.1 | −0.04 | 0.99 |
| | | | 620 | 0.1 | 0.05 | 0.98 |
| | | | 204 | −5.6 | −2.69 | 0.37 |

Example 9: Identifying Phenotypic Changes in Corn Plants Expressing ATHB17Δ113

Corn plants expressing ATHB17Δ113 were assayed to identify phenotypic changes. Field studies were conducted in Illinois, USA in both 2011 and 2012. The studies were established in a randomized complete block design with 10 replications with two testers blocked separately in 2011, and in a GUBD (two testers randomly blocked within trial) with 18 replications in 2012. Three 2-row plots for a total of 6 rows blocked together for each entry was considered an experimental unit for the study. Agronomic practices used to prepare and maintain each study site were characteristic of the region. Maintenance pesticides were applied as needed and all maintenance operations were performed uniformly over the entire production area at a given site.

Biomass samples were collected at the R1 growth stage. In 2011, 10 plants from a given area were harvested and the area measured, while in 2012 all plants from a 1-m row were sampled and plant number counted. Plants were removed by cutting the stalk at soil level, separated into leaf blades, stalks with leaf sheaths, and ear shoots (with husk and shank) and then dried at 70° C. until constant weight was achieved. Components were reported individually and summed for stover (leaves and stalks) and total (stover and ear shoot) biomass. Data from 2011 were presented as $g/m^2$, while the data from 2012 were converted via covariate analysis into plant number adjusted $g/m^2$. The ratio of ear weight to total weight was calculated at R1 to determine early partitioning to the developing ear.

As shown in Table 2, both transgenic corn events expressing ATHB17Δ113 had significantly increased ear dry weight, and the calculated ear partitioning coefficiencies.

Example 10: Identifying Staygreen Phenotype in Corn Plants Expressing ATHB17Δ113

Corn plants expressing ATHB17Δ113 were assayed to identify plants exhibiting a staygreen (or alternatively termed delayed senescence) phenotype. Starting at R5 and then approximately weekly thereafter, the number of green leaves showing at least 50% of its area green below the ear (ear leaf included) were visually assessed and counted on 10 plants per plot.

The staygreen phenotype was observed consistently in corn plants expressing ATHB17Δ113 in different testers with different planting dates over a two year period when this phenotype was tested, even though the results were not always statistically significant.

Example 11: Identifying HD-Zip Class II Transcript Levels Across Corn Tissues

Various corn tissues at different development stages were analyzed for the expression of HD-Zip class II transcripts. Tissue samples were collected from plants grown in the field at various developmental timepoints. RNA was extracted and the transcript expression of 18 HD-Zip class II genes was analyzed. For normalization, the mean expression level for a housekeeping gene was computed across all samples (3 entries×3 replicates). Then a correction/normalization factor was obtained by dividing mean of housekeeping gene by each individual median fluorescence intensity (MFI) of housekeeping gene (Asparaginase). This correction/normalization factor was multiplied with each individual background subtracted MFI for each "trait" (datapoint within that tissue type) and then Log 2 transformed to get the final normalized values for each trait.

Figure 7A:
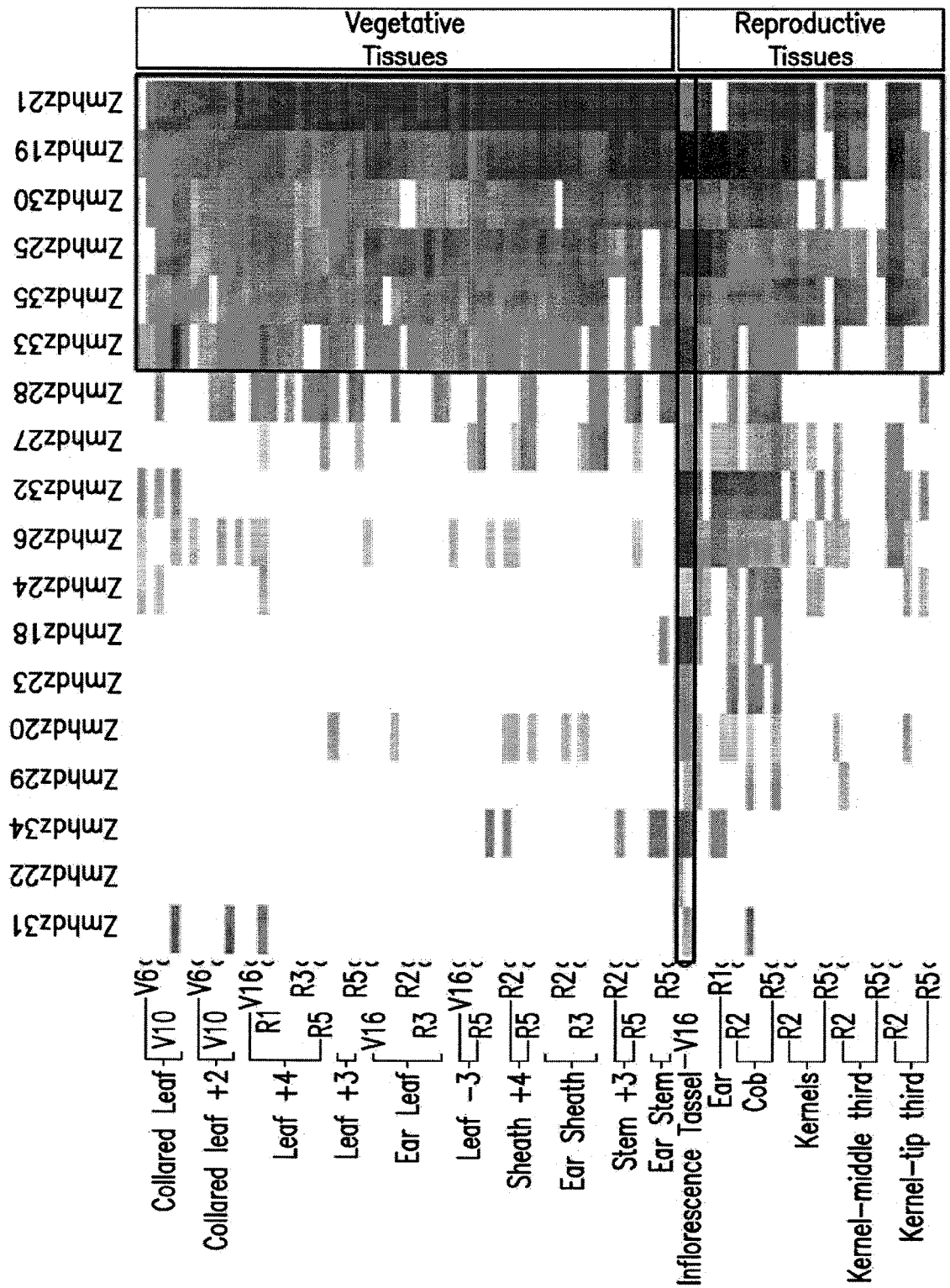
FIGS. 7A-7C—Shows expression levels of corn HD-Zip class II genes across tissues and developmental stages in two hybrids of corn.
Figure 7B:
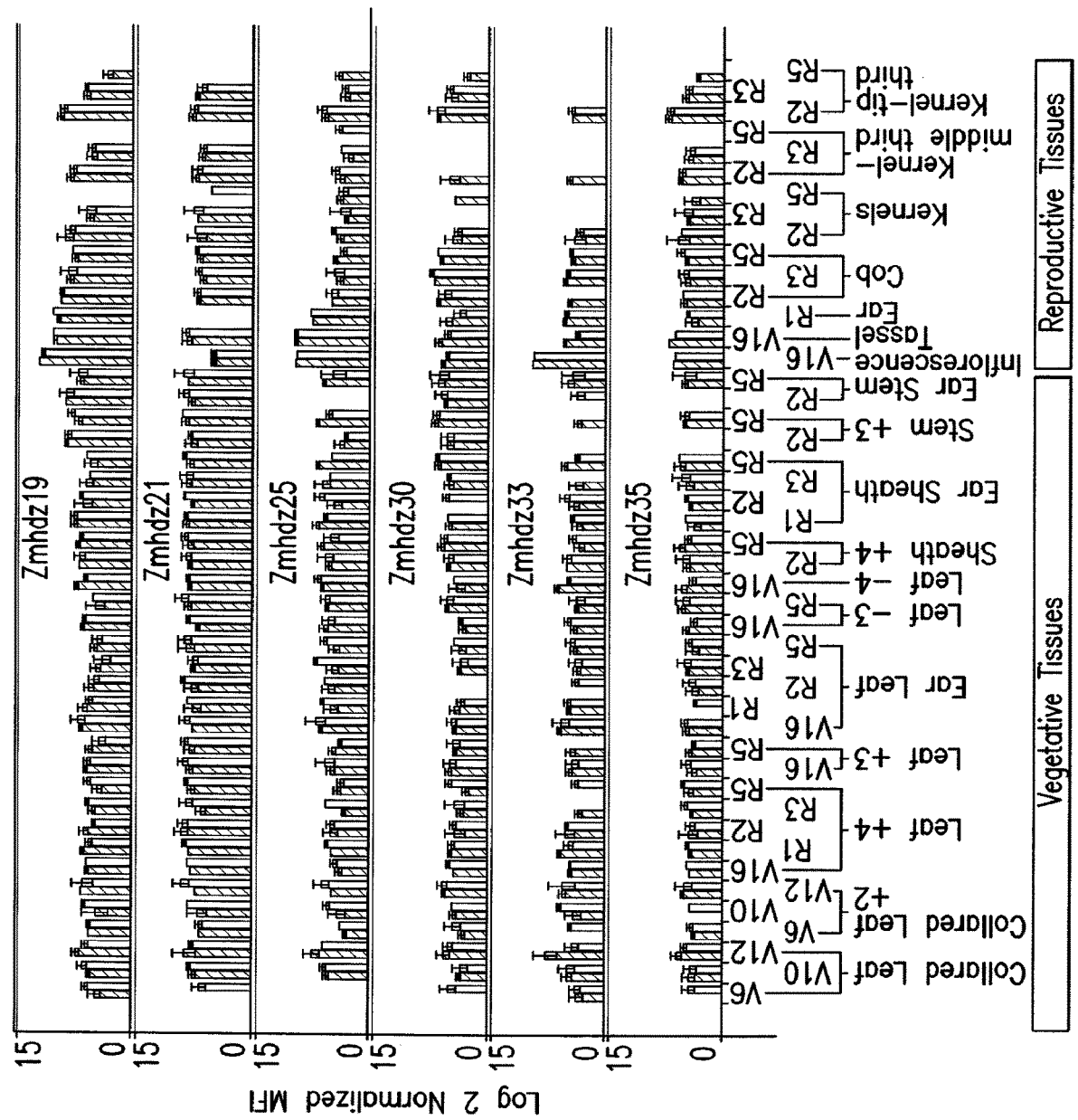
Figure 7C:
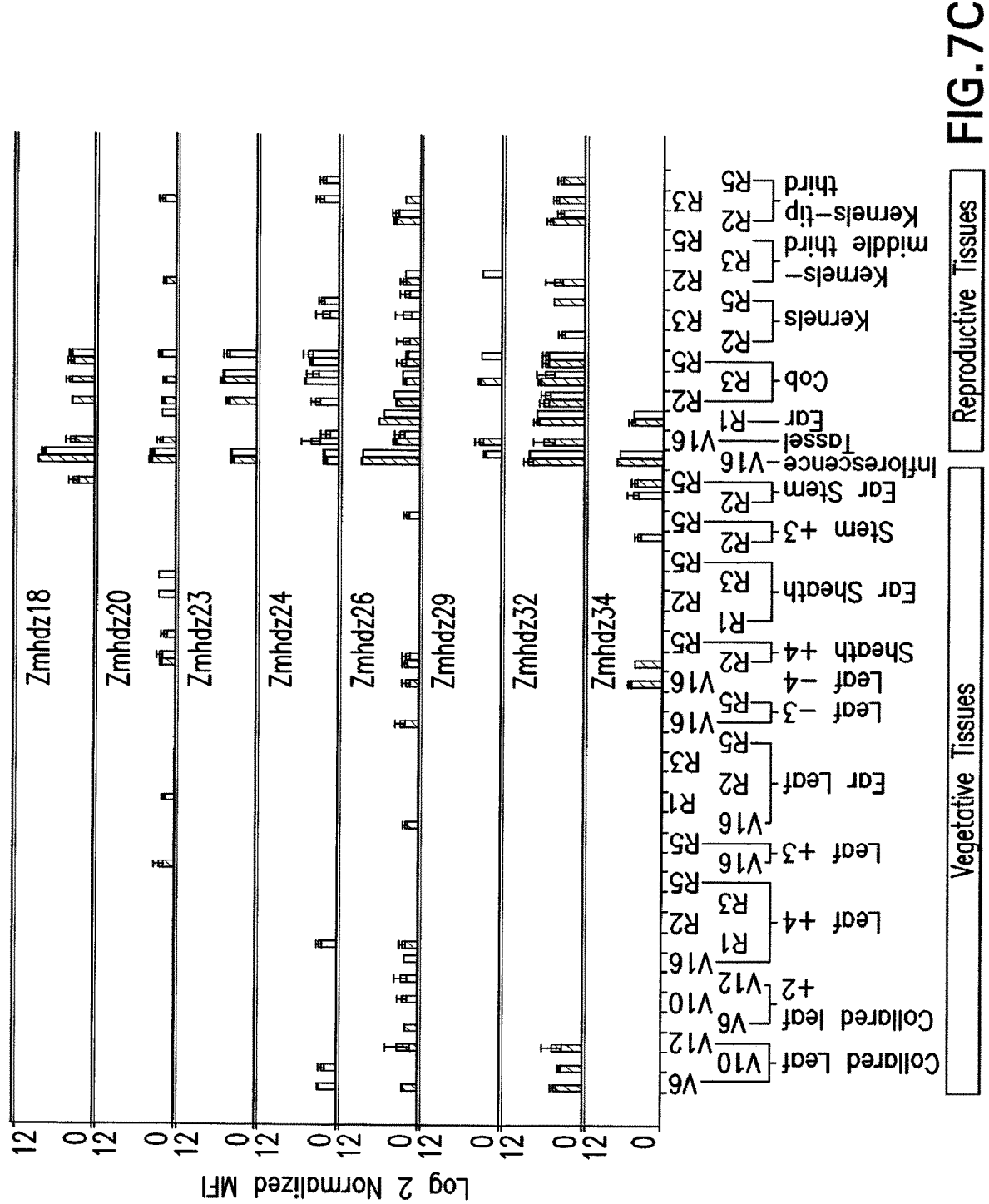

The results of the transcript levels of the corn endogenous HD-Zip II genes are presented in FIG. 7. The heat map in FIG. 7A represents expression of the genes relative to housekeeping genes in the respective tissues and developmental stages. The grey color gradient shows expression values represented on a Log 2 scale normalized MFI; a darker shade indicates a higher expression level. White color represents that expression was below background. The six genes with the highest expression in a given tissue (Zmhdz19, 21, 25, 30, 33 and 35) and the tissue in which each gene is most highly expressed (inflorescence) are boxed. FIG. 7B shows expression levels for Zmhdz19, 21, 25, 30, 33 and 35 in an additional tissue and additional developmental stages in both hybrids. Eight HD-Zip II genes (Zmhdz18, 20, 23, 24, 26 29, 32 and 34) were predominantly expressed in reproductive tissues; FIG. 7C shows expression levels for these genes in additional an additional tissue and additional developmental stages in both hybrids. In FIGS. 7B and 7C, the expression level in one hybrid is shown in black and the other in grey.

Example 12: Phenotypic Evaluation of Corn HD-Zip Class II Transgenic Plants

Figure 8A:
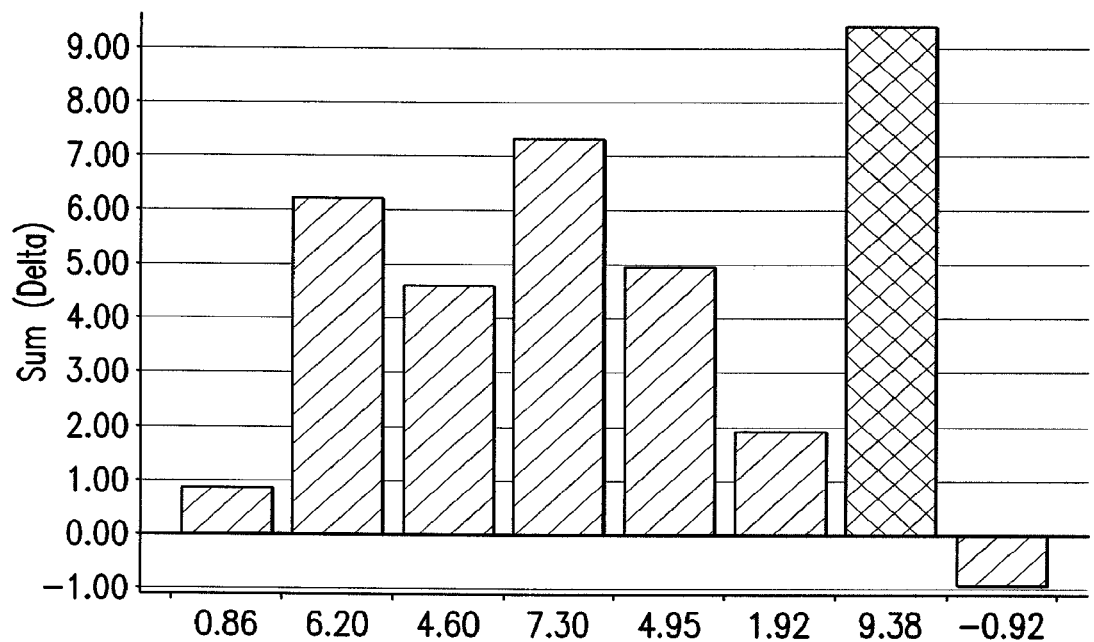
FIG. 8—Shows yield performance in a field of transgenic corn plants comprising the loss-of-function variant Zmhdz25Δ59 (A) and variant Zmhdz18Δ45 (B).
Figure 8B:
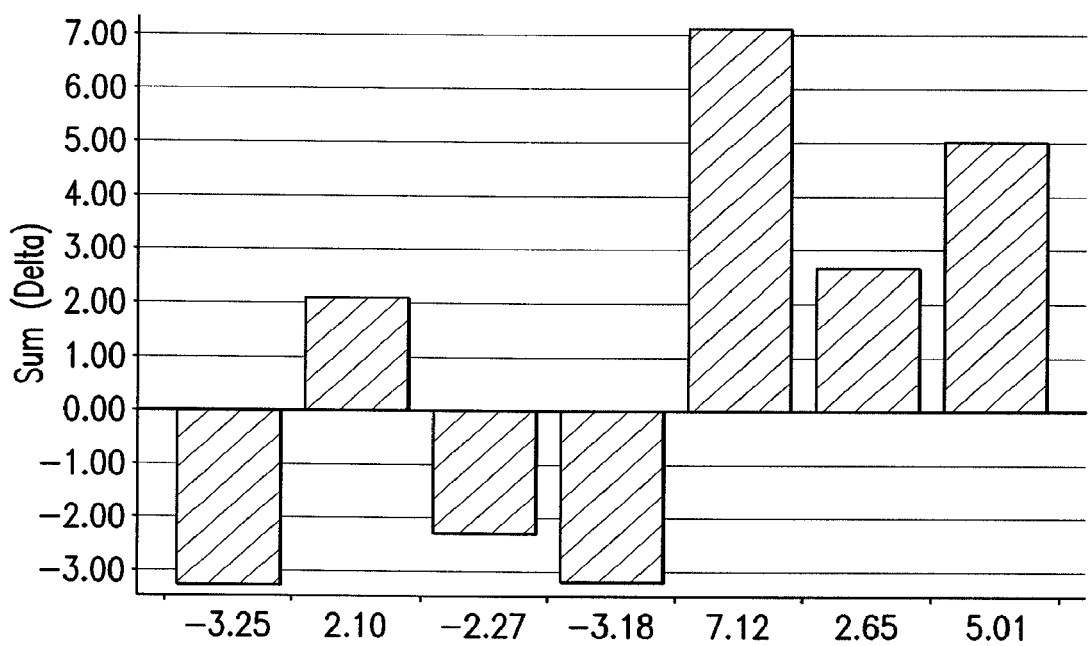

Transgenic corn plants from the loss-of-function variants of two corn HD-Zip class II proteins were generated as described in Example 1 and tested for yield in the field. These variants contained an N-terminal truncation (Zmhdz25Δ59, SEQ ID NO:113 and Zmhdz18Δ45, SEQ ID NO:107), that resulted in partial removal of the repression domain (FIG. 4). Eight events for Zmhdz25D59 and seven events for Zmhdz18D45 were tested in a low power 18-location/2-replication broad acre yield trial under standard agronomic practices. Most events showed neutral yield compared to the control, while one event of Zmhdz25Δ59 showed statistically significant increase in yield (p<0.2) (FIGS. 8A and B).

In another experiment, transgenic corn plants from the N-terminal truncation variants of two corn HD-Zip II proteins were tested for yield in the field: Zmhdz29Δ59, SEQ ID NO:114 and Zmhdz18Δ45, SEQ ID NO:107. Six events were tested in a 6-location broad acre yield trial under standard agronomic practices. Most events showed neutral yield compared to the wild type control, while two Zmhdz18Δ45 events and three Zmhdz29Δ59 events had a statistically significant decrease in yield (p<0.2) (Table 7).

TABLE 7

Broad acre yield of transgenic corn plants with corn HD-Zip II variants.

| Crop | SEQ ID NO: | Event Name | Mean Delta | % Delta | p-Value |
|---|---|---|---|---|---|
| Corn | 107 | 433 | −12.3116 | −5.9 | 0.0483 |
|  |  | 916 | −4.9484 | −2.4 | 0.4241 |
|  |  | 998 | −6.1419 | −2.9 | 0.3227 |
|  |  | 911 | −12.7313 | −6.1 | 0.0409 |
|  |  | 434 | 1.4138 | 0.7 | 0.8182 |
|  |  | 439 | −7.4109 | −3.5 | 0.2347 |
| Corn | 114 | 174 | −1.7264 | −0.8 | 0.795 |
|  |  | 182 | −4.3246 | −2.1 | 0.5225 |
|  |  | 181 | −3.5733 | −1.7 | 0.5622 |
|  |  | 179 | −12.2794 | −5.9 | 0.0483 |
|  |  | 198 | −11.8002 | −5.6 | 0.0581 |
|  |  | 194 | −13.7031 | −6.5 | 0.0276 |

Transgenic rice plants comprising corn HD-Zip class II loss-of-function variants were also produced using methods known in the art, and tested in an automated greenhouse for total seed weight. In experiment one, three corn IID-Zip class II variants with partial truncation in the repression domain were tested under non-stress conditions along with ATHB17Δ113. The results in Table 8 show that while the total seed weight was neutral for Zmhdz33Δ94 and Zmhdz31Δ64, it trended positive for ATHB17Δ113 and Zmhdz35Δ76 compared to the control plants.

TABLE 8

Total seed weight of transgenic rice with corn HD-Zip class II truncation variants.

| Crop | Experiment | Polypeptide SEQ ID NO: | Name Gene | Mean Construct Effect (% over control) |
|---|---|---|---|---|
| Rice | 1 | 59 | ATHB17Δ113 | 18.3 |
| Rice | 1 | 123 | Zmhdz35Δ76 | 14.7 |
| Rice | 1 | 129 | Zmhdz33Δ94 | 8.6 |
| Rice | 1 | 115 | Zmhdz31Δ64 | 6.5 |
| Rice | 2 | 123 | Zmhdz35Δ76 | 10.5* |

*p = 0.05

In another experiment, Zmhdz35Δ76 plants were tested under standard conditions. Eighteen transgene-positive and eighteen transgene-negative plants were sown, but only three events were selected for evaluation. The results shown in Table 8 represent total weight of seeds per plant based on the overall effect of the three selected events. At the construct level, the transgenic plants showed significant increase in total seed weight at p-value of 0.05.

Example 13: TALEN-Mediated Site Directed Genome Modification to Alter Endogenous Regulation This example describes an example of TALEN-mediated site directed genome modification in the promoter region of a corn endogenous HD-Zip class II gene, Zmhdz34 (SEQ ID NO:17), to illustrate generation of mutations in the endogenous genes for altered gene expression. Those skilled in the art can use the same or similar techniques/methods to introduce mutations in the promoter or coding region of this or other endogenous HD-Zip class II genes to alter their expression.

Figure 9:
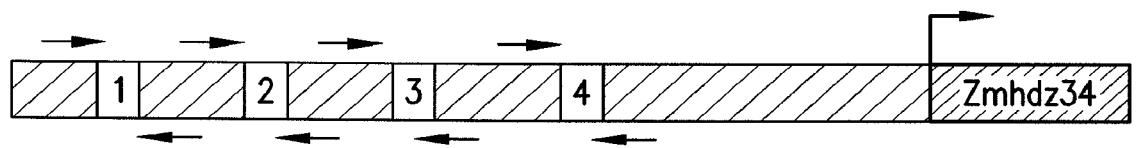
FIG. 9—Shows a schematic representation of the upstream promoter region of Zmhdz34 (SEQ ID NO:17) for TALEN-mediated mutation. Boxes 1 and 2 represent class I DNA binding sites, and Boxes 3 and 4 present class II DNA binding sites used as targets for mutations; the inverted arrow pairs represent pairs of DNA binding sequences.

TALENs are artificial restriction enzymes generated by fusing a TALE DNA binding domain to a DNA cleavage domain. To mutate a specific site, TALEN pairs are designed and engineered to target and cut DNA at the specific site. TALEN target sites are selected comprised of two appropriately oriented TALE binding sites of 19 to 25 bases each, separated by spacer of about 22 bases containing the target site to be mutated. Zmhdz34 gene contains two class II DNA binding sites and two class I DNA binding sites in the ~3 kb upstream promoter region of the gene (FIG. 9). Mutations in the class II or class I DNA binding sites will interfere with the binding of endogenous HD-Zip class II proteins to these sites, including the binding of Zmhdz34 to its promoter. This may lead to a relief in the transcriptional repression caused by Zmhdz34 and/or other endogenous HD-Zip II proteins. Table 9 shows DNA sequences for TALEN pairs and a spacer sequence that may be used to introduce mutations in each of the class I or class II DNA sites. Based on the sequences listed in Table 9, TALENs that comprise the appropriate Repeat Variable Diresidues (RVDs) that bind desired sites can be synthesized by commercial sources, e.g. Life Technologies. Other mutations in the promoter region can also be designed similarly.

Once the TALENs are synthesized, they can be constructed into a plant transformation vector using methods known in the art. Such plant transformation vectors contain two TALEN expression cassettes and a selectable marker cassette. Each cassette may comprise from 5' to 3' a promoter that is functional in plant cells and operably linked to a leader, operably linked to an intron (for monocot transformation vector), that is operably linked to a coding sequence (for a TALEN protein or a selectable marker), operably linked to a 3' UTR.

The plant transformation vectors are introduced into plants by, e.g., Agrobacterium-mediated transformation using methods known in the art. The introduced DNA constructs produce an endonuclease that cleaves the DNA of an endogenous HD-Zip class II gene at the target site, leading to disruption or down-regulation of expression of the gene.

Following selection and regeneration, regenerated events can be screened to identify events with specific mutations using methods well known in the art, such as by DNA sequencing, by PCR with fluorescent oligonucleotides for analysis of fragment length, by measuring transcript levels of Zmhdz34, by the TILLING, or by using SURVEYOR® mutation detection kits.

TABLE 9

TALEN target sequences in the 3 Kb upstream promoter region of Zmhdz34.

TALEN Target Sequence

| Target Site | TALE Binding Site 1 | SEQ ID NO: (5' to 3') | TALEN Spacer Sequence | SEQ ID NO: (5' to 3') | TALE Binding Site 2 | SEQ ID NO: (5' to 3') |
|---|---|---|---|---|---|---|
| 1 | Tagagacacttaa atgctcaaaaat | 80 | cactc*aatgatt*agcgtagat | 81 | Taattaatctaag cactcacaaagt | 82 |
| 2 | Tgaggtgcaatac gcgttatctaag | 83 | ttcaagt*aataatt*agctag | 84 | Tatccaaacattt ttagataataga | 85 |
| 3 | Ttggttggtacca actcga | 86 | aaagcc*aatcatt*ccttcatg | 87 | Tcgcagcacgtag gagcagtg | 88 |
| 4 | Tgcaccaattaag gagcccgccccc | 89 | acaagtt*aatgatt*gctgtccc | 90 | Ttcacacatacgt acgtagtttctg | 91 |

Similar mutations in the promoter regions of other corn HD-Zip class II proteins can also be induced to alter their expression. The mutations can be made in the class I or class II DNA site of these genes. The sequences of the class I and class II DNA binding sites, and methods for identifying these sites in the upstream promoter regions of genes are known in the art. Transformation vectors can also be designed and constructed to target mutations in the promoter regions other than in the class II and class I DNA binding sites, and in the coding sequences of the HD-Zip class II. Transformation, selection and regeneration of plants, and screening of plant can be performed as described above. Sequences of the upstream promoter regions for the 18 corn HD-Zip class II genes were identified and are presented in Table 10.

TABLE 10

Upstream promoter sequences of corn HD-Zip class II genes.

| Polynucleotide SEQ ID NO: | Promoter_Gene Name |
|---|---|
| 37 | Promoter_Zmhdz18 |
| 38 | Promoter_Zmhdz19 |
| 39 | Promoter_Zmhdz20 |
| 40 | Promoter_Zmhdz21 |
| 41 | Promoter_Zmhdz22 |
| 42 | Promoter_Zmhdz23 |
| 43 | Promoter_Zmhdz24 |
| 44 | Promoter_Zmhdz25 |
| 45 | Promoter_Zmhdz26 |
| 46 | Promoter_Zmhdz27 |
| 47 | Promoter_Zmhdz28 |
| 48 | Promoter_Zmhdz29 |
| 49 | Promoter_Zmhdz30 |
| 50 | Promoter_Zmhdz31 |
| 51 | Promoter_Zmhdz32 |
| 52 | Promoter_Zmhdz33 |
| 53 | Promoter_Zmhdz34 |
| 54 | Promoter_Zmhdz35 |

Example 14: Suppression of Endogenous HD-Zip Class II Gene Expression by miRNA

Various methods and techniques for gene suppression are described in the art. This example describes a non-limiting approach to suppress a corn endogenous HD-Zip gene, Zmhdx26, using engineered microRNA (miRNA) merely to illustrate one embodiment of the present disclosure.

DNA molecule encoding an engineered "miRZmhdz26" miRNA precursor (SEQ ID NO:77) is designed and derived from a corn miR159a precursor molecule having the native sequence of SEQ ID NO:75. The corn miR159a precursor molecule has the following sequence:

```
                                          (SEQ ID NO: 75)
GCATCTGCTGTTCTTTATTTCTATACATACATATATACTATCATCGGTTAT

TTGCTTCTCTATTCTGTCCGAGTACTTTACGGTGTTCCGCACATAGATCTC

GTGGCCGGCTGTTTTGCGCTTTCGCTTGCGTTTCTTGGCCCTGCTGGTGTT

GACCGGTCCGAACGGGGCAGATCGATGCTTTGGGTTTGAAGCGGAGCTCC

TATCATTCCAATGAAGGGTCGTTCCGAAGGGCTGGTTCCGCTGCTCGTTCA

TGGTTCCCACTATCCTATCTCATCATGTGTATATATGTAATCCATGGGGA

GGGTTTCTCTCGTCTTTGAGATAGGCTTGTGGTTTGCATGACCGAGGAGCT

GCACCGCCCCCTTGCTGGCCGCTCTTTGGATTGAAGGGAGCTCTGCATCCT

GATCCACCCCTCCATTTTTTTTGCTTGTTGTGTCCTTCCTGGGACCTGAGA

TCTGAGGCTCGTGGTGGCTCACTGTAG,
``` where nucleotides of the mature miRNA (SEQ ID NO:76) are indicated by bold underlined text at nucleotide positions 382 to 402 of SEQ ID NO:75.

The engineered "miRZmhdz26" miRNA precursor has the following sequence:

```
GCATCTGCTGTTCTTTATTTCTATACATACATATATACTATCATCGGTTAT

TTGCTTCTCTATTCTGTCCGAGTACTTTACGGTGTTCCGCACATAGATCTC

GTGGCCGGCTGTTTTGCGCTTTCGCTTGCGTTTCTTGGCCCTGCTGGTGTT

GACCGGTCCGAACGGGGCAGATCGATGCTTTGGGTTTGAAGACTGGAGGA

GCGCTGCAAGGCGAAGGGTCGTTCCGAAGGGCTGGTTCCGCTGCTCGTTCA

TGGTTCCCACTATCCTATCTCATCATGTGTATATATGTAATCCATGGGGA

GGGTTTCTCTCGTCTTTGAGATAGGCTTGTGGTTTGCATGACCGAGGAGCT

GCACCGCCCCCTTGCTGGCCGCTCTCCTTGAAGCTCTCCTCCAGTCATCCT

GATCCACCCCTCCATTTTTTTTGCTTGTTGTGTCCTTCCTGGGACCTGAGA

TCTGAGGCTCGTGGTGGCTCACTGTAG,
``` where nucleotides of the mature miRNA ("miRZmhdz26") are indicated by bold underlined text at nucleotide positions 382-402 of SEQ ID NO: 77 and nucleotides of the corresponding opposite strand designated miRNA* ("miRZmhdz26*") are indicated by italicized underlined text at nucleotide positions 196 to 216 of SEQ ID NO:77. This miRZmhdz26 precursor is processed in planta to an artificial "miRZmhdz26" mature miRNA, which has the sequence (in 5' to 3' direction) TCCTTGAAGCTCTCCTCCAGT (SEQ ID NO: 78, alternatively written in 3' to 5' direction as TGACCTCCTCTCGAAGTTCCT), and which suppresses the corn endogenous gene, Zmhdz26 (SEQ ID NO:9). Zmhdz26 has the following sequence:

```
                                          (SEQ ID NO: 9)
ATGGAGCTGGGGCTGAGCCTGGGCGACGCGGCAGTGCCGGACGCCGGCAGG

GCGGCTCCGGAGCTGGGCCTGGGGCTTGGGGTCGGGATTGGATCCAACGCC

GCCGGAACCGGCAGGGGAAGCAAGGCGGCGGGGACGACGGGAACTACTGGG

TGGTGGGCGGCGCCGGCCACACCGGAGTCGGCAGTGCGGCTCAGCCTCGTG

TCCAGCCTCGGCCTTCAGTGGCCACCTCCGGACGGCGGCATCTGTCATGTA

GGGCGCGACGAGGCGCCGGCGCGCGGCTTCGACGTGAACCGGGCGCCGTCG

GTGGCGGGGAGCGCCCTGGCGCTGGAGGATGACGAGGAGGAGCCGGGCGCC

GCGGCACTGTCGTCGTCGCCCAACGACAGCGCGGGCTCCTTCCCGCTGGAC

CTGGGAGGCCCACGCGCCCACGCCGAGGGCGCCGCGGCGCGGGCCGGCGGC

GAGCGGTCCTCGTCTCGCGCCAGCGATGAGGACGAGGGCGCGTCCGCGCGC

AAGAAGCTGCGCCTCTCCAAGGAGCAGTCTGCGTTCCTGGAGGAGAGCTTC

AAGGAGCACAGCACCCTCAACCCTAAGCAGAAGGCGGCGCTGGCGAAGCAG

CTCAACCTCCGGCCGCGACAGGTAGAAGTCTGGTTCCAGAACCGCCGAGCC

AGGACGAAGCTGAAGCAGACGGAGGTGGACTGCGAGTACCTGAAGCGCTGC

TGCGAGACGCTGACGGAGGAGAACCGGCGGCTGCACAAGGAGCTCGCGGAG

CTGCGCGCGCTCAAGACGGCGCCGCCCTTCTTCATGCGCCTCCCGGCCACC

ACCCTCTCCATGTGCCCCTCCTGCGAGCGCGTCGCCTCCGGCCCCAGCCCT

GCCTCCACCTCGGCACCTGCGTCGTCCACGCCGCCTGCCACAGCCGCCACC
```

-continued

ACCGCCATCTCGTACGCTGCAGCAGCCGCCGCACCCGTGCGAGCCGACCAC

CGGCCCTCGTCGTTCGCCGCGCTGTTCGCGGCGACCCGCAGCTTCCCGCTG

GCGTCCCAGCCGCGGCCGCCCGCGCCGGCGAGCAACTGCCTGTAG, which includes a miRNA recognition site having the sequence CCTGGAGGAGAGCTTCAAGGA (SEQ ID NO:79) and which is also indicated by the bold underlined text at nucleotide positions 546-566 of SEQ ID NO:9.

Recombinant DNA constructs comprising the above described DNA molecule are prepared using methods well known in the art. The recombinant DNA construct may comprise an expression cassette encoding the engineered miRNA precursor, which is under the control of an operably linked promoter, a leader and an intron (for corn transformation vector), and a 3' UTR. It may also comprise a selectable marker cassette. The recombinant DNA construct is introduced into a plant or plant cells by, e.g., *Agrobacterium*-mediated transformation or particle bombardment.

Following selection and regeneration of transformation plants, transgenic plants are analyzed by methods well known in the art, such as by northern blot and PCR for transcript, or by western blot for protein levels. Alternatively, transgenic plants are screen for altered phenotypes.

Example 15: Corn HD-Zip Class II Loss-of-Function Variants

Loss-of-function variants in each of the domains or motifs of corn HD-Zip class II proteins are generated, individually or in combination, by comparison with the sequences of the identified ATHB17 protein variants as described in the previous sections, and/or with the known variants of mammalian HD and other plant HD-Zip transcription factors. The mutations include, but are not limited to, amino acid substitutions or deletions in the N-terminus, EAR or EAR-like motifs in the repression domain or in other domains, HD domain, leucine zipper domain and the CXXCX-like motif-containing C terminus. Exemplary variants are shown in Table 11. These variants can be produced individually or in different combinations to generate additional variants.

Mutations can be introduced into the coding sequences of HD-Zip class II proteins in vitro, e.g., by in vitro DNA synthesis or PCR-based site-directed mutagenesis. Genetically engineered coding sequences are then cloned into plant expression vectors by standard techniques and introduced into plants by, e.g. *Agrobacterium*-mediated transformation, followed by selection and regeneration of transgenic plants using various methods known in the art. Transgenic plants can be screened for the phenotypes disclosed in the present disclosure.

The same or similar mutations can also be introduced into corn endogenous HD-Zip class II proteins using various genome editing technologies such as TALENs as described in Example 13, and other methods known in the art.

TABLE 11

Exemplary mutation variants of corn HD-Zip class II proteins in different domains/motifs.

| Gene | SEQ ID NO: | N-Terminal Deletion* | EAR-Like Motif Mutation** | Homeodomain Mutation | Leucine Zipper Mutation | CXXCX-Like Motif Mutation |
|---|---|---|---|---|---|---|
| Zmhdz18 | 19 | d1-12; d1-40; d1-45; d1-59 | L9A/L11A | V123A/Q126A/N127A | T137A/L144A/L151A/L158A/L165A | C192S/C195S |
| Zmhdz19 | 20 | d1-59; d1-65; d1-67 | L9A/L11A/L13A/L15A/L17A/L19A | V158A/Q161A/N162A | T172A/L179A/L186A/L193A/L200A | C225S/C228S |
| Zmhdz20 | 21 | d1-87; d1-124 | L8A/L10A/L12A | V204A/Q207A/N208A | T218A/L225A/L232A/L239A/L246A | C268S/C271S |
| Zmhdz21 | 22 | d1-15; d1-54 | L6A/L8A/L10A/L12A/L14A | V126A/Q129A/N130A | T140A/L147A/L154A/L161A/L168A | C187S/C190S |
| Zmhdz22 | 23 | d1-28; d-1-68 | L18A/L20A > L166A/L168A/L170A | V131A/Q134A/N135A | T145A/L152A/L159A/L166A/L173A | C203S/C206S |
| Zmhdz23 | 24 | d1-20; d1-59 | L11A/L13A > L166A/L168A/L170A | V131A/Q134A/N135A | T145A/L152A/L159A/L166A/L173A | C204S/C207S |
| Zmhdz24 | 25 | d1-47; d1-86 | L31A/L33A > L244A/L246A | V177A/Q180A/N181A | T191A/L198A/L205A/L212A/L219A | C235S/C238S |
| Zmhdz25 | 26 | d1-59; d1-79; d-1-86; d1-94 | L19A/L21A/L23A/L25A/L27A/L29 A > L262A/L264A | V217A/Q220A/N221A | T231A/L238A/L245A/L252A/L259A | C282S/C285S |
| Zmhdz26 | 27 | d1-96; d1-102 | L3A/L5A/L7A > L22A/L24A/L26A | V214A/Q217A/N218A | T228A/L235A/L242A/L249A/L256A | C277S/C280S |
| Zmhdz27 | 28 | d1-171156 | L20A/L22L5A/L7 A > L52A/L54A/L56A > L97A/L99AL37A/L39A/L41A > L82A/L84A | V209A/Q212A/N213A | T238A/L245A/L252A/L259A/L266AT223A/L230A/L237A/L244A/L251A | C276SC291S/C295SC276S/C280S |
| Zmhdz28 | 29 | d1-28; d1-68 | L15A/L17A > L165A/L167A/L169A > L179A/L181A | V130A/Q133A/N134A | T144A/L151A/L158A/L165A/L172A | C196S/C199S |
| Zmhdz29 | 30 | d1-30; d1-59 | L6A/L8A/L10A/L12A/L14A | V137A/Q140A/N141A | T151A/L158A/L165A/L172A/L179A | C196S/C199S |
| Zmhdz30 | 31 | d1-43, d1-65 | L13A/L15A/L17A/L19A > L40A/L42A | V153A/Q156A/N157A | T167A/L174A/L181A/L188A/L195A | C238S/C241S |
| Zmhdz31 | 32 | d1-32; d1-64; d1-71 | L19A/L21A > L30A/L32A > L182A/L184A/L1186A > | V147A/Q1150A/N151A | T161A/L168A/L175A/L182A/L189A | N/A |
| Zmhdz32 | 33 | d1-68 | L8A/L10A/L12A > L40A/L42A | V147A/Q150A/N151A | T161A/L168A/L175A/L182A/L189A | C215S/C218S |
| Zmhdz33 | 34 | d1-23; d1-94 | L3A/L5A/L7A > L18A/L20A/L22A > L70A/L72A | V210A/Q213A/N214A | T224A/L231A/L238A/L245A/L252A | C273S/C276S |

TABLE 11-continued

Exemplary mutation variants of corn HD-Zip class II proteins in different domains/motifs.

| Gene | SEQ ID NO: | N-Terminal Deletion* | EAR-Like Motif Mutation** | Homeodomain Mutation | Leucine Zipper Mutation | CXXCX-Like Motif Mutation |
|---|---|---|---|---|---|---|
| Zmhdz34 | 35 | d1-28; d1-40 | L8A/L10A/L12A/L14A > L43A/L45A > L165A/L167A | V120A/Q123A/N124A | T134A/L141A/L148A/L155A/L162A | C185S/C188S |
| Zmhdz35 | 36 | d1-76 | L13A/L15A/L17A/L19A > L55A/L57A/L59A > L156A/L158A | V165A/Q168A/N169A | T179A/L186A/L193A/L200A/L207A | C255S/C258S |

*N-terminal truncation variants separated by a ";" represent independent variants. For example, two different variants are listed for Zmhdz34: a variant with an N terminal 28 amino acid truncation, and a variant with an N-terminal 40 amino acid truncation.
**Amino acid substitutions connected by a "/" refer to concurrent substitutions. For example, Zmhdz18 variant L8A/L10A/L12A means the three leucine residues at position 8, 10, and 12 are all mutated to alanine. A ">" separates two independent variants, i.e., a variant before ">" is an independent variant of the one after ">". For example, there are three independent variants listed in the Table for Zmhdz35: variant L13A/L15A/L17A/L19A, variant L55A/L57A/L59A and variant L156A/L158A. Additional variants can be generated using different combinations of the three variants.
N/A = not applicable.

What is claimed is:

1. A recombinant DNA construct comprising a DNA molecule that encodes a N-terminal truncation variant of a HD-Zip class II transcription factor protein that has an amino acid sequence with at least 95% amino acid sequence identity with the full-length amino acid sequence of SEQ ID NO: 113, and operably linked to a heterologous promoter, wherein the N-terminal truncation variant is missing the N-terminal amino acid portion comprising amino acid position 1 to amino acid position 59 of the HD-Zip class II amino acid sequence transcription factor protein relative to the amino acid sequence of SEQ ID NO: 26, and wherein said N-terminal truncation variant of the HD-Zip class II transcription factor protein has a loss-of-function mutation in a transcriptional repression domain.

2. The recombinant DNA construct of claim 1, wherein the N-terminal truncation variant of a HD-Zip class II transcription factor protein has the full-length amino acid sequence of SEQ ID NO: 113.

3. A transgenic plant or transgenic plant cell comprising the recombinant DNA construct of claim 1.

4. The transgenic plant or transgenic plant cell of claim 3, wherein the transgenic plant or a transgenic plant grown from said transgenic plant cell has an enhanced trait relative to a control plant lacking the recombinant DNA construct, and wherein the enhanced trait is increased yield.

5. The transgenic plant of claim 4, wherein the transgenic plant is a corn plant.

6. A method for producing a plant with an enhanced trait comprising the steps of:
(a) transforming a population of plants with a recombinant DNA construct according to claim 1 and expressing said N-terminal truncation variant of a HD-Zip class II transcription factor protein into said transformed population of plants and
(b) selecting a transformed plant from a sub-population of the transformed plants comprising the recombinant DNA construct that has an enhanced trait, wherein the enhanced trait is increased yield, relative to a control plant that does not comprise the recombinant DNA construct.

7. The method of claim 6, wherein, the N-terminal truncation variant of a HD-Zip class II transcription factor protein has the full-length amino acid sequence of SEQ ID NO: 113.

8. The method of claim 6, wherein the transgenic plant is a corn plant.

* * * * *

UNITED STATES PATENT AND TRADEMARK OFFICE
CERTIFICATE OF CORRECTION

PATENT NO. : 11,952,579 B2  
APPLICATION NO. : 17/071231  
DATED : April 9, 2024  
INVENTOR(S) : Griffith et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 175 days.

Signed and Sealed this  
First Day of July, 2025

Coke Morgan Stewart  
*Acting Director of the United States Patent and Trademark Office*